(12) United States Patent
Hariyama et al.

(10) Patent No.: US 10,128,078 B2
(45) Date of Patent: Nov. 13, 2018

(54) PROTECTIVE AGENT FOR ELECTRON MICROSCOPIC OBSERVATION OF BIOLOGICAL SAMPLE IN WATER-CONTAINING STATE, KIT FOR ELECTRON MICROSCOPIC OBSERVATION, METHODS FOR OBSERVATION, DIAGNOSIS, EVALUATION, AND QUANTIFICATION BY ELECTRON MICROSCOPE, AND SAMPLE STAGE

(71) Applicant: JAPAN SCIENCE AND TECHNOLOGY AGENCY, Saitama (JP)

(72) Inventors: Takahiko Hariyama, Shizuoka (JP); Yasuharu Takaku, Shizuoka (JP); Hiroshi Suzuki, Shizuoka (JP); Satoshi Hirakawa, Shizuoka (JP); Hideaki Kawasaki, Shizuoka (JP); Masatsugu Shimomura, Hokkaido (JP); Daisuke Ishii, Aichi (JP); Isao Ohta, Shizuoka (JP); Yoshinori Muranaka, Shizuoka (JP)

(73) Assignee: JAPAN SCIENCE AND TECHNOLOGY AGENCY, Saitama (JP)

( * ) Notice: Subject to any disclaimer, the term of this patent is extended or adjusted under 35 U.S.C. 154(b) by 0 days.

(21) Appl. No.: 15/114,978

(22) PCT Filed: Jan. 28, 2015

(86) PCT No.: PCT/JP2015/052404
§ 371 (c)(1),
(2) Date: Jul. 28, 2016

(87) PCT Pub. No.: WO2015/115502
PCT Pub. Date: Aug. 6, 2015

(65) Prior Publication Data
US 2016/0343539 A1     Nov. 24, 2016

(30) Foreign Application Priority Data

Jan. 29, 2014 (JP) .................................. 2014-014910
Sep. 3, 2014 (JP) .................................. 2014-179660

(51) Int. Cl.
*H01J 37/20* (2006.01)
*G01N 33/483* (2006.01)
*G01N 33/50* (2006.01)
*H01J 37/22* (2006.01)

(52) U.S. Cl.
CPC .......... *H01J 37/20* (2013.01); *G01N 33/4833* (2013.01); *G01N 33/5011* (2013.01); *H01J 37/22* (2013.01); *G01N 2223/612* (2013.01); *G01N 2800/7028* (2013.01); *H01J 2237/2002* (2013.01); *H01J 2237/2007* (2013.01)

(58) Field of Classification Search
CPC ........................................................ H01J 37/20
See application file for complete search history.

(56) References Cited

U.S. PATENT DOCUMENTS

| 2005/0173632 A1 | 8/2005 | Behar et al. |
| 2009/0173882 A1 | 7/2009 | Kuwabata et al. |
| 2012/0120226 A1 | 5/2012 | de Jonge |
| 2014/0227734 A1 | 8/2014 | Hariyama et al. |
| 2014/0264017 A1 | 9/2014 | Nakazawa et al. |

FOREIGN PATENT DOCUMENTS

| JP | 1-258348 | 10/1989 |
| JP | 1-267946 | 10/1989 |
| JP | 2013-235778 | 11/2013 |

OTHER PUBLICATIONS

International Preliminary Report on Patentability dated Aug. 22, 2016 in International Application No. PCT/JP2015/052404.
International Search Report dated Apr. 28, 2015 in International Application No. PCT/JP2015/052404.
Koji Kawai et al., "Hydrophilic Quaternary Ammonium Type Ionic Liquids, Systematic Study of the Relationship among Molecular Structures, Osmotic Pressures, and Water-Solubility", Langmuir, 2011, 27, 9671-9675.
Yasuhito Ishigaki, et al., "Ionic Liquid Enables Simple and Rapid Sample Preparation of Human Culturing Cells for Scanning Electron Microscope Analysis", Microscopy Research and Technique, 2011, 74, 415-420.
Hiroshi Suzuki et al, "In Situ Preparation of Biomimetic Thin Films and Their Surface-Shielding Effect for Organisms in High Vacuum", PLoS ONE, 2013, vol. 8, Issue 11, e78563.
Proceedings of The Japanese Society of Pathology, vol. 103, Issue 1 (published on Mar. 26, 2014).
Poster presentation at The Japanese Society of Pathology (published Apr. 24, 2014).
Proceedings of the 70th Annual Meeting of The Japanese Society of Microscopy (published May 11, 2014).

*Primary Examiner* — Bin Shen
(74) *Attorney, Agent, or Firm* — Wenderoth, Lind & Ponack, L.L.P.

(57) ABSTRACT

Provided are a protective agent for electron microscopic observation in a vacuum which can protect a biological sample in a water-containing state, such as a mammal, a plant tissue or a cultured cell, and a single cell in the living state without deforming it even in a vacuum, a kit using the same, methods for observation, diagnosis, evaluation, and quantification of a sample by an electron microscope, and a sample stage to be used for the observation. The protective agent for electron microscopic observation of the present invention contains a a component to impart the survival environment, a saccharide, and an electrolyte.

25 Claims, 63 Drawing Sheets

(a) TREATMENT OF MCMV PARTICLES WITH POLYBRENE

POLYBRENE
MCVC PARTICLES (b) ADSORPTION OF MCMV BY SANDWICH METHOD

COVER GLASS IRRADIATED WITH PLASMA — Anion glass

MCMV TREATED WITH POLYBRENE

SLIDE GLASS COATED WITH MAS — Cation glass

FIXED AFTER ADSORBED AT 37°C FOR 1 HOUR

MAS COAT
<HYDROPHILICITY>

FIG. 47

ADSORPTION RATE OF MCMV PARTICLES TO GLASS

ADSORPTION RATE
99.65%

★★ $p < 0.01$ (a)

(b)

DERMIC SIDE    EPIDERMAL SIDE (c)

(a)

(b)

DERMIC SIDE   EPIDERMAL SIDE (c)

PROTECTIVE AGENT FOR ELECTRON MICROSCOPIC OBSERVATION OF BIOLOGICAL SAMPLE IN WATER-CONTAINING STATE, KIT FOR ELECTRON MICROSCOPIC OBSERVATION, METHODS FOR OBSERVATION, DIAGNOSIS, EVALUATION, AND QUANTIFICATION BY ELECTRON MICROSCOPE, AND SAMPLE STAGE

TECHNICAL FIELD

The present invention relates to a protective agent for electron microscopic observation of a biological sample in a water-containing state, a kit for electron microscopic observation, an observation method by an electron microscope, and a sample stage.

BACKGROUND ART

It is required to impart vacuum resistance to the sample as the sample is in a vacuum and conductivity required to obtain an image to the sample in order to perform the observation of a sample by a scanning electron microscope and a transmission electron microscope.

The preparation of the sample for a scanning electron microscope is performed by removing the moisture from the sample through vacuum drying in advance, then depositing a conductive material (platinum, carbon, gold, palladium, osmium, or the like) on the sample in order to increase the generation efficiency of a secondary electron by imparting conductivity to the sample, and coating the surface of the sample by a means of a sputtering or the like.

Such a pretreatment is not required for those that are conductive and resistant to a vacuum, such as a metal or a semiconductor, but those that are not conductive are required to be coated with a conductive film formed of a conductive material. In addition, those that are inferior in vacuum resistance or the like, namely those that are deformed by vacuum drying or irradiation with an electron beam in a vacuum at the time of the electron microscopic observation are also required to be coated with a conductive film formed of a conductive material.

A biological sample is often required to be subjected to vacuum drying in advance since it contains a great amount of moisture. Hence, the surface shape of the sample is significantly deformed in some cases and it is difficult to observe it by an electron microscope in the living state.

It is possible to observe the water-containing state of a wet sample such as a gel-like substance or food at room temperature by using a low-vacuum SEM and a cryo-SEM, an environmental controlled SEM (ESEM), or the like. According to these methods, it is possible to observe not only a wet sample but also a sample as it is untreated. However, it is required to put the sample in a high vacuum in order to observe at a high magnification, and thus the sample is required to be resistant to a vacuum or conductive. Hence, it is difficult to obtain an image in the living state at a high magnification even in the observation of a biological sample.

In recent years, a method for an electron microscopic observation using an ionic liquid has been proposed. It is described that a wet sample is observed by using an ionic liquid and a SEM in Patent Literature 1 and Non Patent Literatures 1 and 2. The application of the ionic liquid to a cell is also described in Non Patent Literature 2. In addition, a method to use the technique of an ionic liquid for the transmission electron microscopic observation is disclosed in Patent Literature 2.

CITATION LIST

Patent Literature

Patent Literature 1: WO 2007/083756 A
Patent Literature 2: JP 2009-266741 A

Non Patent Literature

Non Patent Literature 1: Langmuir, 2011, 27, 9671-9675
Non Patent Literature 2: Microsc. Res. Tech. 2011, 74, 415-420

SUMMARY OF INVENTION

Technical Problem

However, it has not been achieved to directly observe a biological sample in the living state at a high magnification by an electron microscope even in the observation using an environmental SEM or the methods according to the respective literatures describe above.

In other words, it has not been achieved to observe the moving appearance of a biological sample as its living state by an electron microscope.

In addition, it has not been possible for the recovered sample to continue growing or living after the observation by an electron microscope. In other words, it has been regarded that electron microscopic observation securing the returning of a sample alive is impossible.

The sample is put in an extremely dry state since the environment for measurement by an electron microscope is a vacuum state. Hence, the sample is deformed or degenerated, and thus it is impossible to observe the sample in a state close to the living state.

Furthermore, a water-containing sample instantaneously freezes when it is put in a vacuum, thus the sample is deformed or degenerated by its ice crystal, and it is impossible to observe the sample in a state close to its original state.

A biological sample is put in a vacuum, and thus the supply of oxygen thereto from the outside world is blocked so as to fall the biological sample in an oxygen deficient state. In addition, the biological sample is put in a dry state, thus it becomes like a dried fish (a squid becomes like a dried squid), and it is difficult for the biological sample to be in the housing of an electron microscope in the living state.

Even in the case of an organism which can withstand a dry state, the water contained in the living body freezes and thus the organism dies before or while a moving state thereof is observed.

A biological sample is irradiated with an electron beam so as to be observed by an electron microscope, but it is required to obtain an electron microscopic image of the biological sample in the living state without causing the deformation or denaturation thereof by an electrical factor, a thermal factor, or the like due to this irradiation with an electron beam.

With regard to the barrier performance, a technique has been proposed so far in which the barrier performance is imparted by forming a film on the sample surface by a means to spin coat, deposit, coat, or the like a sample with an organic, inorganic, or organic/inorganic hybrid material, but there has not been an example to apply such barrier performance to the preparation of a sample for an electron microscope so far.

Accordingly, the present inventors have so far proposed a composition for evaporation inhibition which contains at least one kind selected from an amphiphilic compound, fats and oils, and an ionic liquid and a method in which a thin film is formed by applying this composition for evaporation inhibition to the surface of a biological/living body sample so as to cover the sample with the thin film and the sample that is covered with the thin film and contained in a sample chamber in a vacuum is observed in the living state by an electron microscope (Japanese Patent Application No. 2011-197685, Japanese Patent Application No. 2012-044383, and PCT/JP 2012/072982). In addition, the present inventors have proposed a technique to form a novel thin film by using a biocompatible compound and the like which have been difficult to be shaped into a film as a starting material (PCT/JP2013/074141).

The prior invention by the present inventors described above has mainly made it possible to observe a sample that is prepared by using an insect of which the skin is covered with a strong cuticular layer as a biological/living body sample and contained in the sample chamber in a vacuum in the living state by an electron microscope.

In other words, it cannot be said that the discussion whether the technique of the prior invention is applicable to a biological/living body sample other than the insect described above, for example, a fragile biological sample that does not have a strong layer to cover the surface, such as a mammal, a plant tissue or a cultured cell, and a single cell has been necessarily sufficiently carried out.

The present invention has been achieved as a result of intensive discussions in view of the circumstances as described above, and an object thereof is to provide a protective agent for electron microscopic observation in a vacuum which can protect a biological sample in a water-containing state, such as a mammal, a plant tissue or a cultured cell, and a single cell in the living state without deforming it even in a vacuum, a kit using the same, methods for observation, diagnosis, evaluation, and quantification of a sample by an electron microscope, and a sample stage to be used for the observation.

Solution to Problem

In order to solve the above problem, a protective agent for electron microscopic observation of a biological sample in a water-containing state of the present invention, includes: a a component to impart the survival environment; a saccharide; and an electrolyte.

The a component to impart the survival environment is preferably one or more kinds selected from a polyhydric alcohol and any derivative of the polyhydric alcohol.

The saccharide is preferably one or more kinds selected from a monosaccharide, a disaccharide, an oligosaccharide, a polysaccharide, and any derivative of the monosaccharide, the disaccharide, the oligosaccharide, and the polysaccharide.

The electrolyte is preferably one or more kinds selected from a metal compound, a metal complex, an inorganic salt, an organic salt, and an acid-base.

A kit for electron microscopic observation of a biological sample in a water-containing state of the present invention includes: (A) a protective agent for electron microscopic observation containing a a component to impart the survival environment, a saccharide, and an electrolyte; and (B) a surfactant-containing solution.

The a component to impart the survival environment is preferably one or more kinds selected from a polyhydric alcohol and any derivative of the polyhydric alcohol.

The saccharide is preferably one or more kinds selected from a monosaccharide, a disaccharide, an oligosaccharide, a polysaccharide, and any derivative of the monosaccharide, the disaccharide, the oligosaccharide, and the polysaccharide.

The electrolyte is preferably one or more kinds selected from a metal compound, a metal complex, an inorganic salt, an organic salt, and an acid-base.

A method for observing a biological sample in a water-containing state by an electron microscope of the present invention includes: a step of coating a biological sample in a water-containing state with a protective agent for electron microscopic observation containing a a component to impart the survival environment, a saccharide, and an electrolyte; a step of placing the biological sample in a water-containing state coated with the protective agent for electron microscopic observation on a sample stage and forming a thin film on a surface of the biological sample in a water-containing state by irradiating the biological sample in a water-containing state with an electron beam or plasma to cover the biological sample in a water-containing state; and a step of displaying an electron microscopic image of the biological sample in a water-containing state that is covered with the thin film and contained in a sample chamber in a vacuum on a display device.

In the method for observing a biological sample in a water-containing state by an electron microscope of the present invention, the biological sample in a water-containing state may be coated with a surfactant-containing solution at least before and after the biological sample in a water-containing state is coated with the protective agent for electron microscopic observation.

In the method for observing a biological sample in a water-containing state by an electron microscope of the present invention, a surface of the biological sample in a water-containing state may be washed with water prior to coating of the biological sample in a water-containing state with the protective agent for electron microscopic observation.

In the method for observing a biological sample in a water-containing state by an electron microscope of the present invention, it is preferable to use a sample stage in which the biological sample in a water-containing state on which a thin film is formed is placed on an upper surface of a cylindrical base member, a ring-shaped member having a circular opening that is substantially equal to a diameter of the cylindrical member, an opening having a diameter smaller than the opening at an upper surface portion thereof, and a fixing hole at a side surface portion is covered on the biological sample in a water-containing state placed on the upper surface of the cylindrical base member, and the cylindrical base member and the ring-shaped member are fixed with a fixing material.

In the method for observing a biological sample in a water-containing state by an electron microscope of the present invention, it is preferable to use a sample stage in which the biological sample in a water-containing state on which a thin film is formed is placed on an upper surface of a cylindrical member having a circular recess formed in a center, a disk-shaped member having a circular through hole formed in a center and a plurality of fixing holes opened on the periphery of the through hole is covered on the biological sample in a water-containing state placed on the upper surface of the cylindrical member, and the disk-shaped member and the cylindrical member are fixed with a fixing material.

In the method for observing a biological sample in a water-containing state by an electron microscope of the present invention, a thin film is preferably formed on a surface of a biological sample in a water-containing state by irradiating the biological sample in a water-containing state with an electron beam for sample observation in a sample chamber of an electron microscope.

In the method for observing a biological sample in a water-containing state by an electron microscope of the present invention, a thin film is preferably formed on a surface of a biological sample in a water-containing state by irradiating the sample with an electron beam different from an electron beam in a sample chamber of an electron microscope or plasma in advance before observation of the biological sample in a water-containing state by an electron microscope.

In the method for observing a biological sample in a water-containing state by an electron microscope of the present invention, an electron microscopic image of a biological sample in a water-containing state is preferably displayed on the display device without accompanying destruction of the biological sample in a water-containing state.

In the method for observing a biological sample in a water-containing state by an electron microscope of the present invention, an electron microscopic image of a sample in a water-containing state is preferably displayed on a display device without causing charge-up of the biological sample in a water-containing state by using a scanning electron microscope.

A sample stage used in the observation method of the present invention includes: a cylindrical base member; a ring-shaped member having a circular opening that is substantially equal to a diameter of the cylindrical member, an opening having a diameter smaller than the opening at an upper surface portion of the ring-shaped member, and a fixing hole at a side surface portion; and a fixing material, wherein the biological sample in a water-containing state on which a thin film is formed is placed on an upper surface of the cylindrical base member, the ring-shaped member is covered on the biological sample in a water-containing state placed on the upper surface of the cylindrical base member, and the cylindrical base member and the ring-shaped member are fixed with the fixing material.

A sample stage used in the observation method of the present invention includes: a cylindrical member having a circular recess formed in a center; a disk-shaped member having a circular through hole formed in a center and a plurality of fixing holes opened on the periphery of the through hole; and a fixing material, wherein the biological sample in a water-containing state on which a thin film is formed is placed on an upper surface of the cylindrical member, the disk-shaped member is covered on the biological sample in a water-containing state placed on the upper surface of the cylindrical member, and the disk-shaped member and the cylindrical member are fixed with the fixing material.

A method for diagnosing a cancer cell in a water-containing state by an electron microscope of the present invention includes: a step of coating a cancer cell in a water-containing state or a tissue including the cancer cell which is excised from a living body with a protective agent for electron microscopic observation containing a a component to impart the survival environment, a saccharide, and an electrolyte; a step of placing the cancer cell in a water-containing state or the tissue including the cancer cell which is coated with the protective agent for electron microscopic observation on a sample stage and forming and covering a thin film on a surface of the cancer cell in a water-containing state or the tissue including the cancer cell by irradiating the cancer cell in a water-containing state or the tissue including the cancer cell with an electron beam or plasma; a step of displaying an electron microscopic image of the cancer cell in a water-containing state or the tissue including the cancer cell which is covered with the thin film and contained in a sample chamber in a vacuum on a display device; and a step of performing image diagnosis of the displayed cancer cell in a water-containing state or the displayed tissue including the cancer cell.

In the method for diagnosing a cancer cell in a water-containing state by an electron microscope of the present invention, the cancer cell in a water-containing state is preferably one that is inoculated and cultured on a normal cell or a cell sheet.

In the method for diagnosing a cancer cell in a water-containing state by an electron microscope of the present invention, a cancer cell in a water-containing state or a tissue including the cancer cell which is excised from a living body is preferably chemically fixed immediately after the excision.

A method for evaluating an effect of a physiologically active substance or a drug to a cell in a water-containing state by an electron microscope of the present invention includes: a step of adding a physiologically active substance or a drug to a cell or cell sheet in a water-containing state; a step of coating the cell or cell sheet in a water-containing state to which the physiologically active substance or the drug is added with a protective agent for electron microscopic observation containing a a component to impart the survival environment, a saccharide, and an electrolyte; a step of placing the cell or cell sheet in a water-containing state coated with the protective agent for electron microscopic observation on a sample stage and forming and covering a thin film on a surface of the cell or cell sheet in a water-containing state by irradiating the cell or cell sheet in a water-containing state with an electron beam or plasma; a step of displaying an electron microscopic image of the cell or cell sheet in a water-containing state that is covered with the thin film and contained in a sample chamber in a vacuum on a display device; and a step of performing image diagnosis on an effect of the physiologically active substance or the drug to the displayed cell or cell sheet in a water-containing state.

In the method for evaluating an effect of a physiologically active substance or a drug to a cell in a water-containing state by an electron microscope of the present invention, preferably, the cell is a normal cell in a water-containing state and a physiologically active substance or a drug which has fewer side effects is screened by using a morphological change of the normal cell as an indicator.

In the method for evaluating an effect of a drug to a cell in a water-containing state by an electron microscope of the present invention, the physiologically active substance or the drug is preferably an anti-cancer drug.

In the method for evaluating an effect of a physiologically active substance or a drug to a cell in a water-containing state by an electron microscope of the present invention, preferably, the cell is a diseased cell in a water-containing state and a drug exhibiting activities is screened by using a morphological change of the diseased cell in a water-containing state as an indicator.

In the method for evaluating an effect of a physiologically active substance or a drug to a cell in a water-containing state by an electron microscope of the present invention, preferably, the diseased cell in a water-containing state is a cancer cell and the drug is an anti-cancer drug.

The method for observing a biological sample in a water-containing state by an electron microscope of the present invention includes a step of bringing a cell in a water-containing state into contact with a primary antibody, a step of bringing the primary antibody into contact with a secondary antibody modified with a gold colloid, a step of coating the cell in a water-containing state bound to the primary antibody and the second antibody with a protective agent for electron microscopic observation containing a a component to impart the survival environment, a saccharide, and an electrolyte, a step of placing the cell in a water-containing state coated with the protective agent for electron microscopic observation on a sample stage and forming a thin film on a surface of the cell in a water-containing state by irradiating the cell with an electron beam or plasma to cover the cell in a water-containing state, and a step of displaying an electron microscopic image of the cell in a water-containing state that is covered with the thin film and contained in a sample chamber in a vacuum on a display device, in which a binding site of a cell in a water-containing state with a primary antibody is observed.

In the observation method by an electron microscope of the present invention, preferably, an antigen that reacts with the primary antibody is a membrane protein of the cell in a water-containing state and a binding site of the cell in a water-containing state with the primary antibody is observed.

A method for quantifying viral particles in a water-containing state by an electron microscope of the present invention includes: a step of concentrating viral particles in a water-containing state on a substrate; a step of coating the viral particles in a water-containing state concentrated on the substrate with a protective agent for electron microscopic observation containing a a component to impart the survival environment, a saccharide, and an electrolyte; a step of placing the viral particles in a water-containing state coated with the protective agent for electron microscopic observation on a sample stage together with the substrate and forming a thin film on a surface of the viral particles in a water-containing state by irradiating the viral particles in a water-containing state with an electron beam or plasma to cover the sample; a step of displaying an electron microscopic image of the viral particles in a water-containing state that are covered with the thin film and contained in a sample chamber in a vacuum on a display device; and a step of counting viral particles in the displayed electron microscopic image of the viral particles in a water-containing state.

In the method for quantifying viral particles in a water-containing state by an electron microscope of the present invention, preferably, the step of concentrating viral particles in a water-containing state on a substrate is to concentrate viral particles by charging a surface of the viral particles in a water-containing state with a charge and adsorbing the viral particles in a water-containing state to a substrate having a surface charged with a charge that is opposite to this charged charge.

In the method for quantifying viral particles in a water-containing state by an electron microscope of the present invention, the surface of the viral particles in a water-containing state is preferably charged with a positive charge by being treated with polybrene.

In the method for quantifying viral particles in a water-containing state by an electron microscope of the present invention, the surface of the substrate is preferably charged with a negative charge by irradiating the surface with plasma.

Advantageous Effects of Invention

According to the present invention, it is possible to provide a protective agent for electron microscopic observation in a vacuum which can protect a biological sample in a water-containing state, such as a mammal, a plant tissue or a cultured cell, and a single cell in the living state without deforming it even in a vacuum, a kit using the same, methods for observation, diagnosis, evaluation, and quantification of a sample by an electron microscope, and a sample stage to be used for the observation.

BRIEF DESCRIPTION OF DRAWINGS

FIGS. 1(a) and 1(b) are images of samples which are observed and taken at a magnification of 50-fold by a SEM, respectively.

FIGS. 2(a) and 2(b) are images of the samples illustrated in FIGS. 1(a) and 1(b), which are observed and taken at a magnification of 2000-fold by a SEM, respectively.

FIG. 3(a) is an image of the mouse peritoneal epithelial side in a water-containing state which is treated with a protective agent for electron microscopic observation and a surfactant-containing solution without being chemically fixed and observed and taken at a magnification of 100-fold by a SEM. In addition, FIG. 3(b) is an image of a portion of FIG. 3(a), which is observed and taken at a magnification of 1000-fold by a SEM.

FIG. 4(a) is an image of the pathological section of the human gastric cancer, which is treated with a protective agent for electron microscopic observation and a surfactant-containing solution after the primary chemical fixation of the prior art and observed and taken at a magnification of 500-fold by a SEM. In addition, FIG. 4(b) is an image of a portion of FIG. 4(a), which is observed and taken at a magnification of 1500-fold by a SEM.

FIGS. 6(a) and 6(b) are images of samples which are observed and taken at a magnification of 100-fold by a SEM, respectively.

FIG. 9(a) is an image of the non-metastatic human melanoma cell line which is inoculated on a cell sheet of the human skin-derived fibroblast cell observed and taken at a magnification of 1000-fold by a SEM. In addition, FIG. 9(b) is an image of the microfiber in the marginal region of FIG. 9(a), which is observed and taken at a magnification of 10000-fold by a SEM.

FIG. 10(a) is an image of the metastatic human melanoma cell line which is inoculated on a cell sheet of the human skin-derived fibroblast cell and observed and taken at a magnification of 1000-fold by a SEM. In addition, FIG. 10(b) is an image of the microfiber in the marginal region of FIG. 10(a), which is observed and taken at a magnification of 10000-fold by a SEM.

FIG. 11(a) is an image of the metastatic human melanoma cell line which is inoculated on a cell sheet of the human skin-derived fibroblast cell and observed and taken at a magnification of 2000-fold in 20 minutes after the inoculation by a SEM. In addition, FIG. 11(b) is an image of FIG. 11(a) which is observed and taken at a magnification of 5000-fold by a SEM.

FIG. 13(a) is an image of the metastatic human melanoma cell line which is inoculated on a cell sheet of the human skin-derived fibroblast cell and observed and taken at a magnification of 500-fold in 30 minutes after the inoculation by a SEM. In addition, FIG. 13(b) is an image of FIG. 13(a) which is observed and taken at a magnification of 2000-fold by a SEM.

FIG. 14(a) is an image of the metastatic human melanoma cell line which is inoculated on a cell sheet of the human skin-derived fibroblast cell and observed and taken at a magnification of 1000-fold in 60 minutes after the inoculation by a SEM. In addition, FIG. 14(b) is an image of FIG. 14(a) which is observed at a magnification of 5000-fold and taken by a SEM.

FIG. 17(a) is an image of the metastatic human melanoma cell line which is inoculated on a cell sheet of the human skin-derived fibroblast cell and observed and taken at a magnification of 1000-fold in 60 minutes after sorafenib of a kind of anti-cancer drug is added thereto by a SEM. In addition, FIG. 17(b) is an image of FIG. 17(a) which is observed and taken at a magnification of 5000-fold by a SEM.

FIG. 18A is a photograph which illustrates the artificial human skin being cultured and the culture vessel. In addition, FIG. 18B is a photograph of the HE-stained pathological section of the artificial human skin of FIG. 18A.

FIG. 19(a) is an image of the artificial human skin which is observed and taken at a magnification of 2,500-fold in 60 minutes after gefitinib dissolved in dimethyl sulfoxide (DMSO) is added to the artificial human skin illustrated in FIG. 18A by a SEM. In addition, FIG. 19(b) is an image of the artificial human skin as a control group, which is observed and taken at a magnification of 2,500-fold in 60 minutes after DMSO is added to the artificial human skin illustrated in FIG. 18A by a SEM.

FIG. 21(a) is an image of the metastatic human melanoma cell line by an immunoelectron microscopy, which is inoculated on a cell sheet of the human skin-derived fibroblast cell, bound to a primary antibody and a secondary antibody modified with a gold colloid, treated with a protective agent for electron microscopic observation and a surfactant-containing solution, and then observed and taken at a magnification of 1000-fold by a SEM. In addition, FIG. 21(b) is an image of FIG. 21(a) by an immunoelectron microscopy, which is observed and taken at a magnification of 10,000-fold by a SEM.

FIG. 23(a) illustrates an embodiment of the sample stage that is constituted by a cylindrical member, a ring-shaped member, and a fixing material. In addition, FIG. 23(b) is another embodiment of the sample stage that is constituted by a cylindrical member, a disc-shaped member, and a fixing material.

FIG. 24(a) is an image of the mouse peritoneal epithelial side in a water-containing state which is prepared by placing the peritoneum excised from a mouse on the sample stage illustrated in FIG. 23(a) and immediately treating it with a protective agent for electron microscopic observation and a surfactant-containing solution and observed and taken at a magnification of 100-fold by a SEM. In addition, FIG. 24(b) is an image of a portion of FIG. 24(a), which is observed and taken at a magnification of 1500-fold by a SEM.

FIG. 25(a) is an image of the peritoneum which is excised from a mouse, placed on the sample stage illustrated in FIG. 23(a) after passing through the chemical fixation, dehydration, drying, and metal deposition steps which are a method for preparing a specimen for electron microscopic observation of the prior art, and observed and taken at a magnification of 50-fold by a SEM. In addition, FIG. 25(b) is an image of a portion of FIG. 25(a), which is observed and taken at a magnification of 2000-fold by a SEM.

FIG. 26(a) is an image of the peritoneum in a water-containing state that is excised from a mouse, placed on the sample stage illustrated in FIG. 23(a), immediately treated with a protective agent for electron microscopic observation and a surfactant-containing solution, and observed and taken at a magnification of 100-fold by a SEM. In addition, FIG. 26(b) is an image of a portion of FIG. 26(a), which is observed and taken at a magnification of 1300-fold by a SEM.

FIG. 27(a) is an image of the peritoneum which is excised from a mouse, placed on the sample stage illustrated in FIG. 23(a) after passing through the chemical fixation, dehydration, drying, and metal deposition steps which are a method for preparing a specimen for electron microscopic observation of the prior art, and observed and taken at a magnification of 50-fold by a SEM. In addition, FIG. 27(b) is an image of a portion of FIG. 27(a), which is observed and taken at a magnification of 2000-fold by a SEM.

FIG. 29(a) is an image of the diaphragm in a water-containing state which is excised from a mouse, placed on the sample stage illustrated in FIG. 23(b), immediately treated with a protective agent for electron microscopic observation and a surfactant-containing solution, and observed and taken at a magnification of 500-fold by a SEM. In addition, FIG. 29(b) is an image of a portion of FIG. 29(a), which is observed and taken at a magnification of 2000-fold by a SEM.

FIG. 31(a) is an image of the peritoneum in a water-containing state which is excised from an inflamed mouse, placed on the sample stage illustrated in FIG. 23(a), immediately treated with a protective agent for electron microscopic observation and a surfactant-containing solution, and observed and taken at a magnification of 30-fold by a SEM. In addition, FIG. 31(b) is an image of the peritoneum in a water-containing state which is a control group, excised from a mouse, placed on the sample stage illustrated in FIG. 23(a), immediately treated with a protective agent for electron microscopic observation and a surfactant-containing solution, and observed and taken at a magnification of 30-fold by a SEM.

FIG. 34(a) is an image of the mouse-derived fibroblast cell which is cultured on a glass plate as a cultured cell, withdrawn from the culture medium, then immediately treated with a surfactant-containing solution and a protective agent for electron microscopic observation, and observed and taken at a magnification of 450-fold by a SEM. In addition, FIG. 34(b) is an image of a portion of FIG. 34(a), which is observed and taken at a magnification of 2000-fold by a SEM.

FIG. 35(a) is an image of the mouse-derived fibroblast cell which is cultured on a glass plate as a cultured cell, withdrawn from the culture medium, then introduced into an electron microscope in an untreated state, and observed and taken at a magnification of 1500-fold by a SEM. In addition, FIG. 35(b) is an image of a portion of FIG. 35(a), which is observed and taken at a magnification of 1800-fold by a SEM.

FIG. 36(a) is an image of the human-derived fibroblast cell which is cultured on a glass plate as a cultured cell, withdrawn from the culture medium, then immediately washed with distilled water, treated with a protective agent for electron microscopic observation, and observed and taken at a magnification of 1000-fold by a SEM. In addition, FIG. 36(b) is an image of a portion of FIG. 36(a), which is observed and taken at a magnification of 5000-fold by a SEM.

FIG. 37(a) is an image of the human erythrocyte as a single cell which is contained in physiological saline dropped on a glass plate, introduced into an electron microscope in an untreated state, and observed and taken at a magnification of 1000-fold by a SEM. In addition, FIG. 37(b) is an image of a portion of FIG. 37(a), which is observed and taken at a magnification of 2000-fold by a SEM.

FIG. 38(a) is an image of the human blood cell and platelet in a water-containing state which are prepared by dropping physiological saline containing the human blood cell and platelet as a single cell on a glass plate and immediately treating it with a protective agent for electron microscopic observation and observed and taken at a magnification of 1000-fold by a SEM. FIG. 38(b) is an image of the human erythrocyte in a water-containing state which is prepared by dropping physiological saline containing the human erythrocyte as a single cell on a glass plate and immediately treating it with a protective agent for electron microscopic observation and observed and taken at a magnification of 7000-fold by a SEM. FIG. 38(c) is an image of the human leucocyte in a water-containing state which is prepared by dropping physiological saline containing the human leucocyte as a single cell on a glass plate and immediately treating it with a protective agent for electron microscopic observation and observed and taken at a magnification of 7000-fold by a SEM.

FIG. 39(a) is an image of yeast in a water-containing state which is prepared by dropping a culture medium containing the yeast as a single cell on a glass plate and immediately treating it with a protective agent for electron microscopic observation and observed and taken at a magnification of 5000-fold by a SEM. FIG. 39(b) is an image of a portion of FIG. 39(a), which is observed and taken at a magnification of 20,000-fold by a SEM. FIG. 39(c) is an image of *Bacillus natto* in a water-containing state which is prepared by dropping a culture medium containing the *Bacillus natto* as a single cell on a glass plate and immediately treating it with a protective agent for electron microscopic observation and observed and taken at a magnification of 15,000-fold by a SEM. FIG. 39(d) is an image of *Escherichia coli* in a water-containing state which is prepared by dropping a culture medium containing the *Escherichia coli* as a single cell on a glass plate and immediately treating it with a protective agent for electron microscopic observation and observed and taken at a magnification of 10,000-fold by a SEM.

FIG. 40(a) is an image of the *Dictyostelium discoideum* fruiting body in a water-containing state which is prepared by dropping a culture medium containing the *Dictyostelium discoideum* fruiting body as a single cell on a glass plate and immediately treating it with a protective agent for electron microscopic observation and observed and taken at a magnification of 50-fold by a SEM. FIG. 40(b) is an image of a portion of FIG. 40(a), which is observed and taken at a magnification of 300-fold by a SEM. FIG. 40(c) is an image of a portion of FIG. 40(a), which is observed and taken at a magnification of 3000-fold by a SEM. FIG. 40(d) is an image of a portion of FIG. 40(a), which is observed and taken at a magnification of 6000-fold by a SEM.

FIG. 41(a) is an image thereof taken in 10 minutes after the infection by a SEM, and FIG. 41(b) is an enlarged image of a portion of FIG. 41(a) taken by a SEM.

FIG. 43(a) is an image thereof taken in 10 minutes after the infection by a SEM, FIG. 43(b) is an image of FIG. 43(a) taken in 15 minutes after the infection by a SEM, and FIG. 43(c) is an image of FIG. 43(a) taken in 20 minutes after the infection by a SEM.

FIG. 44(a) is an image thereof taken in 15 minutes after the infection by a SEM, and FIG. 44(b) is an image of the region surrounded by a frame in FIG. 44(a), which is observed and taken by being enlarged by a SEM. FIG. 44(c) is an image of FIG. 44(b) taken in 30 minutes after the infection by a SEM, FIG. 44(d) is an image of FIG. 44(b) taken in 45 minutes after the infection by a SEM, FIG. 44(e) is an image of FIG. 44(b) taken in 60 minutes after the infection by a SEM, and FIG. 44(f) is an image of FIG. 44(b) taken in 75 minutes after the infection by a SEM.

FIG. 45(a) is a photograph of MCMV which is prepared by adsorbing the mouse cytomegalovirus (MCMV) treated with polybrene to the surface of cover glass treated with plasma, observed, and taken. The fluorescent green dot in the drawing indicates the MCMV in a water-containing state adsorbed to the cover glass. FIG. 45(b) is a photograph of MCMV which is prepared by adsorbing the MCMV treated with polybrene to the surface of untreated cover glass as a control group, observed, and taken.

FIGS. 46(a) and 46(b) are schematic diagrams which illustrate the method for concentrating MCMV using the MCMV treated with polybrene and cover glass of Example 27, respectively. FIG. 46(a) illustrates the charge of MCMV treated with polybrene, and FIG. 46(b) schematically illustrates the principle to adsorb the mouse cytomegalovirus (MCMV) treated with polybrene to the surface of cover glass treated with plasma and to concentrate it.

FIG. 47 is a graph which illustrates the measurement results of the adsorption rate of the MCMV particles on the cover glass of Example 28.

FIG. 48(a) is an image of MCMV which is prepared by adsorbing MCMV particles that are positively charged by being treated with polybrene to cover glass that is negatively charged by being irradiated with plasma and concentrating it and observed and taken at a magnification of 15,000-fold by a SEM. FIG. 48(b) is an image of a portion of FIG. 48(a), which is observed and taken at a magnification of 35,000-fold by a SEM.

FIG. 51(a) is an image of MCMV of a control group taken by a SEM, and FIG. 51(b) is an image of MCMV which is treated with uranium acetate and taken by a SEM. In addition, FIG. 51(c) is an image of MCMV which is treated with cisplatin and taken by a SEM, and the arrow in the drawing indicates DNA-containing viral particles. All of the images are observed and taken at a magnification of 10,000-fold by a SEM.

FIG. 53(a) is an image of the petal of *Adonis amurensis* rhizome in a water-containing state, which is prepared by collecting it as a biological tissue of a plant, placing it on the sample stage illustrated in FIG. 23(a), and immediately treating it with a protective agent for electron microscopic observation and a surfactant-containing solution and observed and taken at a magnification of 30-fold by a SEM. In addition, FIG. 53(b) is an image of a portion of FIG. 53(a), which is observed and taken at a magnification of 5000-fold by a SEM.

FIG. 54(a) is an image of the mesophyll cell on the front side of the leaf of dayflower, which is prepared by collecting a leaf of dayflower in a water-containing state as a biological tissue of a plant, subjecting it to a primary chemical fixation treatment, and then treating it with a protective agent for electron microscopic observation and a surfactant-containing solution and observed and taken at a magnification of 30-fold by a SEM. In addition, FIG. 54(b) is an image of the mesophyll cell on the back side of the leaf of dayflower in a water-containing state, which is treated with a protective agent for electron microscopic observation and a surfactant-containing solution after the primary chemical fixation treatment and observed and taken at a magnification of 30-fold by a SEM.

FIG. 55(a) illustrates the front side of the leaf, and FIG. 55(b) illustrates the back side of the leaf.

FIG. 56(a) illustrates the front side of the leaf, and FIG. 56(b) illustrates the back side of the leaf.

FIG. 60(a) is an image of a prokaryotic organism in a water-containing state taken by a SEM. FIG. 60(b) is an image of Nata de coco bacteria in a water-containing state taken by a SEM, FIG. 60(c) is an image of yeast in a water-containing state taken by a SEM, and FIG. 60(d) is an image of *Escherichia coli* in a water-containing state taken by a TEM.

DESCRIPTION OF EMBODIMENTS

Figure 1:
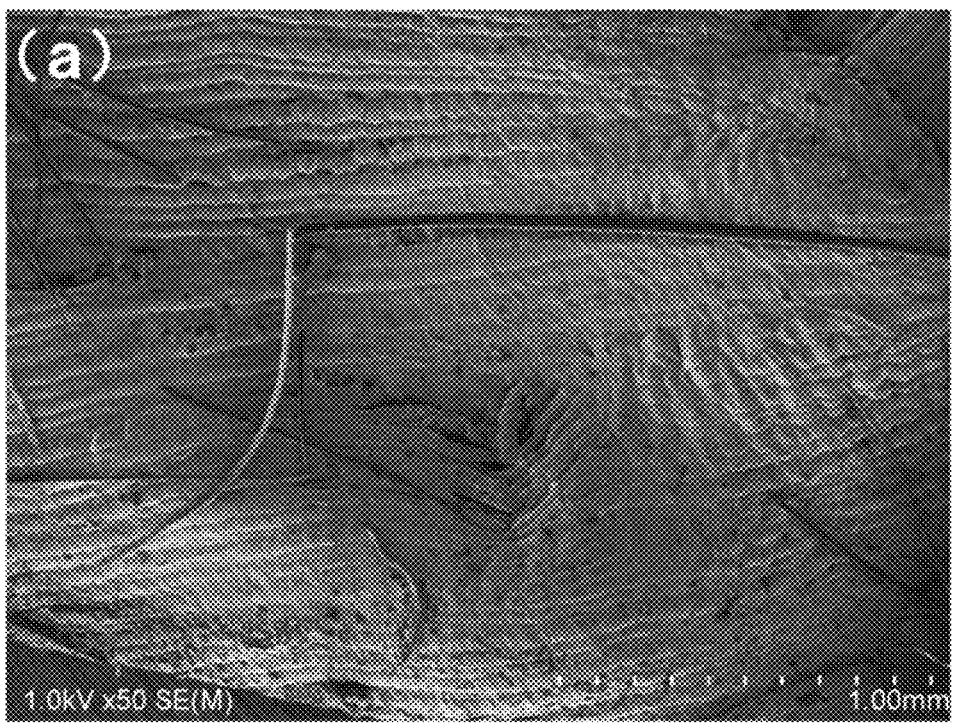
FIG. 1(a) is an image of Example 1 taken by a SEM.
FIG. 1(b) is an image of Comparative Example 1 taken by a SEM.
Figure 1:

Hereinafter, the present invention will be described in detail.

In the prior invention described above, the discussion whether a fragile biological sample which does not have a strong layer to cover the surface, such as a mammal, a plant tissue or a cultured cell, and a single cell can survive in a vacuum in a mirror body of an electron microscope and be observed has not been necessarily sufficiently carried out. Hence, the present inventors have carried out intensive discussions and found out that it is possible to observe a fragile biological sample which does not have a strong layer to cover the surface, such as a mammal, a plant tissue or a cultured cell, and a single cell and has not been necessarily sufficiently discussed in the living state can be observed by an electron microscope by being coated with the protective agent for electron microscopic observation of the present invention. This is a novel finding by the present inventors.

The protective agent for electron microscopic observation of the present invention is referred to as a surface shielding enhancer (SSE) which enhances the water/gas barrier performance (surface shielding effect, SS effect) by the composition for evaporation inhibition of the prior invention by the present inventors.

According to the protective agent for electron microscopic observation of the present invention, it is possible to observe a fragile biological sample which does not have a strong layer to cover the surface, such as a mammal, a plant tissue or a cultured cell, and a single cell in the living state by an electron microscope. In addition, the present invention is not only limited to the provision of a solution for electron microscopic observation of a biological sample, but it provides the composition of a solution (SSE solution) which widely acts as a SSE.

According to the present invention, the SSE solution contains a a component to impart the survival environment of the main component, a saccharide, and an electrolyte, and it can be used in various applications.

Incidentally, in the present invention, the term "a component to impart the survival environment" means a compound that can provide a pseudo-living environment or a survival environment to a biological sample in a water-containing state as it has water-retaining ability even in a vacuum in which the electron microscopic observation is performed.

In addition, in the present invention, the term "vacuum" means, for example $10^{-1}$ Pa or less, further from $10^{-2}$ Pa to $10^{-8}$ Pa, and particularly a range of from $10^{-4}$ Pa to $10^{-8}$ Pa.

Examples of the a component to impart the survival environment may include a polyhydric alcohol and any derivative thereof. A substance which has a hydroxyl group in the molecule and a low vapor pressure is preferable. In addition, it is preferable that the a component to impart the survival environment is viscous. Specific examples thereof may include glycerin, polyethylene glycol, polyvinyl alcohol, a triglyceride, polyresorcinol, polyphenol, tannic acid, urushiol, and a saponin, and particularly it is preferable to use glycerin.

Examples of the saccharide may include a monosaccharide, a disaccharide, an oligosaccharide, a polysaccharide, and any derivative thereof. Specifically, examples of the monosaccharide may include glucose and fructose. Examples of the disaccharide may include sucrose and trehalose, and examples of the polysaccharide may include heparin, chondroitin sulfate, pullulan, pectin, guar gum, xanthan gum, carrageenan, propylene glycol, carboxymethyl cellulose, and inulin. Particularly, a monosaccharide such as glucose is preferable. In addition to these, caramel, honey, beeswax, and the like may be used. In addition, tears of a mammal, wax ester secreted from pores, squalene, triglycerides, sebum such as fatty acids, ceramides, cholesterol, free fatty acids, horny intercellular lipids such as cholesterol sulfate, saliva or digestive fluid secreted from the digestive organs, membrane-type mucin or secretory mucin present on the membrane surface of epithelial cells which mainly constitute the respiratory tract and digestive organs may be used. In addition, a wax component or a water-soluble substance that is secreted on the cuticle surface from invertebrates such as arthropods, fats and oils or a water-soluble substance that is secreted from the pores of vertebrates may be used. In addition, liver oil that is included in the liver of a shark, a cod, a stingray, and the like and the body fluid of a jellyfish, a sea cucumber, and the like may be used. In addition, natural secretions that are secreted from plants and fungi may be used, and as saccharide derived from a plant, oil that can be collected from the seeds of various plants, such as *eucalyptus* oil, peppermint oil, and castor oil, pine oil, and the sap of lacquer, cherry, oak, willow, and the like may be used. The initial secretions that are secreted from prokaryotic organisms and form a biofilm or a bio film itself may be used.

Examples of the electrolyte may include a metal compound, a metal complex, an inorganic salt, an organic salt, and an acid-base.

As the metal compound, those that contain a metal ion may be widely used.

The metal compound may be a salt composed of a cation and an anion (single salt) or a salt composed of two or more kinds (double salt).

The metal compound may be a compound such as an oxide, a hydroxide, a halide, a sulfate, a nitrate, a carbonate, an acetate, a phosphate, or a lactate. Specific examples thereof may include sodium chloride, magnesium chloride, calcium chloride, sodium bicarbonate, potassium chloride, strontium chloride, lithium chloride, hafnium chloride, iron chloride, aluminum chloride, zinc chloride, copper chloride, cobalt chloride, magnesium sulfate, magnesium carbonate, dibasic sodium phosphate, and calcium lactate.

The metal compound may be a metal oxide. A metal alkoxide is a compound represented by MOR, and it is composed of a metal (M) and an alkoxide (RO—) (R is a hydrocarbon). Specific examples of the metal (M) may include silicon, titanium, aluminum, boron, zirconium, vanadium, tungsten, phosphorus, germanium, indium, hafnium, and molybdenum, and a metal alkoxide is obtained from various alcohols. These metal alkoxides may be used as they are, or a reaction product obtained by subjecting these metal alkoxides to a sol-gel reaction in the presence of an acid or an alkali may be used. As the metal alkoxide, two or more kinds may be mixed without using a single component.

The metal compound may be a metal complex. Specific examples thereof may include an ethylenediamine nickel complex and a tetraamine cobalt complex.

Specific examples of the acid-base may include hydrochloric acid, acetic acid, citric acid, maleic acid, succinic acid, fumaric acid, and gluconic acid, and particularly, it is preferable to use citric acid.

In addition, as the electrolyte, it is possible to use a commercially available sports drink powder or Ringer's solution. In particular, a commercially available sports drink powder contains a saccharide, and thus it can be prepared into the protective agent for electron microscopic observation of the present invention by being simply dissolved in glycerin.

The excess liquid is sufficiently wiped off with a filter paper made of paper after the protective agent for electron microscopic observation of the present invention is coated on the entire sample. This makes it possible to observe a fragile biological sample which does not have a strong layer to cover the surface, such as a mammal, a plant tissue or a cultured cell, and a single cell and has not been so far necessarily sufficiently discussed in the living state by an electron microscope. In addition, it is not limited to the coating, and various kinds of methods such as immersion and dropping may be employed. Furthermore, upon use of the protective agent for electron microscopic observation, the stock solution is used by being diluted depending on the characteristics of the sample in some cases. It is preferable to use the protective agent for electron microscopic observation as the stock solution, for example, for the site from which the epithelial tissues and the like are peeled off, or the organs, tissues, and the like that are removed from an individual, and a sample subjected to a treatment by which the original structure is significantly impaired, for example, the organism is scratched in order to obtain a high protective effect. On the other hand, it is preferable to use the protective agent for electron microscopic observation by being diluted in a range of from 10 times to 10,000 times for an organism (for example, cells, tissues, and organs are mentioned) that is excellent in stability and airtightness of the structure as the sample characteristics. In other words, it is effective to thinly coat the protective agent for electron microscopic observation in order to analyze the microstructure and a change thereof by an electron microscope. However, it is not necessarily unsuitable for microstructure observation to use the protective agent for electron microscopic observation as the stock solution. The best conditions for time-dependently observing the sample at a high resolving power and a high resolution while maintaining the surviving state by an electron microscope are obtained by using the protective agent for electron microscopic observation of the present invention at the optimal dilution rate to produce a protective effect for each sample only in view of the sample characteristics.

It is possible to time-dependently observe the developmental process or the regenerative process of the biological sample by an electron microscope while maintaining the surviving state by coating the protective agent for electron microscopic observation of the present invention on the entire sample.

In addition, it is possible to perform the image diagnosis, the evaluation on the effects or side effects of the drug to a cell or a tissue, and the screening of drug by using a disease or the difference or change in morphology of the normal cell and the diseased cell caused by the addition of a physiologically active substance or a drug as an indicator by coating the protective agent for electron microscopic observation of the present invention on the entire sample.

Furthermore, it is possible to perform the immunoelectron microscopy in which the primary antibody against the antigen of a living cell is bound to the secondary antibody that is bound to the primary antibody, modified, and labeled by coating the protective agent for electron microscopic observation of the present invention on the entire sample.

Moreover, it is possible to observe and count living cells, viruses, or the like in an electron microscope and thus to quantify the cells, viruses, and the like by coating the protective agent for electron microscopic observation of the present invention on the entire sample.

Incidentally, the "biological sample" in the above includes prokaryotic organisms and eukaryotic organisms.

The prokaryotic organisms include eubacteria and archaebacteria.

The eubacteria include phylum Acidobacteria, phylum *Aquifex*, phylum Actinobacteria, phylum Elusimicrobia, phylum Caldiserica, phylum *Chlamydia*, phylum *Chlorobium*, phylum *Chloroflexus*, phylum *Chrysiogenes arsenatis*, phylum Thermodesulfobacteria, phylum Thermomicrobia, phylum Cyanobacteria, phylum *Gematimonas*, phylum Synergistetes, phylum Spirochaeta, phylum *Dictyoglomus*, phylum *Thermus-Deinococcus*, phylum Tenericutes, phylum *Deferribacter*, phylum Thermotogae, phylum Nitrospirae, phylum Bacteroidetes, phylum Firmicutes, phylum Fibrobacteres, phylum Fusobacteria, phylum Planctomycetes, phylum Proteobacteria, phylum Verrucomicrobia, and phylum Lentisphaerae.

The archaebacteria include phylum (kingdom) Crenarchaeota, phylum (kingdom) Euryarchaeota, phylum (kingdom) Korarchaeota, phylum Nanoarchaeota, and phylum Thaumarchaeota.

The eukaryotic organisms include kingdom Protista, kingdom Plantae, kingdom Fungi, and kingdom Animalia.

The kingdom Protista includes phylum Myxomycota, *Dictyostelium discoideum*, Labyrinthulomycetes, and phylum Dicontomycetes in addition to the algae (green algae, brown algae, red algae, Bacillariophyceae, division Euglena, division Cryptophyta, division Dinoflagellate), Protozoa (phylum Ciliophora, Rhizopoda (amoeba, foraminifera, heliozoan, and radiolarian), phylum Sporozoa (Apicomplexa, microsporidian, and mucus sporozoan), and flagellate (Trypanosomes, choanoflagellate, hypermastigia, and polymastigote).

The kingdom Plantae includes division Chlorophyta, division Bryophyta, division Charophyta, and subkingdom Tracheophyta (division Psilophyta, division Lycopodiophyta, division Equisetophyta, division Ophioglossales, division Pteridophyta, division Coniferophyta (division Pinophyta), division Cycadophyta, division Ginkgophyta, division Gnetophyta, division Magnoliophyta (division Magnoliophyta (class Dicotyledoneae (class Magnoliopsida), and class Monocotyledoneae (class Liliopsida)).

The kingdom Fungi includes phylum Chytridiomycota (chytrid), phylum Zygomycota (*mucor* and *rhizopus*), phylum Ascomycota (yeast and *Neurospora crassa*), phylum Basidiomycota (mushroom), Fungi imperfecti, and division Lichenes.

The kingdom Animalia includes phylum Porifera, phylum Placozoa (*Trichoplax adhaerens*), phylum Cnidaria (jellyfish, sea anemone, and coral), phylum Ctenophora (comb jelly), phylum Mesozoa (Dicyemida), phylum Platyhelminthes (turbellaria and planarian), phylum Nemertinea (ribbon worm), phylum Gnathostomulida, phylum Gastrotricha, phylum Trochelminthes (rotifer), phylum Kinorhyncha, phylum Acanthocephala, phylum Entoprocta, phylum Nematoda (*ascaris* and *C. elegans*), phylum Nematomorpha (*gordioidea*), phylum Ectoprocta, phylum Phoronida, phylum Brachiopoda, phylum Mollusca (shellfish, squid, and octopus), phylum Priapuloidea, phylum Sipunculida (sipunculid), phylum Echiura, phylum Annelida (earthworm and lugworm), phylum Tardigrada (tardigrade), phylum Pentastoma, phylum Onychophora (velvet worm), phylum Arthropoda (subphylum Chelicerata (superclass Pycnogonida, superclass Xiphosura (horseshoe crab), and superclass Caulogastra (spider and scorpion)), subphylum Crustacea (shrimp and crab), phylum Myriapoda (class Chilopoda (chilopoda and centipede), class Symphyla (Symphyla and symphylan), class Pauropoda (class Pauropoda and pauropoda), and class Diplopoda (class Diplopoda and millipede)), and subphylum Hexapoda (class Entognatha and class Ectognatha (class Incecta)), phylum Pogonophora, phylum Echinodermata (sea urchin, starfish, brittle star, sea cucumber, and crinoid), phylum Chaetognatha (arrow worm), phylum Hemichordata (acorn worm), and phylum Chordata (subphylum Urochordata (sea squirt) and subphylum Cephalochordata (amphioxus), subphylum Vertebrata (superclass Agnatha (class Eptatretus and class Cephalaspidomorphi (*Petromyzon marinus*)), superclass Gnathostomata (class Chondrichthyes (shark, ray, and elephant fish), class Sarcopterygii (coelacanth and lungfish), class Actinopterygii, class Amphibia, class Reptilia, class Mammalia, and class Ayes)).

In particular, examples of Mammals belonging to the class Mammalia may include family Leporidae (hare and rabbit), family Muridae (mouse and rat), family Canidae, family Felidae (cat), family Bovidae (cattle, buffalo, goat, and sheep), family Suidae (wild boar and pig), family Equidae (horse and donkey), family Cercopithecidae such as family Cercopithecidae (Rhesus monkey, cynomolgus monkey, and Japanese monkey) and family Hominidae (human and chimpanzee).

In addition, the "biological sample" includes not only a tissue excised from the living body of the animal described above but also a tissue excised from a plant, a cultured cell, and a single cell.

Examples of the tissue excised from the living body of an animal may include skin, blood vessel, hair, muscle, stomach, intestines, lung, heart, liver, pancreas, kidney, brain, eye, cornea, neuronal, umbilical cord, placenta, peritoneum, diaphragm, fascia, and pericardium.

Examples of the tissue excised from a plant may include flower petal, seed, fruit, leaf, stem, root, root hair, shoot apical meristem, root tip meristem, conduit, phloem, vascular bundle, and mesophyll cell.

Examples of the cultured cell may include those obtained through the primary culture or subculture of a stem cell, a fibroblast cell, a skin cell, a mucosal cell, a liver cell, a pancreatic islet cell, a nerve cell, a chondrocyte, an endothelial cell, an epithelial cell, a bone cell, a muscle cell, and the like which are isolated from a tissue derived from a human or non-human animal, further the sperm of an animal such as livestock or a fish, a reproductive cell, such as an egg or a fertilized egg, a tumor cell, an insect cell, and a plant cell. Furthermore, a cell line that is established and commercially available may be used. In addition, as the cell, an adherent cell or a floating cell may be used. Furthermore, a cell cultured in a flat plate shape or a cell sheet may be used, or a sterically three-dimensionally cultured cell may be used.

Examples of the single cell may include a blood cell, platelet, erythrocyte, and leucocyte. In addition, a singlecelled organism such as yeast, *Escherichia coli, Bacillus subtilis, Bacillus natto*, or cellular slime mold is also exemplified as a single cell.

Furthermore, the "biological sample" includes viruses or viroids. The kind of virus may be a DNA virus or a RNA virus.

Examples of the DNA virus may include family Poxviridae (smallpox virus, monkeypox virus, and the like), family Herpesviridae (herpes simplex virus, varicella-zoster virus, cytomegalovirus, EB virus, and the like), family Adenoviridae (adenovirus), family Papovaviridae (papilloma virus, JC virus, and the like), family Parvoviridae (parvovirus), and family Hepadnaviridae (B hepatitis virus and the like).

Examples of the RNA virus may include family Arenaviridae (Lassa virus and the like), family Orthomyxoviridae (influenza virus and the like), family Caliciviridae (norovirus, Sapovirus, and the like), family Coronaviridae (SARS virus and the like), family Togaviridae (rubella virus and the like), family Nodaviridae (viral nervous necrosis virus and the like), family Paramyxoviridae (mumps virus, measles virus, RS virus, and the like), family Picornaviridae (polio virus, family Coxsackie virus, echo virus, and the like), family Filoviridae (Marburg virus, Ebola virus, and the like), family Bunyaviridae (Crimean-Congo hemorrhagic fever virus, severe fever with thrombocytopenia syndrome virus, and the like), family Flaviviridae (yellow fever virus, dengue virus, C hepatitis virus, G hepatitis virus, and the like), family Rhabdoviridae (rabies virus and the like), family Reoviridae, and family Retroviridae (human immunodeficiency virus, human T-lymphotropic virus, simian immunodeficiency virus, STLV, and the like).

In the case of using a virus or a viroid as the biological sample, it is possible to observe crystalline viral particles. In addition, it is also possible to subject viral particles and a host cell to the electron microscopic observation in a coexisting state and to time-dependently and diligently observe the infection process of the virus to the host cell or the growth process of the virus.

The biological sample may be in a surviving state or one subjected to the primary chemical fixation treatment of the prior art. The change of the tissue excised from the living body an animal stops by a chemical fixation treatment, and thus it is possible to prepare a sample for an electron microscope in a favorable state, and it is also possible to standardize the sample preparation technique for an electron microscope.

The term "developmental process" in the above includes not only the embryonic development but also the differentiation process of a stem cell such as an ES cell or an iPS cell.

The term "regenerative process" in the above includes the process in which the defective part of a tissue or cell of a living body is repaired to the same tissue or cell, and it includes both of the physiological regeneration and pathological regeneration.

The term "diseased cell" in the above includes a cancer cell, an inflammatory cell, and the like.

The term "image diagnosis" in the above includes the pathological diagnosis performed based on an image taken by a SEM or the diagnosis of metastasis and invasion of the diseased cell.

The term "physiologically active substance" in the above includes a neural amino acid, a physiologically active amine, physiologically active nucleotide and nucleoside, a physiologically active peptide, a vascular endothelium-derived relaxing factor, and an eicosanoid and other lipid mediators, a cytokine and a chemokine, a vitamin, and a hormone.

The term "drug" in the above includes a cholinergic agent, an anticholinergic agent, an adrenergic agonist, an anti-adrenergic agonist, a local anesthetic, an antipsychotic drug, an antidepressant drug, a mood stabilizer, a psychostimulant (central nervous system stimulant), a Parkinson's disease agent, an anti-dementia drug, a cerebral circulation and metabolism improving drug, an anti-epileptic drug, a central skeletal muscle relaxant, an anti-anxiety drug, a hypnotic drug, a general anesthetic, a narcotic analgesic, a central depressant, a central stimulant, a *cannabis* drug, a hallucinogenic drug, an organic solvent, nicotine, a non-smoking auxiliary drug, doping, a heart agonist (an anti-arrhythmic drug, a heart failure treatment drug, and an anti-angina drug), an anti-hypertensive drug, a low blood pressure treatment drug, a vasopressor drug, a vasodilator, a headache drug, a hemostatic agent, an anti-thrombotic agent, a hematopoietic agent, a diuretic drug, a urination disorder treatment drug, a benign prostatic hyperplasia treatment drug, a phosphodiesterase-5 (PDE5) inhibitor, a hormone inhibitor, a uterine contraction drug, a uterine relaxant, an immunosuppressant, a cytotoxic agent, an immune stimulant, an anti-allergic drug, a biological product such as a monoclonal antibody, an anti-inflammatory drug and its related drugs (a non-steroidal anti-inflammatory drug, an antipyretic analgesic, a steroidal anti-inflammatory drug, an anti-rheumatic drug, a joint function improving drug, and a feeling dexterity drug), a respiratory agent (a respiratory stimulant, an antitussive, an expectorant drug, a bronchodilator, and a bronchial asthma therapeutic agent), a gastrointestinal agent (a stomach digestive drug, a prokinetic drug, an emetic and an antiemetic, a peptic ulcer treatment drug, and an antidiarrheal drug, an intestinal motility inhibitor, a laxative, a ulcerative colitis treatment drug, a liver disease treatment drug, a biliary tract disease treatment drug, and a pancreatic disease therapeutic agent), a diabetes treatment drug, a lipid-lowering agent, a hyperuricemia and gout treatment drug, an osteoporosis therapeutic agent, an anti-infective drug (an antibiotic, a synthetic antibacterial agent, an anti-tuberculosis drug, an antifungal agent, an anti-viral agent, and a disinfectant), an antineoplastic agent, and a molecular targeted drug.

In the protective agent for electron microscopic observation of the present invention, the blending proportion of the a component to impart the survival environment, the saccharide, and the electrolyte is not particularly limited, but the following compositions are exemplified as preferred ones. Incidentally, the protective agents for electron microscopic observation having these compositions as a stock solution may be diluted depending on the characteristics and the like of the sample. In addition, the composition (the blending proportion of the a component to impart the survival environment, the saccharide, and the electrolyte) of the protective agent for electron microscopic observation of the present invention can be appropriately adjusted in consideration of the kind, content, or the like of the substance (an organic substance, an inorganic substance, and the like) contained in a biological sample in a water-containing state, such as a mammal, a plant tissue or a cultured cell, and a single cell to be the observation target.

(1) A component to impart the survival environment (glycerin):(water):saccharide (glucose):electrolyte (sodium chloride)=from 20:10:0.7:0.03 to 20:10:0.4:0.01

(2) A component to impart the survival environment (glycerin):saccharide (glucose):electrolyte (sodium chloride)=from 20:0.7:0.03 to 20:0.4:0.01

(3) A component to impart the survival environment (glycerin):(water):saccharide (glucose):electrolyte (dibasic sodium phosphate)=from 20:10:0.7:0.03 to 20:10:0.4:0.01

(4) A component to impart the survival environment (glycerin):saccharide (glucose):electrolyte (dibasic sodium phosphate)=from 20:0.7:0.03 to 20:0.4:0.01

(5) A component to impart the survival environment (glycerin):(water):saccharide (glucose):electrolyte (citric acid)=from 20:10:0.7:0.03 to 20:10:0.4:0.01

(6) A component to impart the survival environment (glycerin):saccharide (glucose):electrolyte (citric acid)= from 20:0.7:0.03 to 20:0.4:0.01

(7) A component to impart the survival environment (glycerin):(water):saccharide (glucose):electrolyte (calcium lactate)=from 20:10:1:0.03 to 20:10:0.4:0.01

(8) A component to impart the survival environment (glycerin):saccharide (glucose):electrolyte (calcium lactate)=from 20:1:0.03 to 20:0.4:0.01

Incidentally, the a component to impart the survival environment is preferably those that contain water since the protective agent is easily prepared and easily coated on the sample.

In addition, sodium dihydrogen phosphate may be used as the electrolytic component in the blending proportions (3) and (4) above.

In the SSE, the a component to impart the survival environment such as glycerin itself is a poorly conductive compound, but it is possible to impart conductivity to the a component to impart the survival environment by adding an electrolyte such as sodium chloride to SSE. It is considered that an image taken by a SEM can be obtained at a low magnification and the SSE is equipped with a function equal to that of an ionic liquid used in the prior invention by this. In addition, it is considered that the water retaining property is enhanced as a synergistic effect is obtained by the addition of a saccharide although the a component to impart the survival environment itself has a water retaining property. It is considered that the electron microscopic observation of a fragile biological sample which does not have a strong layer to cover the surface, such as a mammal, a plant tissue or a cultured cell, and a single cell and has not been so far necessarily sufficiently discussed in the living state has become possible by such a a component to impart the survival environment that is equipped with both high water retaining property and conductivity.

In addition, in a case in which a substance to exert the effect (impartation of survival environment, impartation of water retaining property, impartation of conductivity, and the like) equal to that of the component constituting the protective agent for electron microscopic observation of the present invention is present in a biological sample in a water-containing state, such as a mammal, a plant tissue or a cultured cell, and a single cell to be the observation target as the characteristics of the sample, the compositions exemplified above include that the surface of the biological sample after the application of the protective agent for electron microscopic observation of the present invention is in a state which satisfies the compositions exemplified above, and a composition applied in order to obtain such a state is included in the protective agent for electron microscopic observation of the present invention.

Incidentally, as the protective agent for electron microscopic observation of the present invention, for example, a a component to impart the survival environment, a saccharide, and a polymer compound having an electrolyzable functional group may be used in addition to the combination of a a component to impart the survival environment, a saccharide, and an electrolyte as described above. In other words, each of the a component to impart the survival environment, the saccharide, and the electrolyte that are contained in the protective agent for electron microscopic observation of the present invention may be a separate substance, or these constituents may be contained in one substance or the protective agent for electron microscopic observation of the present invention may be a substance that is equipped with a molecular structure having functions equal to those of these constituents.

The protective agent for electron microscopic observation of the present invention may be in a solid state or a liquid state, but it is preferably in a highly viscous liquid state in order to maintain the water environment of the sample tissue in a vacuum. In addition, those in a solid state can be used after being formed into a liquid at the time of use.

The excess liquid is wiped off with soft cloth-like paper, such as the Kimwipes, filter paper, or the like after the protective agent for electron microscopic observation of the present invention is coated on a biological sample. The sample for TEM observation is treated by the applying, attachment, coating, covering, embedding, and the like of a medium.

In addition, according to the present invention, it is also possible to provide a kit for electron microscopic observation that is equipped with (A) a protective agent for electron microscopic observation containing a a component to impart the survival environment, a saccharide, and an electrolyte and (B) a surfactant-containing solution.

The surfactant-containing solution in the present invention is one that replaces the composition for evaporation inhibition in the prior invention, and it is a solution which exerts the water/gas barrier performance (surface shielding effect, SS effect).

The surfactant-containing solution contains a surfactant as the main component (base material). The surfactant is briefly divided into an anionic surfactant, a cationic surfactant, a nonionic surfactant, an amphoteric surfactant, a natural surfactant, and an amphiphilic compound (biosurfactant) derived from microorganisms by the molecular structure. The surfactant is used in various fields such as the industries, the food, and medical products, but basically certain barrier performance can be exhibited even when any surfactant is used.

Among the surfactants described above, the anionic surfactant is classified, for example, into a carboxylic acid type, a sulfuric acid ester type, a sulfonic acid type, and a phosphoric acid ester type. Among these, specific examples thereof may include sodium dodecyl sulfate, sodium laurate, sodium α-sulfo fatty acid methyl ester, sodium dodecylbenzenesulfonate, and sodium dodecyl sulfate-ethoxylated. Among them, it is preferable to use sodium dodecylbenzenesulfonate.

Among the surfactants described above, the cationic surfactant is classified into a quaternary ammonium salt type, an alkyl amine type, and a heterocyclic amine type. Specific examples thereof may include stearyl trimethyl ammonium chloride, distearyl dimethyl ammonium chloride, didecyl dimethyl ammonium chloride, cetyl trimethyl pyridinium chloride, and dodecyl dimethyl benzyl ammonium chloride.

Among the surfactants described above, examples of the nonionic surfactant may include polyoxyethylene alkyl ether, polyoxyethylene hydrogenated castor oil, polyoxyethylene mono-fatty acid ester, polyoxyethylene sorbitan mono-fatty acid ester, sucrose fatty acid ester, polyglycerol fatty acid ester, alkylpolyglycoside, and N-methyl-alkylglucamide. Among them, those that are commercially available under the names of Triton™X (Triton™X-100 and the like), Pluronic® (Pluronic® F-123, F-68, and the like), Tween (Tween 20, 40, 60, 65, 80, 85, and the like), Brij® (Brij® 35, 58, 98, and the like), and Span (Span 20, 40, 60, 80, 83, and 85) are preferable in addition to dodecyl alcohol ethoxylate, nonylphenol ethoxylate, and lauroyl diethanolamide.

Among the surfactants described above, examples of the amphoteric surfactant may include lauryl dimethylaminoacetic acid betaine, dodecyl aminomethyl dimethyl sulfopropyl betaine, and 3-(tetradecyl dimethyl amine niobium) propan-1-sulfonate, but it is preferable to use 3-[(3-cholamidopropyl)dimethylammonio]-1-propanesulfonate (CHAPS), and 3-[(3-cholamidopropyl)dimethyl ammonio]-2-hydroxy-1-propanesulfonate (CHAPSO).

Among the surfactants described above, as the surfactant derived from nature, for example, lecithin and a saponin are preferable, and specifically phosphatidylcholine, phosphatidylethanolamine, phosphatidylinositol, phosphatidylserine, phosphatidic acid, phosphatidylglycerol, and the like are preferable among the compounds referred to as lecithin. In addition, quillaja saponin is preferable as the saponin.

Among the surfactants described above, as the amphiphilic compound (biosurfactant) derived from microorganisms, it is preferable to use rhamnolipid, sophorolipid, mannosylerythritol lipid, and the like.

Among the surfactants which are generally used as a known surfactant other than the surfactants exemplified above, examples of the surfactant which is used particularly in cosmetics may include almond oil PEG-6 esters, Na acyl(C12,14)aspartate, TEA acyl(C12,14)aspartate, arachideth-20, stearyl alcohol, sodium alkyl (C11,13,15) sulfate, TEA alkyl (C11, 13, 15) sulfate, potassium alkyl (C11,13, 15) phosphate, DEA alkyl(C12,13) sulfate, sodium alkyl (C12,13) sulfate, TEA alkyl (C12,13) sulfate, ammonium alkyl (C12,14,16) sulfate, alkyl (C12-14) oxy hydroxypropyl arginine hydrochloride, alkyl (C12-14) diaminoethylglycine hydrochloride, TEA alkyl (C12-14) sulfate, TEA alkyl (C12-15) sulfate, sodium alkyl (C14-18) sulfonate, alkyl (C16,18) trimonium chloride, alkyl (C28) trimonium chloride, isostearamide DEA, isostearyl alcohol, isostearyl glyceryl, isostearyl lauryldimonium chloride, PEG-2 isostearate, PEG-3 isostearate, PEG-4 isostearate, PEG-6 isostearate, PEG-8 isostearate, PEG-10 isostearate, PEG-12 isostearate, PEG-15 glyceryl isostearate, PEG-20 isostearate, PEG-20 glyceryl isostearate, PEG-20 hydrogenated castor oil isostearate, PEG-20 sorbitan isostearate, PEG-30 isostearate, PEG-30 glyceryl isostearate, PEG-40 isostearate, PEG-50 hydrogenated castor oil isostearate, PEG-58 hydrogenated castor oil isostearate, PEG-60 glyceryl isostearate, PG isostearate, sorbitan isostearate, sorbeth-3 isostearate, polyglyceryl-2 isostearate, polyglyceryl-3 isostearate, polyglyceryl-4 isostearate, polyglyceryl-5 isostearate, polyglyceryl-6 isostearate, polyglyceryl-10 isostearate, isosteareth-2, isosteareth-10, isosteareth-15, isosteareth-22, isostearoyl hydrolyzed collagen, AMPD-isostearoyl hydrolyzed collagen, sodium isostearoyl lactylate, isoceteth-10, isoceteth-20, octyl isopalmitate, polyglyceryl-2 isopalmitate, sucrose acetate isobutyrate, potassium undecylenoyl hydrolyzed collagen, ethylenediaminetetrakis(hydroxyisopropyl) dioleate, epoxy ester-1, epoxy ester-2, epoxy ester-3, epoxy ester-4, epoxy ester-5, glyceryl erucate, PEG-4 octanoate, nonoxynol-14, octyldodeceth-2, octyldodeceth-5, octyldodeceth-10, octyldodeceth-30, dextrin TEA octenylsuccinate, octoxynol-1, sodium octoxynol-2 ethanesulfonate, octoxynol-10, octoxynol-25, octoxynol-70, olive oil PEG-6 esters, PEG-3-PPG-20 oligosuccinate, oleamide DEA, oleamine oxide, oleyl betaine, sodium oleyl sulfate, TEA oleyl sulfate, PEG-2 oleate, PEG-10 oleate, PEG-10 glyceryl oleate, PEG-15 glyceryl oleate, PEG-20 glyceryl oleate, PEG-30 glyceryl oleate, PEG-36 oleate, PEG-40 sorbitol oleate, PEG-75 oleate, PEG-150 oleate, PG oleate, sucrose oleate, hydroxy-{bis(hydroxyethyl)amino}propyl oleate, polyglyceryl-2 oleate, polyglyceryl-5 oleate, polyglyceryl-10 oleate, oleoyl hydrolyzed collagen, oleoyl sarcosine, sodium methyl oleoyl taurate, oleth-2, DEA oleth-3 phosphate, sodium oleth-7 phosphate, sodium oleth-8 phosphate, oleth-10, oleth-10 phosphate, DEA oleth-10 phosphate, oleth-20, oleth-20 phosphate, oleth-30, oleth-50, sodium olefin (C14-16) sulfonate, cationic hydrolyzed wheat protein-1, cationic hydrolyzed wheat protein-3, cationic hydrolyzed conchiolin-2, cationic hydrolyzed soy protein-1, cationic hydrolyzed soy protein-2, cationic hydrolyzed soy protein-3, cationic dextran-2, capramide DEA, beef tallow fatty acid glyceryl, apricot kernel oil PEG-6 esters, distearyl citrate, citric acid fatty acid esters of glycerol, quaternium-14, quaternium-18, quaternium-18 hectorite, quaternium-18 bentonite, quaternium-22, quaternium-33, corn oil PEG-6 esters, corn oil PEG-8 esters, cocamide, cocamide DEA, cocamide MEA, cocamidopropyl betaine, cocoamine oxide, sodium cocoamphoacetate, disodium cocoamphodiacetate, sodium polyoxyethylene tridecyl sulfate, disodium cocoamphodipropionate, sodium cocoamphopropionate, cocoyl alanine TEA, PCA ethyl cocoyl arginate, sodium cocoyl isethionate, potassium cocoyl hydrolyzed casein, potassium cocoyl hydrolyzed keratin, potassium cocoyl hydrolyzed yeast, potassium cocoyl hydrolyzed yeast protein, potassium cocoyl hydrolyzed wheat protein, cocoyl hydrolyzed collagen, potassium cocoyl hydrolyzed collagen, sodium cocoyl hydrolyzed collagen, TEA cocoyl hydrolyzed collagen, potassium cocoyl hydrolyzed potato protein, potassium cocoyl hydrolyzed soy protein, potassium cocoyl hydrolyzed corn protein, potassium cocoyl hydrolyzed potato protein, potassium cocoyl glycine, cocoyl glycine TEA, cocoyl glutamic acid, potassium cocoyl glutamate, sodium cocoyl glutamate, TEA cocoyl glutamate, cocoyl sarcosinate, sodium cocoyl sarcosinate, TEA-cocoyl sarcosinate, sodium cocoyl taurate, cocoyl methyl alanine, sodium cocoyl methyl alanine, potassium cocoyl methyl taurate, magnesium cocoyl methyl taurate, sodium cocoyl methyl taurate, sodium coco-glyceryl sulfate, cocodimonium hydroxypropyl hydrolyzed keratin, cocodimonium hydroxypropyl hydrolyzed collagen, cocodimonium hydroxypropyl hydrolyzed silk, coco-betaine, PEG-50 hydrogenated castor oil succinate, succinic acid and fatty acid esters of glycerol, cholestyramine-10, cholestyramine-15, isoceteth-3 acetate, ceteth-3 acetate, isobutyl acetate, ethyl acetate, glyceryl, acetic acid and fatty acid esters of glycerol, sucrose acetate stearate, trideceth-3 acetate, trideceth-15 acetate, butyl acetate, glyceryl acetate monostearate, laneth-9 acetate, diacetyl tartaric acid and fatty acid esters of glycerol, dialkyl (C12-15) dimonium chloride, dialkyl (C12-18) dimonium chloride, PEG-8 diisostearate, PG diisostearate, polyglyceryl-2 diisostearate, PEG-4 dioleate, PEG-10 dioleate, PEG-32 dioleate, PEG-75 dioleate, PEG-120 methyl glucose dioleate, PEG-150 dioleate, PG dioleate, glycol dioleate, polyglyceryl-6 dioleate, ditallow alkyl dimonium cellulose sulfate, dicocodimonium chloride, glyceryl diacetate stearate, distearyldimonium chloride, PEG-2 distearate, PEG-12 distearate, PEG-20 methyl glucose distearate, PEG-120 distearate, PEG-250 distearate, PEG-trimethylolpropane distearate, PG distearate, PPG-20 methyl glucose distearate, glycol distearate, glyceryl distearate, sucrose distearate, sorbitan distearate, polyglyceryl-6 distearate, polyglyceryl-10 distearate, dicetyldimonium chloride, MEA dicetearyl phosphate, dihydroxyethyl stearyl betaine, PEG-3 dipalmitate, dihydroxyethyl lauramine oxide, (dihydroxy-methyl silyl propoxyphene) hydroxypropyl hydrolyzed casein, (dihydroxymethyl silyl propoxyphene) hydroxypropyl hydrolyzed collagen, (dihydroxy-methyl silyl propoxy) hydroxypropyl hydrolyzed silk, dihydrocoleth-15, fatty acid (C8-22) esters of polyglyceryl-10, dimethicone copolyol, ethyl dimethicone copolyol, butyl dimethicone copolyol, dimethyl stearamine, PEG-4 dilaurate, PEG-12 dilaurate, PEG-32 dilaurate, sucrose dilaurate, dilaureth-4 phosphate, dilaureth-10 phosphate, magnesium dilauroyl glutamate, lecithin hydroxide, hydrogenated coco-glycerides, hydrogenated soybean fatty acid esters of glycerol, hydrogenated tallowamide DEA, disodium hydrogenated tallow glutamate, TEA hydrogenated tallow glutamate, hydrogenated lanolin, hydrogenated lanolin alcohol, hydrogenated lysolecithin, hydrogenated lecithin, stearamide, stearamide DEA, stearamide MEA, stearamide ethyl diethylamine, stearamidopropyl dimethylamine, stearamine oxide, stearalkonium chloride, stearalkonium hectorite, sodium stearyl dimethyl betaine, stearyltrimonium saccharin, stearyltrimonium bromide, stearyl betaine, sodium stearyl sulfate, stearate PEG-2, PEG-6 sorbitol stearate, PEG-10 stearate, PEG-10 glyceryl stearate, PEG-14 stearate, PEG-20 glyceryl stearate, PEG-23 stearate, PEG-25 stearate, PEG-40 stearate, PEG-100 stearate, PEG-120 glyceryl stearate, PEG-150 stearate, PEG-200 glyceryl stearate, PG stearate, TEA stearate, glycol stearate, glyceryl stearate, sucrose stearate, steareth-4 stearate, stearoyl dihydroxy isobutyramide stearate, sorbitan stearate, polyoxyethylene cetyl ether stearate, polyglyceryl-2 stearate, polyglyceryl-10 stearate, glyceryl stearate/malate, steardimonium hydroxydicarboxylic propyl hydrolyzed keratin, steardimonium hydroxydicarboxylic propyl hydrolyzed collagen, steardimonium hydroxydicarboxylic propyl hydrolyzed silk, steartrimonium chloride, steareth-2 phosphate, steareth-3, steareth-10, steareth-16, steareth-50, steareth-80, steareth-100, potassium stearoyl hydrolyzed collagen, sodium stearoyl hydrolyzed collagen, stearoylglutamic acid, disodium stearoylglutamate, potassium stearoylglutamate, sodium stearoylglutamate, dioctyl dodecyl stearoylglutamate, stearoyl colaminoformyl methyl pyridinium chloride, calcium stearoyl lactate, sodium stearoyl lactylate, sodium stearoyl methyl taurate, (C12-14) pareth disodium sulfosuccinate, PEG-2 oleamidopropyl disodium sulfosuccinate, PEG-4 cocoil isopropanolamide disodium sulfosuccinate, PEG-5 lauramide disodium sulfosuccinate, dioctyl sodium sulfosuccinate, Shitosutereth 14-2 sodium sulfosuccinic acid, lauryl disodium sulfosuccinate, laureth disodium sulfosuccinate, sorbitan sesquiisostearate, glyceryl sesquioleate, sorbitan sesquioleate, diglyceryl sesquioleate, PEG-20 methyl glucose sesquistearate, sorbitan sesquistearate, methyl glucose sesquistearate, cetyl dimethicone copolyol, cetylpyridinium chloride, sodium cetyl sulfate, DEA cetyl phosphate, potassium cetyl phosphate, cetearyl alcohol, cetearyl glucoside, cetearyl alcohol, sodium cetearyl sulfate, ceteareth-10, ceteareth-15, ceteareth-22, ceteareth-34, ceteareth-55, ceteareth-60, ceteareth-60 myristyl glycol, ceteareth-100, ceteth-8 phosphate, ceteth-10, ceteth-10 phosphate, ceteth-12, ceteth-24, ceteth-45, cetrimonium chloride, cetrimonium saccharin, cetrimonium bromide, cetoleth-10, cetoleth-20, cetoleth-25, tallowamide MEA, polyglyceryl-10 decaisostearate, polyglyceryl-10 decaoleate, polyglyceryl-10 decasteareate, decyl glucoside, diglycerol sorbitan tetraoctanoate, sorbeth-30 tetraoleate, sorbeth-40 tetraoleate, sorbeth-60 tetraoleate, sorbeth-60 tetrastearate, TEA dodecyl benzene sulfonate, triPEG-8 alkyl (C12-15) phosphate, tri(PEG-3 isostearate) trimethylolpropane, PEG-10 glyceryl triisostearate, PEG-15 hydrogenated castor oil triisostearate, PEG-20 hydrogenated castor oil triisostearate, PEG-30 glyceryl triisostearate, PEG-30 hydrogenated castor oil triisostearate, PEG-50 glyceryl triisostearate, PEG-50 hydrogenated castor oil triisostearate, PEG-160 sorbitan triisostearate, polyglyceryl-2 triisostearate, sorbitan trioleate, polyglyceryl-10 trioleate, PEG-3 sorbitol tristearate, PEG-140 glyceryl tristearate, PEG-160 sorbitan tristearate, sucrose tristearate, sorbitan tristearate, polyglyceryl-10 tristearate sodium trideceth triacetate, sodium trideceth hexaacetate, trideceth-9, trideceth-10, trideceth-11, trideceth-20, trideceth-21, trihydroxystearin, sucrose tribehenate, trilaurylamine, trilaureth tetraphosphoric acid, sodium trilaureth tetraphosphate, lactic acid and fatty acid esters of glycerol, nonyl nonoxynol-10, nonyl nonoxynol-100, nonoxynol-3, sodium nonoxynol-4 sulfate, nonoxynol-6 phosphoric acid, sodium nonoxynol-6 phosphate, nonoxynol-10, nonoxynol-10 phosphorus acid, nonoxynol-23, nonoxynol-50, nonoxynol-120, perfluoroalkyl PEG phosphate, DEA perfluoroalkyl phosphate, palm kernel fatty acid amide DEA, sodium palm kernel fatty acid amide ethyl hydroxyethyl amino propionate, palm kernel fatty acid amide propyl betaine, sodium palm fatty acid glutamate, palmitamide MEA, PEG-6 palmitate, PEG-18 palmitate, PEG-20 palmitate, sucrose palmitate, sorbitan palmitate, di-TEA palmitoyl aspartate, sodium palmitoyl methyl taurate, peanut oil PEG-6 esters, glyceryl hydroxystearate, hydroxypropyltrimonium hydrolyzed casein, hydroxypropyltrimonium hydrolyzed keratin, hydroxypropyltrimonium hydrolyzed wheat protein, hydroxypropyltrimonium hydrolyzed collagen, hydroxypropyltrimonium hydrolyzed silk, hydroxy lanolin, PPG-2 myristyl propionate, polyglyceryl-10 heptastearate, heptadecylimidazole hydroxyethyl carboxylate methyl imidazolinium, behenamidopropyl PG dimonium chloride, behenamine oxide, beheneth-10, beheneth-30, glyceryl behenate, behentrimonium chloride, benzalkonium chloride, polyglyceryl-10 pentaisostearate, diglycerol sorbitan pentaoctanoate, PEG-40 sorbitol pentaoleate, polyglyceryl-6 pentaoleate, polyglyceryl-10 pentaoleate, polyglyceryl-10 pentastearate, potassium polyacrylate, sodium polyacrylate, ammonium polyacrylate, TEA polyoxyethylene alkyl phenyl ether phosphate, sodium polyoxyethylene ether phosphate, polyoxyethylene octyl ether phosphoric acid, polyoxyethylene cetyl stearyl diether, polyoxyethylene phytostanol, polyoxyethylene butyl ether, polyoxyethylene coconut fatty acid diethanolamide, TEA polyoxyethylene lauryl ether phosphate, polyoxypropylene carboxyalkyl (C14-18) diglucoside, polyoxypropylene glyceryl ether phosphate, polyoxypropylene sorbitol, sucrose polyoleate, polyglyceryl-2 oleyl, sucrose polystearate, cetyl acetate, acetic acid lanolin alcohol, poly-palm fatty acid esters of sucrose, sucrose polylaurate, polyglyceryl polyricinoleate, sucrose poloxamer-181 polylinoleate, poloxamer-333, poloxamine 304, poloxamine 901, poloxamine 1104, poloxamine 1302, poloxamine 1508, maltitol hydroxyalkyl (C12,14), myristamide DEA, myristamine oxide, myristalconium chloride, myristyl PG hydroxyethyl decanamide, myristyl betaine, sodium myristyl sulfate, PEG-8 myristate, PEG-20 myristate, glyceryl myristate, sucrose myristate, polyglyceryl-10 myristate, myreth-3 myristate, myristoyl hydrolyzed collagen, potassium myristoyl hydrolyzed collagen, potassium myristoyl glutamate, myristoyl glutamate, sodium myristoyl glutamate, sodium myristoyl sarcosinate, sodium myristoyl methyl alanine, sodium myristoyl methyl taurate, myreth-3, sodium myreth-3 sulfate, glyceryl monoacetate monostearate, coconut fatty acid esters of TEA, coconut fatty acid esters of glyceryl, palm fatty acid esters of sucrose, coconut fatty acid esters of sorbitan, coconut fatty acid esters of lysine, lauramide DEA, lauramide MEA, lauramide propyl betaine, sodium lauraminodiacetate, lauraminopropionic acid, sodium lauraminopropionate, lauramine oxide, sodium lauraminodipropionate, lauryl DEA, lauryl isoquinolinium saccharin, lauryl isoquinolinium bromide, lauryl glucoside, sodium lauryl diaminoethyl glycine, lauryl dimonium hydroxypropyl hydrolyzed keratin, lauryl dimonium hydroxypropyl hydrolyzed collagen, lauryl dimonium hydroxypropyl hydrolyzed silk, sodium lauryl sulfoacetate, sodium lauryl hydroxy acetic acid amide sulfate, lauryl hydroxy sultaine, lauryl pyridinium chloride lauryl betaine, DEA lauryl sulfate, potassium lauryl sulfate, MEA lauryl sulfate, magnesium lauryl sulfate, sodium lauryl sulfate, TEA lauryl sulfate, ammonium lauryl sulfate, lauryl phosphoric acid, disodium lauryl phosphate, sodium lauryl phosphate, PEG-2 laurate, PEG-4DEA laurate, PEG-6 laurate, PEG-8, PEG-8 glyceryl laurate, PEG-9 laurate, PEG-10 laurate, PEG-12 glyceryl laurate, PEG-23 glyceryl laurate, PEG-32 laurate, PEG-75 laurate, PEG-150 laurate, PEG sorbitol laurate, PG laurate, TEA laurate, glyceryl laurate, sucrose laurate, polyoxyethylene hydrogenated castor oil laurate, polyglyceryl-6 laurate, polyglyceryl-10 laurate, maltitol laurate, laurtrimonium chloride, laurtrimonium bromide, laureth-2 sulfate, ammonium laureth-3, TEA laureth-3 sulfate, laureth-3 sulfate, ammonium laureth-3 phosphate, laureth-4 phosphate, sodium laureth-4 phosphate, potassium laureth-4.5 acetate, laureth-5 acetate, sodium laureth-5 sulfate, laureth-6 acetate, sodium laureth-6 acetate, laureth-7 phosphate, laureth-9, laureth-10, laureth-10 acetate, potassium laureth-10 acetate, sodium laureth-16 acetate, sodium laureth-17 acetate, laureth-40, TEA laureth sulfate, sodium lauroampho PG-acetate phosphate, sodium lauroamphoacetate, lauroyl aspartic acid, potassium lauroyl hydrolyzed collagen, sodium lauroyl hydrolyzed collagen, sodium lauroyl hydrolyzed silk, lauroyl glutamic acid, potassium lauroyl glutamate, sodium lauroyl glutamate, TEA lauroyl glutamate, dioctyl dodecyl lauroyl glutamate, dioctyl dodeceth-2 lauroyl glutamate, dioctyl dodecyl lauroyl glutamate, dicholesteryl lauroyl glutamate, disteareth-2 lauroyl glutamate, disteareth-5 lauroyl glutamate, lauroyl sarcosine, sodium lauroyl sarcosinate, TEA lauroyl sarcosinate, potassium lauroyl threonate, sodium lauroyl lactate, lauroyl methyl alanine, sodium lauroyl methyl alanine, TEA lauroyl methyl alanine, sodium lauroyl methyl taurate, laneth-10, laneth-25, laneth-40, laneth-75, lanolin fatty acid esters of PEG-4, lanolin fatty acid esters of PEG-12, lanolin fatty acid amide DEA, lanolin fatty acid esters of isopropyl, lanolin fatty acid esters of octyl dodecyl, lanolin fatty acid esters of glyceryl, lanolin fatty acid esters of cholesteryl, lapirium chloride, ricinoleic acid amide propyl betaine, glyceryl ricinoleate, sucrose ricinoleate, polyoxypropylene sorbitol ricinoleate, polyglyceryl-6 ricinoleate, lanolyl linoleate, linoleamide DEA, sulfated castor oil, malic acid lauramide, rosin hydrolyzed collagen, and AMPD rosin hydrolyzed collagen.

In addition to the surfactants described above, it is also possible to use a fluorine-based surfactant. Specific examples thereof may include ammonium heptadecafluoro-1-octanesulfonate, ammonium pentadecafluorooctanoate, heptadecafluorooctanesulfonic acid, lithium heptadecafluoro-1-octanesulfonate, pentadecafluorooctanoic acid, pentadecafluorooctanoic acid hydrate, and potassium heptadecafluoro-1-octanesulfonate.

In addition to the surfactants described above, it is also possible to use, for example, an anionic surfactant such as a salt of N-long-chain acylamino acid such as a salt of N-long-chain acyl neutral amino acid such as a salt of N-long-chain acyl glutamic acid, a salt of N-long-chain acyl aspartic acid, a salt of N-long-chain acyl glycine, a salt of N-long-chain acyl alanine, a salt of N-long-chain acyl threonine, or a salt of N-long-chain acyl sarcosine, a salt of N-long-chain fatty acyl-N-methyl taurine, an alkyl sulfate and an alkylene oxide adduct thereof, a fatty acid amide ether sulfate, a metal salt of fatty acid, a sulfosuccinic acid-based surfactant, an alkyl phosphate and an alkylene oxide adduct thereof, an ester salt of a higher alkyl sulfuric acid, an ester salt of alkyl ether sulfuric acid, a salt of alkyl hydroxy ether carboxylic acid, or alkyl ether carboxylic acid, a nonionic surfactant such as an ether type surfactant such as a glycerin ether and an alkylene oxide adduct thereof, an ester type surfactant such as a glycerol ester and an alkylene oxide adduct thereof, an ether ester type surfactant such as a sorbitan ester and an alkylene oxide adduct thereof, a fatty acid alkylol amide such as fatty acid monoethanolamide or fatty acid diethanolamide, an ester type surfactant such as polyoxyalkylene fatty acid ester, a polyoxyalkylene polyhydric alcohol fatty acid ester, a polyoxyalkylene sorbitan fatty acid ester, polyoxyalkylene hydrogenated castor oil, glyceryl monostearate, a glyceryl ester, a polyglyceryl ester of fatty acid, a polyglycertl ester of acylamino acid, a sorbitan ester, or a sucrose ester of fatty acid, or a nitrogen-containing type nonionic surfactant such as an alkyl glucoside, a diester of hardened castor oil pyroglutamic acid and an ethylene oxide adduct thereof, or a fatty acid alkanolamide, an amphoteric surfactant such as a cationic amphiphilic compound such as an aliphatic amine salt such as an alkyl ammonium chloride, a dialkyl ammonium chloride, an alkyl trimethyl ammonium chloride (C16-C22), a dialkyldimethylammonium methosulfate salt, a quaternary ammonium salt thereof, an aromatic quaternary ammonium salt such as benzalkonium salt, a fatty acid acyl arginine ester, a salt of N-long-chain acyl arginine ethyl pyrrolidone carboxylic acid, an amidoamine, a salt of stearamidopropyldimethyl amine glutamine acid, a salt of stearamidopropyl dimethylamine lactic acid, a salt of stearamidopropyl dimethyl amine pyrrolidone carboxylic acid, a salt of behenamidopropyl dimethylamine glutamine acid, a salt of behenamidopropyl dimethylamine lactic acid, or a salt of behenamidopropyl dimethylamine pyrrolidone carboxylic acid as well as a betaine-type amphipathic compound such as an alkyl betaine, an alkylamido betaine, a sulfobetaine, an imidazolinium betaine, an amino propionate, or carboxybetaine, N-long chain acyl arginine, N-(3-alkyl (12,14) oxy-2-hydroxypropyl) arginine hydrochloride, an aminocarboxylic acid type surfactant, or an imidazoline type surfactant.

In addition, the surfactant-containing solution may also contain a metal compound in addition to a surfactant. As the metal compound, those that contain a metal ion may be widely used.

The metal compound may be a salt composed of a cation and an anion (single salt) or a salt (double salt) composed of two or more kinds.

The metal compound may be a compound such as an oxide, a hydroxide, a halide, a sulfate, a nitrate, a carbonate, an acetate, a phosphate, or a lactate. Specific examples thereof may include sodium chloride, magnesium chloride, calcium chloride, sodium bicarbonate, potassium chloride, strontium chloride, lithium chloride, hafnium chloride, iron chloride, aluminum chloride, zinc chloride, copper chloride, cobalt chloride, magnesium sulfate, magnesium carbonate, dibasic sodium phosphate, and calcium lactate.

The metal compound may be a metal oxide. A metal alkoxide is a compound represented by MOR, and it is composed of a metal (M) and an alkoxide (RO—) (R is a hydrocarbon). Specific examples the metal (M) may include silicon, titanium, aluminum, boron, zirconium, vanadium, tungsten, phosphorus, germanium, indium, hafnium, and molybdenum, and a metal alkoxide is obtained from various alcohols. These metal alkoxides may be used as they are, or a reaction product obtained by subjecting these metal alkoxides to a sol-gel reaction in the presence of an acid or an alkali may be used. As the metal alkoxide, two or more kinds may be mixed without using a single component.

The metal compound may be a metal complex. Specific examples thereof may include an ethylenediamine nickel complex and a tetraamine cobalt complex.

In addition, the surfactant-containing solution may also contain a saccharide. As the saccharide, a disaccharide, an oligosaccharide, a polysaccharide, and any derivative thereof are blended. Specifically, examples of the monosaccharide may include glucose and fructose. Examples of the disaccharide may include sucrose and trehalose, and examples of the polysaccharide may include heparin, chondroitin sulfate, pullulan, pectin, guar gum, xanthan gum, carrageenan, propylene glycol, carboxymethyl cellulose, and inulin. Particularly, a polysaccharide such as pullulan, is preferable. In addition to these, caramel, honey, beeswax, and the like may be used. In addition, tears of a mammal, wax ester secreted from pores, squalene, triglycerides, sebum such as fatty acids, ceramides, cholesterol, free fatty acids, horny intercellular lipids such as cholesterol sulfate, saliva or digestive fluid secreted from the digestive organs, membrane-type mucin or secretory mucin present on the membrane surface of epithelial cells which mainly constitute the respiratory tract and digestive organs may be used. In addition, a wax component or a water-soluble substance that is secreted on the cuticle surface by invertebrates such as arthropods, fats and oils or a water-soluble substance that is secreted from the pores of vertebrates may be used. In addition, liver oil that is included in the liver of a shark, a cod, a stingray, and the like and the body fluid of a jellyfish, a sea cucumber, and the like may be used. In addition, natural secretions that are secreted by plants and fungi may be used, and as saccharide derived from a plant, oil that can be collected from the seeds of various plants, such as *eucalyptus* oil, peppermint oil, and castor oil, pine oil, and the sap of lacquer, cherry, oak, willow, and the like may be used. The initial secretions that are secreted by prokaryotic organisms and form a biofilm or bio film itself may be used.

In addition, the surfactant-containing solution may also contain fats and oils.

Examples of the fats and oils may include silicone oil. Silicone oil functions as a water retaining agent to maintain the water environment of the tissue or cell of a biological sample, and the dynamic observation of a biological sample as its living state is achieved by this. In other words, silicone oil can be used as a material having barrier performance that the water of a tissue or cell is not lost even in a vacuum.

As the silicone oil, for example, those that have a viscosity at 25° C. of from 1 to 100,000 mP·s may be used. For example, the "636-04001" manufactured by Wako Pure Chemical Industries, Ltd. and the "KF-54" and "KF-96" manufactured by Shin-Etsu Chemical Co., Ltd., and the like can be used.

The surfactant-containing solution of the present invention using silicone oil contains silicone oil preferably at 10% by weight with respect to the total amount of the composition, and as a component other than that, components as to be exemplified below may be blended.

In addition, the surfactant-containing solution may contain an ionic liquid.

Examples of the ionic liquid may include an imidazolium salt, a pyridinium salt, a piperidinium salt, a pyrrolidinium salt, a quaternary ammonium salt, a phosphonium, a sulfonium, and a pyrazolium.

Examples of the imidazolium salt may include 1-alkyl-3-alkylimidazolium, 1,3-dimethylimidazolium, 1-ethyl-3-methylimidazolium, 1-butyl-3-methylimidazolium, 1-hexyl-3-methylimidazolium, 3-methyl-1-octylimidazolium, 1-dodecyl-3-methylimidazolium, 1-dodecyl-3-methylimidazolium, 1-methyl-3-tetradecyl-imidazolium, 1-hexadecyl-3-imidazolium, 1-octadecyl-3-methylimidazolium, 1-allyl-3-methylimidazolium, 1-allyl-3-ethyl-imidazolium, 1-allyl-3-butylimidazolium, 1, 3-diallylimidazolium, 1-benzyl-3-methylimidazolium, and 1-(2-hydroxyethyl)-3-methylimidazolium.

Examples of the 1-alkyl-2,3-dialkylimidazolium salt may include 1-ethyl-2,3-dimethylimidazolium, 1,2,3,-tri-ethylimidazolium, 1,2-dimethyl-3-propylimidazolium, 1-butyl-2,3-dimethylimidazolium, 1-hexyl-2,3-dimethylimidazolium, and 1,3-didecyl-2-methylimidazolium.

Examples of the pyridinium salt may include 1-methylpyridinium, 1-ethylpyridinium, 1-butylpyridinium, 1-hexylpyridinium, 1-ethyl-3-methylpyridinium, 1-methyl-4-methylpyridinium, 1-propyl-4-methylpyridinium, 1-propyl-3-methylpyridinium, 1-butyl-2-methylpyridinium, 1-butyl-3-methylpyridinium, 1-ethyl-3-hydroxymethylpyridinium, and 1-(3-hydroxypropyl)pyridinium, Examples of the piperidinium salt may include 1-methyl-1-propylpiperidinium, 1-butyl-1-methylpiperidinium, and 1-(methoxyethyl)-1-methylpiperidinium.

Examples of the pyrrolidinium salt may include 1,1-dimethylpyrrolidinium, 1-ethyl-1-methylpyrrolidinium, 1-methyl-1-propylpyrrolidinium, 1-butyl-1-methylpyrrolidinium, and 1-(methoxyethyl)-1-methylpyrrolidinium.

Examples of the quaternary ammonium salt may include choline, N,N-diethyl-N-methyl-N-(2-methoxyethyl)ammonium, trimethylamine oxide in addition to tetramethylammonium, tetrabutylammonium, butyltrimethylammonium, ethyl -dimethyl-propylammonium, tributylammonium, methyltrioctylammonium, and 2-hydroxyethylammonium.

Examples of the phosphonium may include tetrabutylphosphonium, tributylhexadecylphosphonium, triethylpentylphosphonium, triethyloctylphosphonium, tetraoctylphosphonium, triisobutylmethylphosphonium, tributyltetradecylphosphonium, and triethyltetradecylphosphonium.

Examples of the sulfonium may include triethyl sulfonium and diethyl methyl sulfonium.

Examples of the pyrazolium may include guanidinium and N-(methoxyethyl)-N-methylmorpholinium in addition to 1-ethyl-2,3,5-trimethylpyrazolium, 1-propyl-2,3,5-trimethylpyrazolium, and 1-butyl-2,3,5-trimethylpyrazolium.

Above, the anionic site in the compound that is referred to as the ionic liquid may be those described below. In other words, it may be an aromatic hydrocarbon group, an ether group, an alkyl hydroxyl group, a chloride, a bromide, an iodide, an acetate, a lactate, methoxy sulfonate, ethoxy sulfonate, dimethoxy phosphate, n-butyl sulfonate, diethoxy phosphate, ethyl sulfonate, n-hexyl phosphate, a hydrogen phosphate, a thiocyanate, octyl sulfonate, 2-(2-methoxyethoxy)ethyl sulfate, tricyanomethane, a tetrafluoroborate, a hexafluorophosphate, triflate, bis(trifluoromethylsulfonyl) imide, trifluoromethanesulfonate, bis(fluorosulfonyl)imide, bis(nonafluorobutanesulfonyl)imide, ethyl sulfate, perfluorobutanesulfonate, dicyanamide, trifluoroacetate, a formate, a dihydrogen phosphate ion (dihydrogen phosphate), hydrogen carbonate, methyl carbonate, dibutyl phosphate, tris(pentafluoroethyl) trifluorophosphate, bis[oxalate(2-)-O,O'] borate, a decanoate, bis(2,4,4-trimethylpentyl) phosphinate, dodecylbenzene sulfonate, p-trienesulfonate, diethyl phosphonate, a benzoate, a thiosalicylate, tetrachloro ferrite, tetrachloro aluminate, or a hexafluoroantimonate in addition to a saturated/unsaturated hydrocarbon group.

In addition, the anionic site may be an arbitrary amino acid obtained through the ion exchange by the method described in J. Am., Chem. Soc., 2005, 127, 2398-2399. The amino acid referred to herein may be a monomer, a dipeptide, or an oligopeptide.

In addition, the surfactant-containing solution contains a surfactant as the main component, or contains a surfactant and a metal compound or a saccharide, or contains oils and fats, or contains an ionic liquid, but an amino acid and any derivative thereof, a polyhydric alcohol, a vitamin and any derivative thereof, a fatty acid and any derivative thereof, and a polymer material which are mentioned in the following sections may be added to the surfactant-containing solution at an arbitrary proportion in addition to these components.

As a component of the surfactant-containing solution to provide the water/gas barrier performance described above, an amino acid and any derivative thereof may be blended. Examples of the amino acid may include a simple substance of glycine, alanine, valine, leucine, isoleucine, serine, threonine, cysteine, methionine, asparagine, glutamine, proline, phenylalanine, tyrosine, tryptophan, aspartic acid, glutamic acid, lysine, arginine, histidine, and the like, a hydrochloride thereof, those obtained by bonding two or more molecules thereof, a polymer thereof, and the like thereof. These may be a single kind or a mixture of two or more kinds. Furthermore, it may be any derivative of these.

As a component of the surfactant-containing solution to provide the water/gas barrier performance described above, a polyhydric alcohol and any derivative thereof may be blended. A substance which has a hydroxyl group in the molecule and a low vapor pressure is preferable. Specific examples thereof may include glycerin, a triglyceride, polyresorcinol, polyphenol, tannic acid, and urushiol, and particularly it is preferable to use tannic acid.

As a component of the surfactant-containing solution to provide the water/gas barrier performance described above, a vitamin, any derivative thereof, and a related substance thereof may be blended. Specific examples thereof may include vitamin B1, vitamin B2, vitamin B3, vitamin B5, vitamin B6, vitamin B7, vitamin B9, vitamin B12, vitamin A, vitamin D, vitamin E, vitamin K, or any derivative thereof. Among them, retinal, β-carotene, vitamin B3 (nicotinic acid and nicotinamide), vitamin B6 (pyridoxine, pyridoxal, and pyridoxamine), and vitamin B9 (folic acid) are preferable. In addition to these, examples of the vitamin derivative may include D-araboascorbic acid, setoflavine T, 4-deoxypyridoxine hydrochloride, dibenzoyl thiamine, 2,6-di-O-palmitoyl-L-ascorbic acid, flavin adenine dinucleotide disodium salt hydrate, (+)-5,6-O-isopropylidene-L-ascorbic acid, 6-O-palmitoyl-L-ascorbic acid, proflavine hemisulfate salt hydrate, pyridoxal hydrochloride, 5-pyridoxal phosphate monohydrate, pyridoxine 3,4-dipalmitate, sodium isoascorbate monohydrate, thiamine disulfide hydrate, and thiamine disulfide nitrate. Examples of the vitamin-related substance may include choline chloride, choline bromide, choline dihydrogen citrate, choline coenzyme Q10 bitartrate, coenzyme Qo, methionine methylsulfonyl chloride, and an inositol.

Examples of the polymer material may include polyvinyl alcohol, Teflon (registered trademark) polyvinylidene fluoride, tetraethoxysilane, tetramethoxysilane, titanium isopropoxide, and zirconium butoxide.

As a component of the surfactant-containing solution to provide the water/gas barrier performance described above, the following components may be blended in addition to the components exemplified above, such as the metal compound and the saccharide.

Coordination compound: crown ether, cyclodextrin, resorcinol cyclic tetramer, calixarene, dendrimer, and the like.

Fatty acid and any derivative thereof: linoleic acid, oleic acid, palmitic acid, linolenic acid, and the like.

Derivative of saccharide and fatty acid: hyaluronic acid, ceramide, an amphiphilic compound, collagen, an amino acid, essential oil, petroleum jelly, and the like.

Gelling agent: Poly(pyridinium-1,4-diyliminocarbonyl-1,4-phenylenemethylene chloride, and the like.

Coloring matter: paprika pigment, malachite green, and the like in addition to chlorophyll, carotenoid (lycopene), phycobilin, melanin, and the like.

Conductive polymer: Nafion (registered trademark) and the like in addition to polyacetylene, polyaniline, polythiophene, and the like.

Nanoclay: those that are commercialized in the name of Nanoclay Nanomer® Laponite, montmorillonite, or the like.

Matrix material that is a reagent for mass analysis and used mainly in the MALDI method: 3-amino-4-hydroxybenzoic acid, sinapic acid, esculetin, 4-hydroxy-azobenzene-2'-carboxylic acid, 3-hydroxy-2-pyridinecarboxylic acid, nicotinic acid, 2',4',6'-trihydroxyacetophenone, α-cyano-4-hydroxycinnamic acid, 2,5-dihydroxybenzoic acid, and the like.

The surfactant-containing solution may be in a solid state or a liquid state, but it is preferably in a highly viscous liquid state in order to maintain the water environment of the sample tissue in a vacuum. In addition, those in a solid state can be used after being prepared in a liquid state at the time of use.

The surfactant-containing solution can form a very thin film on the surface of a sample when the respective components described above are dissolved in water, an organic solvent, or the like and directly coated on the sample, for example.

In the surfactant-containing solution, the blending proportion of the surfactant, a metal compound, and the saccharide is not particularly limited, but the following compositions are exemplified as preferred ones.

(1) Surfactant (sodium dodecylbenzenesulfonate):metal compound (ethylene diamine nickel complex)=from 0.005:0.001 to 0.05:0.01

(2) Surfactant (sodium dodecyl sulfate):metal compound (ethylene diamine nickel complex)=from 0.005:0.0001 to 0.05:0.001

(3) Surfactant (sodium dodecylbenzenesulfonate):metal compound (tetraamine cobalt complex)=from 0.005:0.001 to 0.05 to 0.01

(4) Surfactant (Tween 20)/saccharide (trehalose)=from 3/1 to 20/2

(5) Surfactant (Tween 20)/saccharide (pullulan)=from 3/0.2 to 20/2

(6) Surfactant (Tween 20)/saccharide (inulin)=from 3/0.1 to 20/7

The excess liquid is wiped off with soft cloth-like paper, such as the Kimwipes, filter paper, or the like after the surfactant-containing solution is coated on a sample. The sample for TEM observation is treated by the coating, attachment, coating, covering, embedding, and the like of a medium.

The film thickness of the thin film formed on the sample surface in this manner can be set, for example, to be in a range of from 5 nm to 1000 nm.

The kit for electron microscopic observation of the present invention contains the protective agent for electron microscopic observation and the surfactant-containing solution which are described above. The kit for electron microscopic observation of the present invention makes it possible to conveniently observe a fragile biological sample which does not have a strong layer to cover the surface, such as a mammal, a plant tissue or a cultured cell, and a single cell and has not been so far necessarily sufficiently discussed in the living state by an electron microscope by only using the two kinds of solutions described above.

According to the method for observing a sample by an electron microscope of the present invention, it is possible to observe a biological sample in a water-containing state as its living state by coating the biological sample in a water-containing state with the protective agent for electron microscopic observation, placing the biological sample in a water-containing state coated with the protective agent for electron microscopic observation on a sample stage, forming a thin film on the surface of the biological sample in a water-containing state by irradiating the biological sample in a water-containing state with an electron beam or plasma so as to cover the biological sample in a water-containing state, and displaying an electron microscopic image of the biological sample in a water-containing state that is covered with the thin film and contained in a sample chamber in a vacuum on a display device.

In addition, according to the method for observing a sample by an electron microscope of the present invention, it is preferable to apply a surfactant-containing solution to a biological sample in a water-containing state at least before and after the biological sample in a water-containing state is coated with the protective agent for electron microscopic observation.

In other words, the timing to coat the surfactant-containing solution may be before or after the biological sample in a water-containing state is coated with the protective agent for electron microscopic observation depending on the kind of the biological sample in a water-containing state.

In addition, in the method for observing a sample by an electron microscope of the present invention, it is preferable to wash the surface of the biological sample in a water-containing state with water prior to coating of the biological sample in a water-containing state.

Water used for water washing is not particularly limited as long as it does not affect the biological sample in a water-containing state. Specific examples thereof may include ultrapure water, deionized water, and distilled water.

Usually, it has been considered that osmotic pressure abnormality is caused to rupture the cell when the water described above is dropped on a cell. However, the present inventors have found out that any abnormality of the cell is not acknowledged even when the washing treatment to drop distilled water on a cell and to leave the cell to stand still for 1 minute is repeated 2 times. Furthermore, in some cells, it has been confirmed that the image that is obtained by adding the water washing step and taken by a SEM is clearer as compared to the image that is obtained by coating the protective agent for electron microscopic observation after the treatment with the surfactant-containing solution and taken by a SEM. It is considered by the present inventors that a substance having similar properties with those of the surfactant-containing solution is present on the surface of a cultured cell, the concentration thereof is higher than that of the surfactant-containing solution, and thus the concentration of the substance is lowered to a concentration at which the secretion of the cultured cell can form a thin film suitable for observation by the water washing.

In the method for observing a sample in a water-containing state by an electron microscope of the present invention, it is preferable to form a thin film on the surface of the biological sample in a water-containing state by irradiating the biological sample in a water-containing state with an electron beam for sample observation in the sample chamber of an electron microscope.

In the method for observing a sample in a water-containing state by an electron microscope of the present invention, it is preferable to form a thin film on the surface of the biological sample in a water-containing state by irradiating the biological sample in a water-containing state with an electron beam different from the electron beam in the sample chamber of an electron microscope or plasma in advance before the biological sample in a water-containing state is observed by the electron microscope.

In particular, it is possible to observe a biological sample in a water-containing state as its living state by coating the surface of a biological sample in a water-containing state with the protective agent for electron microscopic observation or the surfactant-containing solution, then forming a thin film on the surface of the biological sample in a water-containing state by irradiating the biological sample in a water-containing state with an electron beam or plasma so as to cover the biological sample in a water-containing state, and displaying an electron microscopic image of the biological sample in a water-containing state that is covered with the thin film and contained in a sample chamber in a vacuum on a display device.

This thin film can be formed on the surface of a biological sample in a water-containing state by irradiating the biological sample in a water-containing state with an electron beam for sample observation in the sample chamber of an electron microscope.

Alternatively, this thin film can be formed on the surface of a biological sample in a water-containing state by irradiating the biological sample in a water-containing state with an electron beam different from the electron beam for sample observation of an electron microscope or plasma in advance before the biological sample in a water-containing state is observed by the electron microscope.

The irradiation condition is appropriately selected depending on the protective agent for electron microscopic observation, the surfactant-containing solution, or the like to be used, and it is not particularly limited, but as an example, it is possible to observe a biological sample as its living state in a high vacuum (for example, from $10^{-4}$ to $10^{-7}$ Pa) by a SEM, for example, a usual FE-SEM by irradiating the biological sample in a water-containing state that is covered with the protective agent for electron microscopic observation or the surfactant-containing solution without being subjected to the pretreatment of the prior art with the electron beam (for example, about 5.0 kV) of the SEM for 60 minutes in the sample chamber.

In addition, it is possible to observe a biological sample as its living state in a high vacuum by a SEM or a TEM by irradiating a biological sample in a water-containing state that is covered with the protective agent for electron microscopic observation or the surfactant-containing solution without being subjected to the pretreatment of the prior art with plasma for 3 minutes in advance in another example.

The surface of a biological sample in a water-containing state is covered with a thin film by such irradiation with an electron beam or plasma. The thickness of this thin film can be set, for example, to be in a range of from 5 nm to 1000 nm in the case of forming the thin film on the surface of a biological sample.

The polymerization by irradiation with plasma can be conducted, for example, by using an ion sputtering apparatus or the like of the prior art under the conditions having a pressure of from $10^{-3}$ to $10^5$ Pa, a temperature of from −20 to +80° C., a voltage of from 1 to 10 kV, and a DC. Alternatively, it can be conducted by an apparatus such as a reaction tube or a method which is used in the plasma polymerization of the prior art.

In the present invention, the biological sample in a water-containing state for SEM observation is treated by the coating, attachment, coating, covering, and the like of a surfactant-containing solution in order to be subjected to the observation by an electron microscope. For example, in the case of the coating, the excess liquid is wiped off with soft cloth-like paper, such as the Kimwipes, filter paper, or the like after the coating. The biological sample in a water-containing state for TEM observation is treated by the coating, attachment, coating, covering, embedding, and the like of a surfactant-containing solution.

In addition, with regard to some of the cultured cells and single cell, the atrophy of cells by irradiation with plasma is acknowledged in some cases, and thus it is preferable to form a thin film by irradiation with an electron beam.

When the sample is introduced into the sample chamber, for example, a sample stage may be used in which a biological sample in a water-containing state on which a thin film is formed is placed on the upper surface of a cylindrical base member, a ring-shaped member having a circular opening that is substantially equal to the diameter of the cylindrical member, an opening having a diameter smaller than the opening at the upper surface portion thereof, and a fixing hole at the side surface portion is covered on the biological sample in a water-containing state placed on the upper surface of the cylindrical base member, and the cylindrical base member and the ring-shaped member are fixed with a fixing material.

In addition, a sample stage may be used in which the biological sample in a water-containing state on which a thin film is formed is placed on the upper surface of a cylindrical member having a circular recess formed in the center, a disk-shaped member having a circular through hole formed in the center and a plurality of fixing holes opened in the periphery of the through hole is covered on the biological sample in a water-containing state placed on the upper surface of the cylindrical member, and the disk-shaped member and the cylindrical member are fixed with a fixing material.

It is possible to observe a sample in a state close to the form in the organism as the tension is applied to the sample of the membrane-like animal tissue, the atrophy of the tissue is suppressed, and the membrane surface is more spread by using the sample stage equipped with the structure as described above.

The method for diagnosing of a cancer cell in a water-containing state by an electron microscope of the present invention includes a step of coating a cancer cell in a water-containing state or a tissue including this which is excised from a living body with a protective agent for electron microscopic observation containing a a component to impart the survival environment, a saccharide, and an electrolyte, a step of placing the cancer cell in a water-containing state or the tissue including this which is coated with a protective agent for electron microscopic observation on a sample stage and forming and covering a thin film on the surface of the cancer cell in a water-containing state, or the tissue including this by irradiating it with an electron beam or plasma, a step of displaying an electron microscopic image of the cancer cell in a water-containing state or the tissue including this which is covered with a thin film and contained in a sample chamber in a vacuum on a display device, and a step of performing image diagnosis of the displayed cancer cell in a water-containing state or the displayed tissue including this.

By applying the method for diagnosing of a cancer cell in a water-containing of the present invention, it is confirmed that the cells are regularly arranged and the shape of the cells is also smooth in a normal cell, but the cells are irregularly present and piled in a multi-layered and there are a great number of apophyses on the cell surface in a cancer cell. Hence, it is possible to perform the image diagnosis of the cancer cell or a tissue including this by paying attention to the difference in external form between the normal cells and the cancer cells even without using a special cell marker or the like. In addition to this, a cancer cell that is highly invasive and metastatic extends a microfiber to a near normal cell in some cases, and thus it is possible to perform the image diagnosis of the cancer cell or a tissue including this by also paying attention to such a specific morphological change of the cancer cell.

In the method for diagnosing of a cancer cell in a water-containing state by an electron microscope of the present invention, the cancer cells in a water-containing state is preferably one that is inoculated and cultured on a normal cell or a cell sheet.

A cell sheet is a form of cultured cells obtained by culturing a normal cell in a plate shape. By using such a normal cell or cell sheet, it is possible to time-dependently observe the process of invasion and metastasis of the cancer cell to a normal cell and it is also possible to observe the specific morphological change of the cancer cell when the cancer cell invades and metastasizes to a normal cell. As such a specific morphological change of the cancer cell when the cancer cell invades and metastasizes to a normal cell, the extension of a microfiber by the cancer cell is exemplified. A cancer cell extends a microfiber to a normal cell, and it invades and metastasizes to the interior of the normal cell by using this microfiber as a foothold. It is possible to observe the extension of this microfiber as the normal cell and cancer cell in a water-containing state are alive by using the method for diagnosing of a cancer cell in a water-containing state by an electron microscope of the present invention.

In the method for diagnosing of a cancer cell in a water-containing state by an electron microscope of the present invention, a cancer cell in a water-containing state or a tissue including this which is excised from a living body can be observed without being chemically fixed after the excision. It is possible to observe the morphological change associated with the invasion and metastasis of the cancer cell in real-time by observing the cancer cell in a water-containing state or a tissue including this which is excised from a living body without chemically fixing it in this manner.

In addition, in the method for diagnosing of a cancer cell in a water-containing state by an electron microscope of the present invention, it is also possible to chemically fix a cancer cell in a water-containing state or a tissue including this which is excised from a living body immediately after the excision as it is performed in a medical institution in the prior art. It is possible to minimize a change of the cell and to provide a highly reproducible diagnostic technique by quickly chemically fixing the cancer cell or the tissue in this manner, and thus the present invention is considered to contribute to the standardization of diagnostic techniques.

The method for evaluating an effect of a physiologically active substance or a drug to a cell in a water-containing state by an electron microscope of the present invention includes a step of adding a physiologically active substance or a drug to a cell or cell sheet in a water-containing state, a step of coating the cell or cell sheet in a water-containing state to which the physiologically active substance or the drug is added with a protective agent for electron microscopic observation containing a a component to impart the survival environment, a saccharide, and an electrolyte, a step of placing the cell or cell sheet in a water-containing state which is coated with the protective agent for electron microscopic observation on a sample stage and forming and covering a thin film on the surface of the cell or cell sheet in a water-containing state by irradiating it with an electron beam or plasma, a step of displaying an electron microscopic image of the cell or cell sheet in a water-containing state which is covered with a thin film and contained in a sample chamber in a vacuum on a display device, and a step of performing image diagnosis on the effect of the physiologically active substance or the drug to the displayed cell or cell sheet in a water-containing state.

By using the method for evaluating an effect of a physiologically active substance or a drug to a cell in a water-containing state by an electron microscope of the present invention, it is possible to time-dependently observe the morphological change caused by adding a drug to a normal cell or cell sheet in a water-containing state as the cell is alive. For example, it is possible to observe at which time the physiologically active substance or the drug effectively acts after the administration by coating the protective agent for electron microscopic observation of the present invention to the cells having different elapsed times of 20 minutes, 30 minutes, and 60 minutes after the physiologically active substance or the drug is added thereto.

In the method for evaluating an effect of a physiologically active substance or a drug to a cell in a water-containing state by an electron microscope of the present invention, it is preferable that the cell is a normal cell in a water-containing state and a physiologically active substance or a drug which has fewer side effects is screened by using the morphological change of the normal cell as an indicator.

In the method for evaluating an effect of a physiologically active substance or a drug to a cell in a water-containing state by an electron microscope of the present invention, the physiologically active substance or the drug is preferably a newly developed medical product in the drug discovery field. Examples of the newly developed medical product may include an anti-cancer drug.

In the method for evaluating an effect of a physiologically active substance or a drug to a cell in a water-containing state by an electron microscope of the present invention, it is preferable that the cell is a diseased cell in a water-containing state and a physiologically active substance or a drug which exhibits activities is screened by using the morphological change of the diseased cell in a water-containing state as an indicator.

In the method for evaluating an effect of a physiologically active substance or a drug to a cell in a water-containing state by an electron microscope of the present invention, it is preferable that the diseased cell in a water-containing state is a cancer cell and the physiologically active substance or the drug is a newly developed medical product in the drug discovery field. Examples of the newly developed medical product may include an anti-cancer drug.

The physiologically active substance and the drug which is added to a normal cell or cell sheet in a water-containing state is not limited to an anti-cancer drug, and, for example, it can be applied to various drugs which exhibit physiological activities or pharmacological activities such as histamine and growth factors, anti-inflammatory agents, and antineoplastic agents. When these various drugs are a drug which causes a change in morphology of a cell, it is possible to observe and evaluate the effect and activity of the drug so as to screen the drug.

The method for observing a biological sample in a water-containing state by an electron microscope of the present invention includes a step of bringing a cell in a water-containing state into contact with a primary antibody, a step of bringing the primary antibody into contact with a secondary antibody modified with a gold colloid, a step of coating the cell in a water-containing state bound to the primary antibody and the second antibody with a protective agent for electron microscopic observation containing a a component to impart the survival environment, a saccharide, and an electrolyte, a step of placing the cell in a water-containing state coated with the protective agent for electron microscopic observation on a sample stage and forming a thin film on the surface of the cell in a water-containing state by irradiating it with an electron beam or plasma to cover the cell in a water-containing state, and a step of displaying an electron microscopic image of the cell in a water-containing state that is covered with the thin film and contained in a sample chamber in a vacuum on a display device, in which the binding site of the cell in a water-containing state with the primary antibody is observed.

In the method for observing a biological sample in a water-containing state by an electron microscope of the present invention, it is preferable that the antigen that reacts with the primary antibody is a membrane protein of a cell in a water-containing state and the binding site of the cell in a water-containing state with the primary antibody is observed.

In the immunoelectron microscopy of the prior art, a multi-step sample preparation method including chemical fixation is required and it takes a whole day to prepare the sample for a SEM and it takes a few days to prepare the sample for a TEM. However, in the method for observing the binding site of a cell in a water-containing state with a primary antibody of the present invention, the cell is not required to be chemically fixed and those that are added other than the antibody are only the protective agent for electron microscopic observation and the surfactant-containing solution. Hence, it is possible to observe the binding site of a cell in a water-containing state with a primary antibody in a few hours.

In addition, in the immunoelectron microscopy of the prior art, it is required to select a site exhibiting favorable ultrastructural preservation and stainability. Moreover, the antigen ability of a cell in a water-containing state deteriorates and a decrease in sensitivity is caused when the chemical fixation is enhanced in order to maintain the microstructure. Problems are pointed out that are hardly solved at the same time since the microstructure of the cell is damaged when the chemical fixation is weakened in order to improve sensitivity. However, in a method for observing the binding site of a cell in a water-containing state with a primary antibody of the present invention, it is possible to remarkably decrease the deactivation of antigen ability by chemical fixation and it is also possible to improve the sensitivity to about 100 times that of the method of the prior art.

Furthermore, in the immunoelectron microscopy of the prior art, the artifacts upon sample preparation are hardly distinguished from the signals of the original purpose, and the confirmation of the accurate localization of the antigen protein is greatly dependent on the skill and proficiency of the experimenter. In addition, the operation of the experimental instrument to be used in the immunostaining method is also difficult, and thus adequate training is required. However, in the method for observing the binding site of a cell in a water-containing state with a primary antibody of the present invention, as described above, high sensitivity is obtained as compared to the method of the prior art, and thus it is possible to conduct the antibody treatment at a low concentration and there is an advantage that a non-specific signal is hardly detected.

By using the protective agent for electron microscopic observation of the present invention, an image which has fewer non-specific signals, obtained by the immunoelectron microscopy, and taken by a SEM is obtained at a high sensitivity in a significantly short time since the primary antibody and the secondary antibody act without chemical fixation of the cell. By performing the observation using this novel immunoelectron microscopy, it is possible to quickly and conveniently realize the cancer diagnosis and cancer pathology at a high accuracy, for example, by using a tumor marker as the antigen. Incidentally, the diseased cell is not limited to a cancer cell, and it is also possible to diagnose an inflammatory disease or an autoimmune disease.

The method for observing the binding site of a cell in a water-containing state with a primary antibody of the present invention is referred to as live immunoelectron microscopy of a novel immunoelectron microscopy by the present inventors.

It is also possible to observe and count the viral particles in a water-containing state by using an electron microscope so as to quantify the concentration of virus by using the protective agent for electron microscopic observation of the present invention.

As the virus quantification method of the prior art, plaque assay, a quantitative PCR method, or the like has been utilized. However, the plaque assay requires a long time for preparation and is inferior in reproducibility, and thus a more favorable measurement method is desired. The quantitative PCR method is a highly effective measurement method, but it has a problem that the loss of DNA in the step of extracting the viral DNA is unavoidable. In addition, the virus quantification by the quantitative PCR method measures the amount of all the viral genomes contained in the sample solution, and thus the actual number of viral particles is only estimated.

Hence, it is ideal to quantitatively and directly measure the viral particles, but there is a technical difficulty for quantitativity in the virus quantification method using a TEM and a cryo-electron microscope, which is a direct measurement method.

As a means for solving the above problems, the present inventors have devised a method for quantifying viral particles in a water-containing state by an electron microscope of the present invention.

In other words, the method for quantifying viral particles in a water-containing state by an electron microscope of the present invention includes a step of concentrating viral particles in a water-containing state on a substrate, a step of coating the viral particles in a water-containing state concentrated on a substrate with a protective agent for electron microscopic observation containing a a component to impart the survival environment, a saccharide, and an electrolyte, a step of placing the viral particles in a water-containing state coated with the protective agent for electron microscopic observation on a sample stage together with the substrate and forming a thin film on the surface of the viral particles in a water-containing state by irradiating the viral particles in a water-containing state with an electron beam or plasma to cover the sample, a step of displaying an electron microscopic image of the viral particles in a water-containing state which are covered with the thin film and contained in a sample chamber in a vacuum on a display device, and a step of counting the viral particles in the displayed electron microscopic image of the viral particles in a water-containing state.

In the method for quantifying viral particles in a water-containing state by an electron microscope of the present invention, the step of concentrating viral particles in a water-containing state on a substrate is preferably to concentrate viral particles by charging the surface of the viral particles in a water-containing state with a charge and adsorbing the viral particles in a water-containing state to a substrate having a surface charged with a charge that is opposite to this charged charge.

In the method for quantifying viral particles in a water-containing state by an electron microscope of the present invention, it is preferable to charge the surface of the viral particles with a positive charge by treating it with polybrene.

In the method for quantifying viral particles in a water-containing state by an electron microscope of the present invention, it is preferable to charge the surface of the substrate with a negative charge by irradiating it with plasma. In other words, the functional group on the substrate surface is broken and the hydrophilic group is exposed onto the surface by irradiating the substrate surface with plasma. Examples of these hydrophilic groups may include a hydroxyl group, and the substrate surface can be charged with a negative charge by the hydrophilic group.

In embodiments of the present invention, it is preferable to recover the virus which has been propagated in a host cell in advance. As the method for recovering a virus, it is possible to suitably use a known method in which a host cell is infected with a viral particle and the viral particle present in the culture supernatant is recovered or a cell infected with a virus is ground in a buffer solution and the homogenate of the virus-infected cell thus obtained is filtered through a filter and treated by the sucrose density gradient ultracentrifugation method. In addition, these methods may be used singly or a plurality thereof may be combined.

As the method for concentrating viral particles in a water-containing state on a substrate, the viral particles are charged with a positive charge and the substrate is charged with a negative charge, but the viral particles may be charged with a negative charge and the substrate may be charged with a positive charge.

In addition, the compound for charging the viral particles with a positive charge is not particularly limited as long as it does not to cause a morphological change of the viral particles in a water-containing state. As illustrated in FIG. 46(a), polybrene is preferably used since it is a polyvalent quaternary amine polymer compound, plays a role as glue in between the glass substrate surface that is negatively charged and the virus, and has a remarkable effect to prevent leakage of the virus.

Incidentally, the method for concentrating viral particles in a water-containing state on a substrate is not particularly limited to the method using a charge as described above as long as it does not to cause a morphological change of the virus sample in a water-containing state.

The substrate is not limited to glass, and it is also possible to use a metal sample stage or ceramics.

In the method for quantifying viral particles in a water-containing state by an electron microscope of the present invention, it is possible to determine the concentration of virus by counting the viral particles in a plurality of visual fields by an electron microscope, calculating the average value, and multiplying the parameter such as the dilution ratio of the dispersion of the viral particles of the measurement sample, the dropped amount of the dispersion of the virus particles, or the like. Moreover, the concentration of virus determined by the method for quantifying viral particles in a water-containing state by an electron microscope of the present invention is consistent with the viral concentration determined by the plaque assay or quantitative PCR method that is a method of the prior art.

In addition, by combining the method for quantifying viral particles in a water-containing state by an electron microscope of the present invention and the method for observing the binding site of a cell in a water-containing state with a primary antibody of the present invention, it is considered that it is possible to distinguish a DNA virus from a RNA virus, for example, by using an anti-DNA antibody as the primary antibody.

The method for observing a biological sample in a water-containing state by an electron microscope of the present invention can be applied to the analysis and assay performed by combining an electron microscope with another analytical method.

The method for observing a biological sample in a water-containing state by an electron microscope of the present invention can be applied to, for example, the combination of a scanning electron microscope with energy dispersive X-ray analysis (SEM-EDS) and the combination of a transmission electron microscope with energy dispersive X-ray analysis (TEM-EDS). By the combination with EDS, for example, it is possible to analyze the element distribution across the depth from the surface up to about several hundreds µm of a cell in a water-containing state without chemically fixing the cell.

In addition, by combining the element distribution obtained by the above EDS analysis with the method for evaluating an effect of a physiologically active substance or a drug to a cell in a water-containing state by an electron microscope of the present invention, for example, it is possible to time-dependently analyze the mechanism of action caused by adding a physiologically active substance or a drug to a normal cell or cell sheet in a water-containing state as the cell is alive by taking the viewpoint of a change in element distribution into account as well in addition to a morphological change of the cell.

The protective agent for electron microscopic observation of the present invention functions as a favorable protective agent for electron microscopic observation for observing a biological sample in a water-containing state, such as a mammal, a plant tissue or a cultured cell, and a single cell by an electron microscope. In other words, the protective agent for electron microscopic observation of the present invention makes it possible to place a living biological sample in a water-containing state, such as a mammal, a plant tissue or a cultured cell, and a single cell in the mirror body of an electron microscope in the living state without subjecting the biological sample to dehydration, chemical fixation, and electron staining of the prior art, and even at the time of observation, it suppresses drying and ice crystals of the biological sample under reduced pressure and the damage caused by the temperature change and enhances the surface shielding effect (SS effect) that blocks the water/gas in the sample.

According to the present invention, it is possible to observe a biological sample in a water-containing state, such as a mammal, a plant tissue or a cultured cell, and a single cell, which has not been necessarily sufficiently discussed in the prior invention by the present inventors without deforming the sample and impairing the state of the sample itself. In other words, it is possible to enhance the surface shielding effect (SS effect) that blocks the water/gas in the sample and is indicated in the prior invention.

In other words, the protective agent for electron microscopic observation of the present invention functions as a favorable visualizing agent for observing a biological sample in a water-containing state, such as a mammal, a plant tissue or a cultured cell, and a single cell by an electron microscope, and thus it is suitably utilized in the sample observation by a scanning electron microscope and a transmission electron microscope.

In the case of coating a cultured cell with the protective agent for electron microscopic observation and surfactant-containing solution of the present invention, not only it is possible to cover the cell surface as the cell is alive but also the cell survives after the cell surface is covered.

By covering the surface of a biological sample in a water-containing state, such as a mammal, a plant tissue or a cultured cell, and a single cell with the protective agent for electron microscopic observation and surfactant-containing solution of the present invention, it is possible to observe the living state of the biological sample in a water-containing state, such as a mammal, a plant tissue or a cultured cell, and a single cell and the structure such as a fine surface of an organism by a scanning electron microscope.

Moreover, by covering the surface of a biological sample in a water-containing state, such as a mammal, a plant tissue or a cultured cell, and a single cell with the protective agent for electron microscopic observation of the present invention, it is possible to directly observe the living state of the biological sample in a water-containing state without charging (charge-up) it in a scanning electron microscope.

In addition, the protective agent for electron microscopic observation of the present invention makes it possible to observe a biological sample in a water-containing state at a high magnification without passing through the procedure of chemical fixation→conductive staining→dehydration drying→coating or chemical fixation→dehydration→embedding→ultra-slicing→electron staining→coating which is required for the sample preparation of a biological sample in a water-containing state in the observation by an electron microscope in the prior art.

The protective agent for electron microscopic observation of the present invention suppresses the deformation and degeneration of the sample even during the measurement by an electron microscope and does not significantly damage the sample before and after the measurement. By using the protective agent for electron microscopic observation of the present invention for a biological sample in a water-containing state, such as a mammal, a plant tissue or a cultured cell, and a single cell, which has not been necessarily sufficiently discussed in the composition for evaporation inhibition of the prior invention by the present inventors, it is possible to enhance the water/gas barrier performance in a vacuum and to suppress a significant decrease of temperature in the sample. In addition, even a biological sample in a water-containing state, such as a mammal, a plant tissue or a cultured cell, and a single cell is irradiated with an electron beam in a vacuum, the water/gas barrier performance is enhanced, a significant decrease of temperature in the sample is suppressed, and also it is possible to enhance the action such as prevention of charging of the sample by irradiation with an electron beam and suppression of the thermal damage. In a case in which the sample is a biological sample in a water-containing state, a biological sample in the living state can be observed as its living state and no change is seen in the sample even when it is taken out of the mirror body.

In particular, by using the protective agent for electron microscopic observation of the present invention, when a cultured cell is observed as its living state by an electron microscope and then returned into the medium, the cultured cell does not perish immediately after the observation but can continuously survive for a certain period.

In the present invention, the sample observation by a scanning electron microscope and a transmission electron microscope can be performed by an apparatus having a configuration which has been known so far.

A scanning electron microscope is generally constituted by a lens-barrel unit (mirror body) and an operating unit. In the lens-barrel unit, the generation of an electron beam by the electron gun, the narrowing of the electron beam by the electron lens, the trimming of the electron probe, and the scanning of the electron probe in the observation region of the sample surface by the deflecting coil are carried out. The sample chamber in which the sample is placed is equipped with a sample stage, a detector to detect the signal emitted from the sample. This lens-barrel unit is required to be maintained in a clean vacuum, and thus it is provided with a vacuum pumping mechanism operated depending on the purpose.

The operating unit controls the generation of an electron beam, the lens action of the electron lens, the astigmatism correction, the scanning range (magnification) or scanning speed of the electron probe on the sample surface, and the like, and it also displays the detected signal on the CRT as a video.

In addition, it is general to observe and take a low-scan image with fewer noises in the still image by a scanning electron microscope, but the observation in the TV mode, namely, the video of a moving image is the main in the observation of a living biological sample by a scanning electron microscope. Accordingly, it is also considerable to display and record an image by a scanning electron microscope in a high quality TV mode by adding a display and recording circuit for a TV-mode image with fewer noises (having a small S/N) to the scanning electron microscope.

EXAMPLES

Hereinafter, the present invention will be described in more detail with reference to Examples, but the present invention is not limited to these Examples in any way.

In the following Examples, the SEM observation was typically performed at an accelerating voltage of 5.0 kV by using a field emission scanning electron microscope (FE-SEM, S-8000 (Hitachi)).

Example 1

A protective agent for electron microscopic observation was prepared by mixing glycerin and water as a a component to impart the survival environment, glucose as a saccharide, and sodium chloride as an electrolyte at a blending proportion of a component to impart the survival environment (glycerin):(water):saccharide (glucose):electrolyte (sodium chloride)=20:10:0.7:0.03.

In addition, a 1% (v/v) Tween 20 solution was prepared as a surfactant-containing solution.

The peritoneum was excised from a living mouse and subjected to the primary chemical fixation with 10% (w/w) neutral buffered formalin, and then immersed in the protective agent for electron microscopic observation for 1 minute as the pretreatment. The peeled peritoneal site of mouse thus pretreated was immersed in the surfactant-containing solution for 1 minute and then withdrawn therefrom, and the excess was wiped off, thereby covering the surface of the peeled peritoneal site of mouse with the surfactant-containing solution. Thereafter, the peeled peritoneal site of mouse was introduced into the sample chamber of the SEM such that the mouse peritoneal epithelial side covered with the surfactant-containing solution was to be the upper surface, irradiated with an electron beam to polymerize the surfactant-containing solution and thus to form a thin film, and subjected to the SEM observation.

Figure 2:
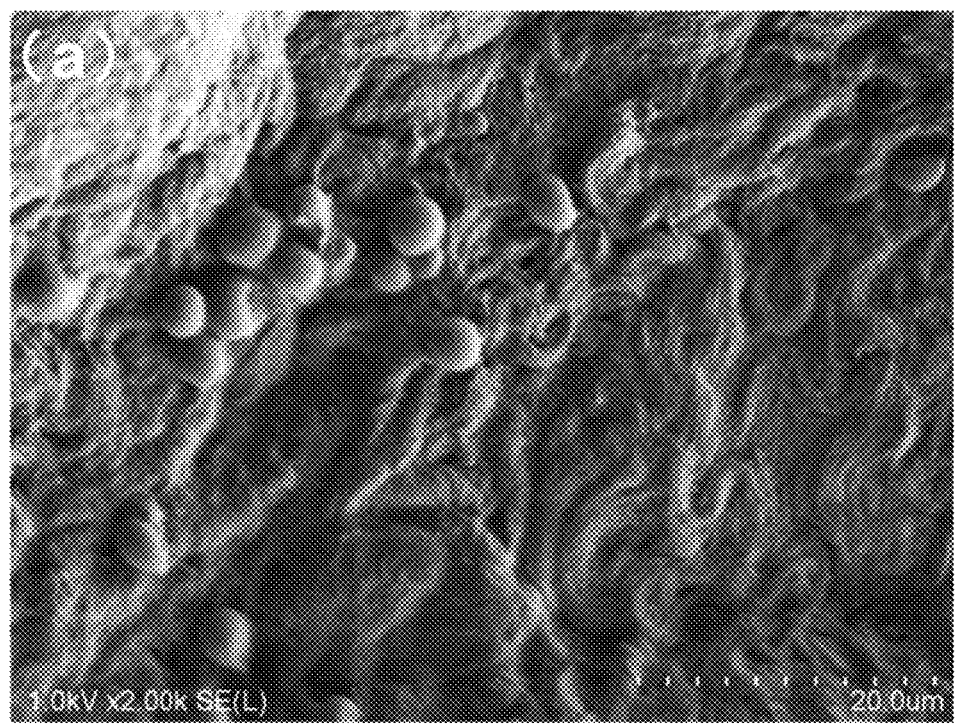
FIG. 2(a) is an image of Example 1 taken by a SEM.
FIG. 2(b) is an image of Comparative Example 1 taken by a SEM.
Figure 2:

FIG. 1(a) is an image of the mouse peritoneal epithelial side in a water-containing state which was treated with the protective agent for electron microscopic observation and the surfactant-containing solution after the primary chemical fixation of the prior art, and observed and taken at a magnification of 50-fold by a SEM. In addition, FIG. 2(a) is an image the sample of FIG. 1(a), which was observed and taken at a magnification of 2000-fold by a SEM.

In Example 1, charge-up or the cleavage of peritoneum has not been acknowledged at all, but a great number of apophyses on the peritoneal surface have been confirmed. From this fact, it has been confirmed that the normal morphology of a biological sample can be maintained in a vacuum even when the biological sample is a biological tissue of a mammal by treating the biological tissue with the protective agent for electron microscopic observation of the present invention prior to the thin film formation.

Comparative Example 1

The peritoneum was excised from a living mouse and subjected to the primary chemical fixation with 10% (w/w) neutral buffered formalin in the same manner as in Example 1, then introduced into the sample chamber of the SEM without being treated with the protective agent for electron microscopic observation and surfactant-containing solution of the present invention, and subjected to the SEM observation.

FIG. 1(b) is an image of the mouse peritoneal epithelial side which was not treated with the protective agent for electron microscopic observation and surfactant-containing solution of the present invention after the primary chemical fixation, and observed and taken at a magnification of 50-fold by a SEM. In addition, FIG. 2(b) is an image the sample of FIG. 1(b), which was observed and taken at a magnification of 2000-fold by a SEM.

In Comparative Example 1, it has been confirmed that the image taken by a SEM is charged up and the peritoneal surface is broken. Hence it can be seen that it is difficult to

47 maintain the normal morphology of a biological tissue of a mammal in a vacuum by the chemical fixation treatment method of the prior art.

Example 2

A protective agent for electron microscopic observation and a surfactant-containing solution were prepared in the same manner as in Example 1.

The peritoneum excised from a living mouse was immediately treated with the protective agent for electron microscopic observation as the pretreatment without being chemically fixed, and immersed in the surfactant-containing solution for 1 minute.

The mouse peritoneum thus pretreated was immersed in the surfactant-containing solution for 1 minute and then withdrawn therefrom, and the excess was wiped off, thereby covering the surface of the mouse peritoneum with the surfactant-containing solution. Thereafter, the mouse peritoneum covered with the surfactant-containing solution was introduced into the sample chamber of the SEM, irradiated with an electron beam to polymerize the surfactant-containing solution and thus to form a thin film, and subjected to the SEM observation.

Figure 3:
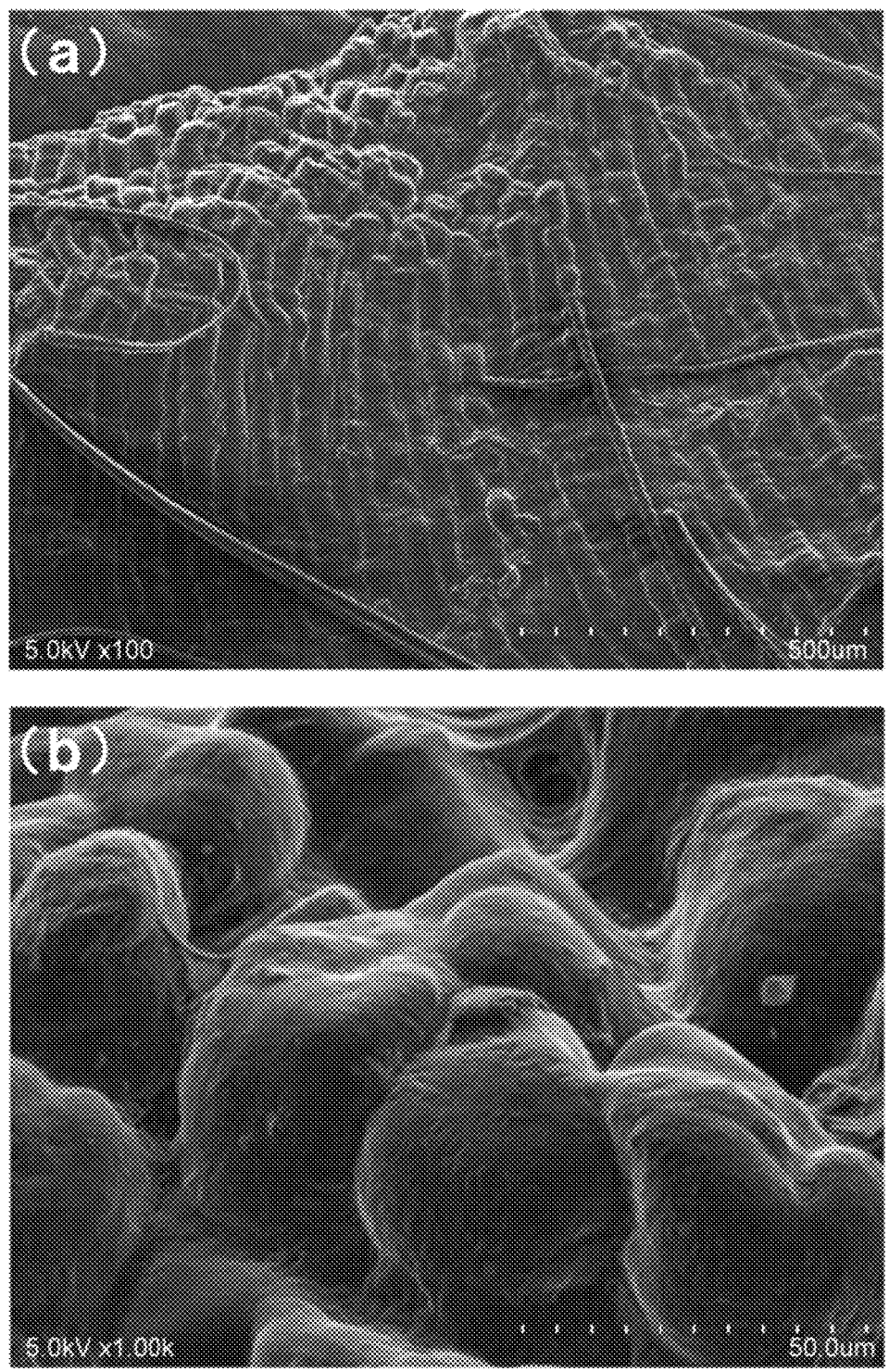
FIGS. 3(a) and 3(b) are images of Example 2 taken by a SEM, respectively.

FIG. 3(a) is an image which was observed and taken at a magnification of 100-fold by a SEM, and FIG. 3(b) is an image of the sample of FIG. 3(a), which was observed and taken at a magnification of 1000-fold by a SEM.

In Example 2, peritoneal surface has maintained the normal morphology and a great number of apophyseal structures have been confirmed in the same manner as in Example 1. From this fact, it has been confirmed that the normal morphology of a biological sample can be maintained in a vacuum even when the biological sample is a biological tissue of a mammal by treating the biological tissue with the protective agent for electron microscopic observation of the present invention prior to the thin film formation.

Example 3

A protective agent for electron microscopic observation and a surfactant-containing solution were prepared in the same manner as in Example 1.

The pathological specimen of the human gastric cancer subjected to the primary chemical fixation with 10% (w/w) neutral buffered formalin was treated with the protective agent for electron microscopic observation and immersed in the surfactant-containing solution for 1 minute. The excess surfactant-containing solution was wiped off, the sample was introduced into the sample chamber of the SEM, irradiated with an electron beam to polymerize the surfactant-containing solution and thus to form a thin film, and subjected to the SEM observation.

Figure 4:
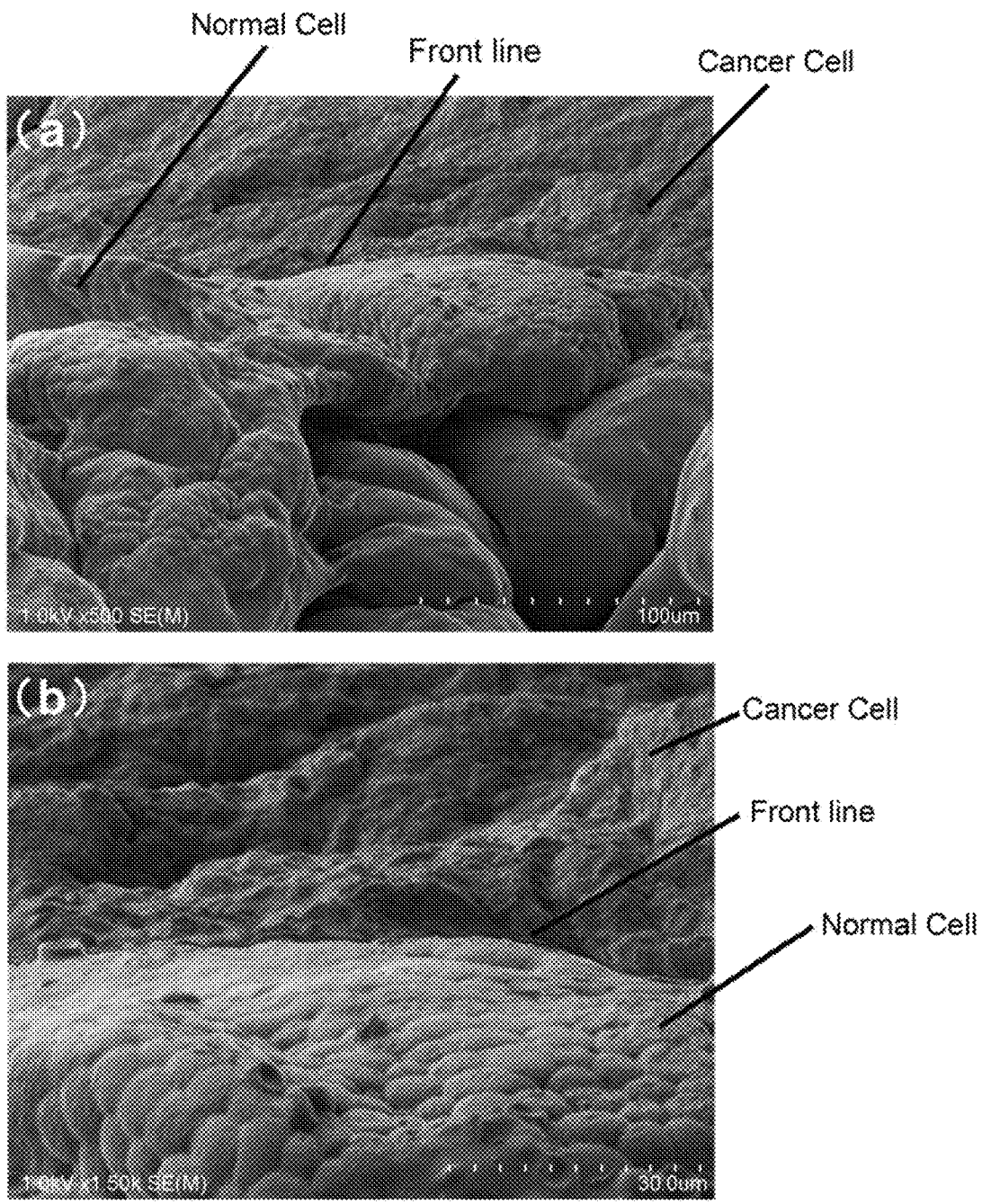
FIGS. 4(a) and 4(b) are images of Example 3 taken by a SEM, respectively.
Figure 5:
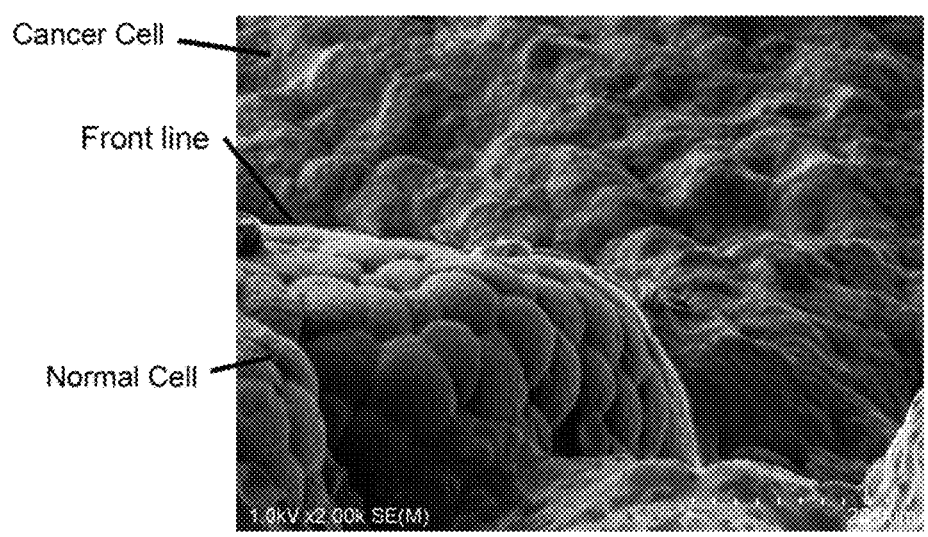
FIG. 5 is an image of a portion of the pathological section of the human gastric cancer of Example 3 illustrated in FIGS. 4(a) and 4(b), which is observed and taken at a magnification of 2000-fold by a SEM.

FIG. 4(a) is an image of the pathological specimen of the human gastric cancer in a water-containing state, which was treated with the protective agent for electron microscopic observation and the surfactant-containing solution after the primary chemical fixation of the prior art, and observed and taken at a magnification of 500-fold by a SEM. In addition, FIG. 4(b) is an image of the sample of FIG. 4(a), which was observed and taken at a magnification of 1500-fold by a SEM. Furthermore, FIG. 5 is an image of the sample of FIG. 4(a), which was observed and taken at a magnification of 2000-fold by a SEM.

In Example 3, it has been possible to clearly confirm the difference in morphology between a cancer cell having

48 irregular apophyses on the surface and a normal cell having a regular structure, and the boundary surface (front line) between a cancer cell and a normal cell has also been acknowledged.

Example 4

A protective agent for electron microscopic observation and a surfactant-containing solution were prepared in the same manner as in Example 1.

The pathological specimen of the human gastric cancer subjected to the primary chemical fixation with 10% (w/w) neutral buffered formalin was treated with the protective agent for electron microscopic observation and immersed in the surfactant-containing solution for 1 minute. The excess surfactant-containing solution was wiped off, the sample was introduced into the sample chamber of the SEM, irradiated with an electron beam to polymerize the surfactant-containing solution and thus to form a thin film, and subjected to the SEM observation.

Figure 6:
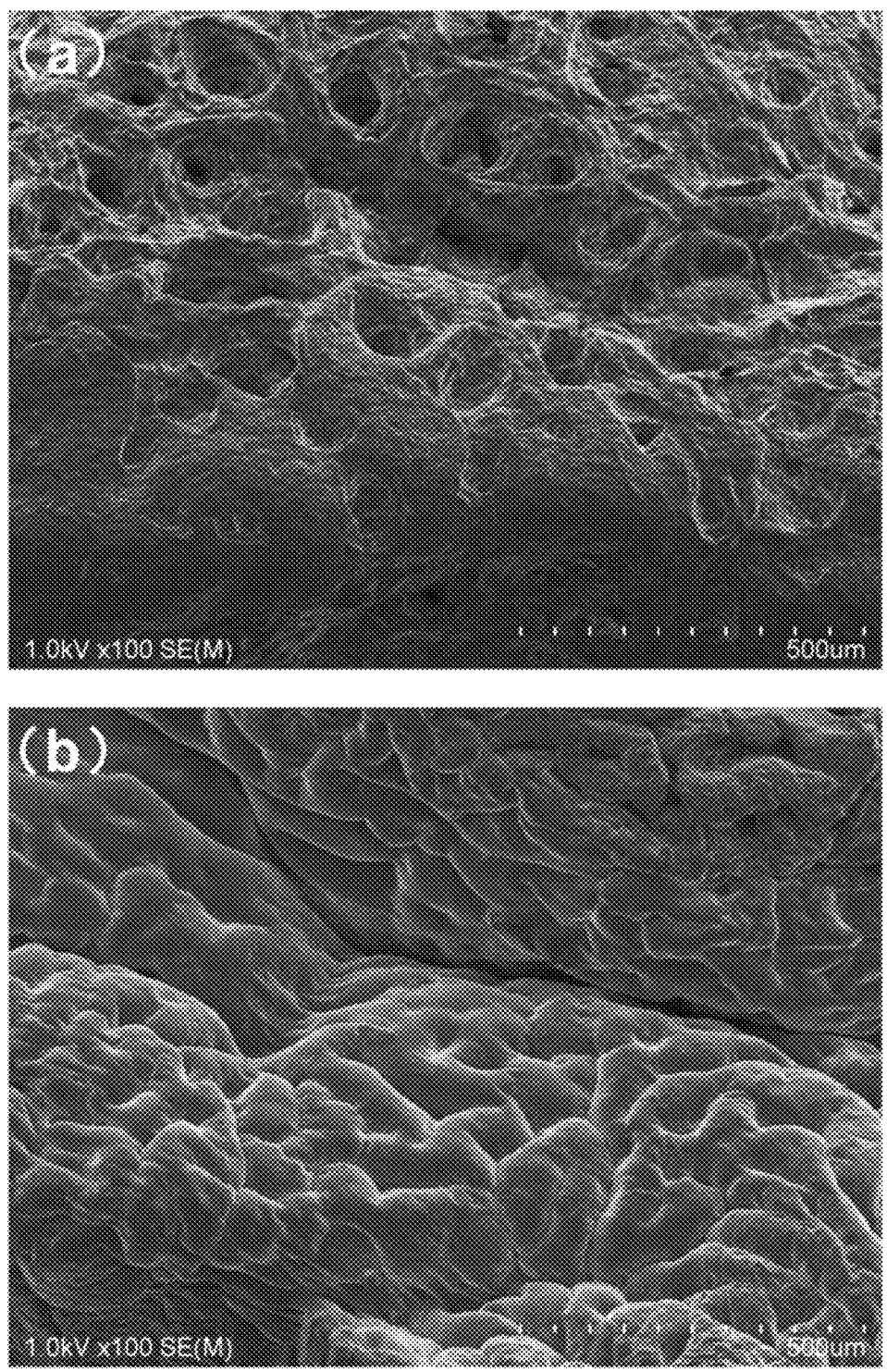
FIG. 6(a) is an image of Example 4 taken by a SEM.
FIG. 6(b) is an image of Comparative Example 2 taken by a SEM.
Figure 7:
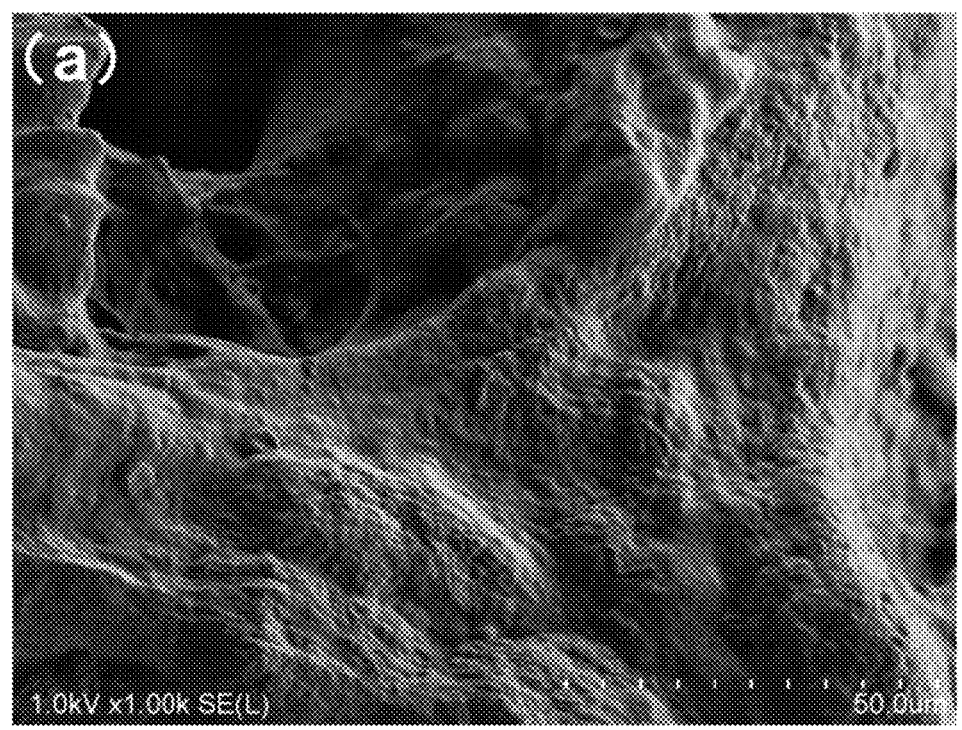
FIG. 7(a) is an image of a portion of Example 4 illustrated in FIG. 6(a), which is observed and taken at a magnification of 1000-fold by a SEM.
FIG. 7(b) is an image of a portion of Comparative Example 2 illustrated in FIG. 6(b), which is observed and taken at a magnification of 1000-fold by a SEM.
Figure 7:
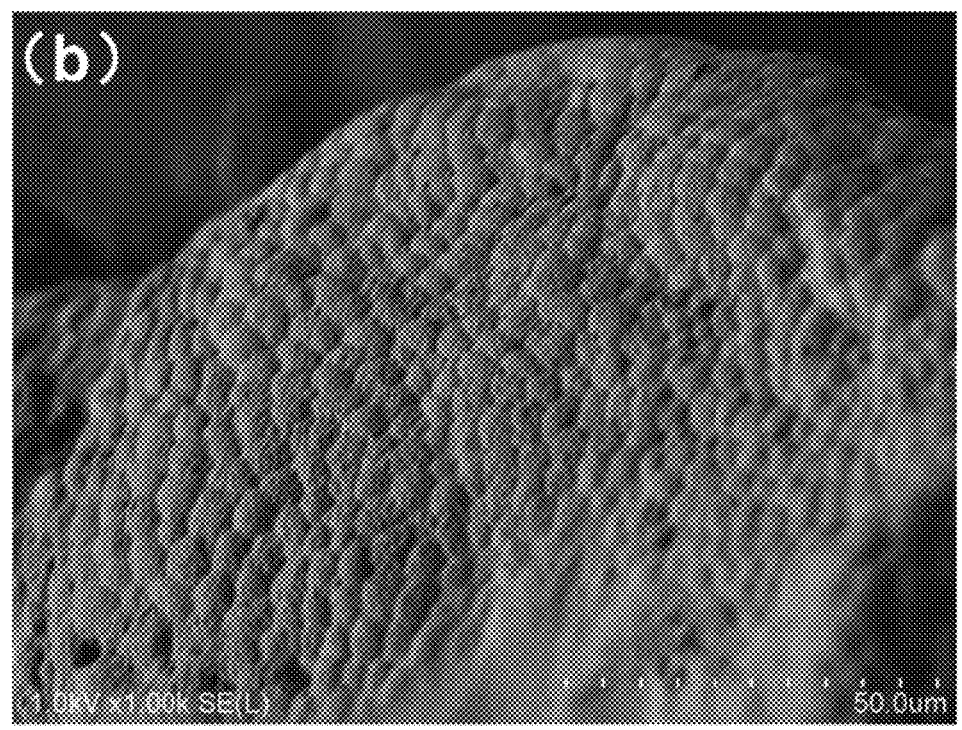
Figure 8:
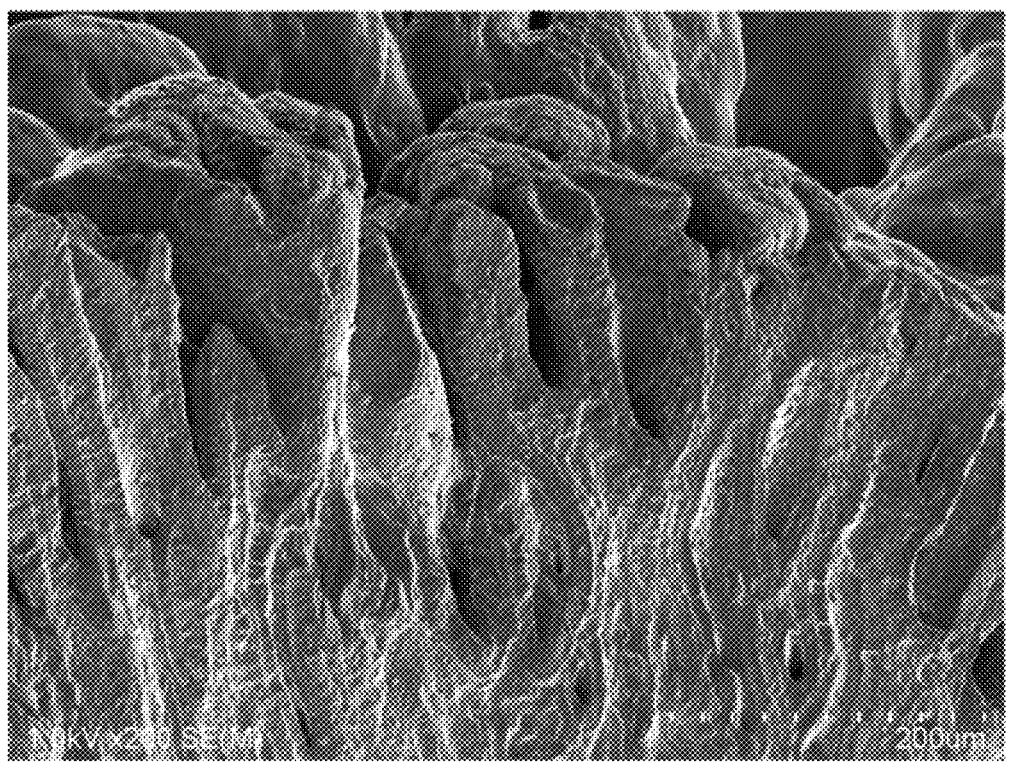
FIG. 8 is an image of the cross section which is obtained by cutting the pathological section of human gastric cancer of Example 4 illustrated in FIG. 6(a) in a thickness direction and observed and taken at a magnification of 200-fold, by a SEM.

FIG. 6(a) is an image of the pathological specimen of the human gastric cancer in a water-containing state, which was treated with the protective agent for electron microscopic observation and the surfactant-containing solution after the primary chemical fixation of the prior art, and observed and taken at a magnification of 100-fold by a SEM. In addition, FIG. 7(a) is an image of the sample of FIG. 6(a), which was observed and taken at a magnification of 1000-fold by a SEM. Furthermore, FIG. 8 is an image of the cross section which was obtained by cutting the pathological specimen of the human gastric cancer illustrated in FIG. 6(a) in a thickness direction and observed and taken at a magnification of 200-fold by a SEM.

In Example 4, it has been possible to clearly confirm the cancer cell having irregular apophyses and perforations on the surface. In addition, as illustrated in FIG. 8, it has also been confirmed that it is possible to cut the pathology specimen subjected to the surface observation in the thickness direction, to cut the same pathology specimen in the thickness direction, which has been difficult in the prior art, and to observe the cross section of the pathology specimen. It is considered that this makes it possible to easily obtain the information on how deeply the cancer cell has spread from the surface of an organ.

Comparative Example 2

A protective agent for electron microscopic observation and a surfactant-containing solution were prepared in the same manner as in Example 1.

The pathological specimen of a normal human stomach subjected to the primary chemical fixation with 10% (w/w) neutral buffered formalin was treated with the protective agent for electron microscopic observation and immersed in the surfactant-containing solution for 1 minute. The excess surfactant-containing solution was wiped off, the sample was introduced into the sample chamber of the SEM, irradiated with an electron beam to polymerize the surfactant-containing solution and thus to form a thin film, and subjected to the SEM observation.

FIG. 6(b) is an image of the pathological specimen of a normal human stomach in a water-containing state, which was treated with the protective agent for electron microscopic observation and the surfactant-containing solution after the primary chemical fixation of the prior art, and observed and taken at a magnification of 100-fold by a SEM.

In addition, FIG. 7(b) is an image of the sample of FIG. 6(b), which was observed and taken at a magnification of 1000-fold by a SEM.

Example 5

A protective agent for electron microscopic observation and a surfactant-containing solution were prepared in the same manner as in Example 1.

A cell sheet obtained by culturing a normal human skin cell in a plate shape was inoculated with a non-metastatic human melanoma cell line, cultured, and then treated with the protective agent for electron microscopic observation and the surfactant-containing solution. Thereafter, the non-metastatic melanoma line covered with the surfactant-containing solution was introduced into the sample chamber of the SEM, irradiated with an electron beam to polymerize the surfactant-containing solution and thus to form a thin film, and subjected to the SEM observation.

Figure 9:
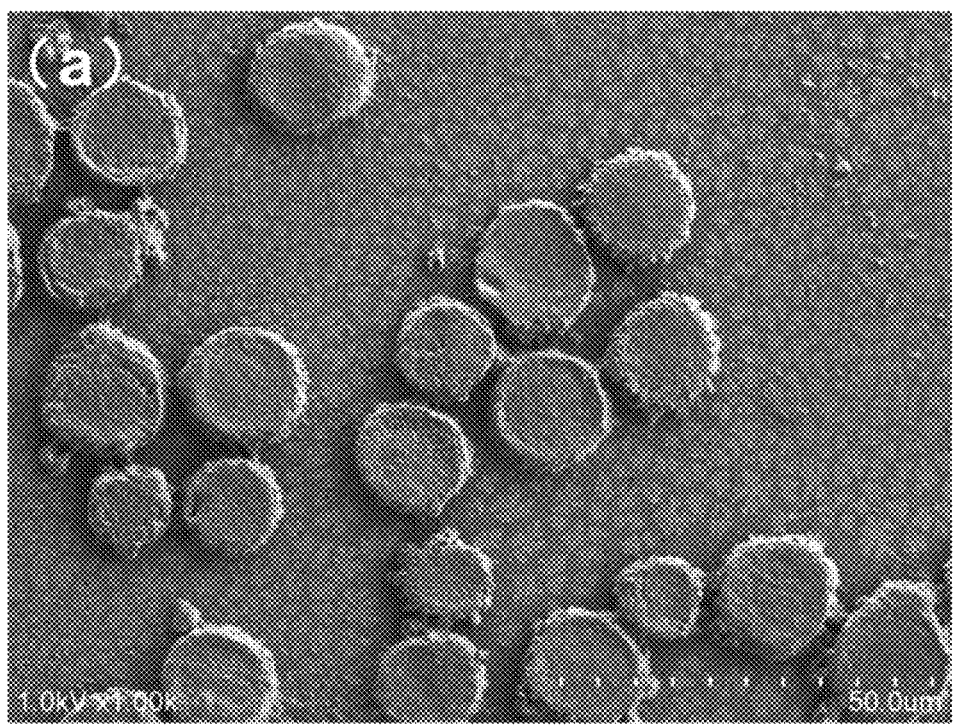
FIGS. 9(a) and 9(b) are images of Example 5 taken by a SEM, respectively.
Figure 9:
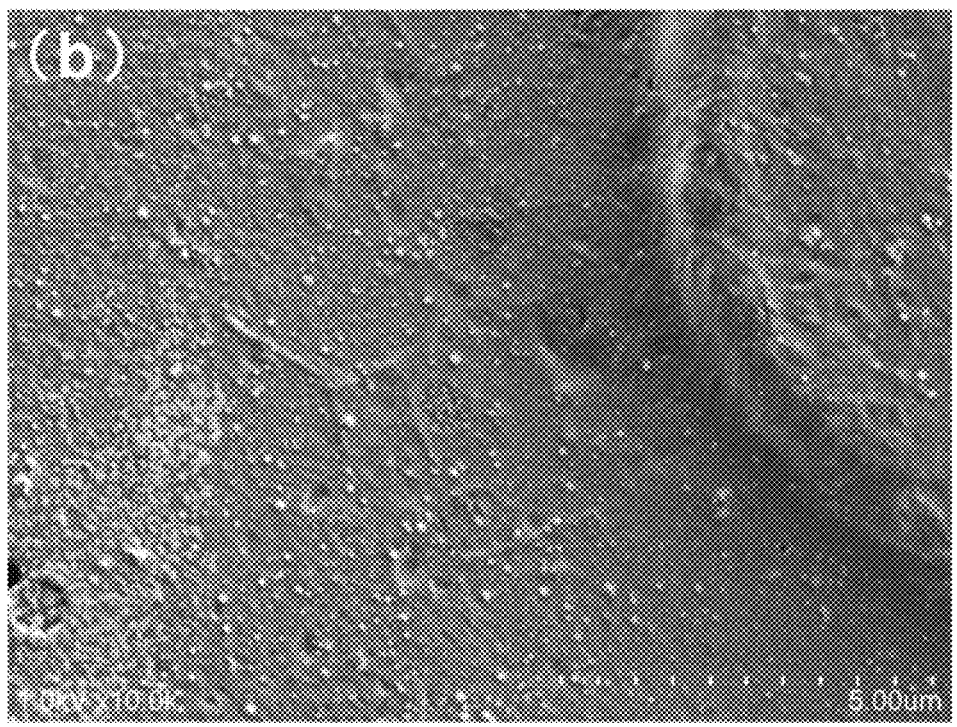

FIG. 9(a) is an image of the non-metastatic human melanoma cell line which was inoculated onto a cell sheet of the human skin-derived fibroblast cell and observed and taken at a magnification of 1000-fold by a SEM. In addition, FIG. 9(b) is an image of the microfiber in the marginal region of FIG. 9(a), which was observed and taken at a magnification of 10000-fold by a SEM.

In Example 5, it has been confirmed that the non-metastatic melanoma cell line remains on the surface of a normal skin cell but does not invade the normal skin cell since it does not almost extends a microfiber. In addition, it is possible to clearly distinguish the boundary between the human skin-derived fibroblast cell and the human melanoma cell.

Example 6

A protective agent for electron microscopic observation and a surfactant-containing solution were prepared in the same manner as in Example 1.

A cell sheet obtained by culturing a normal human skin cell in a plate shape was inoculated with a metastatic human melanoma cell line, cultured, and then treated with the protective agent for electron microscopic observation and the surfactant-containing solution. Thereafter, the metastatic human melanoma cell line covered with the surfactant-containing solution was introduced into the sample chamber of the SEM, irradiated with an electron beam to polymerize the surfactant-containing solution and thus to form a thin film, and subjected to the SEM observation.

Figure 10:
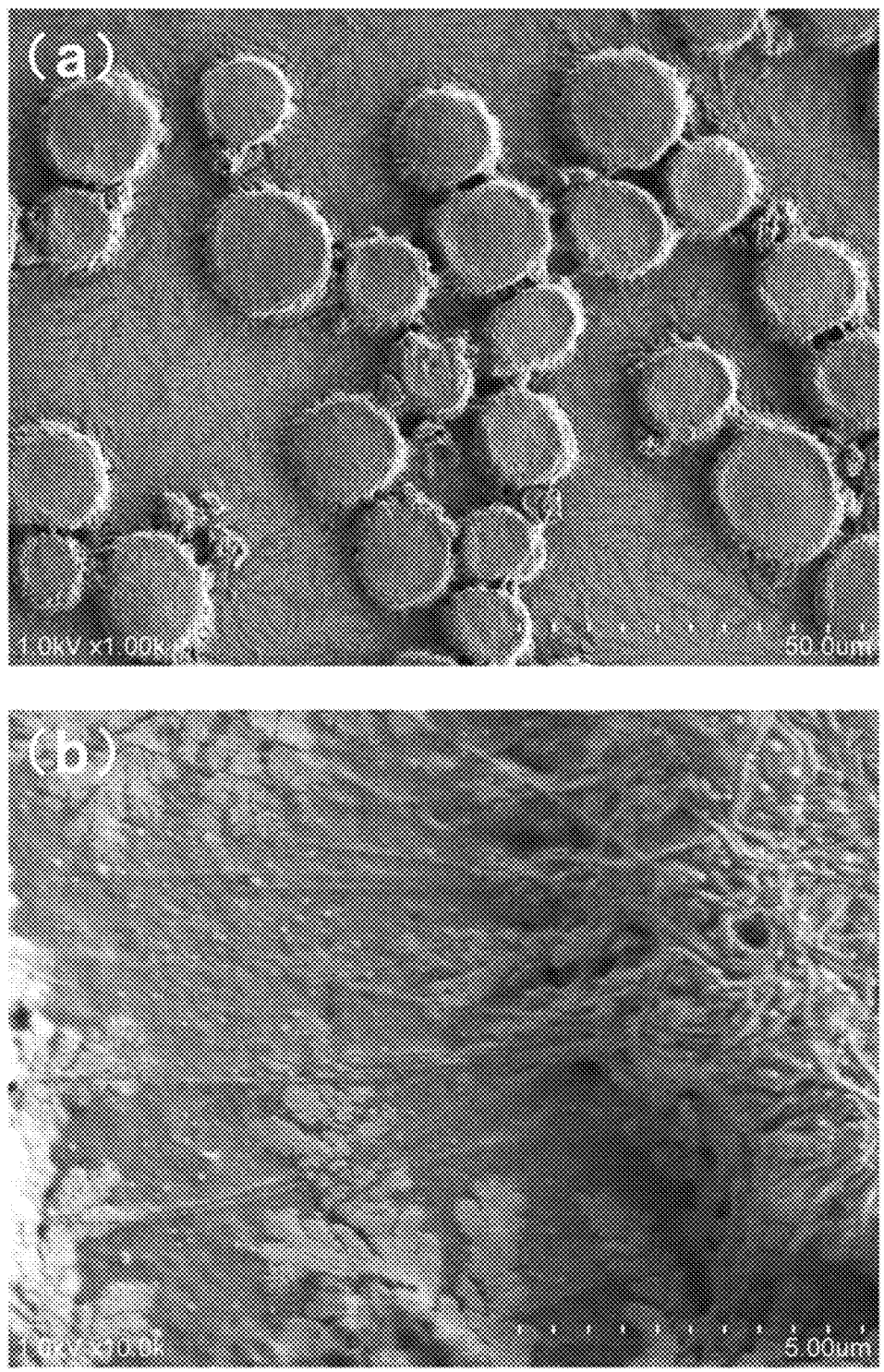
FIGS. 10(a) and 10(b) are images of Example 6 taken by a SEM, respectively.

FIG. 10(a) is an image of the metastatic human melanoma cell line which was inoculated onto a cell sheet of the human skin-derived fibroblast cell, and observed and taken at a magnification of 1000-fold by a SEM. In addition, FIG. 10(b) is an image of the microfiber in the marginal region of FIG. 10(a), which was observed and taken at a magnification of 10000-fold by a SEM.

In Example 6, it has been confirmed that the metastatic melanoma cell line extends a microfiber to a normal skin cell and invades the normal skin cell by using this microfiber as a foothold.

Example 7

A protective agent for electron microscopic observation and a surfactant-containing solution were prepared in the same manner as in Example 1.

A cell sheet obtained by culturing a normal human skin cell in a plate shape was inoculated with a metastatic human melanoma cell line and treated with the protective agent for electron microscopic observation and the surfactant-containing solution in 20 minutes after the inoculation. Thereafter, the metastatic human melanoma cell line covered with the surfactant-containing solution was introduced into the sample chamber of the SEM, irradiated with an electron beam to polymerize the surfactant-containing solution and thus to form a thin film, and subjected to the SEM observation.

Figure 11:
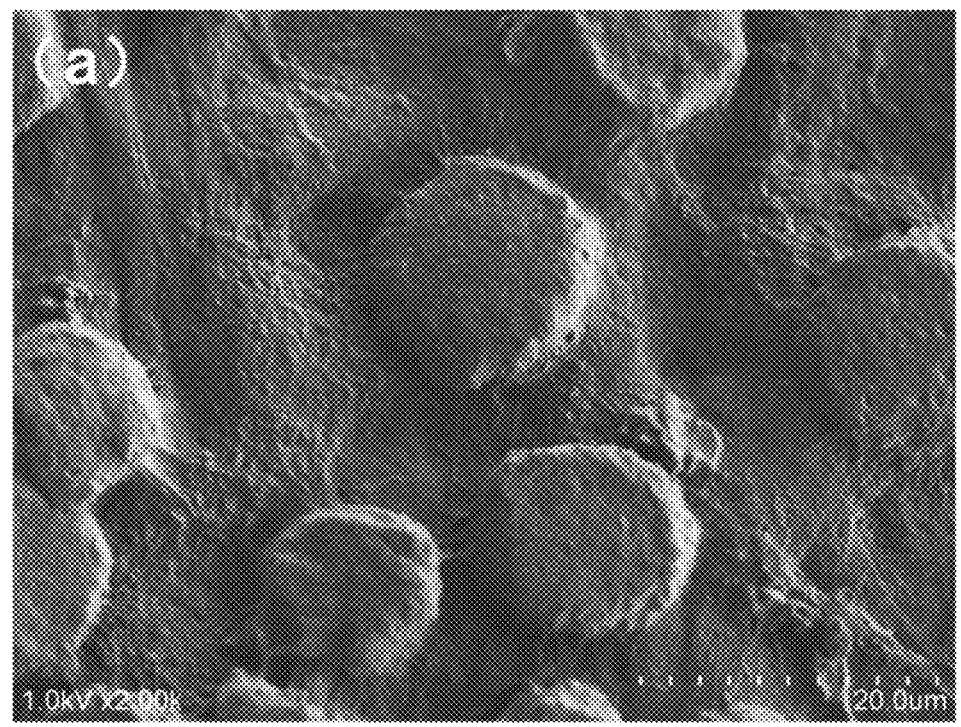
FIGS. 11(a) and 11(b) are images of Example 7 taken by a SEM, respectively.
Figure 11:
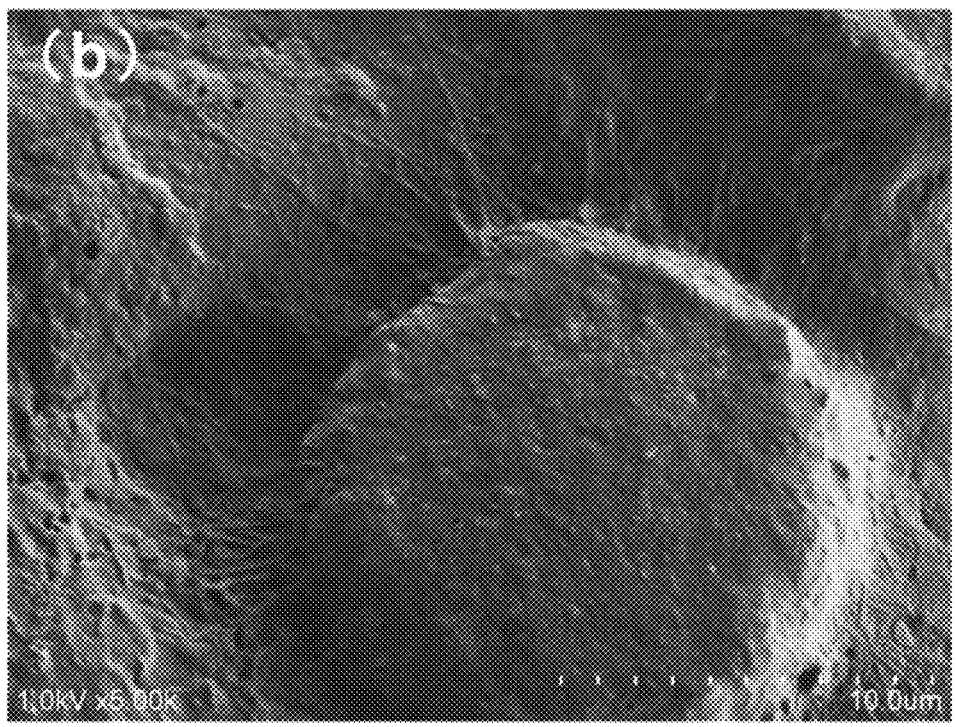
Figure 12:
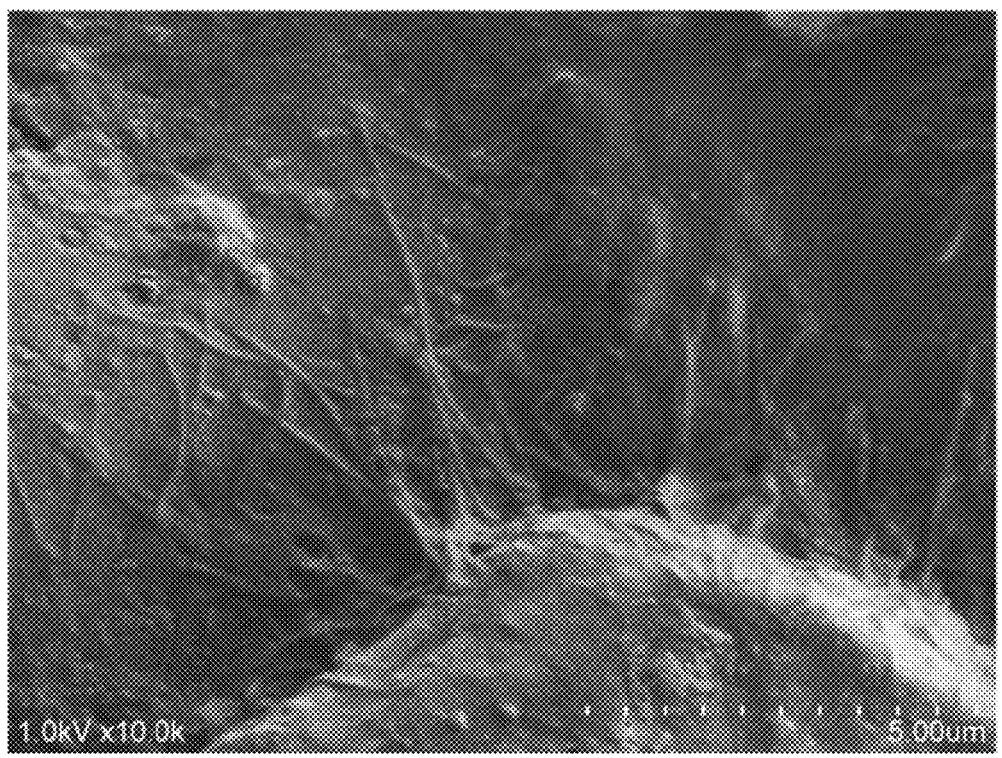
FIG. 12 is an image of the microfiber in the marginal region of the human melanoma cell line of Example 7 illustrated in FIG. 11(a), which is observed and taken at a magnification of 10000-fold by a SEM.

FIG. 11(a) is an image of the metastatic human melanoma cell line which was inoculated onto a cell sheet of the human skin-derived fibroblast cell and observed and taken at a magnification of 2000-fold by a SEM. In addition, FIG. 11(b) is an image of FIG. 11(a) which was observed and taken at a magnification of 5000-fold by a SEM. FIG. 12 is an image of FIG. 11(a) which was observed and taken at a magnification of 5000-fold by a SEM.

In Example 7, it has been confirmed that the metastatic melanoma cell line extends a microfiber to a normal skin cell in 20 minutes after the inoculation and starts to invade the normal skin cell by using this microfiber as a foothold.

Example 8

A protective agent for electron microscopic observation and a surfactant-containing solution were prepared in the same manner as in Example 1.

A cell sheet obtained by culturing a normal human skin cell in a plate shape was inoculated with a metastatic human melanoma cell line and treated with the protective agent for electron microscopic observation and the surfactant-containing solution in 30 minutes after the inoculation. Thereafter, the metastatic human melanoma cell line covered with the surfactant-containing solution was introduced into the sample chamber of the SEM, irradiated with an electron beam to polymerize the surfactant-containing solution and thus to form a thin film, and subjected to the SEM observation.

Figure 13:
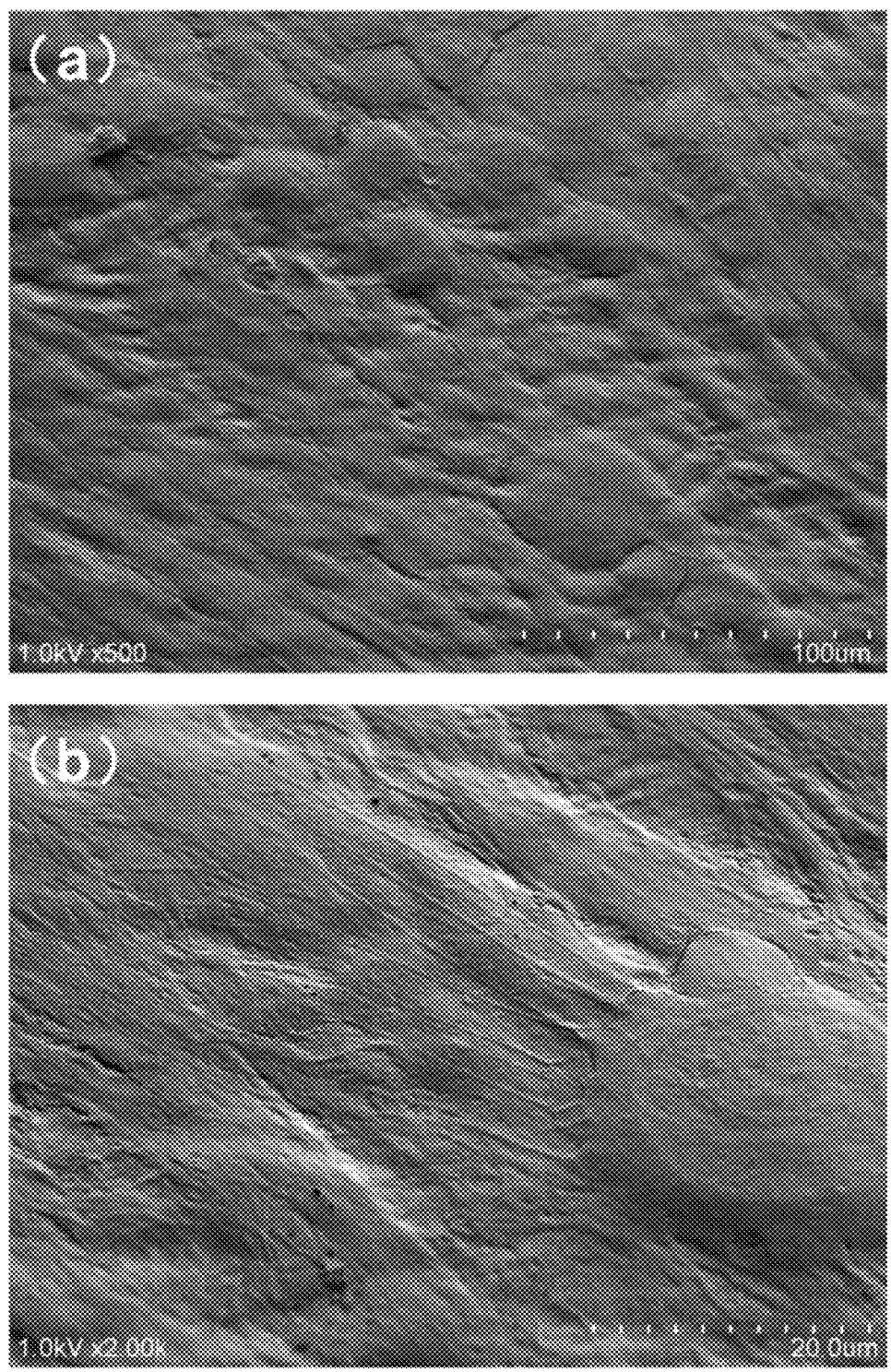
FIGS. 13(a) and 13(b) are images of Example 8 taken by a SEM, respectively.

FIG. 13(a) is an image of the metastatic human melanoma cell line which was inoculated onto a cell sheet of the human skin-derived fibroblast cell and observed and taken at a magnification of 500-fold by a SEM. In addition, FIG. 13(b) is an image of FIG. 13(a) which was observed and taken at a magnification of 2000-fold by a SEM.

In Example 8, it has been confirmed that the invasion of the metastatic melanoma cell line to a normal skin cell is progressed in 30 minutes after the inoculation and the metastatic melanoma cell line is being gradually integrated with the normal skin cell, and it has been confirmed that the microfiber of the metastatic melanoma cell line has further extended as compared to that in 20 minutes after the inoculation.

Example 9

A protective agent for electron microscopic observation and a surfactant-containing solution were prepared in the same manner as in Example 1.

A cell sheet obtained by culturing a normal human skin cell in a plate shape was inoculated with a metastatic human melanoma cell line and treated with the protective agent for electron microscopic observation and the surfactant-containing solution in 60 minutes after the inoculation. Thereafter, the metastatic human melanoma cell line covered with the surfactant-containing solution was introduced into the sample chamber of the SEM, irradiated with an electron beam to polymerize the surfactant-containing solution and thus to form a thin film, and subjected to the SEM observation.

Figure 14:
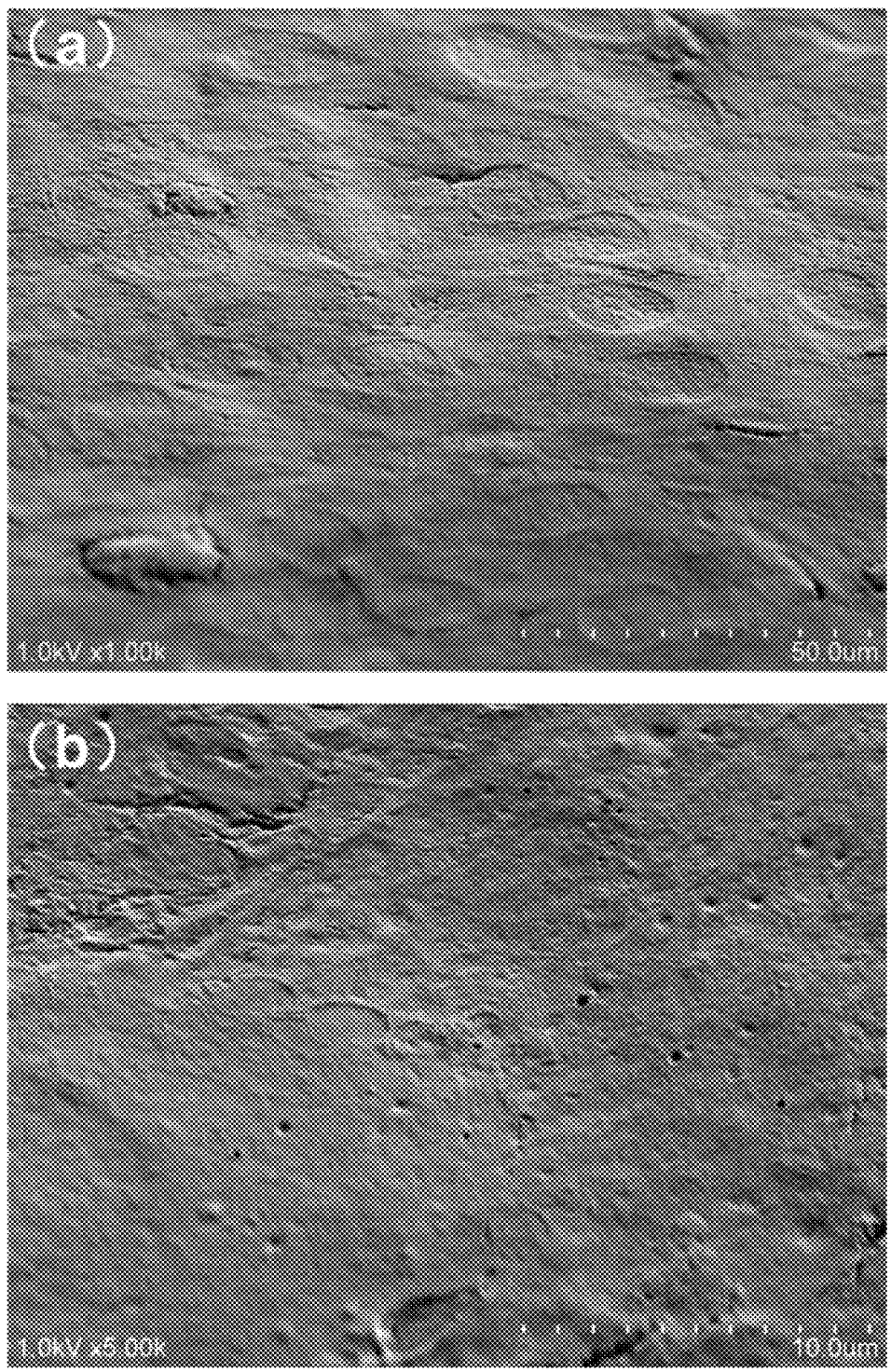
FIGS. 14(a) and 14(b) are images of Example 9 taken by a SEM, respectively.

FIG. 14(a) is an image of the metastatic human melanoma cell line which was inoculated onto a cell sheet of the human skin-derived fibroblast cell and observed and taken at a magnification of 1000-fold by a SEM. In addition, FIG. 14(b) is an image of FIG. 14(a) which was observed and taken at a magnification of 5000-fold by a SEM.

In Example 9, it has been confirmed that the invasion of the metastatic melanoma cell line to a normal skin cell is further progressed in 60 minutes after the inoculation and the metastatic melanoma cell line is completely integrated with the normal skin cell, and it has been confirmed that the microfiber of the metastatic melanoma cell line has further extended as compared to that in 30 minutes after the inoculation.

Example 10

A protective agent for electron microscopic observation and a surfactant-containing solution were prepared in the same manner as in Example 1.

A cell sheet obtained by culturing a normal human skin cell in a plate shape was inoculated with a non-metastatic human melanoma cell line and treated with the protective agent for electron microscopic observation and the surfactant-containing solution in 60 minutes after the inoculation. Thereafter, the non-metastatic human melanoma cell line covered with the surfactant-containing solution was introduced into the sample chamber of the SEM, irradiated with an electron beam to polymerize the surfactant-containing solution and thus to form a thin film, and subjected to the SEM observation.

Figure 15:
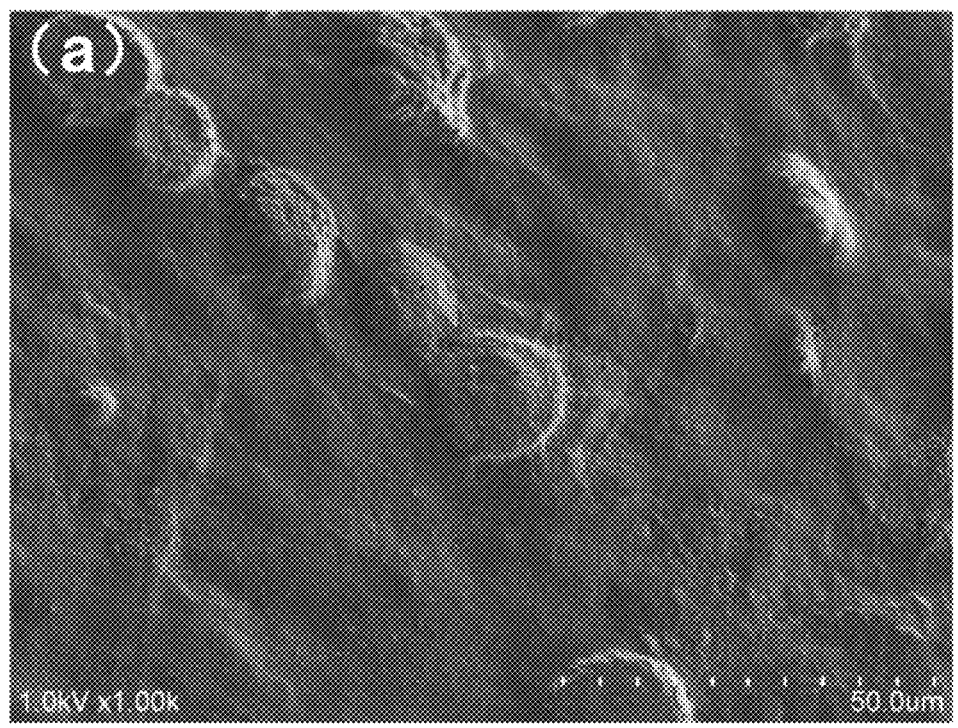
FIGS. 15(a) and 15(b) are images of Example 10 taken by a SEM, respectively, and they are images of the non-metastatic human melanoma cell line which is inoculated on a cell sheet of the human skin-derived fibroblast cell and observed and taken at a magnification of 1000-fold in 60 minutes after the inoculation, by a SEM.
Figure 15:
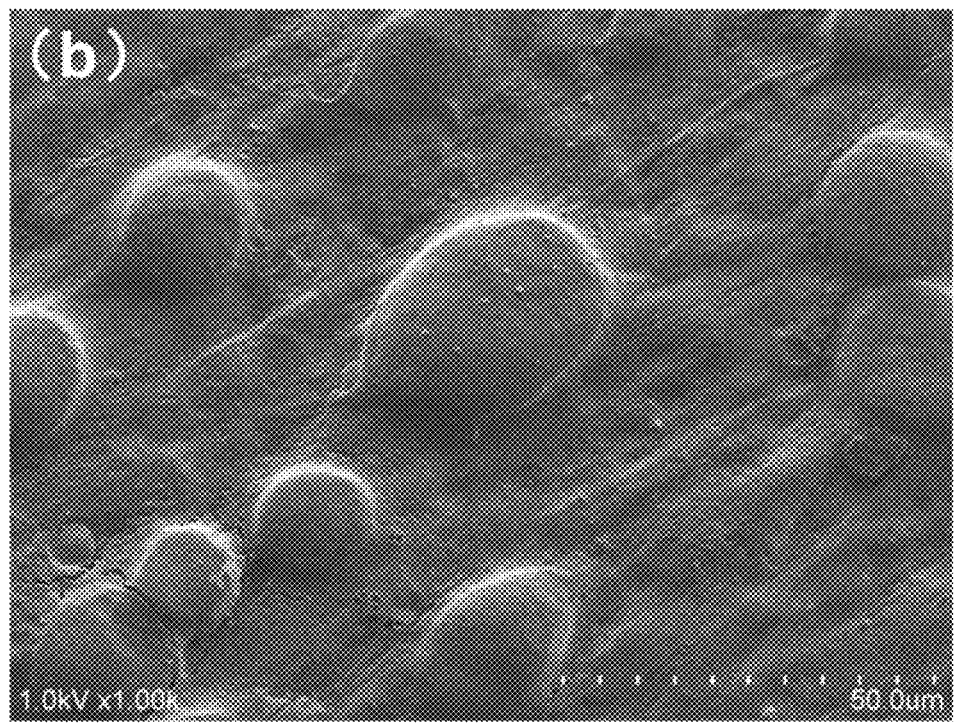
Figure 16:
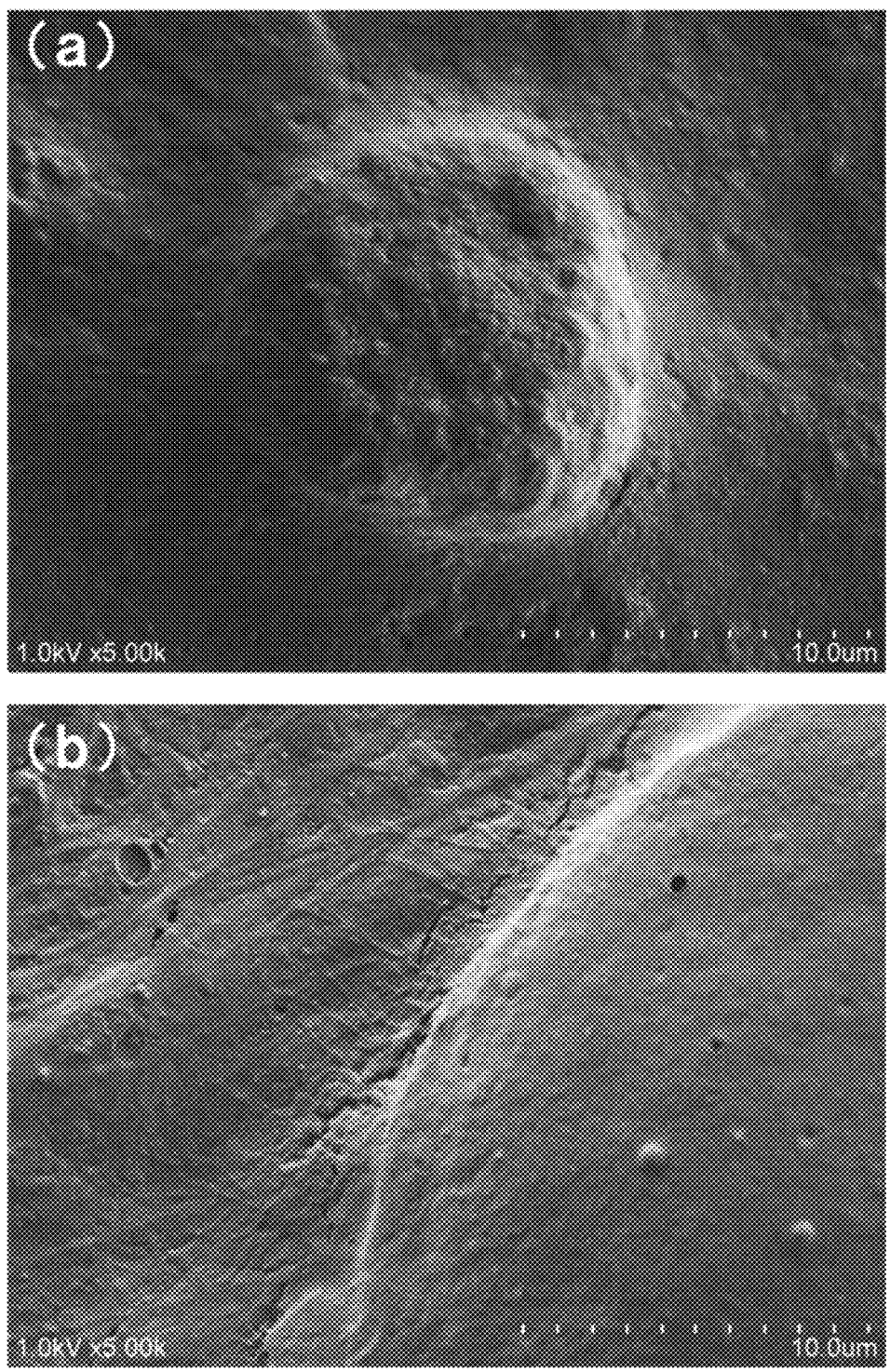
FIGS. 16(a) and 16(b) are images of the non-metastatic human melanoma cell lines respectively illustrated in FIGS. 15(a) and 15(b), which are observed and taken at a magnification of 5000-fold by a SEM.

FIGS. 15(a) and 15(b) are images of the non-metastatic human melanoma cell line which was inoculated onto a cell sheet of the human skin-derived fibroblast cell and observed and taken at a magnification of 1000-fold by a SEM, respectively. In addition, FIGS. 16(a) and 16(b) are images of FIGS. 14(a) and 14(b) which were observed and taken at a magnification of 5000-fold by a SEM.

In Example 10, the extension of a microfiber and the invasion of the melanoma cell have not been confirmed even when 60 minutes has elapsed after a normal skin cell has been inoculated with the non-metastatic human melanoma cell line.

From the results of Examples 7 to 10 described above, it has been demonstrated that the time required for the human melanoma cell to invade a normal skin cell is as short as only from 20 minutes to 60 minutes after the inoculation. In addition, in the case of melanoma cell, it is possible to morphologically identify the non-metastatic melanoma cell line and the metastatic melanoma cell line by using the extension of microfiber as an indicator, and it is possible to diagnose whether the cancer cell of a patient is a metastatic line or a non-metastatic line by culturing the cancer cell collected from a skin cancer patient for several tens of minutes and observing it by using the protective agent for electron microscopic observation of the present invention and a SEM. Furthermore, it is also considered that it is possible to suppress the removal range to the minimum when a cancer cell is surgically removed by confirming the range in which a microfiber is extended.

Example 11

A protective agent for electron microscopic observation and a surfactant-containing solution were prepared in the same manner as in Example 1.

A cell sheet obtained by culturing a normal human skin cell in a plate shape was inoculated with a metastatic human melanoma cell line and treated with the protective agent for electron microscopic observation and the surfactant-containing solution in 60 minutes after sorafenib of a kind of anti-cancer drug was added the cell sheet. Thereafter, the metastatic human melanoma cell line covered with the surfactant-containing solution was introduced into the sample chamber of the SEM, irradiated with an electron beam to polymerize the surfactant-containing solution and thus to form a thin film, and subjected to the SEM observation.

Figure 17:
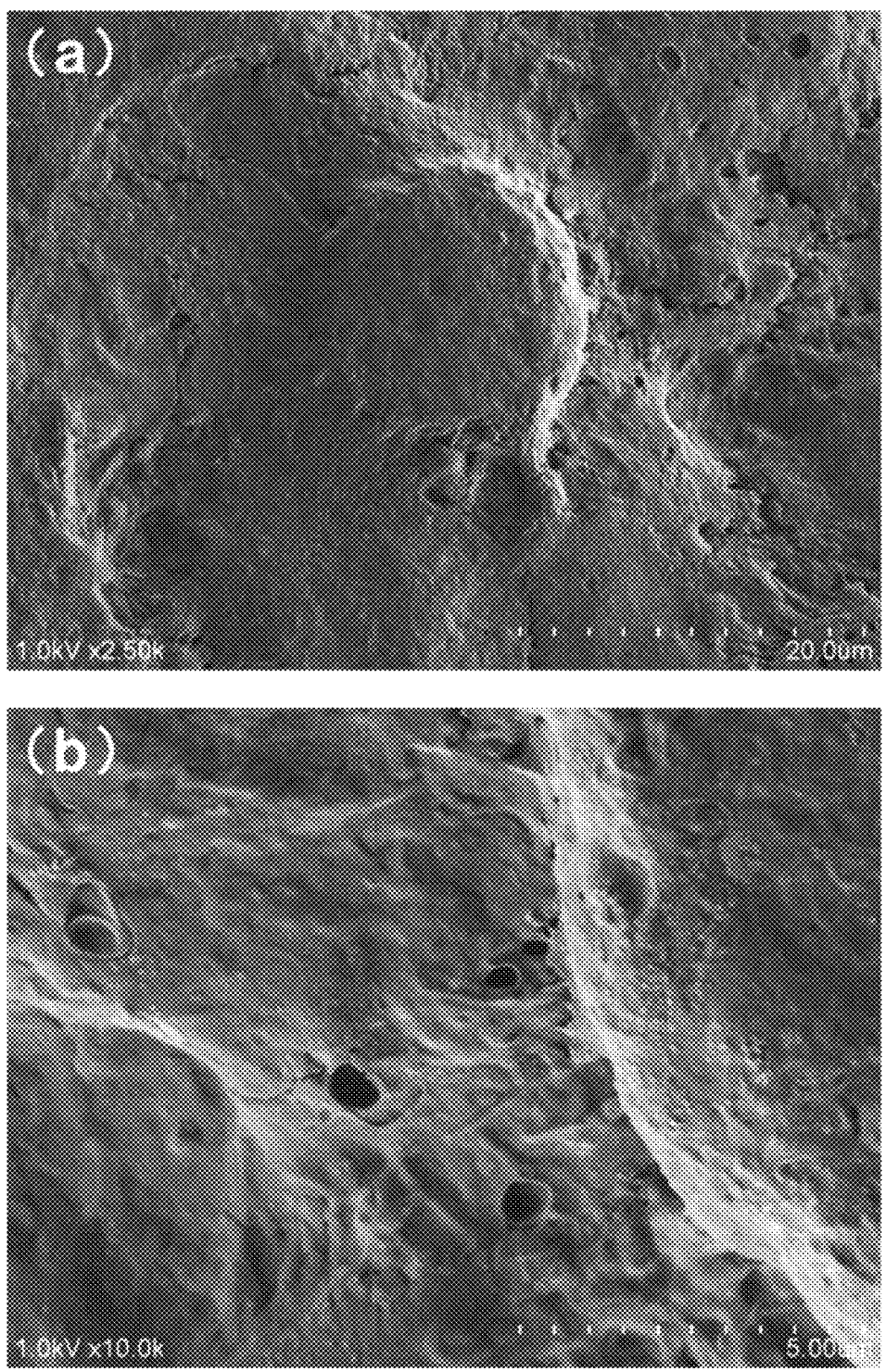
FIGS. 17(a) and 17(b) are images of Example 11 taken by a SEM, respectively.

FIG. 17(a) is an image of the metastatic human melanoma cell line which was inoculated onto a cell sheet of the human skin-derived fibroblast cell, to which sorafenib was added, and which was observed and taken at a magnification of 1000-fold by a SEM. In addition, FIG. 17(b) is an image of FIG. 17(a) which was observed and taken at a magnification of 5000-fold by a SEM.

In Example 11, it has been confirmed that even a metastatic melanoma cell line is not able to extend a microfiber so that the invasion thereof is suppressed by adding sorafenib.

Consequently, it is possible to diagnose whether the added anti-cancer drug is effective for the cancer cell of a patient by observing a cancer cell which is collected from a skin cancer patient, to which an anti-cancer drug is added, and which is cultured and then observed by using the protective agent for electron microscopic observation of the present invention and a SEM. In addition, it is also possible to perform the drug screening whether the added anti-cancer drug candidates actually have anti-cancer activities by observing a cancer cell to which an anti-cancer drug is added and which is cultured and then observed by using the protective agent for electron microscopic observation of the present invention and a SEM.

Example 12 and Comparative Example 3

A protective agent for electron microscopic observation and a surfactant-containing solution were prepared in the same manner as in Example 1.

The artificial human skin obtained by sterically three-dimensionally culturing a normal human skin cell was treated with the protective agent for electron microscopic observation and the surfactant-containing solution in 60 minutes after gefitinib was added the artificial human skin. Thereafter, the artificial human skin covered with the surfactant-containing solution was introduced into the sample chamber of the SEM, irradiated with an electron beam to polymerize the surfactant-containing solution and thus to form a thin film, and subjected to the SEM observation (Example 12).

Figure 18:
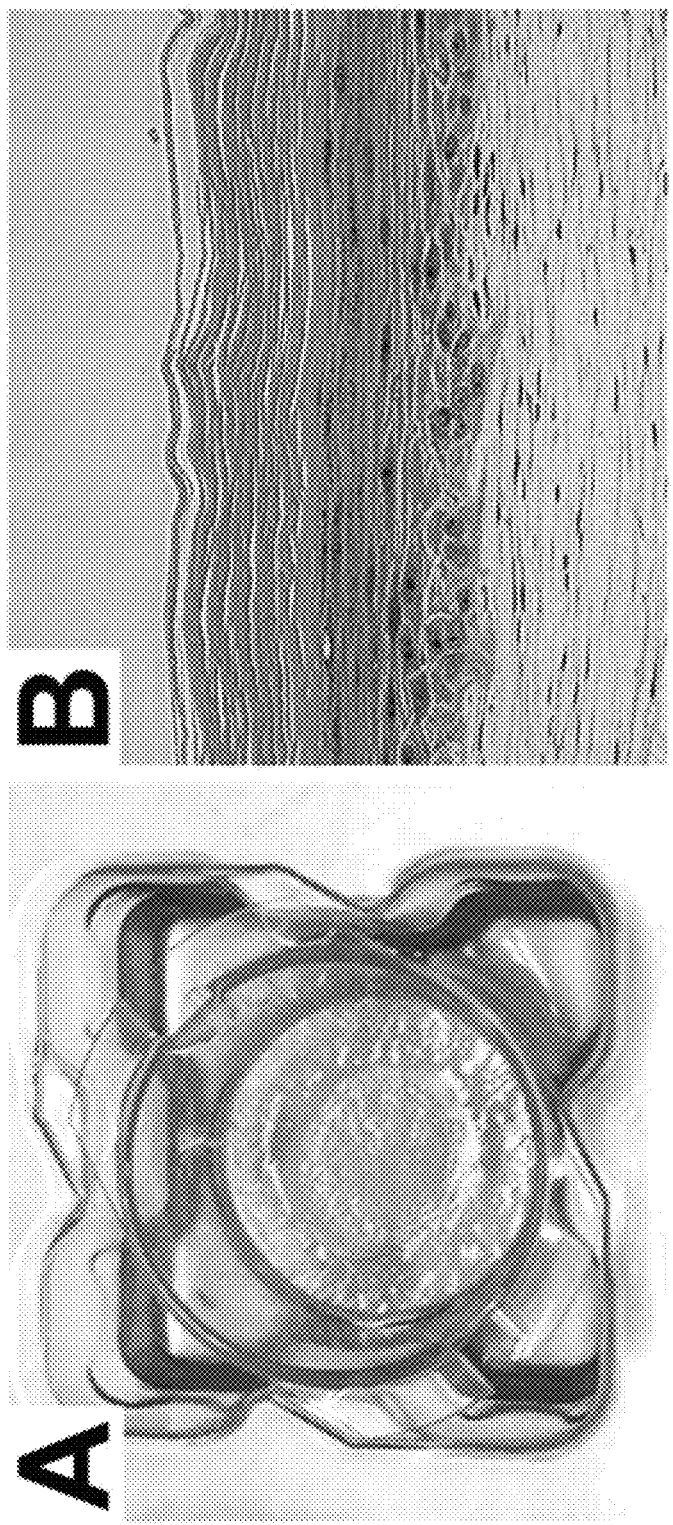
FIGS. 18A and 18B are photographs of an artificial human skin to be used in Example 12 to be described later, respectively.
Figure 19:
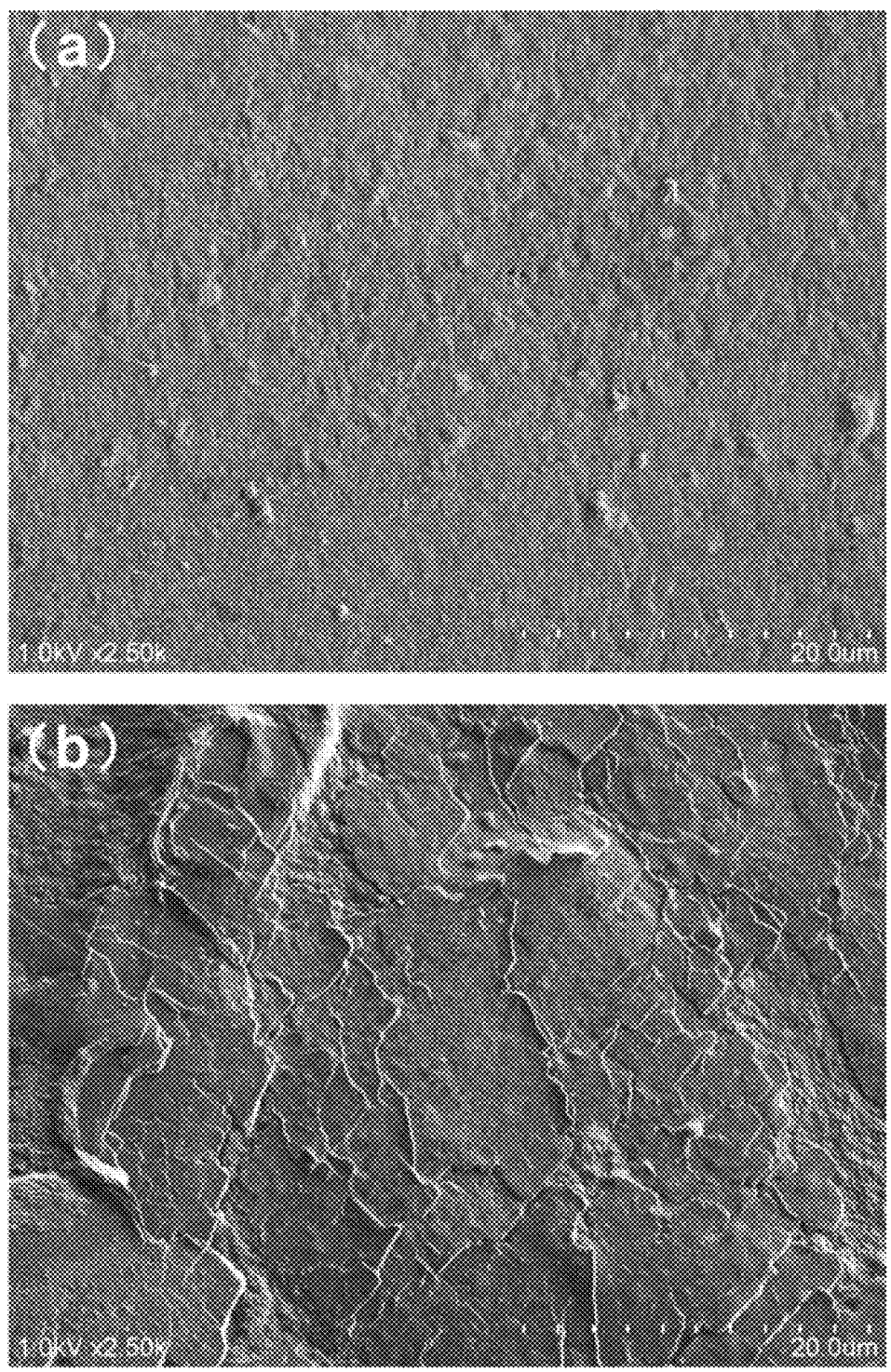
FIG. 19(a) is an image of Example 12 taken by a SEM.
FIG. 19(b) is an image of Comparative Example 3 taken by a SEM.

FIGS. 18A and 18B are photographs of the three-dimensionally cultured artificial human skin. FIG. 18A is a photograph which illustrates the artificial human skin being cultured and the culture vessel. In addition, FIG. 18B is a photograph of the HE-stained pathological section of the artificial human skin of FIG. 18A. FIG. 19(a) is an image of the artificial human skin which was observed and taken at a magnification of 2,500-fold by a SEM after gefitinib dissolved in dimethyl sulfoxide (DMSO) was added the artificial human skin. In addition, FIG. 19(b) is an image of the artificial human skin illustrated in FIG. 19(a), which was observed and taken at a magnification of 2,500-fold by a SEM after the artificial human skin was treated with the protective agent for electron microscopic observation and the surfactant-containing solution in 60 minutes after DMSO was added the artificial human skin as a control group (Comparative Example 3).

In Example 12, it has been confirmed that the epidermis of the artificial skin cell to which gefitinib was added is peeled off in a scale shape as illustrated in FIG. 19(a). On the other hand, a normal morphology has been maintained in the artificial skin cell of the control group. From the results described above, it has become possible to evaluate the surface change of a skin cell which is a side effect of gefitinib in a cultured cell system by observing a three-dimensionally cultured artificial skin cell by using the protective agent for electron microscopic observation of the present invention and a SEM after adding gefitinib thereto. In addition, it is possible to screen a drug which has fewer side effects by adding various kinds of anti-cancer drugs. Furthermore, it is possible to screen drug candidates which exhibit activities by observing a three-dimensionally cultured artificial skin cell by using the protective agent for electron microscopic observation of the present invention and a SEM after adding drug candidates thereto without being limited to anti-cancer drugs and culturing it.

Example 13

A protective agent for electron microscopic observation and a surfactant-containing solution were prepared in the same manner as in Example 1.

The human neonatal dermal fibroblast cell was cultured in a cell culture filter made of polyethylene terephthalate (PET) so as to be layered in four layers, subsequently the cultured human neonatal dermal fibroblast cell was inoculated with the human skin-derived lymphatic endothelial cell and co-cultured. A primary antibody solution having the membrane protein of the human skin-derived lymphatic endothelial cell as the antigen was dropped on the co-cultured cells by adjusting its concentration with an appropriate antibody dilution buffer, and the co-cultured cells were cultured at 37° C. for 30 minutes. The excess primary antibody which did not bind to the co-cultured cells was washed off with an appropriate washing buffer, and a secondary antibody which exhibited binding property to the primary antibody and was modified with a gold colloid was dropped on the co-cultured cells by adjusting its concentration with an appropriate antibody dilution buffer, and the co-cultured cells were cultured at 37° C. for 30 minutes. The excess second antibody which did not bind to the co-cultured cells was washed off with an appropriate washing buffer, and the co-cultured cells were then treated with the protective agent for electron microscopic observation and the surfactant-containing solution. Thereafter, the antibody-biding cultured cell which was covered with the surfactant-containing solution was introduced into the sample chamber of the SEM, irradiated with an electron beam to polymerize the surfactant-containing solution and thus to form a thin film, and subjected to the SEM observation.

Figure 20:
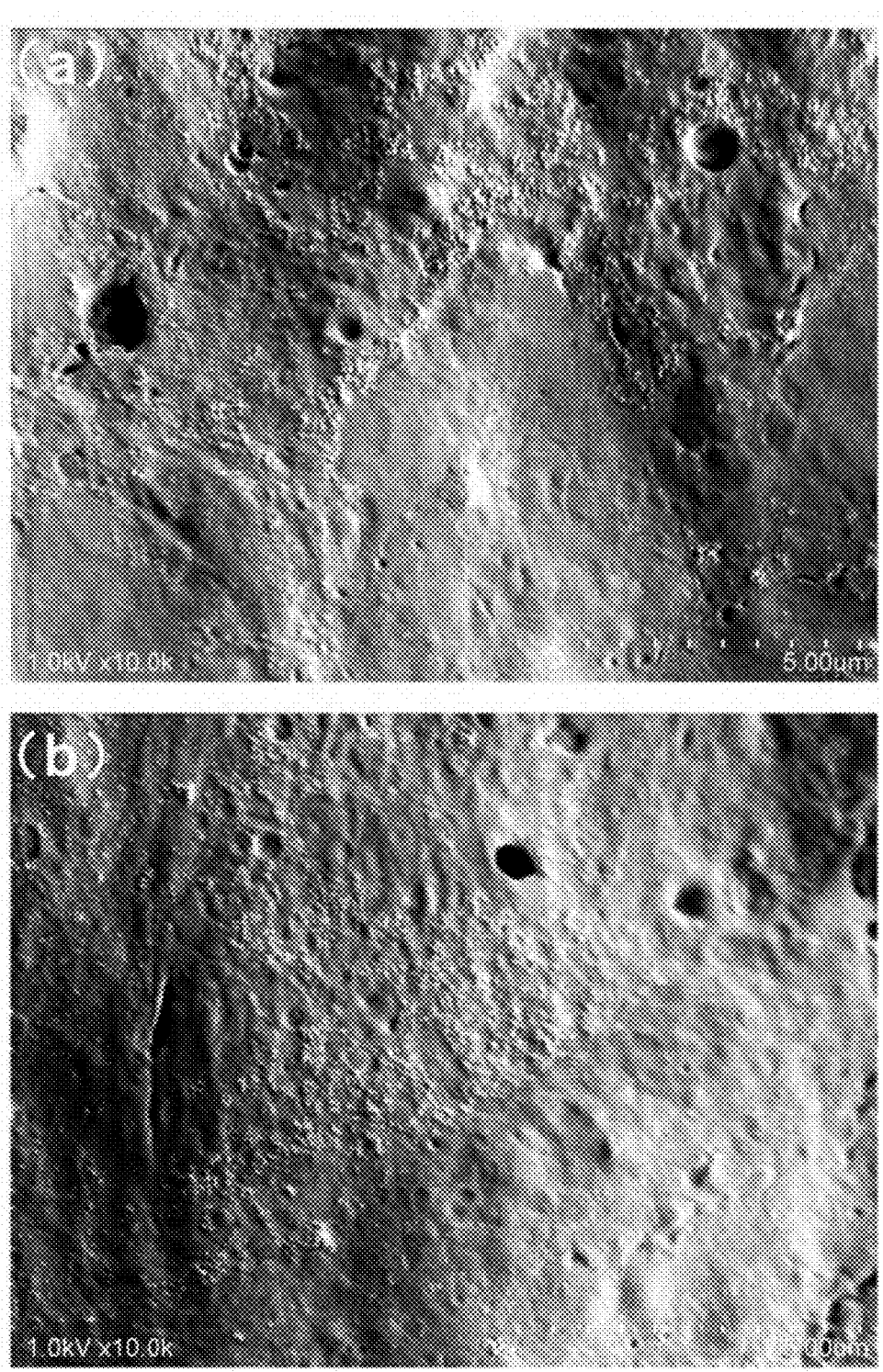
FIGS. 20(a) and 20(b) are images of Example 13 by an immunoelectron microscopy taken by a SEM, respectively, and they are images of the human skin-derived fibroblast cell by an immunoelectron microscopy, which is bound to a primary antibody and a secondary antibody modified with a gold colloid, treated with a protective agent for electron microscopic observation and a surfactant-containing solution, and then observed and taken at a magnification of 10,000-fold by a SEM.

FIGS. 20(a) and 20(b) are images of the human skin-derived lymphatic endothelial cell by the immunoelectron microscopy, which was bound to a primary antibody and a secondary antibody modified with a gold colloid, treated with the protective agent for electron microscopic observation and the surfactant-containing solution, and then observed and taken at a magnification of 10,000-fold by a SEM.

From this result, it has been confirmed that an image by the immunoelectron microscopy, which has fewer non-specific signals and is taken by a SEM is obtained at a high sensitivity in a significantly short time since the primary antibody and the secondary antibody act without chemically fixing the cell by using the protective agent for electron microscopic observation of the present invention.

Example 14

A protective agent for electron microscopic observation and a surfactant-containing solution were prepared in the same manner as in Example 1.

In the same manner as in Example 11, a cell sheet obtained by culturing a normal human skin cell in a plate shape was inoculated with a metastatic human melanoma cell line, a primary antibody solution having the membrane protein of the human melanoma cell as the antigen was dropped on the cell sheet by adjusting its concentration with an appropriate antibody dilution buffer, and the cell sheet was cultured at 37° C. for 30 minutes. The excess primary antibody which did not bind to the human melanoma cell was washed off with an appropriate washing buffer, and a secondary antibody which exhibited binding property to the primary antibody and was modified with a gold colloid was dropped on the cell sheet by adjusting its concentration with an appropriate antibody dilution buffer, and the cell sheet was cultured at 37° C. for 30 minutes. The excess second antibody which did not bind to the primary antibody was washed off with an appropriate washing buffer, and the cell sheet was then treated with the protective agent for electron microscopic observation and the surfactant-containing solution. Thereafter, the metastatic human melanoma cell line covered with the surfactant-containing solution was introduced into the sample chamber of the SEM, irradiated with an electron beam to polymerize the surfactant-containing solution and thus to form a thin film, and subjected to the SEM observation.

Figure 21:
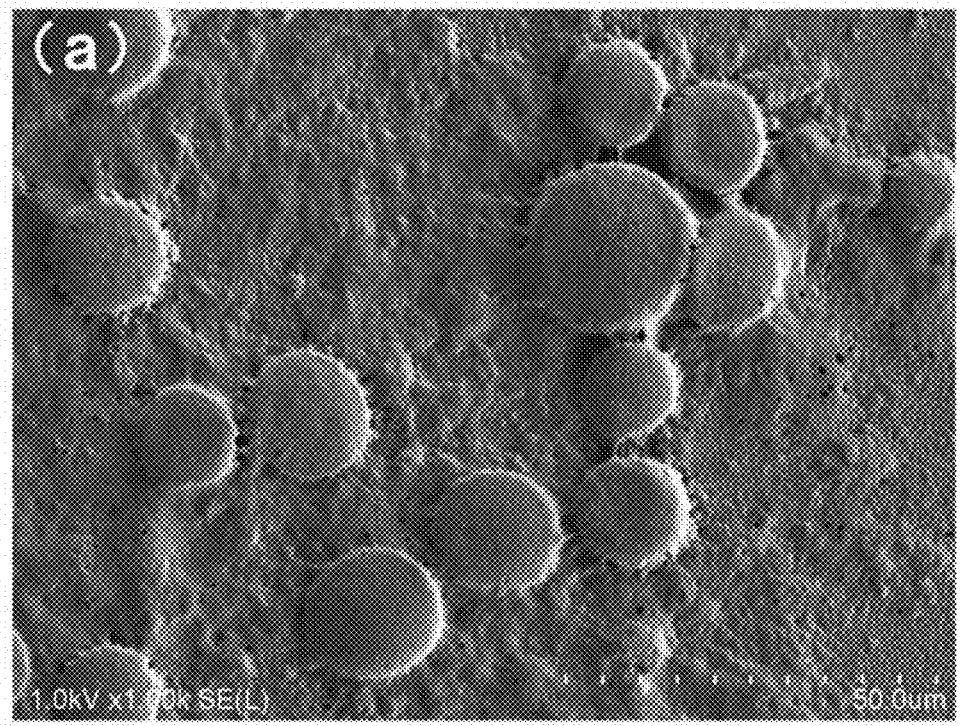
FIGS. 21(a) and 21(b) are images of Example 14 by an immunoelectron microscopy taken by a SEM, respectively.
Figure 21:
Figure 22:
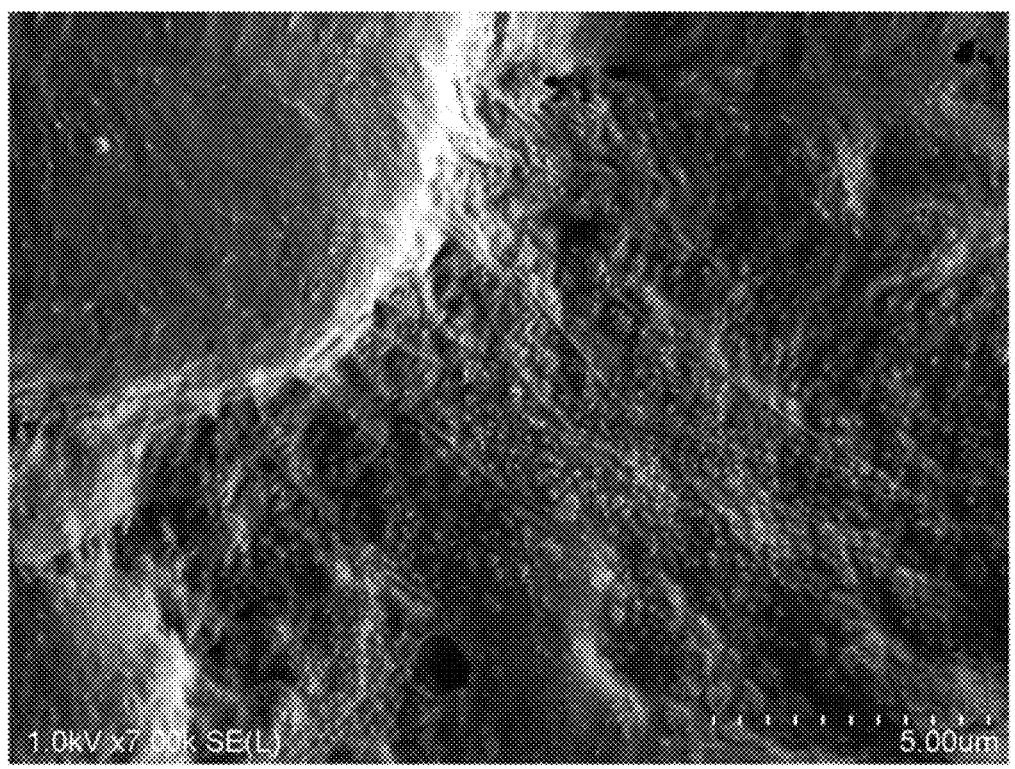
FIG. 22 is an image of the microfiber in the marginal region of the human melanoma cell line by an immunoelectron microscopy illustrated in FIG. 21(a), which is observed and taken at a magnification of 7000-fold by a SEM.

FIG. 21(a) is an image of the living human melanoma cell by the immunoelectron microscopy, which was bound to a primary antibody and a secondary antibody modified with a gold colloid, treated with the protective agent for electron microscopic observation and the surfactant-containing solution, and then observed and taken at a magnification of 1000-fold by a SEM. In addition, FIG. 21(b) is an image of the cell of FIG. 21(a) by an immunoelectron microscopy, which was observed and taken at a magnification of 10,000-fold by a SEM. In addition, FIG. 22 is an image of the microfiber in the marginal region of the melanoma cell of FIG. 21(a) by an immunoelectron microscopy, which was observed and taken at a magnification of 7000-fold by a SEM.

From these results it has been confirmed that an image by the immunoelectron microscopy, which has fewer non-specific signals and is taken by a SEM is obtained at a high sensitivity in a significantly short time since the primary antibody and the secondary antibody act without chemically fixing the cell by using the protective agent for electron microscopic observation of the present invention. By performing the observation using this novel immunoelectron microscopy, it is possible to quickly and conveniently realize the cancer diagnosis and cancer pathology at a high accuracy, for example, by using a tumor marker as the antigen. Incidentally, the diseased cell is not limited to a cancer cell, and it is also possible to diagnose an inflammatory disease or an autoimmune disease.

Example 15

A protective agent for electron microscopic observation and a surfactant-containing solution were prepared in the same manner as in Example 1.

The peritoneum excised from a living mouse was placed on the sample stage (a) illustrated in FIGS. 23(a) and 23(b) such that the epithelial side was to be the upper surface and the protective agent for electron microscopic observation and the surfactant-containing solution were immediately dropped on the peritoneum and left to stand still for 1 minute as the pretreatment.

The surfactant-containing solution was dropped on the mouse peritoneum thus pretreated and left to stand still for 1 minute, and the excess was then wiped off, thereby covering the surface of the mouse peritoneum with the surfactant-containing solution. Thereafter, the mouse peritoneum covered with the surfactant-containing solution was introduced into the sample chamber of the SEM, irradiated with an electron beam to polymerize the surfactant-containing solution and thus to form a thin film, and subjected to the SEM observation.

Figure 24:
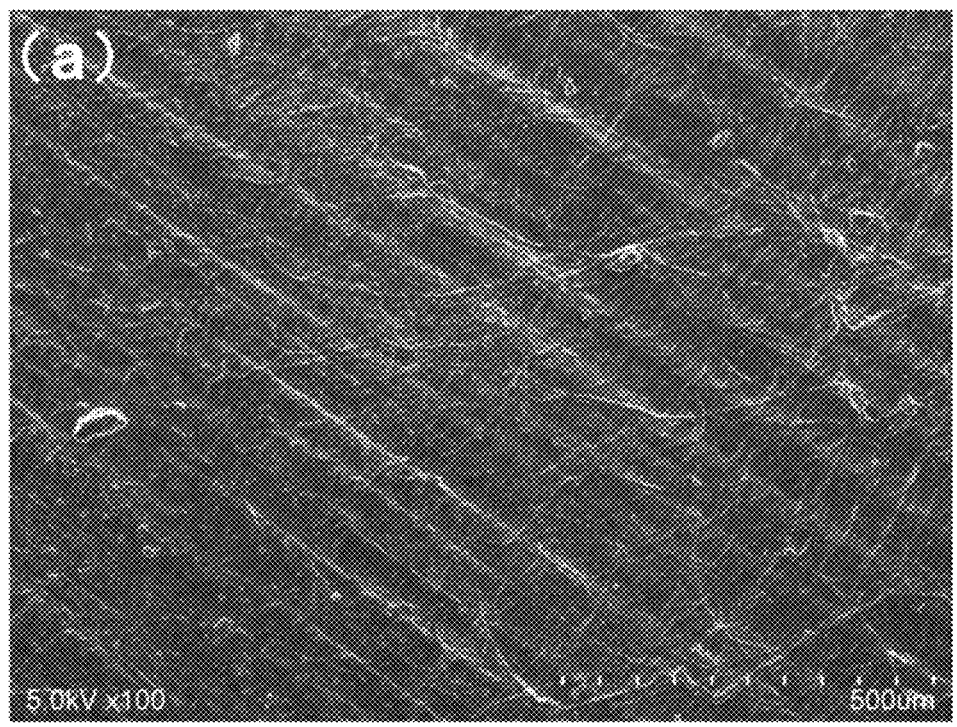
FIGS. 24(a) and 24(b) are images of Example 15 taken by a SEM, respectively.
Figure 24:
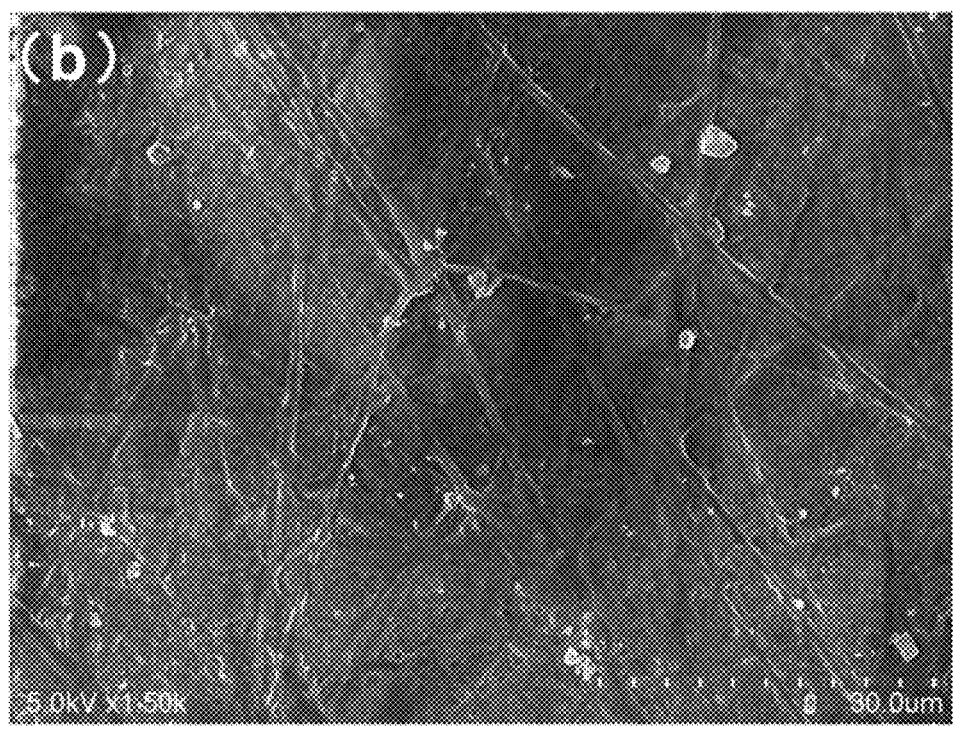

FIG. 24(a) is an image which was observed and taken at a magnification of 100-fold by a SEM, and FIG. 24(b) is an image of the sample of FIG. 24(a), which was observed and taken at a magnification of 1500-fold by a SEM.

The sample stage illustrated in FIGS. 23(a) and 23(b) is a jig for observing a membrane-like tissue such as peritoneum or diaphragm in a state of being tensioned. In other words, a tension is applied to the sample by applying weight from above, and thus it is possible to observe a membrane-like tissue such as peritoneum or diaphragm which shrinks with time after being excised from a living body in the same manner as it is in the organism.

In the image of Example 15 using this sample stage taken by a SEM, a great number of apophyses on the peritoneal surface which have been observed in Examples 1 and 2 have not been confirmed, and it has been possible to observe a fine network structure at a high magnification. In addition, cleavage of the peritoneum or exposure of the filament which exists below the surface of the peritoneum has not been acknowledged at all. Hence, it is considered that a sample can be observed while maintaining the morphology closer to the state present in the living body as a tension is applied to the sample by using the sample stage illustrated in FIGS. 23(a) and 23(b).

Comparative Example 4

The peritoneum excised from a living mouse was subjected to the primary chemical fixation with 10% (w/w) neutral buffered formalin, and the sample was then dried and subjected to the metal deposition (JEOL JFC-1100). The mouse peritoneal specimen prepared in accordance with such a method for preparing a specimen for electron microscopic observation of the prior art was placed on the sample stage illustrated in FIG. 23(a) such that the epithelial side was to be the upper surface and subjected to SEM observation.

Figure 25:
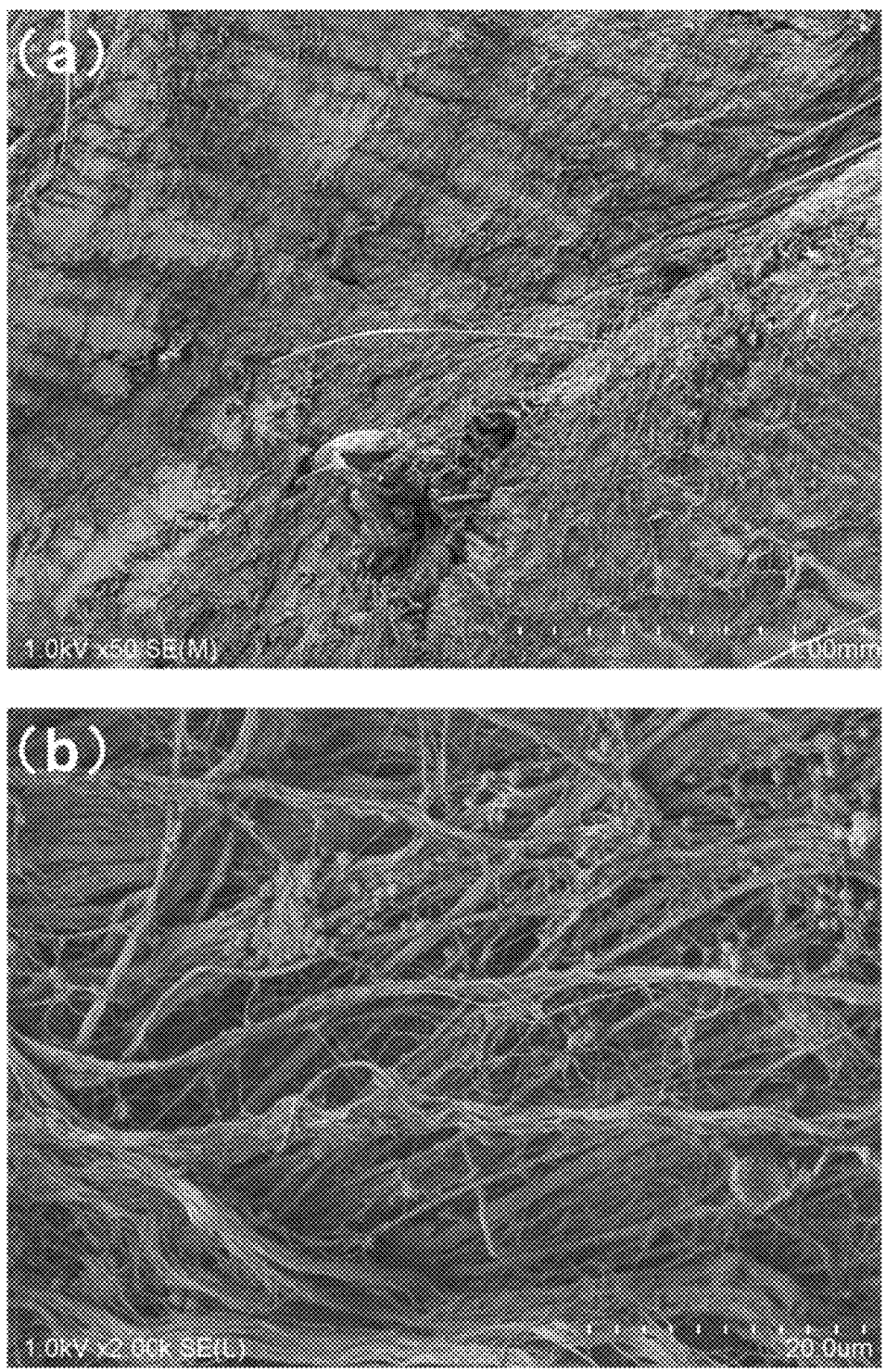
FIGS. 25(a) and 25(b) are images of Comparative Example 4 taken by a SEM, respectively.

FIG. 25(a) is an image which was observed and taken at a magnification of 50-fold by a SEM, and FIG. 25(b) is an image of the sample of FIG. 25(a), which was observed and taken at a magnification of 2000-fold by a SEM.

In the image of Comparative Example 4 taken by a SEM, cleavage of the peritoneum or exposure of the filament which exists below the surface of the peritoneum has been confirmed.

Example 16

A protective agent for electron microscopic observation and a surfactant-containing solution were prepared in the same manner as in Example 1.

A sample of mouse peritoneal visceral side was prepared in the same manner as in Example 15 except that the peritoneum excised from a mouse was placed on the sample stage (a) illustrated in FIGS. 23(a) and 23(b) such that the visceral side was to be the upper surface, and it was subjected to the SEM observation.

Figure 26:
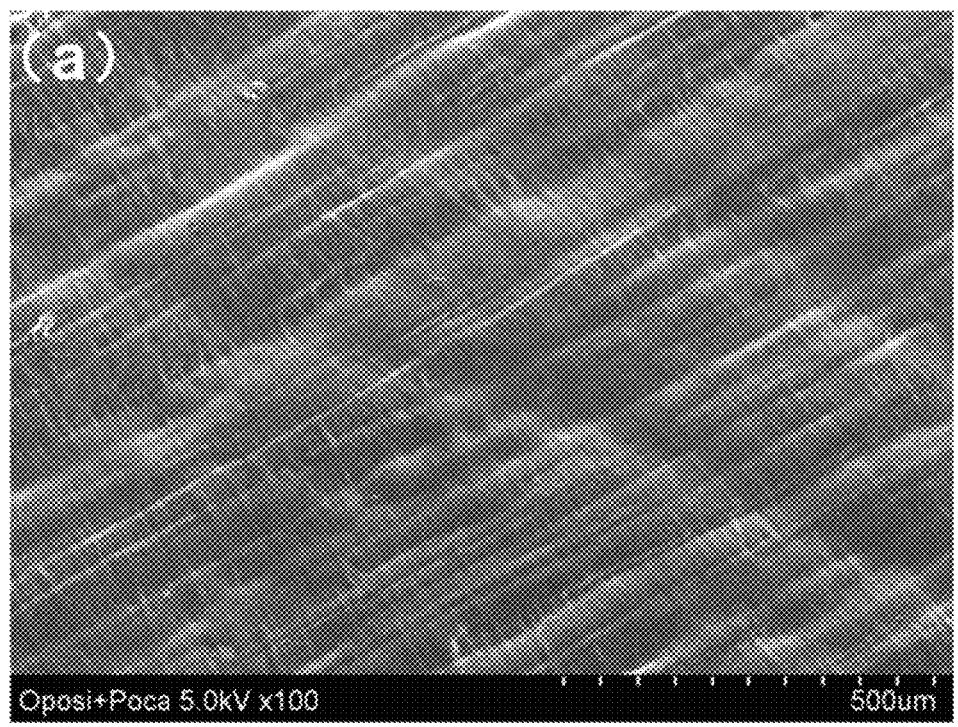
FIGS. 26(a) and 26(b) are images of Example 16 taken by a SEM, respectively.
Figure 26:
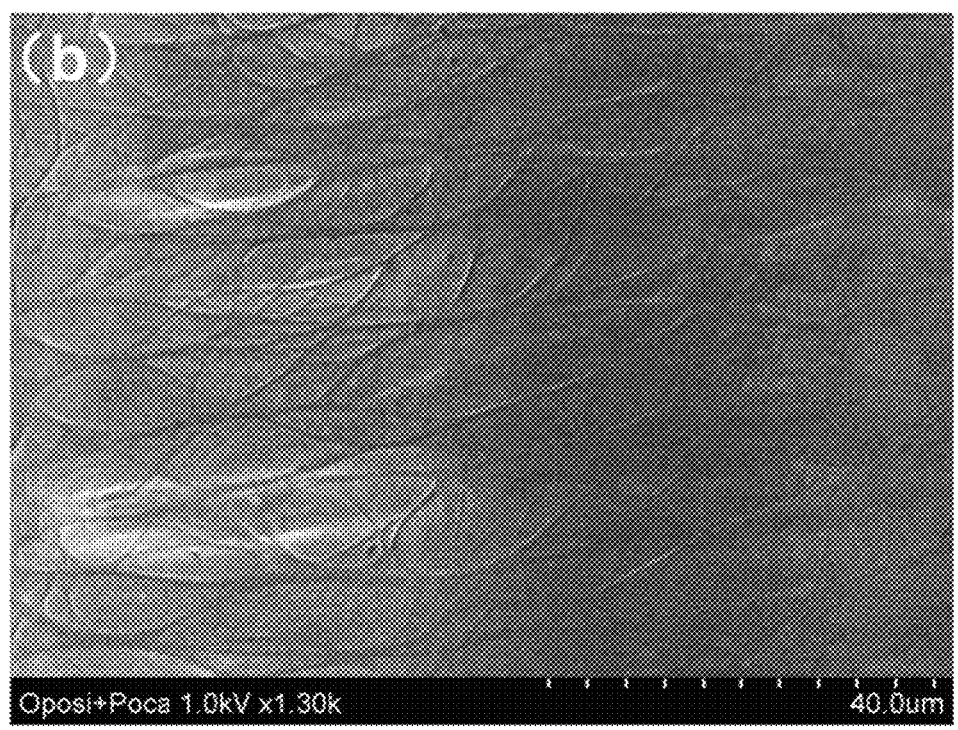

FIG. 26(a) is an image which was observed and taken at a magnification of 100-fold by a SEM, and FIG. 26(b) is an image of the sample of FIG. 26(a), which was observed and taken at a magnification of 1300-fold by a SEM.

In the image of Example 16 taken by a SEM, in the same manner as in Example 15, the apophyses have not been clearly confirmed and it has been possible to observe a fine network structure at a high magnification. In addition, cleavage of the peritoneum or exposure of the filament which exists below the surface of the peritoneum has not been acknowledged at all.

Comparative Example 5

A sample of mouse peritoneal visceral side was prepared in the same manner as in Comparative Example 4 except that the peritoneum excised from a mouse was placed on the sample stage (a) illustrated in FIGS. 23(a) and 23(b) such that the visceral side was to be the upper surface, and it was subjected to the SEM observation.

Figure 27:
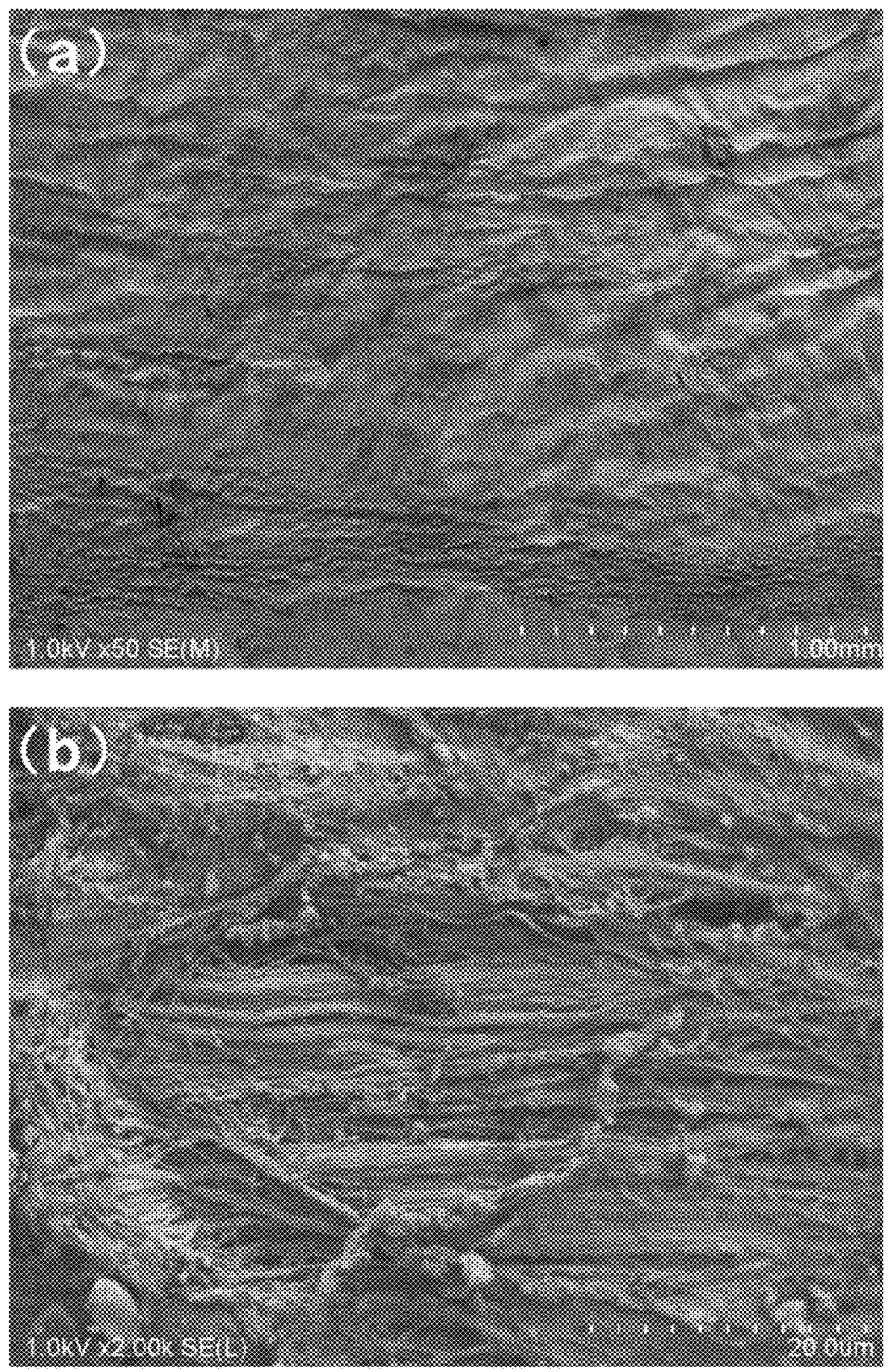
FIGS. 27(a) and 27(b) are images of Comparative Example 5 taken by a SEM, respectively.

FIG. 27(a) is an image which was observed and taken at a magnification of 50-fold by a SEM, and FIG. 27(b) is an image of the sample of FIG. 27(a), which was observed and taken at a magnification of 2000-fold by a SEM.

In the image of Comparative Example 5 taken by a SEM, cleavage of the peritoneum or exposure of the filament which exists below the surface of the peritoneum has been confirmed in the same manner as in Comparative Example 4.

Comparative Example 6

Figure 28:
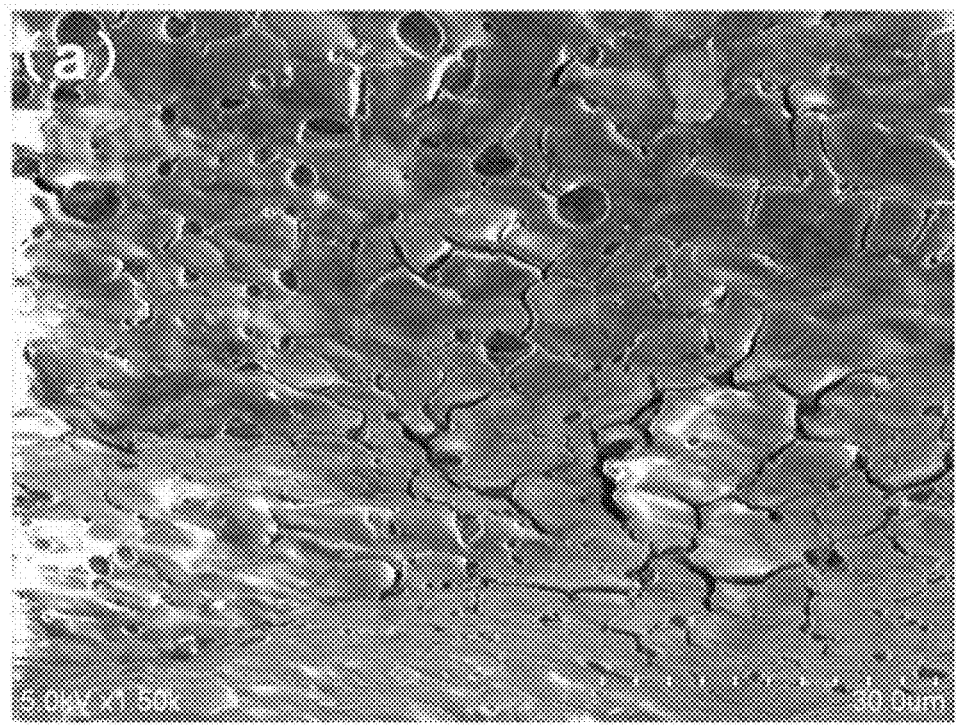
FIGS. 28(a) and 28(b) are images of Comparative Example 6 taken by a SEM, respectively, and they are images of the peritoneum which is excised from a mouse, placed on the sample stage illustrated in FIG. 23(a), introduced into an electron microscope in an untreated state, and observed and taken at a magnification of 1500-fold by a SEM.
Figure 28:
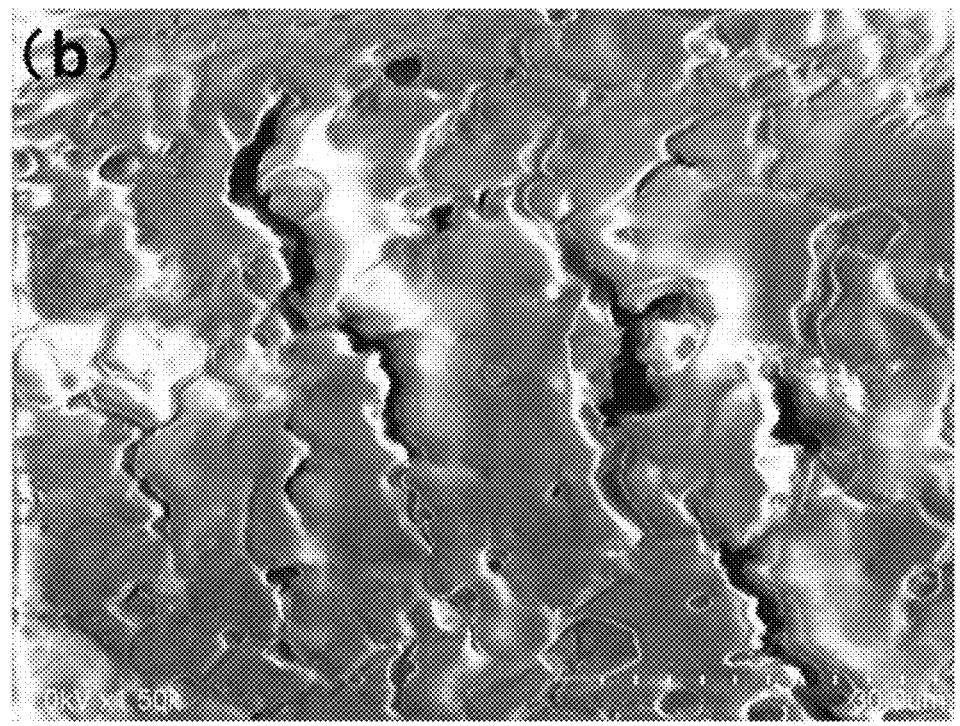

The peritoneum excised from a living mouse in the same manner as in Example 15 was placed on the sample stage illustrated in FIG. 23(a) and introduced into the electron microscope in an untreated state. FIGS. 28(a) and 28(b) are images which were both observed and taken at a magnification of 1500-fold by a SEM.

In the images of Comparative Example 6 taken by a SEM, the sample is wholly charged up so as not to be normally observed. In addition, it has been confirmed that the peritoneal surface is broken and the tissue is collapsed as the sample is exposed to a vacuum.

Example 17

A protective agent for electron microscopic observation and a surfactant-containing solution were prepared in the same manner as in Example 1.

A sample of mouse diaphragm peeled site was prepared in the same manner as in Example 15 except that the tissue excised from a mouse was the diaphragm peeled site, and it was subjected to the SEM observation.

Figure 29:
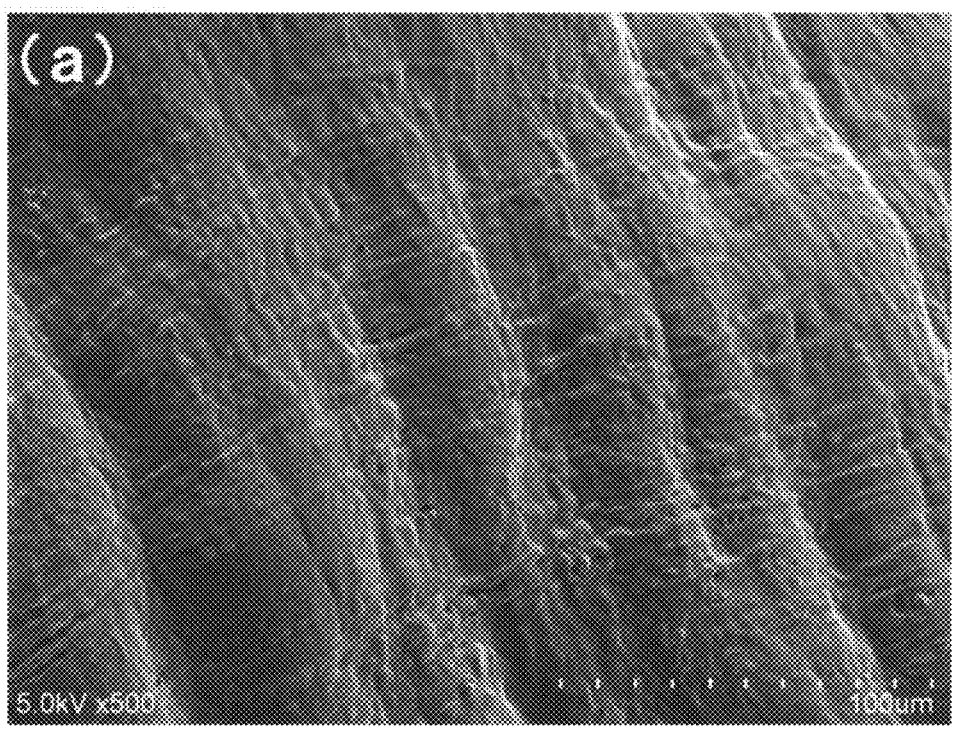
FIGS. 29(a) and 29(b) are photographs which illustrate images of Example 17 taken by a SEM, respectively.
Figure 29:
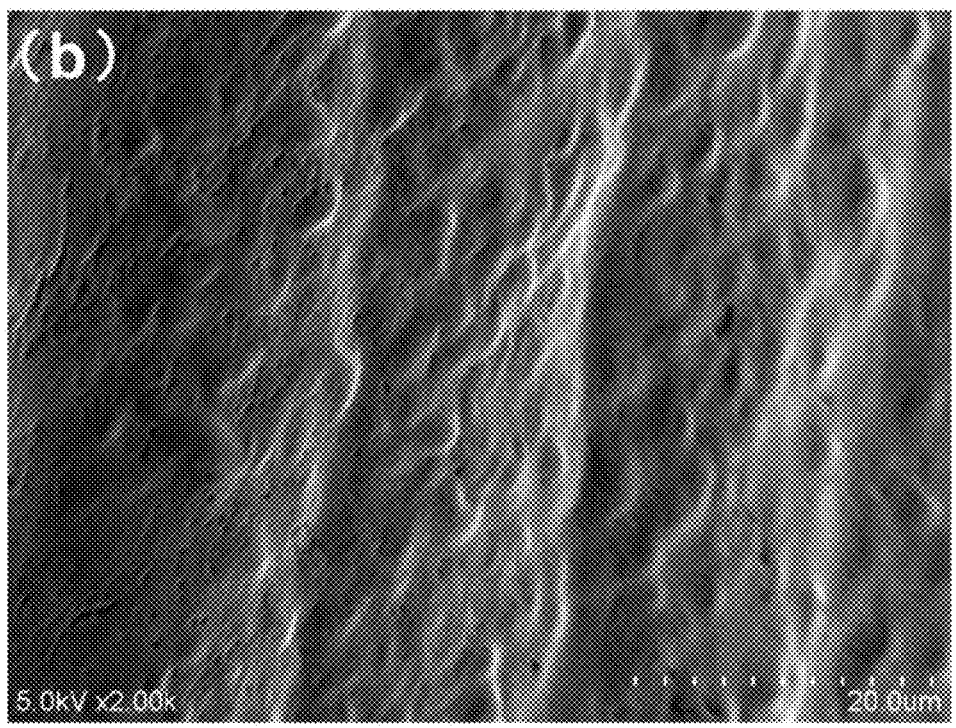
Figure 30:
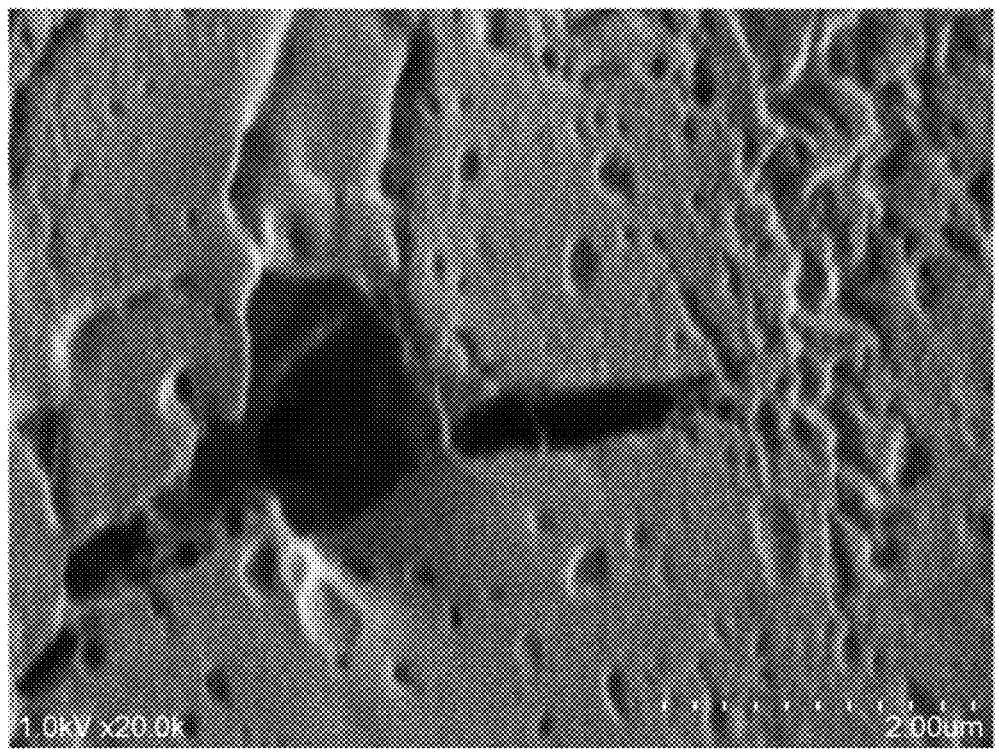
FIG. 30 is an image of the mouse diaphragm ventral in a water-containing state illustrated in FIGS. 29(a) and 29(b), which is observed and taken at a magnification of 20,000-fold by a SEM.

FIG. 29(a) is an image which was observed and taken at a magnification of 500-fold by a SEM, and FIG. 29(b) is an image of the sample of FIG. 29(a), which was observed and taken at a magnification of 2000-fold by a SEM. FIG. 30 is an image of the sample of FIG. 29(a), which was observed and taken at a magnification of 20000-fold by a SEM.

In the image of Example 17 using the sample stage taken by a SEM, surface of the diaphragm peeled site maintains a normal morphology in the same manner as the peritoneal surface which has been observed in Example 15 and a plurality of apophyseal fine pores have been confirmed in the image of FIG. 29(b) taken at a magnification of 2000-fold by a SEM. In addition, cleavage of the diaphragm or exposure of the filament which exists below the surface of the diaphragm has not been acknowledged at all. Furthermore, in FIG. 30 that is the image taken at an ultra-high magnification of 20000-fold by a SEM, the fine pores confirmed in FIG. 29(b) look like a secretory tissue, but the diaphragm in such a state has been observed by the present inventors for the first time, and it is difficult to estimate the function or the like of the above fine pores at the present moment. Hence, a possibility that can provide a new finding to the medical and biological fields is suggested since a fine structure on the surface of a membrane-like tissue which has not been able to be observed under an electron microscope in the prior art can be observed by applying the present invention.

Example 18

A protective agent for electron microscopic observation and a surfactant-containing solution were prepared in the same manner as in Example 1.

For the purpose of causing inflammation to a mouse, an adjuvant was repeatedly injected into the abdominal cavity of the mouse once a week, and the peritoneum was excised from the living mouse after 3 weeks. A sample was prepared in the same manner as in Example 15 except that the inflamed mouse peritoneum was used, and it was subjected to the SEM observation.

Figure 31:
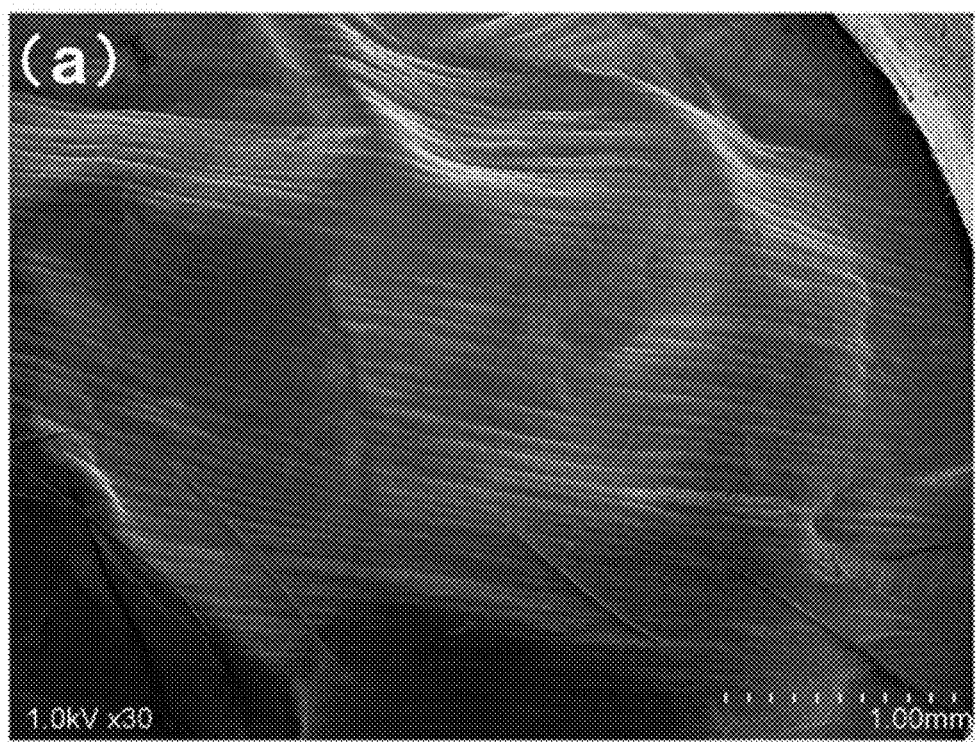
FIG. 31(a) is an image of Example 18 taken by a SEM.
FIG. 31(b) is an image of Comparative Example 7 taken by a SEM.
Figure 31:
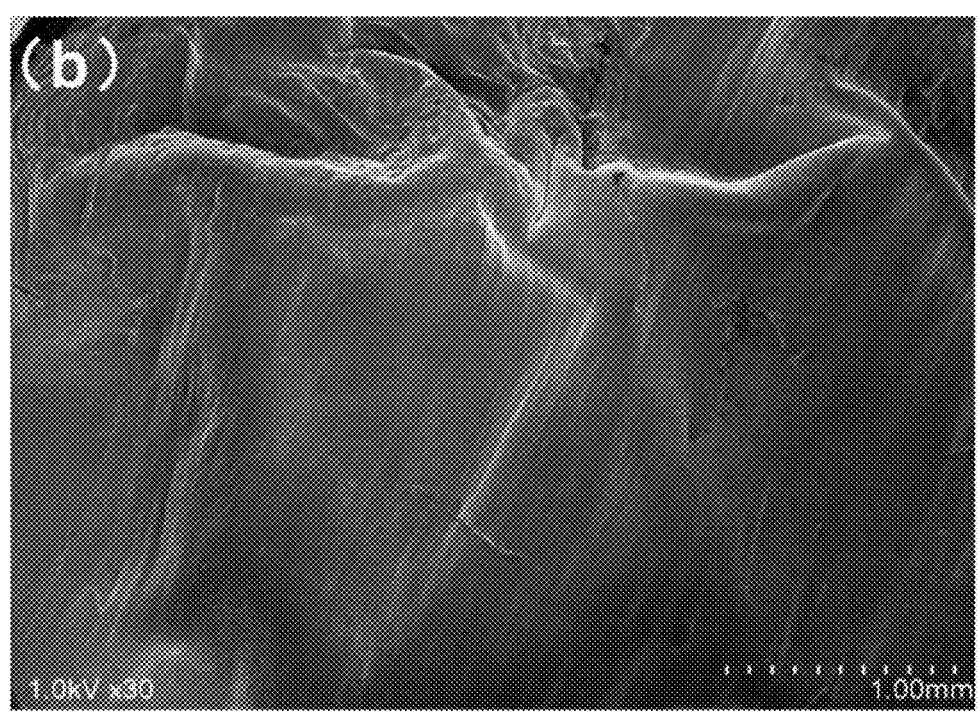
Figure 32:
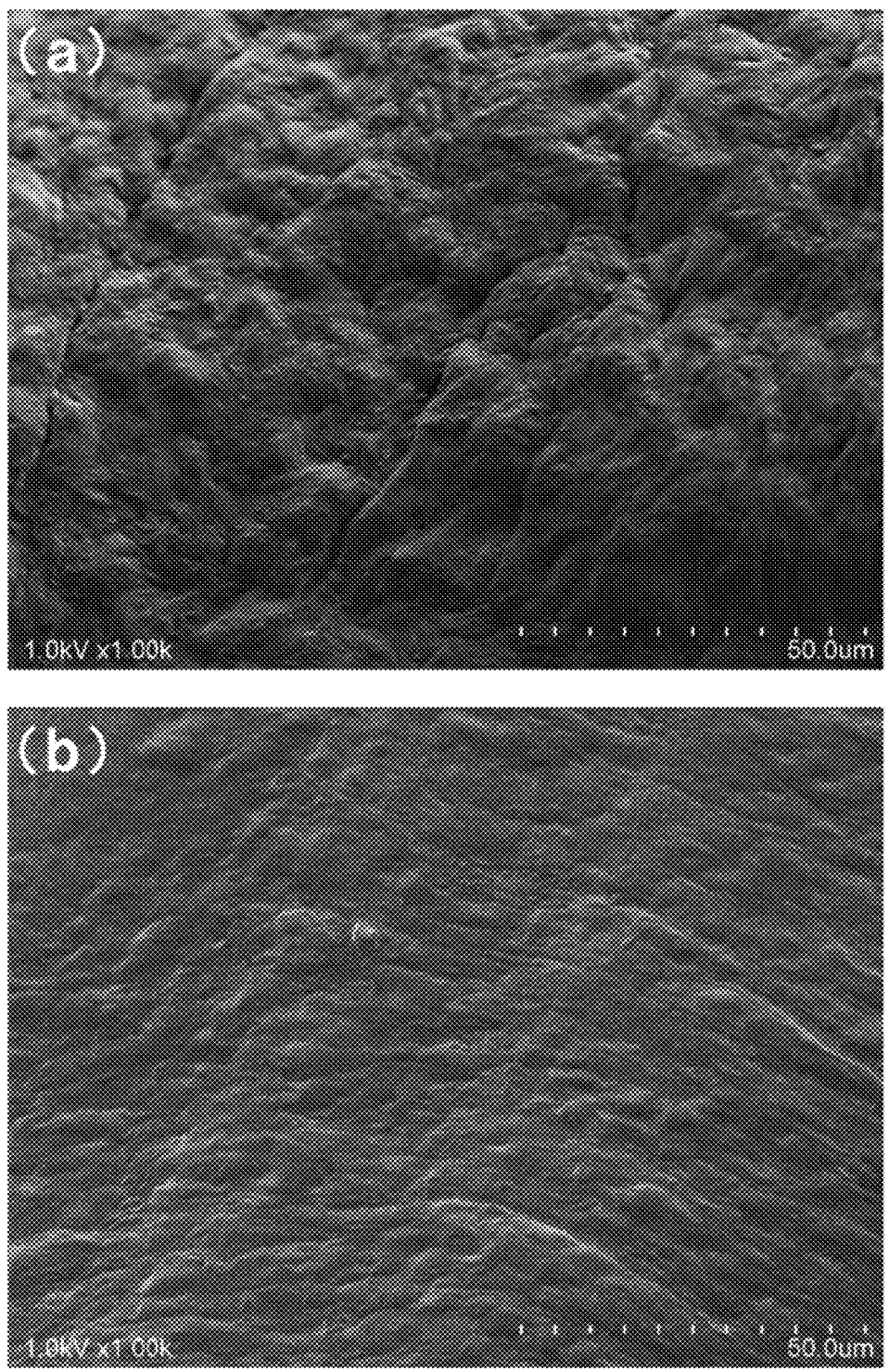
FIGS. 32(a) and 32(b) are images of the mouse peritoneal epithelial sides in a water-containing state respectively illustrated in FIGS. 31(a) and 31(b), which are observed and taken at a magnification of 1000-fold by a SEM.
Figure 33:
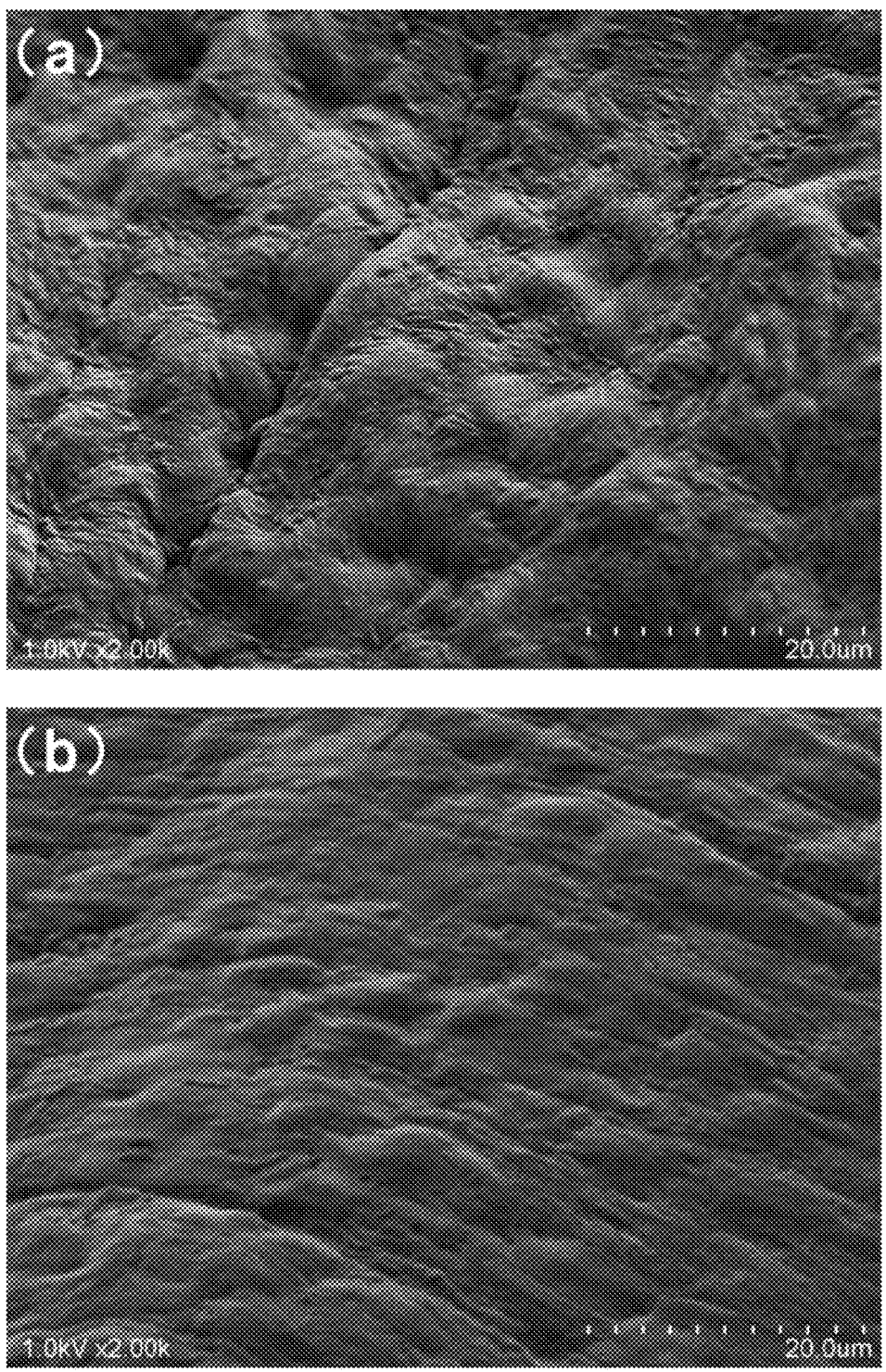
FIGS. 33(a) and 33(b) are images of the mouse peritoneal epithelial sides in a water-containing state respectively illustrated in FIGS. 31(a) and 31(b), which are observed and taken at a magnification of 2000-fold by a SEM.

FIG. 31(a) is an image which was observed and taken at a magnification of 30-fold by a SEM, and FIG. 32(a) is an image of the sample of FIG. 31(a), which was observed and taken at a magnification of 1000-fold by a SEM. In addition, FIG. 33(a) is an image of the sample of FIG. 31(a), which was observed and taken at a magnification of 2000-fold by a SEM.

In the image of Example 18 taken by a SEM, it has been confirmed that a pathological change of the peritoneum of an inflamed mouse can be observed in a water-containing state. A streaky change on the peritoneal surface is acknowledged in the image taken at a magnification of 30-fold by a SEM of FIG. 31(a), but a great number of irregular apophyses are acknowledged in the image taken at a magnification of 1000-fold by a SEM of FIG. 32(a) and the image taken at a magnification of 2000-fold by a SEM of FIG. 33(a). It is considered that such a change is caused by propagation or fibrillization of the cells that are assembled in order to repair the inflammation site. Hence, a possibility that can provide a new finding to the medical and biological fields is suggested since a pathological change in the animal body which has not been able to be observed under an electron microscope in the prior art can be observed in a significantly close state to the interior of the living body by applying the present invention.

Comparative Example 7

As a control group of Example 18, an adjuvant was not injected into a mouse but physiological saline was repeatedly injected into the abdominal cavity of the mouse once a week, and the peritoneum was excised from the living mouse after 3 weeks. A specimen of the mouse peritoneum was prepared in the same manner as in Example 15 except that the mouse peritoneum of the control group was used, and it was subjected to the SEM observation.

FIG. 31(b) is an image which was observed and taken at a magnification of 30-fold by a SEM, and FIG. 32(b) is an image of the sample of FIG. 31(b), which was observed and taken at a magnification of 1000-fold by a SEM. In addition, FIG. 33(b) is an image of the sample of FIG. 31(b), which was observed and taken at a magnification of 2000-fold by a SEM.

In the image of Comparative Example 7 taken by a SEM, it has been confirmed that the peritoneum maintains a normal morphology and the cells are regularly arranged on the contrary to the image of Example 18 taken by a SEM.

Example 19

A protective agent for electron microscopic observation was prepared by mixing glycerin and water as a a component to impart the survival environment, glucose as a saccharide, and sodium chloride as an electrolyte at blending proportion of a component to impart the survival environment (glycerin):(water):saccharide (glucose):electrolyte (sodium chloride)=20:10:0.09:0.01.

The mouse-derived fibroblast cell was cultured on a glass plate as a cultured cell and withdrawn from the culture medium together with the glass plate, the surfactant-containing solution was then immediately dropped on the mouse-derived fibroblast cell, and the mouse-derived fibroblast cell was left to stand still for 1 minute. Thereafter, the protective agent for electron microscopic observation that was diluted 100 times with the culture medium of mouse-derived fibroblast cell was dropped on the mouse-derived fibroblast cell treated with the surfactant-containing solution, and the mouse-derived fibroblast cell was left to stand still for 1 minute. The mouse-derived fibroblast cell on which the protective agent for electron microscopic observation was dropped was introduced into the sample chamber of the SEM together with the glass plate, irradiated with an electron beam to polymerize the surfactant-containing solution and thus to form a thin film, and subjected to the SEM observation.

Figure 34:
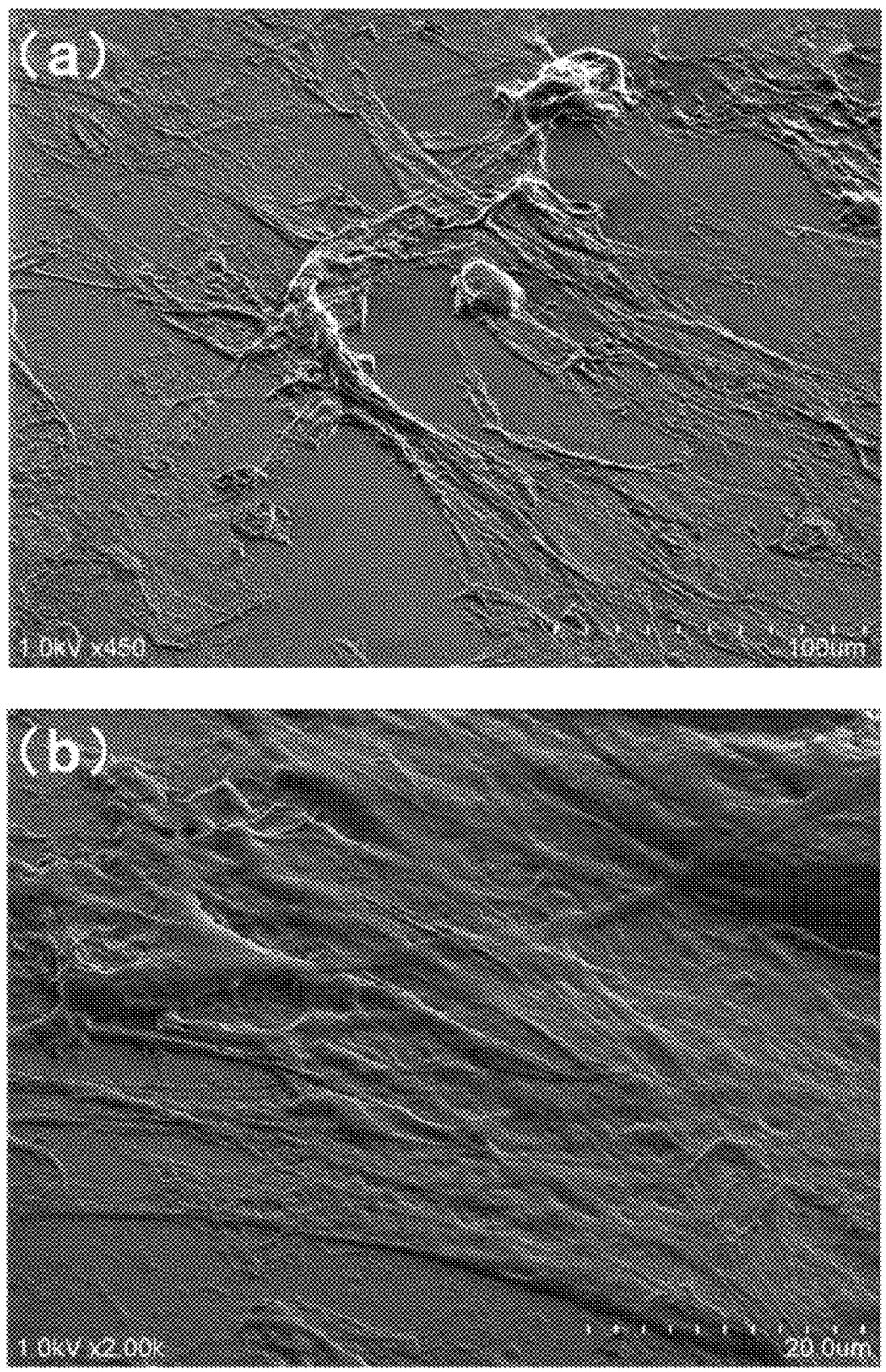
FIGS. 34(a) and 34(b) are images of Example 19 taken by a SEM, respectively.

FIG. 34(a) is an image which was observed and taken at a magnification of 450-fold by a SEM, and FIG. 34(b) is an image of the sample of FIG. 34(a), which was observed and taken at a magnification of 2000-fold by a SEM.

It has been confirmed that a cultured cell which has been ruptured at the time of evacuation in the sample chamber of a SEM in the prior art can be observed in a normal morphology in a vacuum by treating a cultured cell with the protective agent for electron microscopic observation of the present invention after applying the surfactant-containing solution to the cultured cell. In particular, it is noteworthy that it has become possible to observe a state in which a pseudopodium is stretched from a fibroblast cell.

Furthermore, it has been confirmed that the cell continues living when the glass plate was returned into the culture medium after the observation. In this way, a technique capable of observing a cell in a surviving state under an electron microscope and returning the cell alive from a vacuum is absolutely a new one, and it is considered to be a significantly important technique in life science research.

Comparative Example 8

In the same manner as in Example 19, the mouse-derived fibroblast cell cultured on a glass plate was used as a cultured cell, and the mouse-derived fibroblast cell was withdrawn from the culture medium together with the glass plate and then introduced into an electron microscope in an untreated state.

Figure 35:
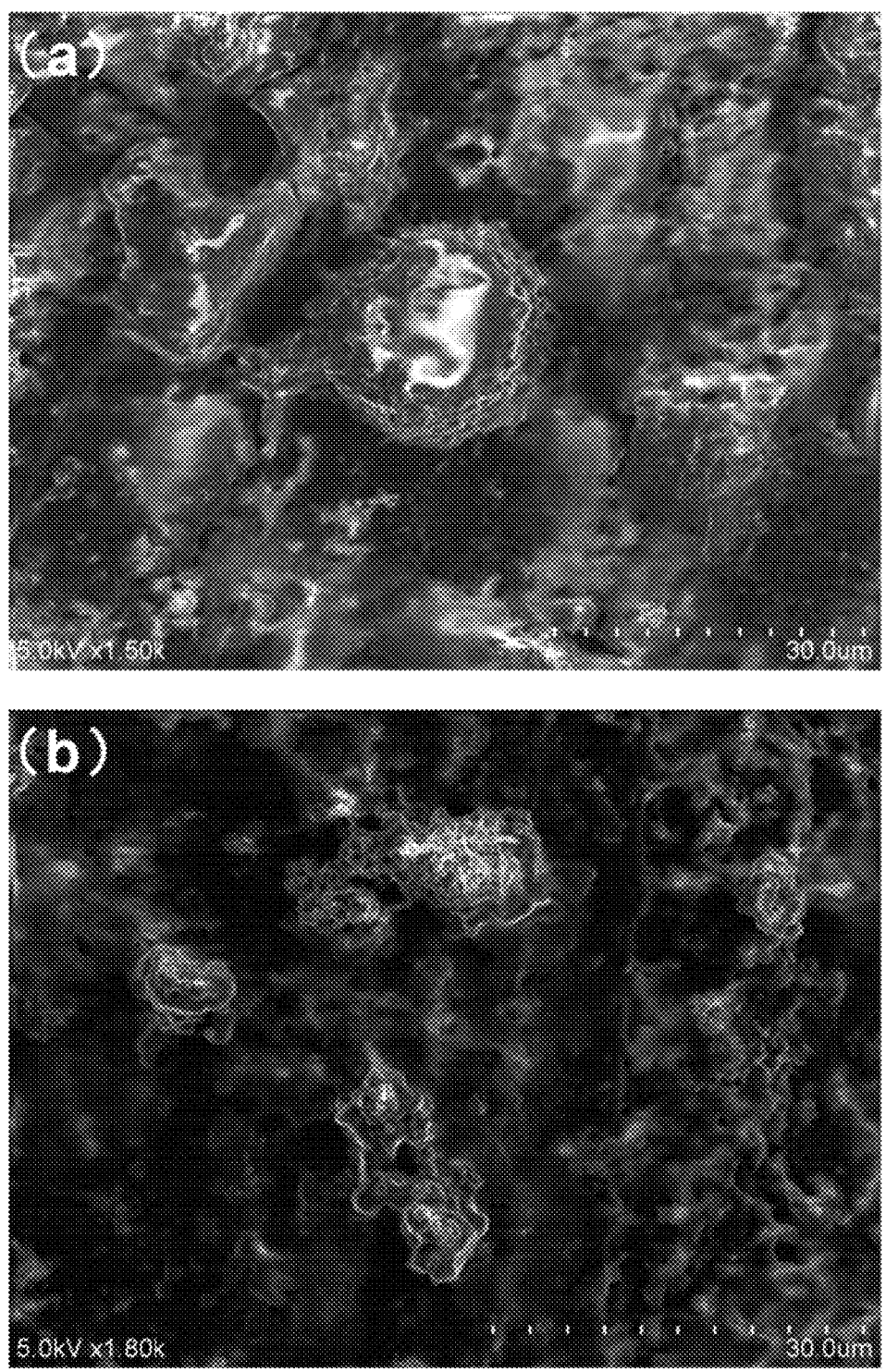
FIGS. 35(a) and 35(b) are images of Comparative Example 8 taken by a SEM, respectively.

FIG. 35(a) is an image which was observed and taken at a magnification of 1500-fold by a SEM, and FIG. 35(b) is an image of the sample of FIG. 35(a), which was observed and taken at a magnification of 1800-fold by a SEM.

In both of the images taken by a SEM, the cells are atrophied and deformed, and thus it has been confirmed that the observation of the cells in a surviving state is impossible.

Example 20

A protective agent for electron microscopic observation was prepared in the same manner as in Example 19.

The human-derived fibroblast cell cultured on a glass plate was used as a cultured cell, the human-derived fibroblast cell was withdrawn from the culture medium together with the glass plate, and a washing treatment to drop distilled water on the human-derived fibroblast cell and to leave it to stand still for 1 minute was immediately repeated 2 times, thereafter, the protective agent for electron microscopic observation that was diluted 100 times with the culture medium of human-derived fibroblast cell was dropped on the human-derived fibroblast cell, and the human-derived fibroblast cell was left to stand still for 1 minute. The human-derived fibroblast cell on which the protective agent for electron microscopic observation was dropped was introduced into the sample chamber of the SEM together with the glass plate, irradiated with an electron beam, and subjected to the SEM observation.

Figure 36:
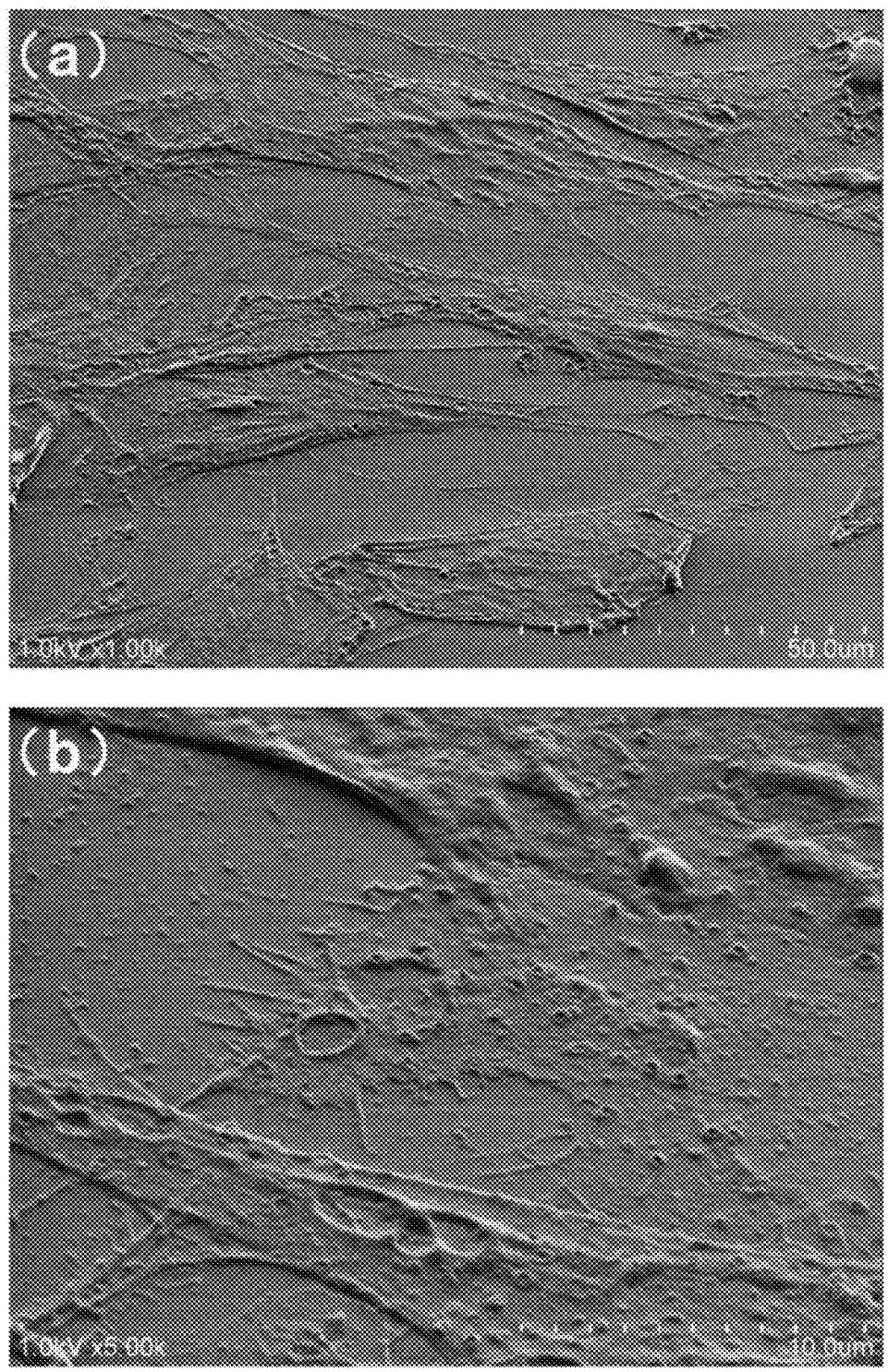
FIGS. 36(a) and 36(b) are images of Example 20 taken by a SEM, respectively.

FIG. 36(a) is an image which was observed and taken at a magnification of 1000-fold by a SEM. In addition, FIG. 36(b) is an image of the sample of FIG. 36(a), which was observed and taken at a magnification of 5000-fold by a SEM.

In Example 20, it has been possible to observe a cultured cell in a surviving state in a vacuum even though the cultured cell is not treated with a surfactant-containing solution, and a state in which a pseudopodium is stretched from a fibroblast cell has been confirmed in the same manner as in Example 19.

Comparative Example 9

Physiological saline containing human erythrocyte as a single cell was dropped onto a glass plate and introduced into an electron microscope in an untreated state.

Figure 37:
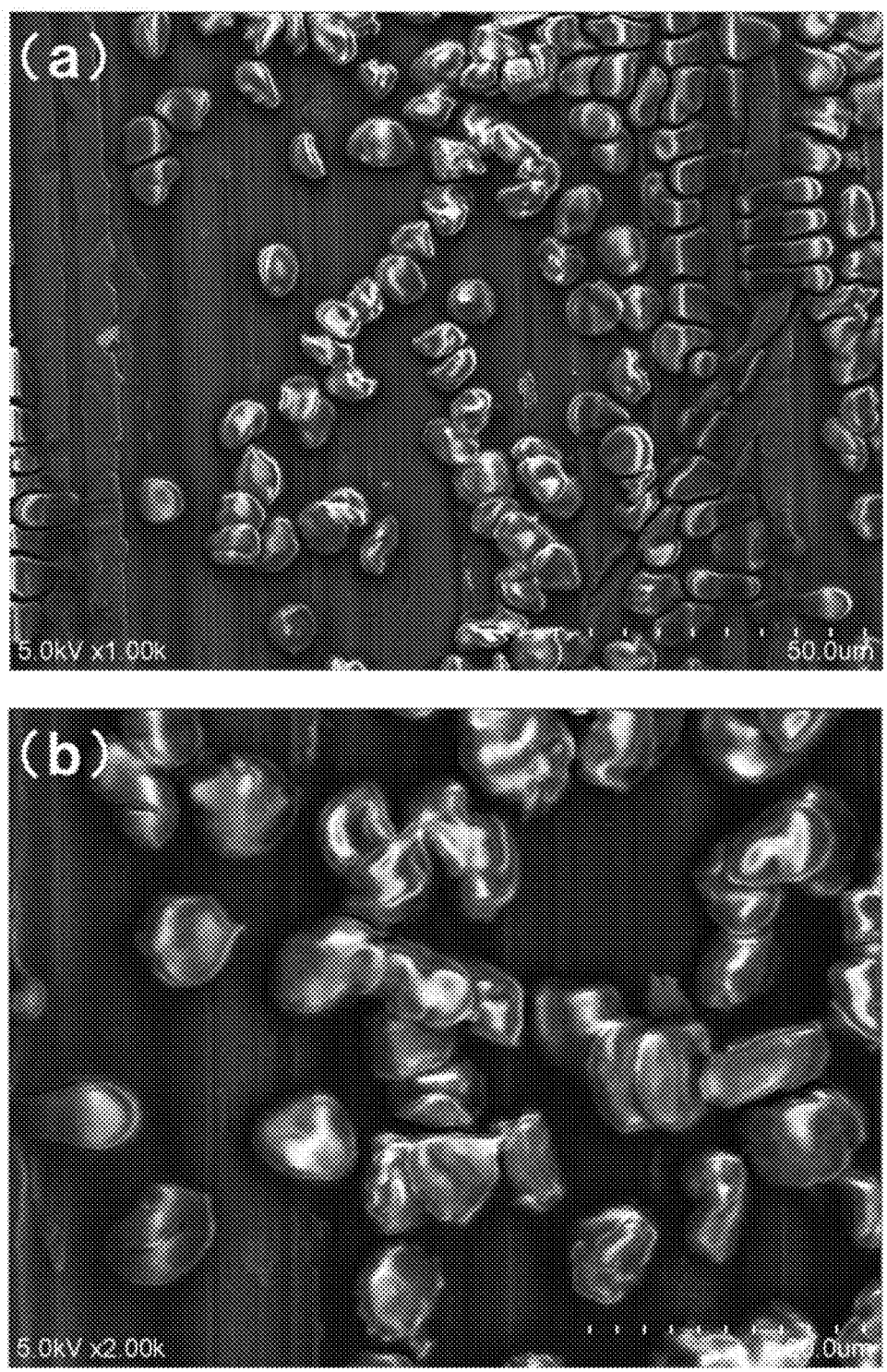
FIGS. 37(a) and 37(b) are images of Comparative Example 9 taken by a SEM, respectively.

FIG. 37(a) is an image which was observed and taken at a magnification of 1000-fold by a SEM. In addition, FIG. 37(b) is an image of a portion of FIG. 37(a), which was observed and taken at a magnification of 2000-fold by a SEM.

In both of the images taken by a SEM, charge-up is caused, also the erythrocyte is atrophied and deformed, and thus it has been confirmed that the observation of the erythrocyte in a surviving state is impossible.

Example 21

A protective agent for electron microscopic observation was prepared in the same manner as in Example 19.

Physiological saline containing the human blood cell, platelet, erythrocyte, and leucocyte as a single cell was dropped on a glass plate, the protective agent for electron microscopic observation was immediately dropped on the physiological saline, and the physiological saline was left to stand still for 1 minute. The human blood cell, platelet, erythrocyte, and leucocyte on which the protective agent for electron microscopic observation was dropped was introduced into the sample chamber of a SEM together with the glass plate, irradiated with an electron beam, and subjected to the SEM observation.

Figure 38:
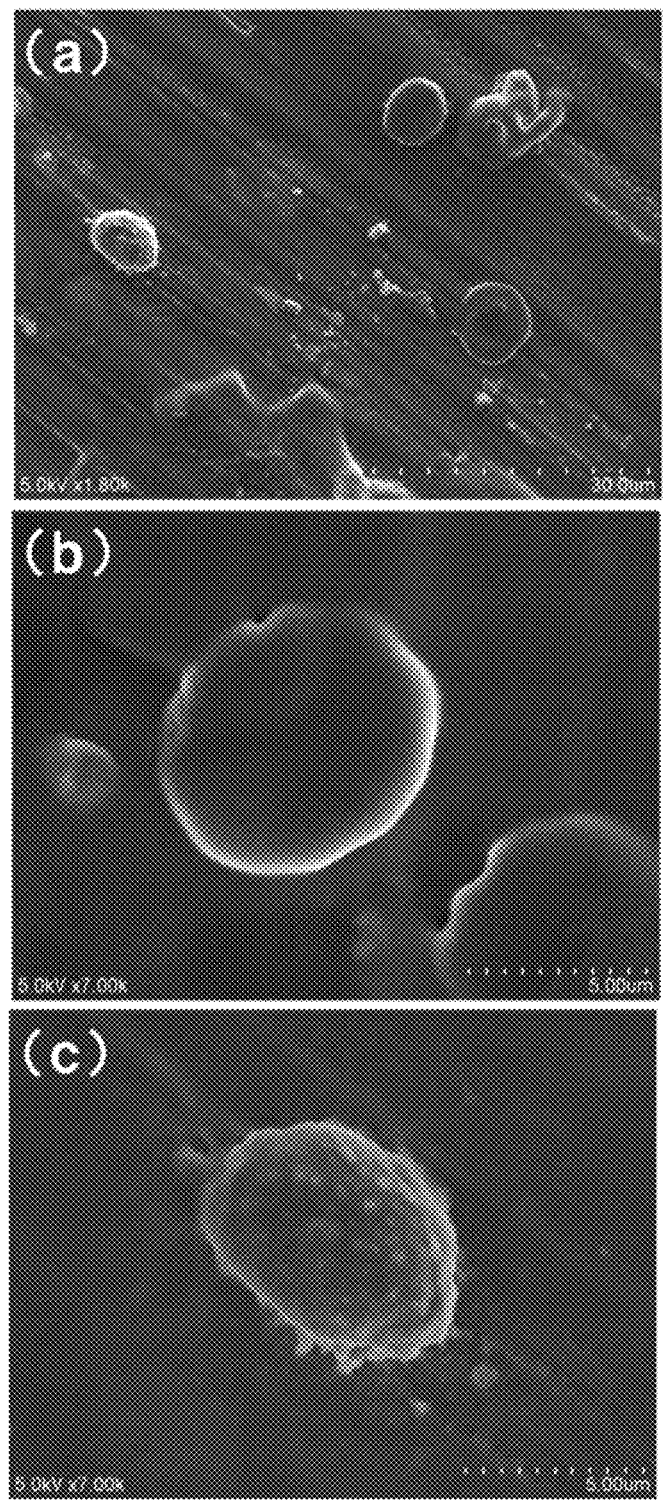
FIGS. 38(a), 38(b), and 38(c) are images of Example 21 taken by a SEM, respectively.

FIG. 38(a) is an image of the human blood cell and platelet which were observed and taken at a magnification of 1800-fold by a SEM. In addition, FIG. 38(b) is an image of the human erythrocyte which was observed and taken at a magnification of 7000-fold by a SEM, and FIG. 38(c) is an image of the human leucocyte which was observed and taken at a magnification of 7000-fold by a SEM.

In Example 21, it has been possible to confirm a cell in a surviving state of all of the human blood cell, and platelet, erythrocyte, and leucocyte under an electron microscope.

Example 22

A protective agent for electron microscopic observation was prepared in the same manner as in Example 19.

A culture medium containing yeast, *Bacillus natto*, and *Escherichia coli* as a single cell was dropped on a glass plate and immediately treated with the protective agent for electron microscopic observation. The yeast, *Bacillus natto*, and *Escherichia coli* on which the protective agent for electron microscopic observation was dropped was introduced into the sample chamber of a SEM together with the glass plate, irradiated with an electron beam, and subjected to the SEM observation.

Figure 39:
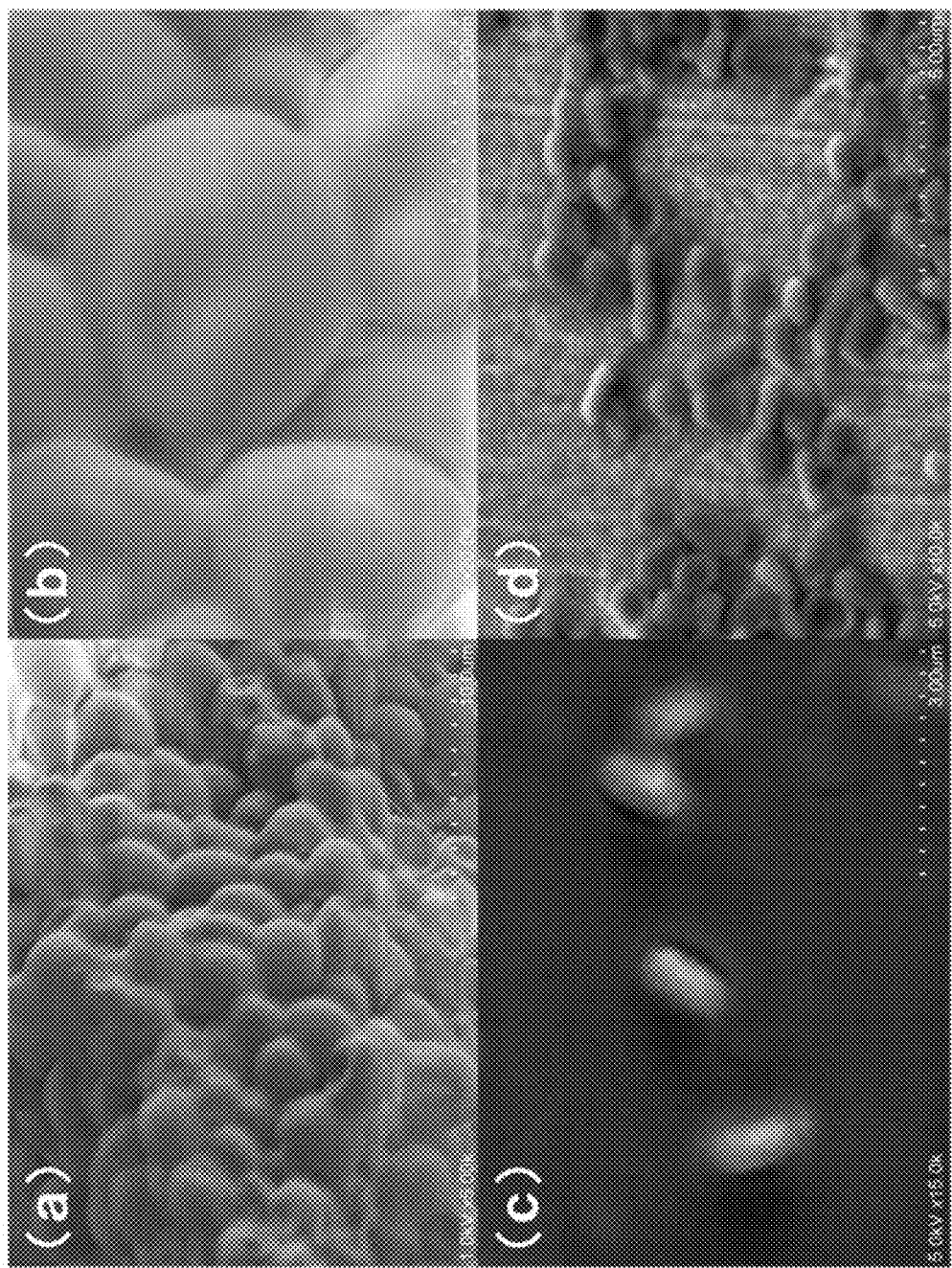
FIGS. 39(a), 39(b), 39(c), and 39(d) are images of Example 22 taken by a SEM, respectively.

FIG. 39(a) is an image of yeast in a water-containing state which was observed and taken at a magnification of 5000-fold by a SEM. In addition, FIG. 39(b) is an image of a portion of FIG. 39(a), which was observed and taken at a magnification of 20,000-fold by a SEM. FIG. 39(c) is an image of *Bacillus natto* in a water-containing state which was observed and taken at a magnification of 15,000-fold by a SEM. FIG. 39(d) is an image of *Escherichia coli* in a water-containing state which was observed and taken at a magnification of 10,000-fold by a SEM.

In Example 22, it has been possible to confirm a cell in a surviving state of all of yeast, *Bacillus natto*, and *Escherichia coli* under an electron microscope.

Example 23

A protective agent for electron microscopic observation was prepared in the same manner as in Example 19.

A culture medium containing the *Dictyostelium discoideum* fruiting body that is one of cellular slime mold as a single cell was dropped on a glass plate and immediately treated with the protective agent for electron microscopic observation. The *Dictyostelium discoideum* fruiting body on which the protective agent for electron microscopic observation was dropped was introduced into the sample chamber of a SEM together with the glass plate, irradiated with an electron beam, and subjected to the SEM observation.

Figure 40:
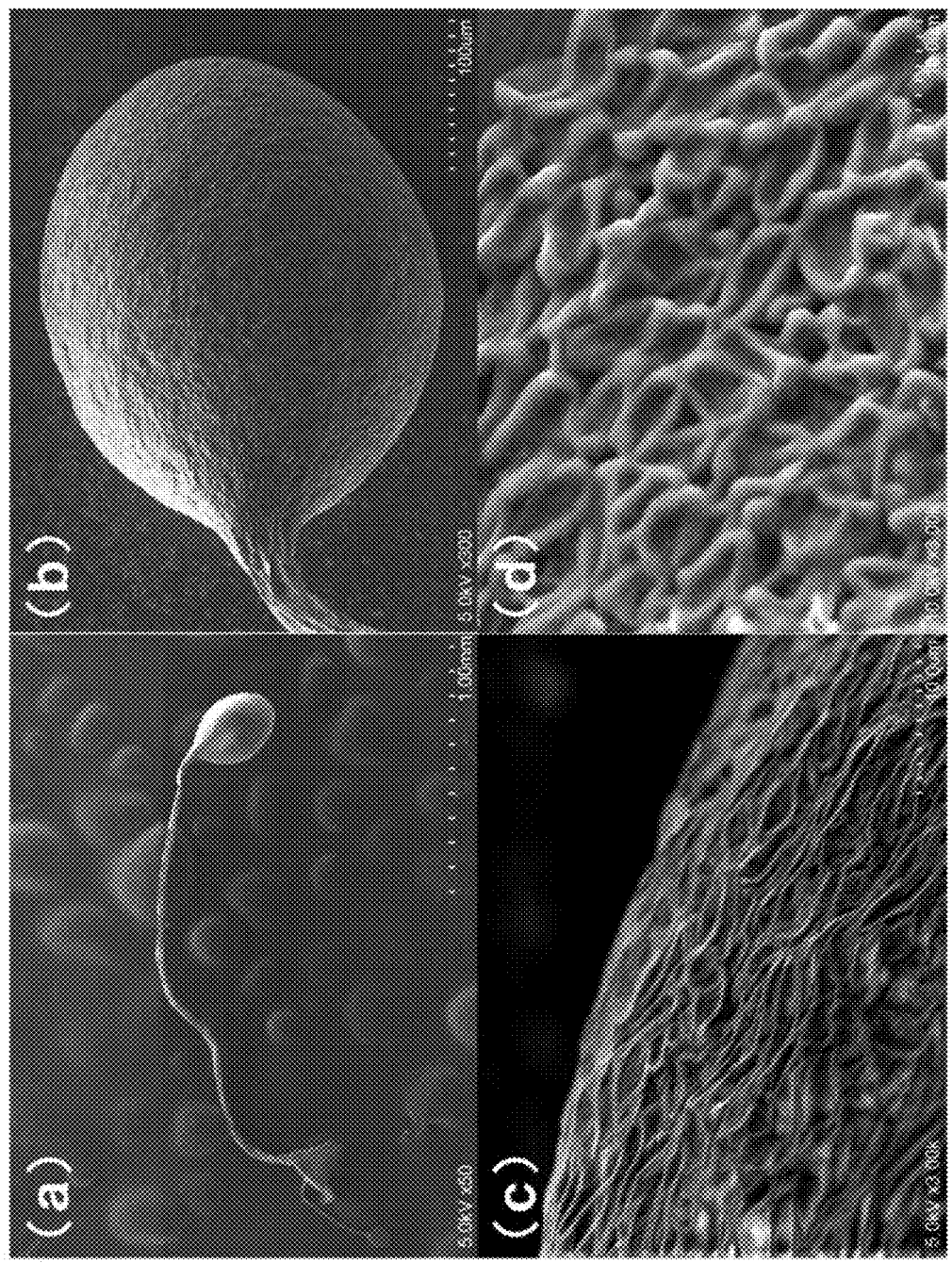
FIGS. 40(a), 40(b), 40(c), and 40(d) are images of Example 23 taken by a SEM, respectively.

FIG. 40(a) is an image of the *Dictyostelium discoideum* fruiting body in a water-containing state which was observed and taken at a magnification of 50-fold by a SEM. In addition, FIG. 40(b) is an image of a portion of FIG. 40(a), which was observed and taken at a magnification of 300-fold by a SEM, FIG. 40(c) is an image of a portion of FIG. 40(a), which was observed and taken at a magnification of 3000-fold by a SEM, and FIG. 40(d) is an image of a portion of FIG. 40(a), which was observed and taken at a magnification of 6000-fold by a SEM.

In Example 23, it has been possible to confirm a cell in a surviving state of the *Dictyostelium discoideum* fruiting body in a water-containing state under an electron microscope. In particular, it has been confirmed that there are fine network apophyses on the surface of the fruiting body in the observation at a high magnification.

Example 24

A protective agent for electron microscopic observation was prepared in the same manner as in Example 19.

The mouse fibroblast cell cultured on a glass plate was infected with the mouse cytomegalovirus (MCMV) and immediately treated with the protective agent for electron microscopic observation. The MCMV-infected mouse fibroblast cell on which the protective agent for electron microscopic observation was dropped was introduced into the sample chamber of a SEM together with the glass plate, irradiated with an electron beam, and subjected to the SEM observation.

Figure 41:
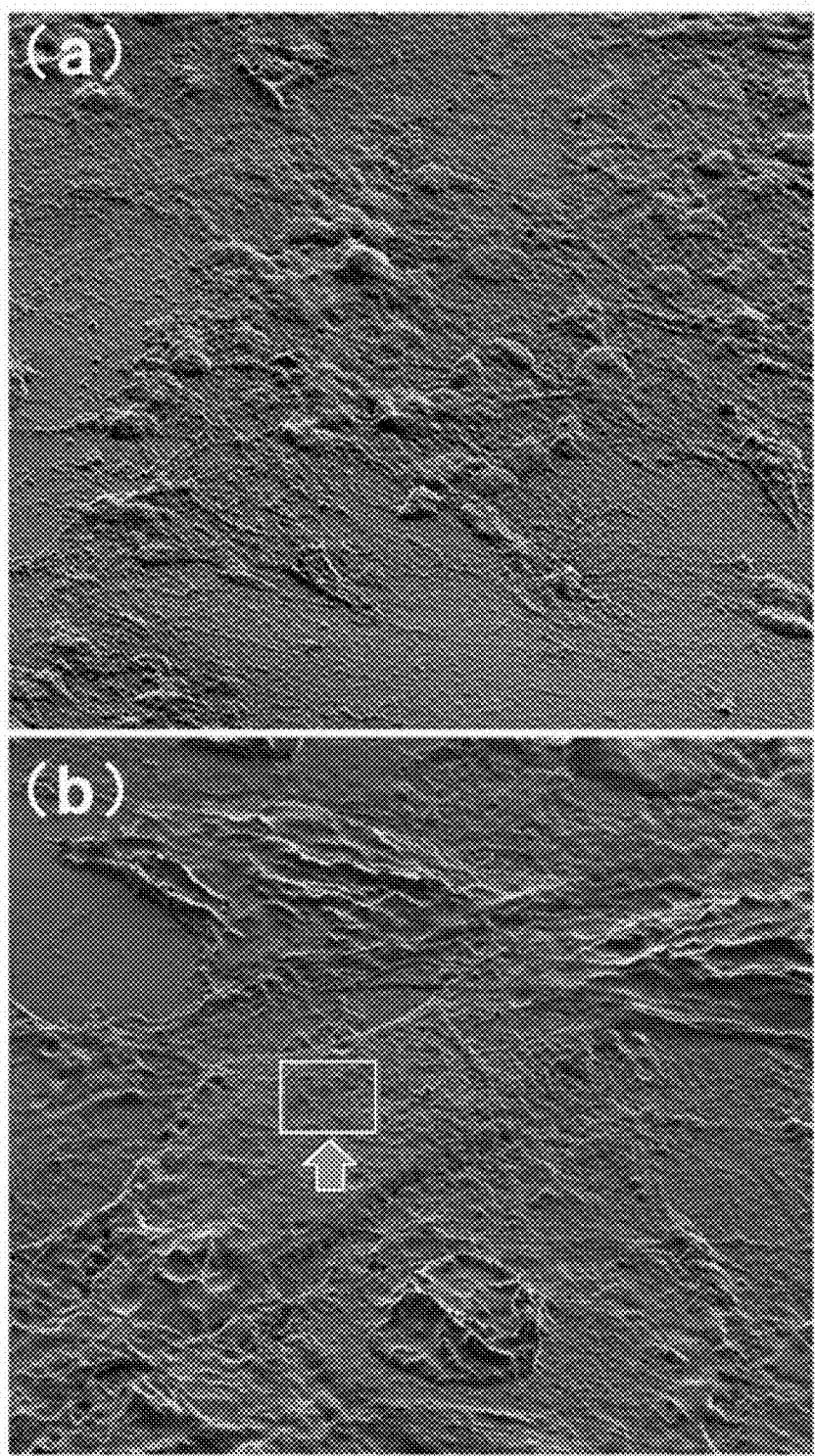
FIGS. 41(a) and 41(b) are images of the MCMV-infected mouse fibroblast cell in a water-containing state of Example 24 taken by a SEM, respectively.
Figure 42:
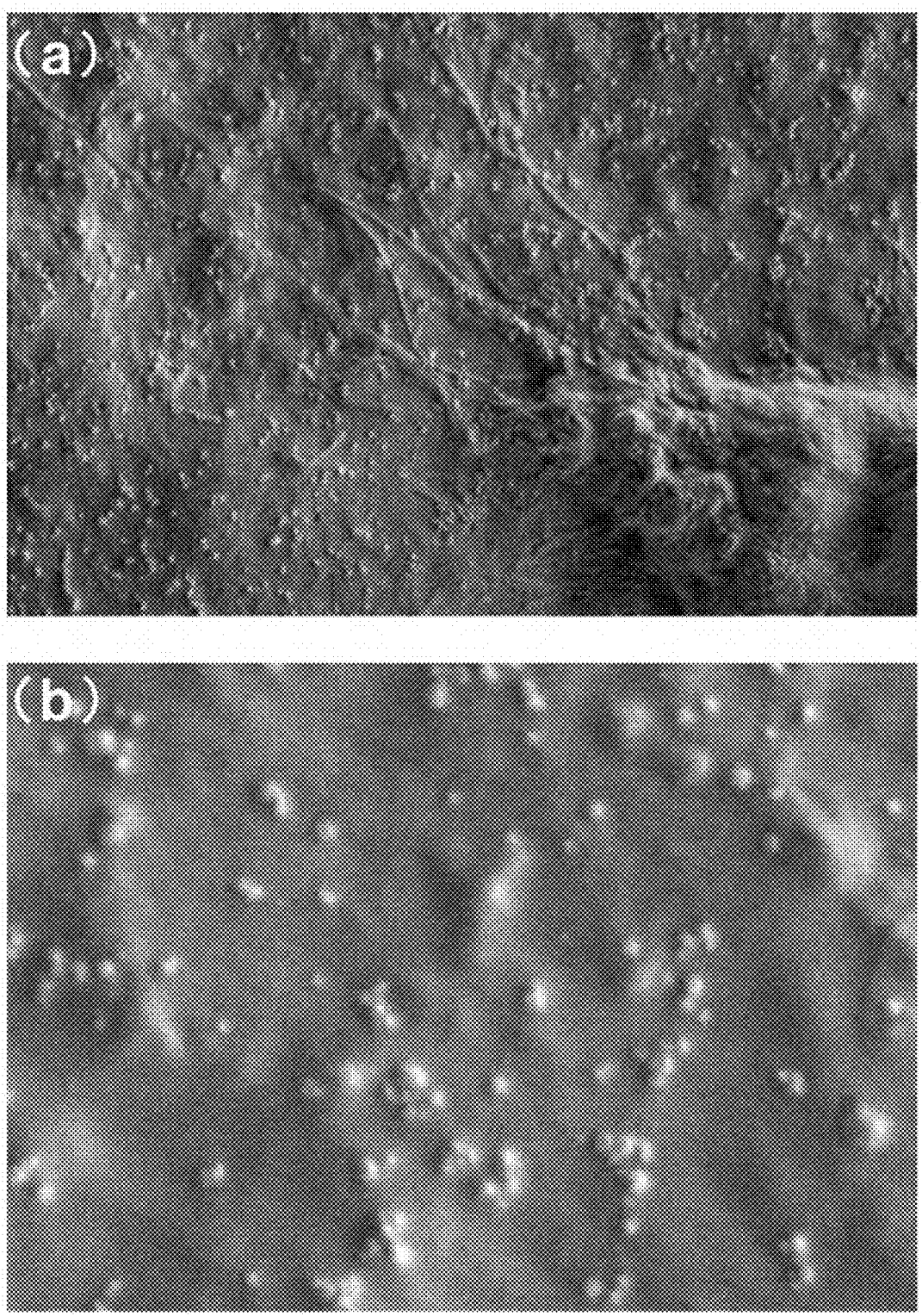
FIGS. 42(a) and 42(b) are images of the MCMV-infected mouse fibroblast cell in a water-containing state illustrated in FIGS. 41(a) and 41(b), which are observed and taken at a high magnification by a SEM, respectively.

FIG. 41(a) is an image of the MCMV-infected mouse fibroblast cell of Example 24 taken in 10 minutes after the infection by a SEM. FIG. 41(b) is an image of a portion of FIG. 41(a), which was observed and taken by being enlarged by a SEM, and FIGS. 42(a) and 42(b) are images of FIG. 41(b) which was observed and taken at a higher magnification by a SEM.

In Example 24, it has been confirmed that it is possible to clearly observe the viral particles on the surface of the MCMV-infected mouse fibroblast cell in a water-containing state. In addition, it has been also confirmed that the infection of a fibroblast cell by the MCMV proceeds within 10 minutes.

Example 25

A protective agent for electron microscopic observation was prepared in the same manner as in Example 19.

In the same manner as in Example 24, the mouse fibroblast cell cultured on a glass plate was infected with the mouse cytomegalovirus (MCMV) and immediately treated with the protective agent for electron microscopic observation. The MCMV-infected mouse fibroblast cell on which the protective agent for electron microscopic observation was dropped was introduced into the sample chamber of a SEM together with the glass plate, irradiated with an electron beam, and subjected to the SEM observation.

Figure 43:
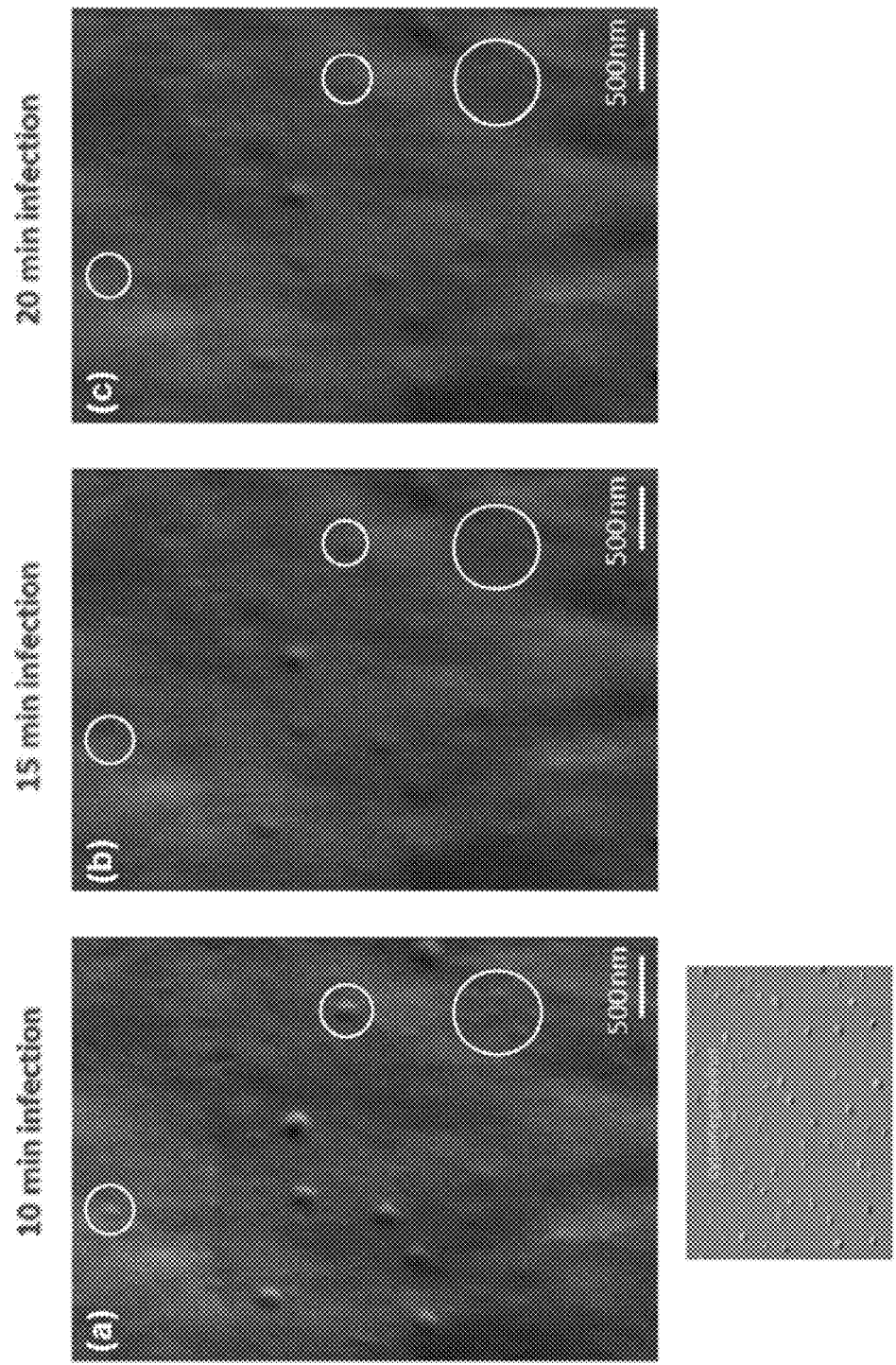
FIGS. 43(a), 43(b), and 43(c) are images of the MCMV-infected mouse fibroblast cell in a water-containing state of Example 25 taken by a SEM, respectively.

FIG. 43(a) is an image of the MCMV-infected mouse fibroblast cell of Example 25 taken in 10 minutes after the infection by a SEM. FIG. 43(b) is an image of FIG. 43(a) taken in 15 minutes after the infection by a SEM, and FIG. 43(c) is an image of FIG. 43(a) taken in 20 minutes after the infection by a SEM.

In Example 25, it has been confirmed that it is possible to observe the process in which the viral particles time-dependently penetrate from the surface of the host cell into the interior of the cell by endocytosis on the surface of the MCMV-infected mouse fibroblast cell in a water-containing state by using a SEM.

Example 26

A protective agent for electron microscopic observation was prepared in the same manner as in Example 19.

In the same manner as in Example 24, the Hep-2 cell of human pharyngeal cancer cell cultured on a glass plate was infected with the human poliovirus and immediately treated with the protective agent for electron microscopic observation. The human poliovirus-infected Hep-2 cell on which the protective agent for electron microscopic observation was dropped was introduced into the sample chamber of a SEM together with the glass plate, irradiated with an electron beam, and subjected to the SEM observation.

Figure 44:
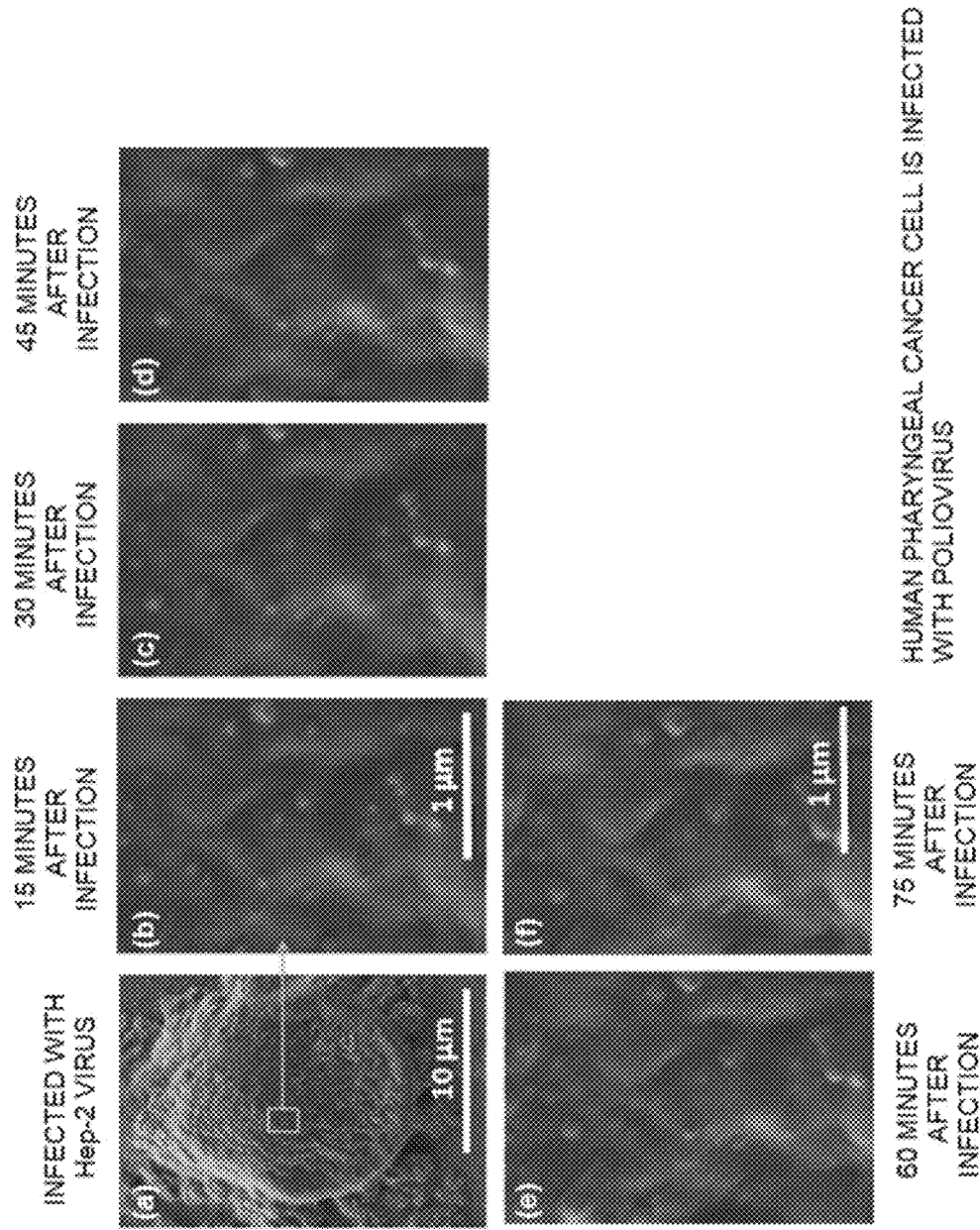
FIGS. 44(a) to 44(f) are images of the human poliovirus-infected human pharyngeal cancer cell (Hep-2 cell) in a water-containing state of Example 26 taken by a SEM, respectively.

FIG. 44(a) is an image of the human poliovirus-infected Hep-2 cell of Example 26 taken in 15 minutes after the infection by a SEM. FIG. 44(b) is an image of the region surrounded by a frame in FIG. 44(a), which was observed and taken by being enlarged by a SEM. In addition, FIG. 44(c) is an image of FIG. 44(b) taken in 30 minutes after the infection by a SEM, FIG. 44(d) is an image of FIG. 44(b) taken in 45 minutes after the infection by a SEM, FIG. 44(e) is an image of FIG. 44(b) taken in 60 minutes after the infection by a SEM, and FIG. 44(f) is an image of FIG. 44(b) taken in 75 minutes after the infection by a SEM.

In Example 26, it has been confirmed that it is possible to observe the process in which the viral particles time-dependently penetrate from the surface of the host cell into the interior of the cell by endocytosis on the surface of the human poliovirus-infected Hep-2 cell in a water-containing state by using a SEM.

Example 27

The mouse cytomegalovirus expressing GFP (GFP-M32-MCMV) was prepared as a virus, a dispersion containing the viral particles was inoculated onto a slide glass, and polybrene to charge the MCMV with a positive charge was added to the dispersion. Subsequently, the surface of the cover glass was treated with plasma to improve its hydrophilicity by exposing the hydroxyl group onto the surface, whereby the cover glass having a surface charged with a negative charge was prepared as an experimental group. In addition, an untreated cover glass was used as a control group. It was investigated whether there was a difference in amount of the MCMV particles adsorbed to the two kinds of cover glass of the experimental group and the control group by the polybrene treatment.

Figure 45:
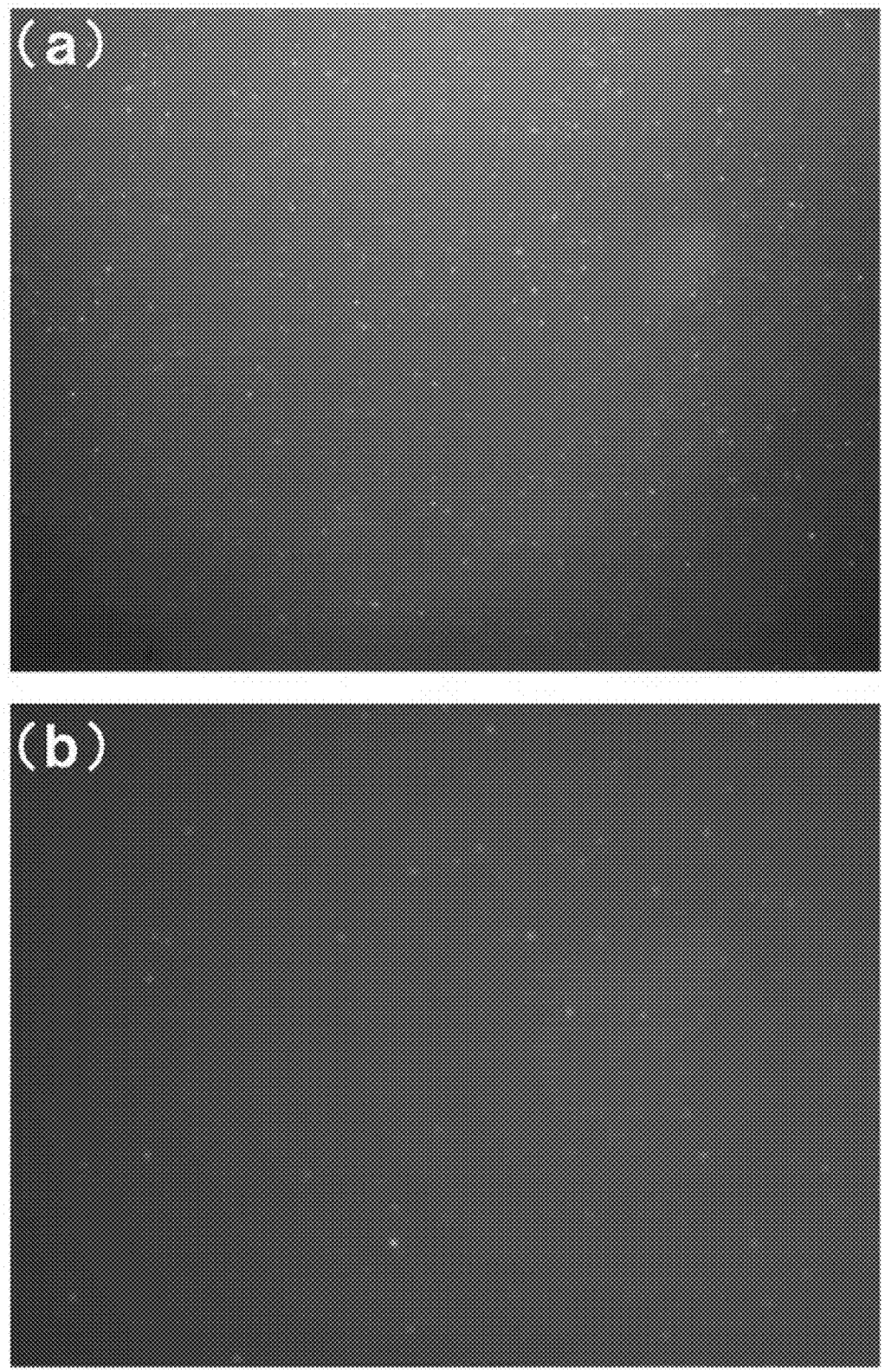
FIGS. 45(a) and 45(b) are photographs of MCMV of Example 27, which is prepared by adsorbing the MCMV treated with polybrene to the surface of cover glass and observed and taken by a fluorescence microscope, respectively.

FIGS. 45(a) and 45(b) are photographs of the MCMV of Example 27 taken by a fluorescence microscope. FIG. 45(a) is a photograph of the mouse cytomegalovirus (MCMV) treated with polybrene, which was adsorbed to the surface of the cover glass treated with plasma, observed, and taken. The fluorescent green dot in the drawing indicates the MCMV in a water-containing state adsorbed to the cover glass. FIG. 45(b) is a photograph of the MCMV treated with polybrene, which was adsorbed to the surface of the untreated cover glass as a control group, observed, and taken.

In Example 27, from the photograph of FIG. 45(a) taken by a fluorescence microscope, it has been confirmed that the cover glass is strongly negatively charged by enhancing the hydrophilicity of the cover glass through the plasma treatment as compared to the untreated cover glass and it can electrostatically adsorb and concentrate the MCMV particles which are positively charged through the polybrene treatment. On the other hand, from the photograph of FIG. 45(b) taken by a fluorescence microscope, it has been confirmed that the amount of the MCMV particles adsorbed to the cover glass which is not treated with plasma is smaller as compared to that of the slide glass that is the experimental group of FIG. 45(a). This demonstrates that MCMV particles can be concentrated to a level in which the MCMV particles can be observed under a microscope.

Example 28

A protective agent for electron microscopic observation and a surfactant-containing solution were prepared in the same manner as in Example 1.

As illustrated in FIG. 46(b), the mouse cytomegalovirus (MCMV) treated with polybrene was adsorbed to and concentrated on the surface of the cover glass treated with plasma. The MCMV which was adsorbed to and concentrated on the cover glass was treated with the protective agent for electron microscopic observation and the surfactant-containing solution. The MCMV on which the surfactant-containing solution was dropped was introduced into the sample chamber of a SEM together with the cover glass, irradiated with an electron beam, and subjected to the SEM observation.

FIG. 47 is a graph which illustrates the measurement results of the adsorption rate of the MCMV particles to the cover glass. The data on the left of the graph represents the concentration of virus in the dispersion of the viral particles before the MCMV particles which are positively charged through the polybrene treatment is adsorbed to the cover glass which is negatively charged by being irradiated with plasma. On the other hand, the data on the right of the graph represents the concentration of virus in the washing solution after the adsorption. The concentration of virus before and after the adsorption was subjected to the t-test and statistically analyzed, and it has been confirmed that it is $p<0.01$ and the concentration of the MCMV particles contained in the dispersion of viral particles is significantly decreased before and after the adsorption. From this result, the adsorption rate of the MCMV particles to the cover glass is determined to be 99.65% and thus almost all of the MCMV particles contained in the dispersion of viral particles have been confirmed to be adsorbed to the cover glass.

Figure 48:
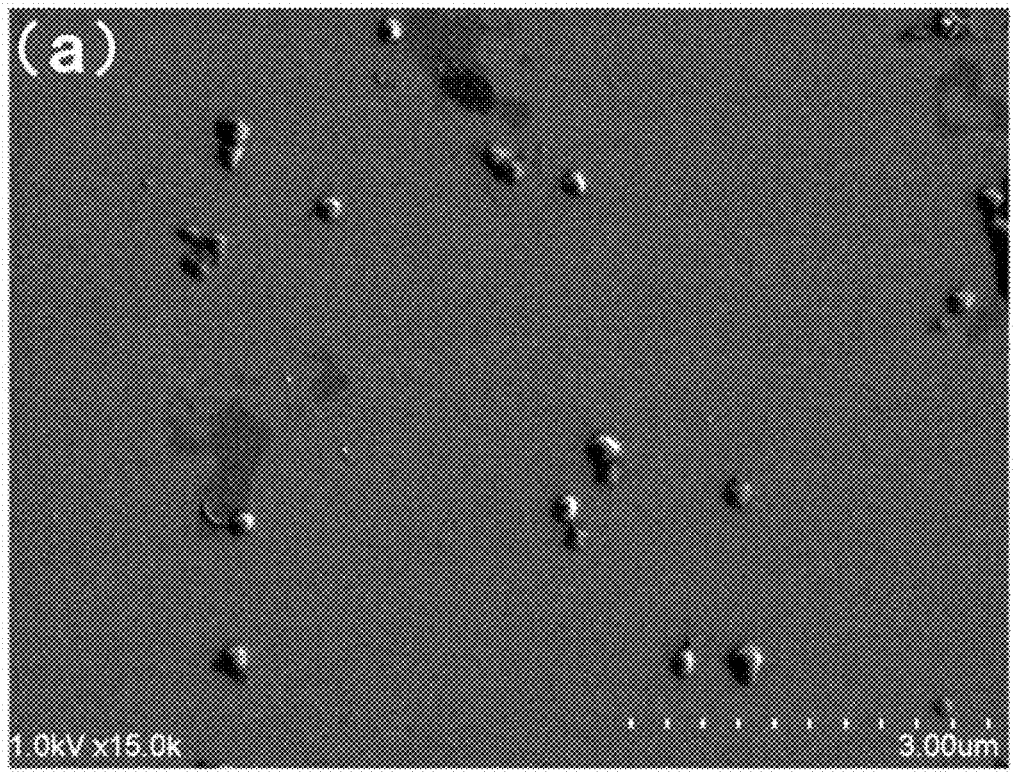
FIGS. 48(a) and 48(b) are images of MCMV of Example 28, which is adsorbed to cover glass, concentrated, and taken by a SEM, respectively.
Figure 48:
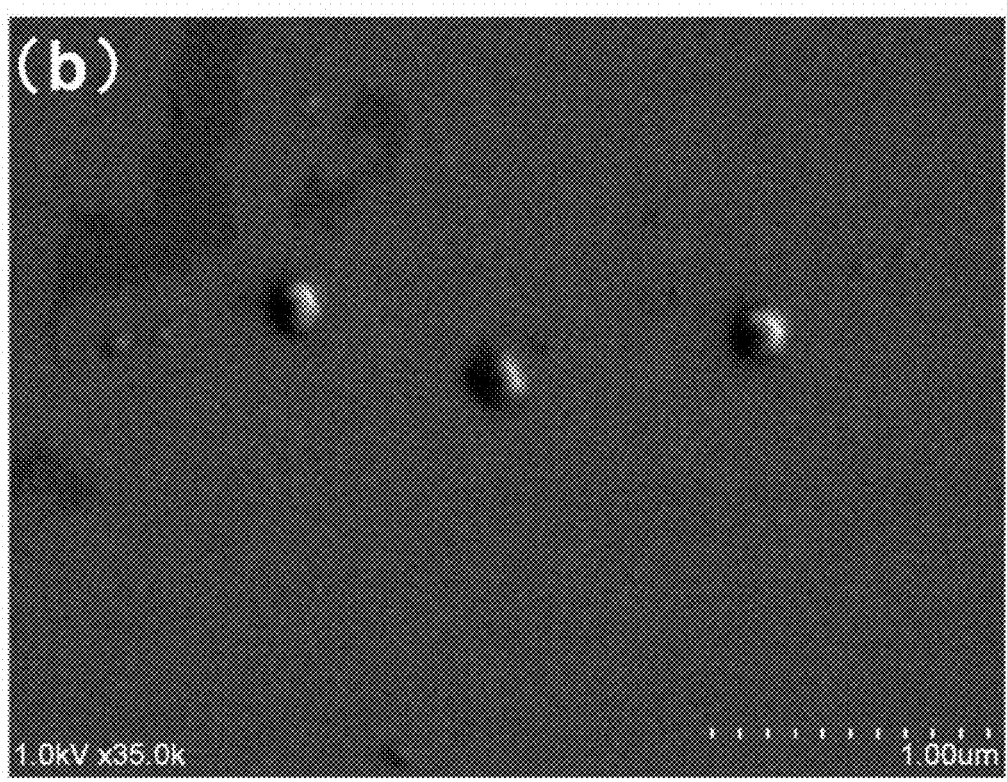
Figure 49:
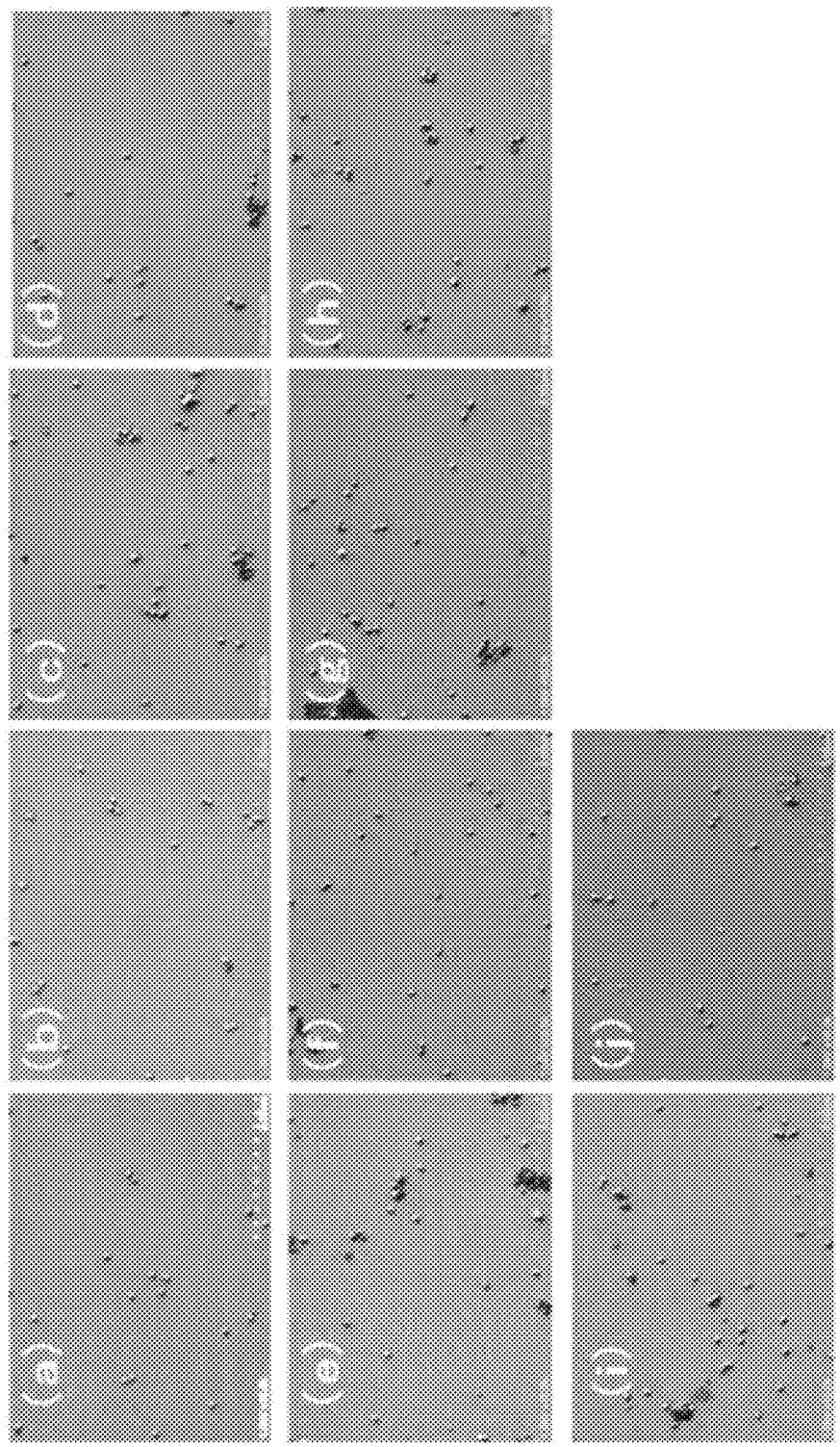
FIGS. 49(a) to 49(j) are images of viral particles of Example 29 taken in a plurality of different visual fields by a SEM, respectively.

FIGS. 48(a) and 48(b) are images of Example 28 taken by a SEM. FIG. 48(a) is an image of the MCMV which was prepared by adsorbing MCMV particles that were positively charged by being treated with polybrene to the cover glass that is negatively charged by being irradiated with plasma and concentrating it, and observed and taken at a magnification of 15,000-fold by a SEM. FIG. 48(b) is an image of a portion of FIG. 48(a), which was observed and taken at a magnification of 35,000-fold by a SEM.

In Example 28, it has been confirmed that the vital particles of the MCMV in a water-containing state can be adsorbed to the cover glass that is negatively charged by being irradiated with plasma and observed under an electron microscope by being positively charged through the polybrene treatment.

Example 29

A protective agent for electron microscopic observation and a surfactant-containing solution were prepared in the same manner as in Example 1.

In advance, the mouse fibroblast cell infected with MCMV was cultured, the culture supernatant containing MCMV particles was recovered, and this was used as Sample A. In addition, the culture supernatant containing MCMV particles was recovered and subjected to ultracentrifugation to separate the viral particles from the dense body, and only the viral particles thus recovered was used as Sample B. In the same manner as in Example 28, the MCMV which was adsorbed to and concentrated on the cover glass was treated with the protective agent for electron microscopic observation and the surfactant-containing solution. The MCMV on which the surfactant-containing solution was dropped was introduced into the sample chamber of a SEM together with the cover glass, irradiated with an electron beam, and subjected to the SEM observation.

FIGS. 49(a) to 49(j) are images of Example 29 taken by a SEM, and they are images of viral particles taken in a plurality of different visual fields by a SEM, respectively. In the images of FIGS. 49(a) to 49(j) taken by a SEM, the number of viral particles in the visual field was counted and the average value of viral particles in the 10 visual fields was calculated. As a result, in the case of using the dispersion of viral particles of sample B, the number of viral particles was 17 in FIG. 49(a), 21 in FIG. 49(b), 35 in FIG. 49(c), 20 in FIG. 49(d), 15 in FIG. 49(e), 32 in FIG. 49(f), 25 in FIG. 49(g), 17 in FIG. 49(h), 36 in FIG. 49(i), and 14 in FIG. 49(j), and the average number of viral particles in the 10 visual fields was 23.2 particles/field. The concentration of virus in the virus dispersion was calculated based on the average number of viral particles in these 10 visual fields, and it was $8.35 \times 10^{10}$ particles/ml. Incidentally, although it is not illustrated, the concentration of virus was $6.35 \times 10^9$ particles/ml in the case of using the dispersion of viral particles of Sample A.

Figure 50:
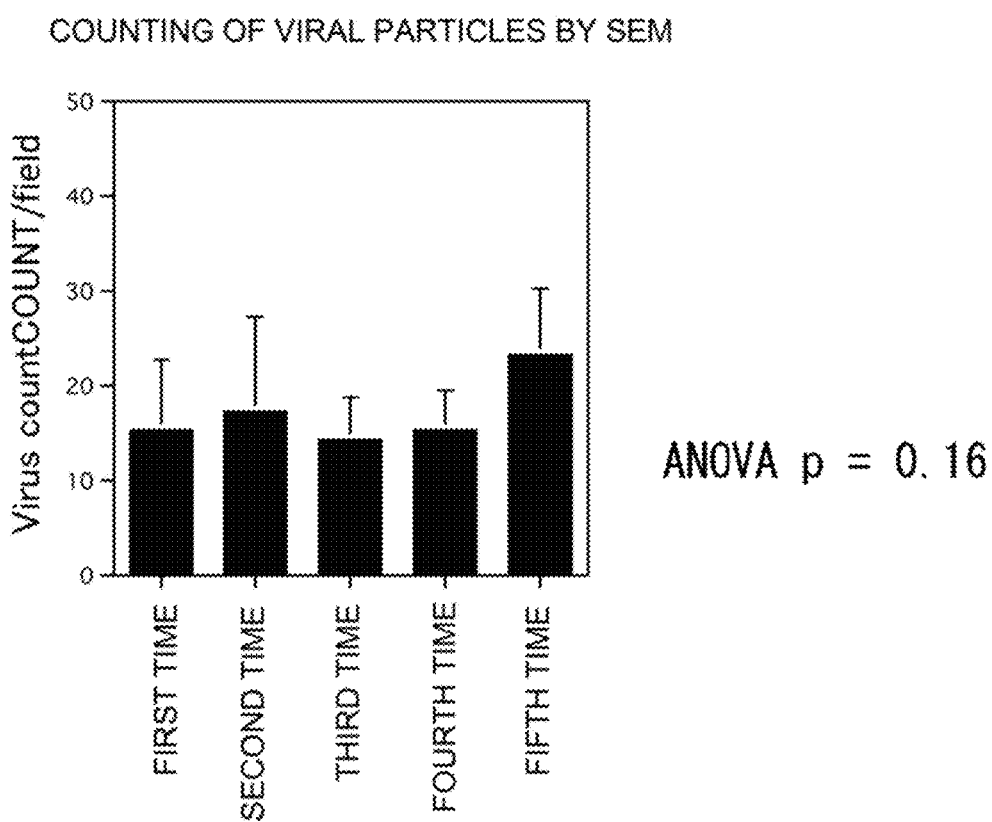
FIG. 50 is a graph which illustrates the average number of viral particles when the same experiment as in Example 29 is repeated 5 times.

FIG. 50 is a graph which illustrates the number of viral particles when the same experiment is repeated 5 times by using Sample B. The average value for the 5 times of experiments was calculated, and the average number of viral particles was $17.2 \pm 2.5$ particles/field. The concentration of virus in the virus dispersion of the MCMV virus was calculated based on the average number of viral particles for these 5 times of experiments, and it was $6.55 \times 10^{10} \pm 2.56 \times 10^{10}$ particles/ml. Incidentally, although it is not illustrated, the concentration of virus was $8.73 \times 10^9 \pm 7.14 \times 10^9$ particles/ml in the case of using the dispersion of viral particles of Sample A.

In addition, the concentration of virus by the plaque assay and the quantitative PCR method which are methods of the prior art was quantified by using the same dispersion of viral particles as a sample. The results are presented in Table 1.

TABLE 1

| | Sample A | Sample B |
|---|---|---|
| Plaque assay | $1.3 \times 10^8 \pm 7 \times 10^7$ PFU/ml | $2.2 \times 109 \pm 6 \times 10^8$ PFU/ml |
| Quantitative PCR method (MCMV copy numbers) | $1.09 \times 10^{11} \pm 9.5 \times 10^9$ copies/ml | $1.35 \times 10^{10} \pm 1.0 \times 10^9$ copies/ml |
| Example 29 | $8.73 \times 10^9 \pm 7.14 \times 10^9$ particles/ml | $6.55 \times 10^{10} \pm 2.56 \times 10^{10}$ particles/ml |

As a result, the concentration of virus has been confirmed to be $1.3 \times 10^8 \pm 7 \times 10^7$ PFU/ml by the plaque assay and $1.09 \times 10^{11} \pm 9.5 \times 10^9$ copies/ml by the quantitative PCR method in the case of using the dispersion of viral particles of Sample A. On the other hand, the concentration of virus has been confirmed to be $2.2\times10^9\pm6\times10^8$ PFU/ml by the plaque assay and $1.35\times10^{10}\pm1.0\times10^9$ copies/ml by the quantitative PCR method in the case of using the dispersion of viral particles of Sample B. When these results are compared with the results of Example 29, the concentration of viral particles calculated by the counting and quantitative method by the electron microscopic observation of viral particles using the protective agent for electron microscopic observation of the present invention is consistent with the result by the plaque assay or quantitative PCR method that is a method of the prior art.

Furthermore, the characteristics of the methods of the prior art and the counting and quantitative method by the electron microscopic observation of viral particles using the protective agent for electron microscopic observation of the present invention are presented in Table 2.

TABLE 2

| Virus quantification method | Detection principle | Reproducibility | Time | Labor | Cost | Quantitativity |
|---|---|---|---|---|---|---|
| Plaque assay | Infecting capability | Medium | Week | High degree | Inexpensive | +Indirect |
| Quantitative PCR method | Viral DNA | Medium | One day | Medium degree | Moderate | +Indirect |
| Flow virometry assay | Viral particles | High | Several hours | Medium degree | High | +Indirect |
| TEM method | Viral particles | Medium | Several days | High degree | High | −Direct |
| Example 29 | Viral particles | High | Several hours | Low degree | Moderate | +Direct |

Consequently, it is possible to accurately quantify the concentration of virus in a short time by using the counting and quantitative method by the electron microscopic observation of viral particles using the protective agent for electron microscopic observation of the present invention.

Example 30

A protective agent for electron microscopic observation and a surfactant-containing solution were prepared in the same manner as in Example 1.

In Example 30, it was tried to detect DNA-containing viral particles in the electron microscopic observation of viral particles in a water-containing state. In the same manner as in Example 28, the MCMV that was adsorbed to and concentrated on the cover glass was treated with only the protective agent for electron microscopic observation and the surfactant-containing solution as a control group. As an experimental group, the MCMV that was adsorbed to and concentrated on the cover glass was treated with the protective agent for electron microscopic observation and the surfactant-containing solution after being treated with uranium acetate. Uranium acetate is able to stain the DNA and peptide. In addition, as an experimental group, the MCMV that was adsorbed to and concentrated on the cover glass was treated with the protective agent for electron microscopic observation and the surfactant-containing solution after being treated with cisplatin. Cisplatin is able to stain the DNA and peptide. The MCMV subjected to each of these treatments was introduced into the sample chamber of a SEM together with the cover glass, irradiated with an electron beam, and subjected to the SEM observation.

Figure 51:
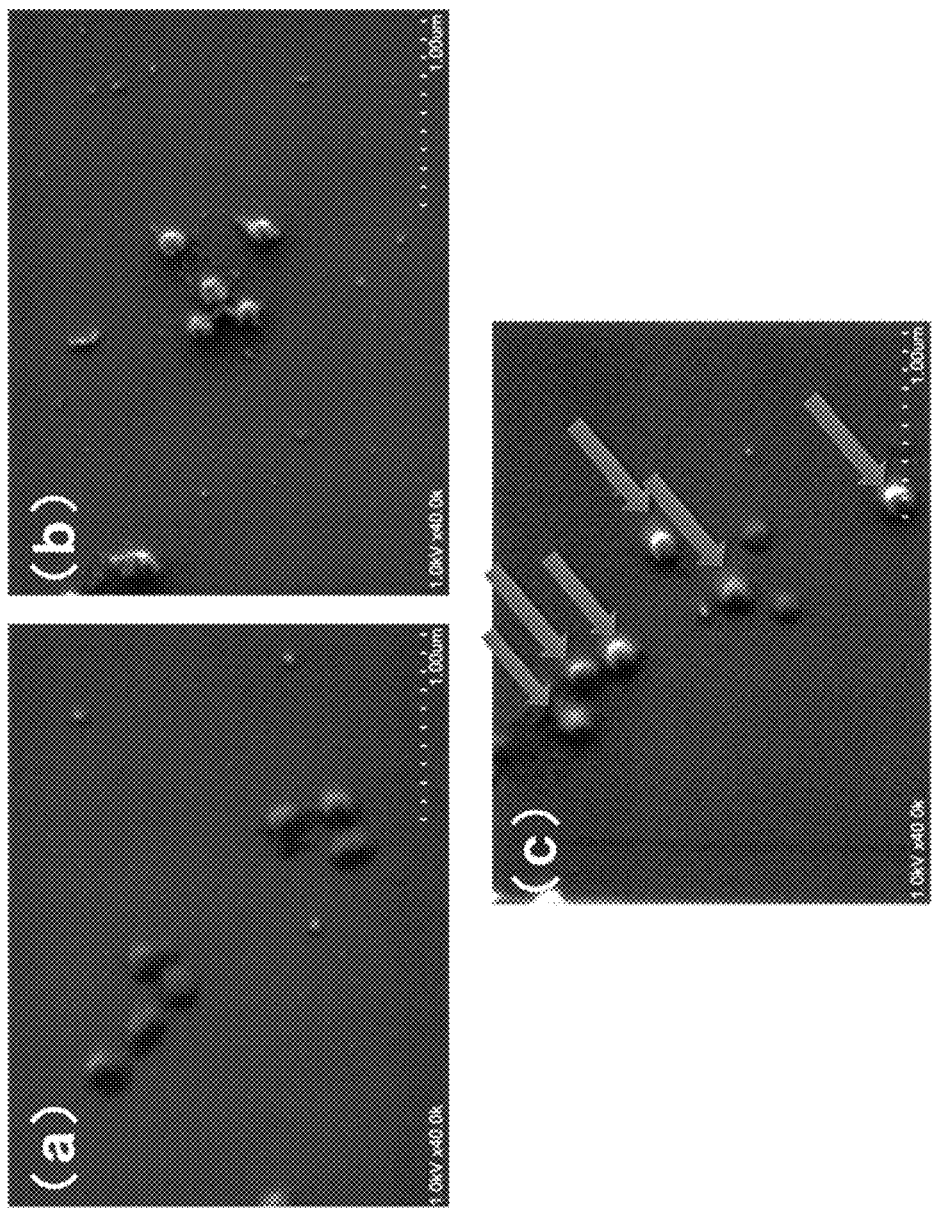
FIGS. 51(a), 51(b), and 51(c) are images of MCMV in a water-containing state of Example 30 taken by a SEM, respectively.

FIG. 51(a) is an image of the MCMV of a control group taken by a SEM, and FIG. 51(b) is an image of the MCMV which was treated with uranium acetate and taken by a SEM. In addition, FIG. 51(c) is an image of the MCMV which was treated with cisplatin and taken by a SEM, and the arrow in the drawing indicates the DNA-containing viral particles.

All of them are images of the MCMV in a water-containing state which was observed and taken at a magnification of 10,000-fold by a SEM.

In Example 30, it has been confirmed that the observation of viral particles by an immunoelectron microscopy in a water-containing state is also possible. In addition, it is considered that it can be confirmed that the MCMV treated with the protective agent for electron microscopic observation and the surfactant-containing solution contains the DNA.

Example 31

A protective agent for electron microscopic observation and a surfactant-containing solution were prepared in the same manner as in Example 1.

In the same manner as in Example 28, the MCMV that was adsorbed to and concentrated on the cover glass was bound to an anti-DNA antibody as a primary antibody and then to an antibody which exhibited binding property to the primary antibody and was modified with a gold colloid as a secondary antibody, and then treated with the protective agent for electron microscopic observation and the surfactant-containing solution. The two antibodies-bound MCMV on which the surfactant-containing solution was dropped was introduced into the sample chamber of a SEM together with the cover glass, irradiated with an electron beam, and subjected to the SEM observation.

Figure 52:
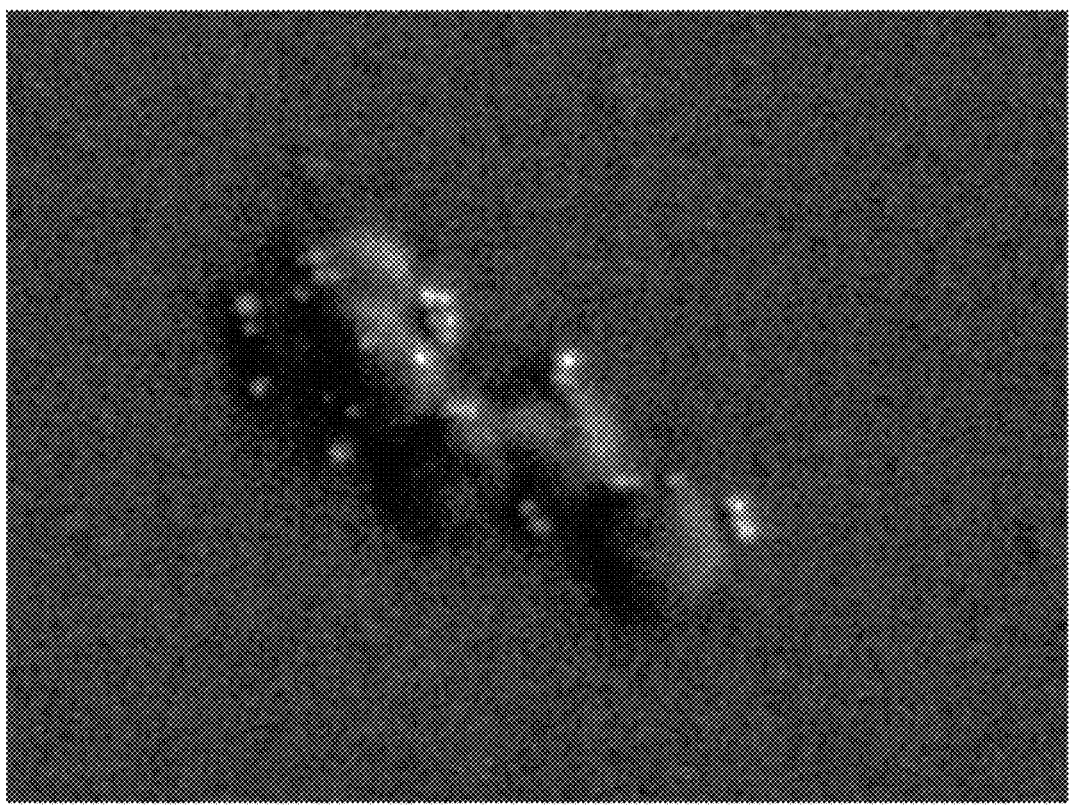
FIG. 52 is an image of Example 31 taken by a SEM, it is an image of MCMV in a water-containing state which is prepared by binding the anti-DNA antibody as a primary antibody to the MCMV, binding an antibody which exhibits binding property to the primary antibody and modified with a gold colloid to the MCMV as a secondary antibody, and then treating it with a protective agent for electron microscopic observation and an surfactant-containing solution and observed and taken by a SEM.

FIG. 52 is an image of the two antibodies-bound MCMV in a water-containing state which was observed and taken at a magnification of 10,000-fold by a SEM.

In Example 31, it has been confirmed that the observation of viral particles by an immunoelectron microscopy, namely the live immunoelectron microscopy in a water-containing state is also possible. In addition, it is considered that the distinguishment of a DNA virus from a RNA virus by the electron microscopic observation is also possible since an anti-DNA antibody is used as the primary antibody.

Example 32

A protective agent for electron microscopic observation and a surfactant-containing solution were prepared in the same manner as in Example 1.

The petal of *Adonis amurensis* rhizome was collected as a biological tissue of a plant, placed on the sample stage illustrated in FIG. 23(a), and immediately treated with the protective agent for electron microscopic observation and the surfactant-containing solution. The petal of *Adonis amurensis* rhizome on which the surfactant-containing solution was dropped was introduced into the sample chamber of a SEM, irradiated with an electron beam, and subjected to the SEM observation.

Figure 53:
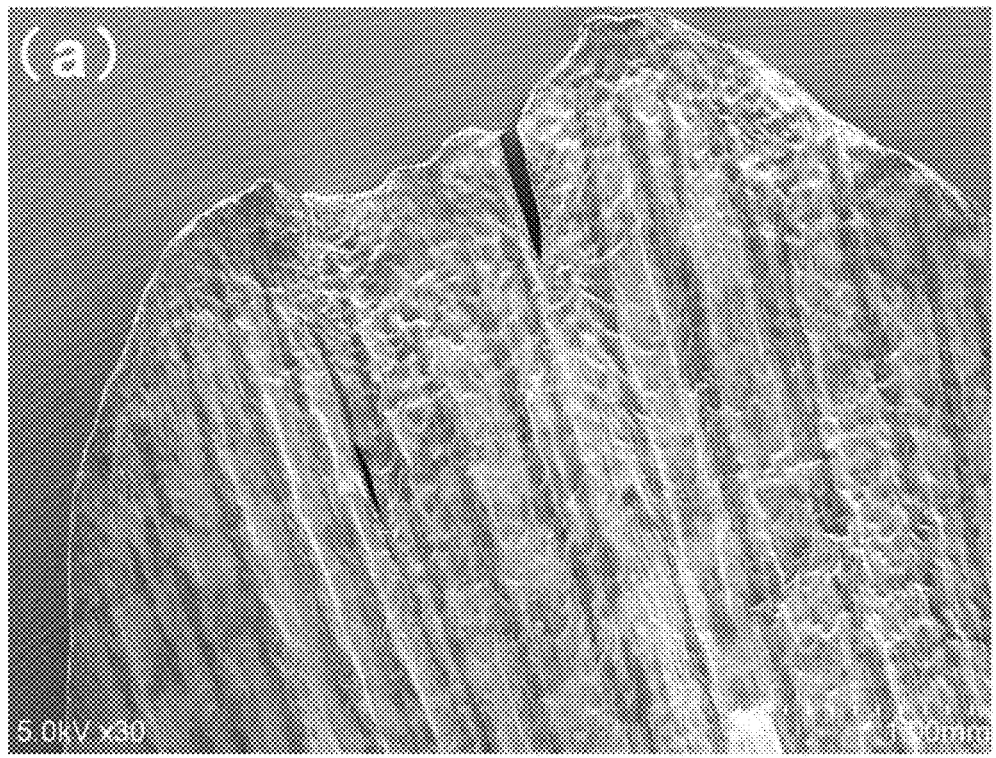
FIGS. 53(a) and 53(b) are images of Example 32 taken by a SEM, respectively.
Figure 53:
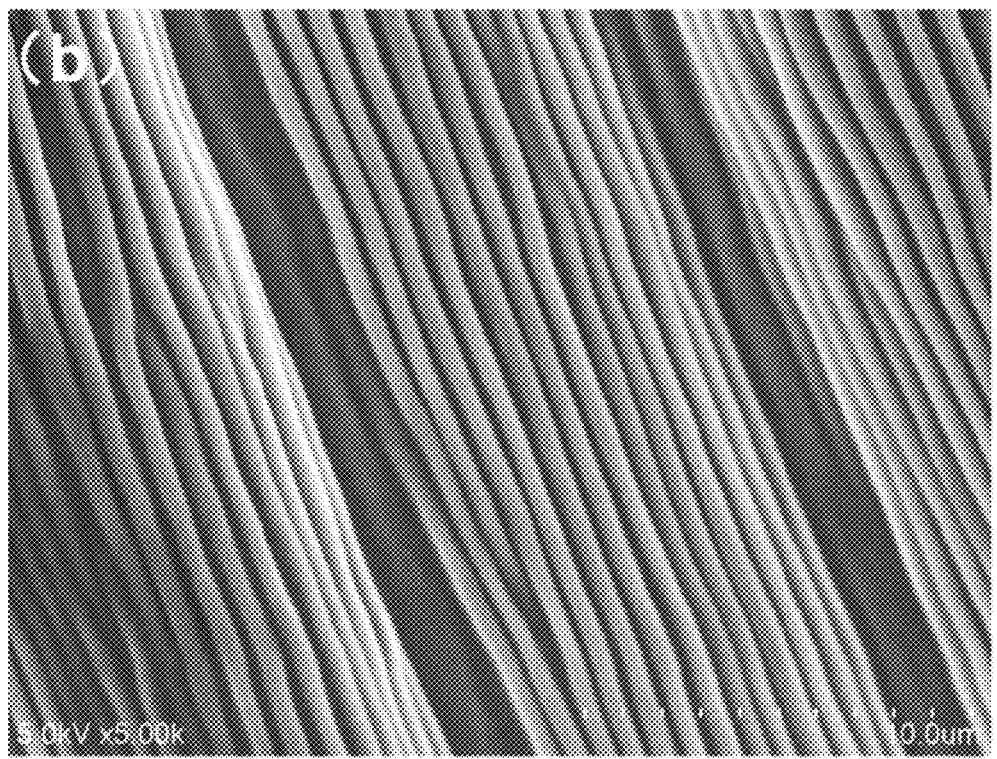

FIG. 53(a) is an image of the petal of *Adonis amurensis* rhizome in a water-containing state, which was observed and taken at a magnification of 30-fold by a SEM. In addition, FIG. 53(*b*) is an image of a portion of FIG. 53(*a*), which was observed and taken at a magnification of 5000-fold by a SEM.

In Example 32, it has been possible to confirm the cell in a surviving state of the petal of *Adonis amurensis* rhizome in a water-containing state under an electron microscope. In particular, it has been confirmed that a groove-like compositional arrangement is regularly formed on the surface of the petal in the observation at a high magnification.

Example 33

A protective agent for electron microscopic observation and a surfactant-containing solution were prepared in the same manner as in Example 1.

A leaf of dayflower was collected as a biological tissue of a plant, subjected to a primary chemical fixation treatment with 10% (w/w) neutral buffered formalin, and then immersed in the protective agent for electron microscopic observation for 1 minute as a pretreatment. The leaf of dayflower treated with the protective agent for electron microscopic observation was treated with the surfactant-containing solution. The leaf of dayflower on which the surfactant-containing solution was dropped was introduced into the sample chamber of a SEM, irradiated with an electron beam, and subjected to the SEM observation.

Figure 54:
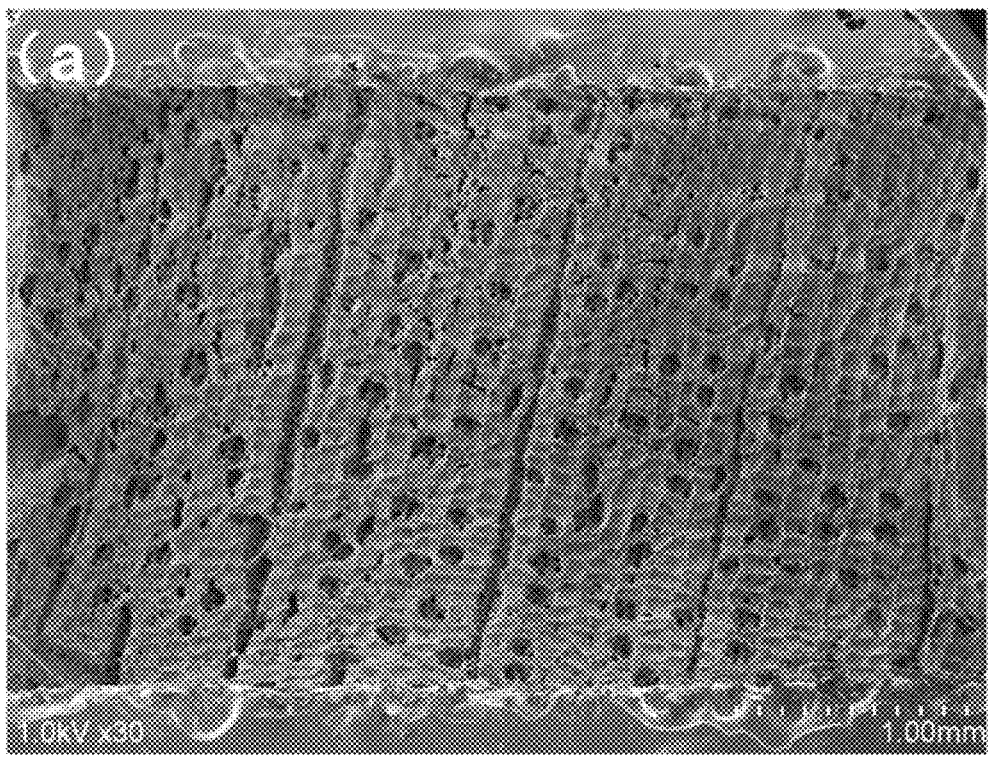
FIGS. 54(a) and 54(b) are images of Example 33 taken by a SEM, respectively.
Figure 54:
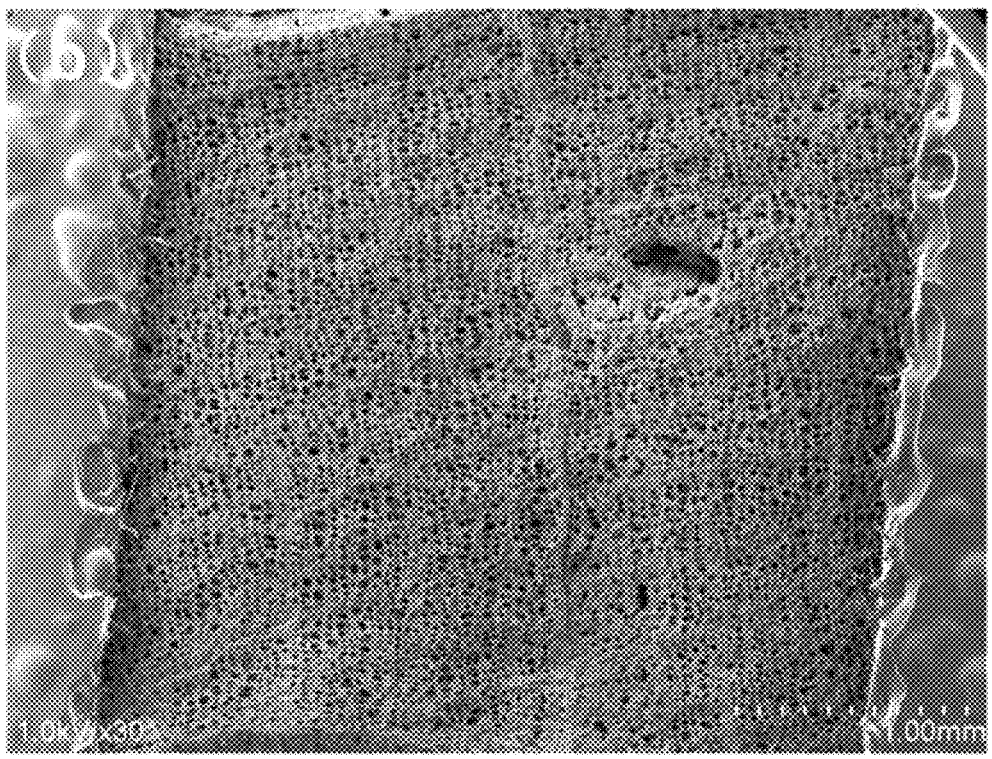

FIG. 54(*a*) is an image of the mesophyll cell on the front side of the leaf of dayflower, which was observed and taken at a magnification of 30-fold by a SEM. In addition, FIG. 54(*b*) is an image of the mesophyll cell on the back side of the leaf of dayflower, which was observed and taken at a magnification of 30-fold by a SEM.

Figure 55:
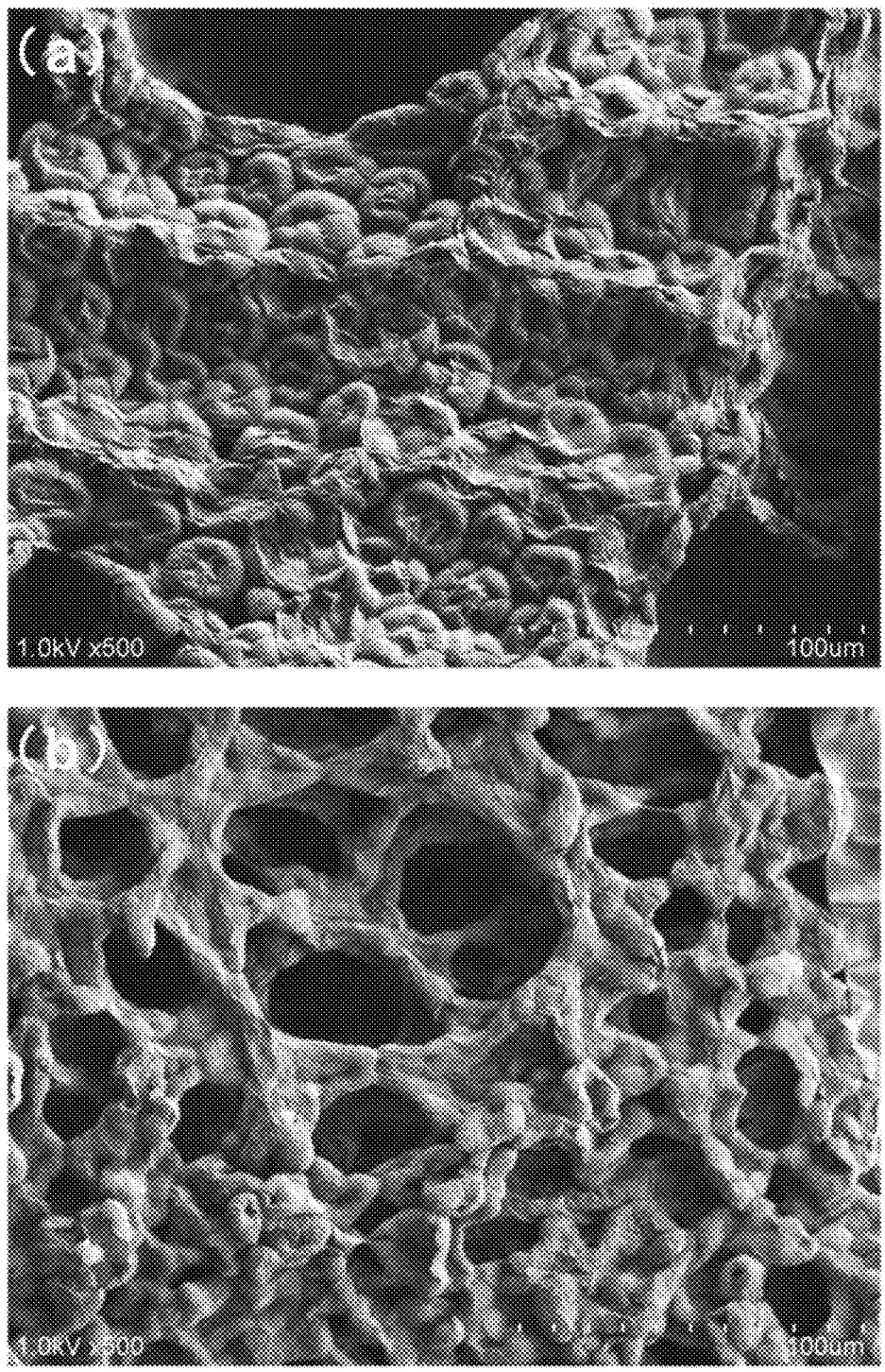
FIGS. 55(a) and 55(b) are images of the mesophyll cells of the leaf of dayflower in a water-containing state illustrated in FIGS. 54(a) and 54(b), which are observed and taken at a magnification of 500-fold by a SEM.
Figure 56:
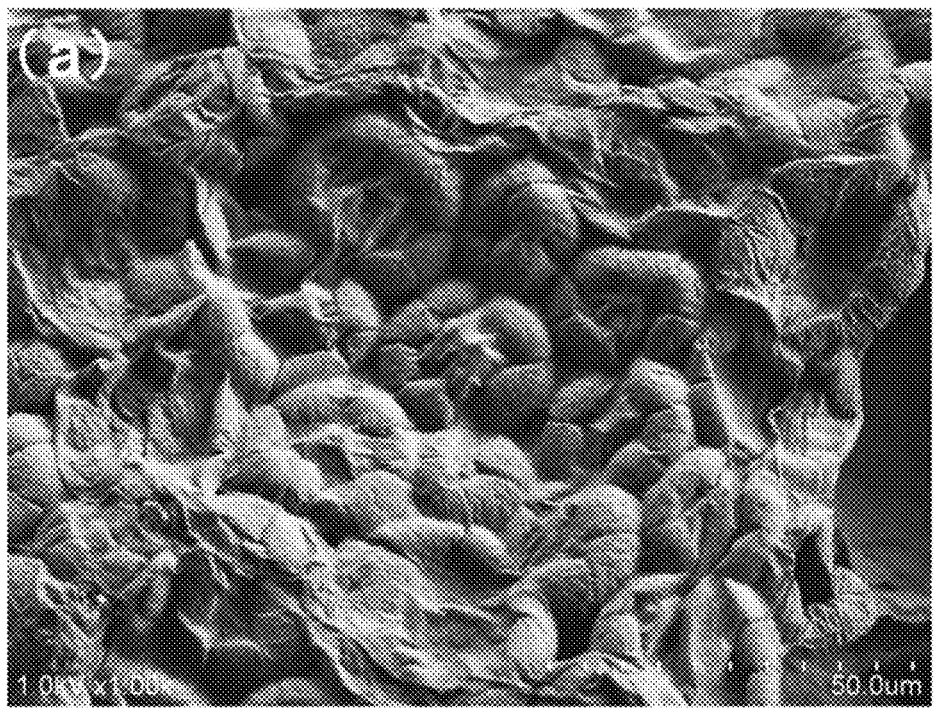
FIGS. 56(a) and 56(b) are images of the mesophyll cells of the leaf of dayflower in a water-containing state illustrated in FIGS. 54(a) and 54(b), which are observed and taken at a magnification of 1000-fold by a SEM.
Figure 56:
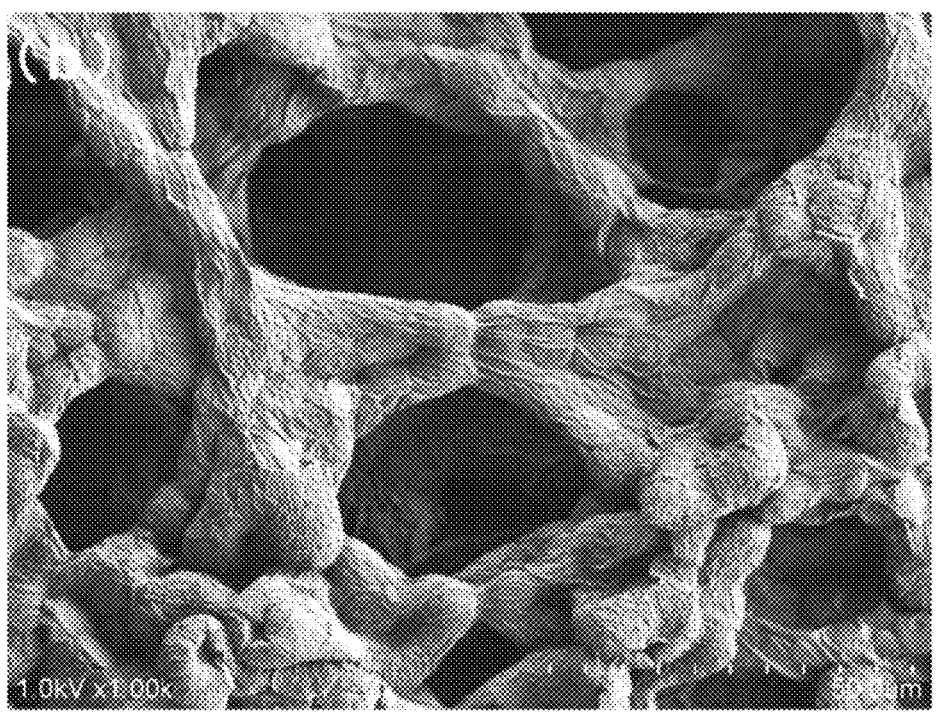

FIGS. 55(*a*) and 55(*b*) are images of the samples of FIGS. 54(*a*) and 54(*b*), which were observed and taken at a magnification of 500-fold by a SEM. In addition, FIGS. 56(*a*) and 56(*b*) are images of the samples of FIGS. 54(*a*) and 54(*b*), which were observed and taken at a magnification of 1000-fold by a SEM.

In Example 33, it has been possible to confirm the cell in a water-containing state of the leaf of dayflower under an electron microscope. In particular, it has been confirmed that the shape or density of the mesophyll cell is greatly different on the front side and the back side and the density of the mesophyll cell is sparser on the back side of the leaf in the observation at a high magnification.

Example 34

A protective agent for electron microscopic observation and a surfactant-containing solution were prepared in the same manner as in Example 1.

Figure 23:
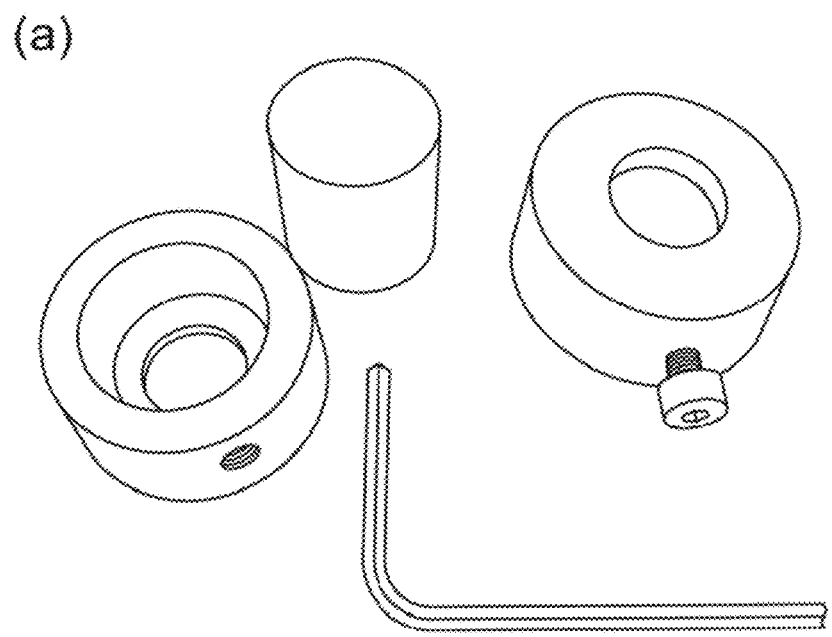
FIGS. 23(a) and 23(b) are photographs which illustrate a sample stage for electron microscopic observation of the present invention, respectively.
Figure 23:
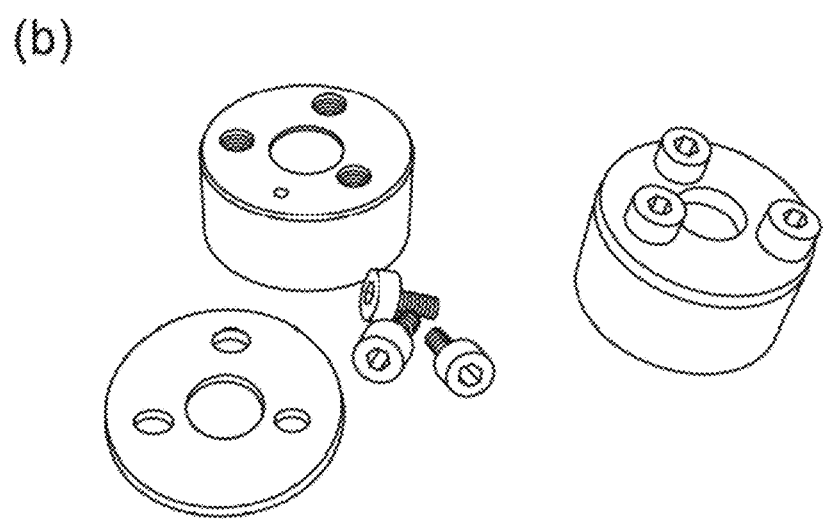

A living planarian was placed on the sample stage illustrated in FIG. 23(*a*), and immediately treated with the protective agent for electron microscopic observation and the surfactant-containing solution. The living planarian on which the surfactant-containing solution was dropped was introduced into the sample chamber of a SEM, irradiated with an electron beam, and subjected to the SEM observation.

Figure 57:
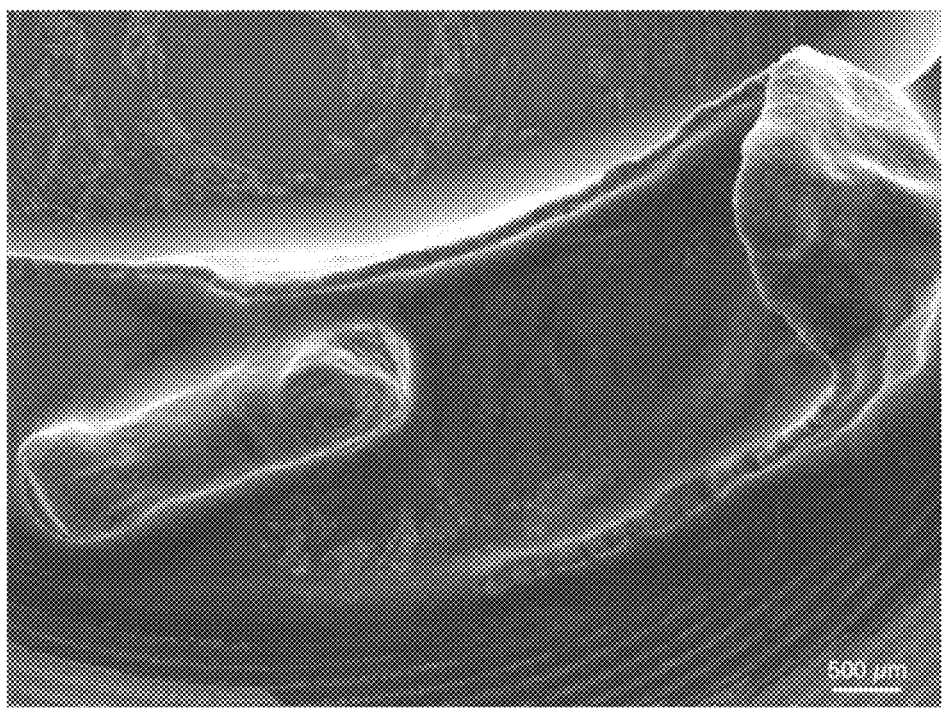
FIG. 57 is a photograph which illustrates an image of Example 34 taken by a SEM. It is an image of a planarian in a water-containing state which is prepared by dropping a protective agent for electron microscopic observation onto a living planarian and treating it with a surfactant-containing solution and observed and taken by a SEM.

FIG. 57 is an image of a planarian which was observed and taken in a water-containing state by a SEM. The scale bar in the drawing represents 500 μm.

In Example 34, it has been possible to confirm the survival of a planarian in a water-containing state under an electron microscope.

Example 35

A protective agent for electron microscopic observation and a surfactant-containing solution were prepared in the same manner as in Example 1.

A living *Drosophila* in the compound eye developmental process of *Drosophila* was immediately treated with the protective agent for electron microscopic observation and the surfactant-containing solution. The living *Drosophila* on which the surfactant-containing solution was dropped was introduced into the sample chamber of a SEM, irradiated with an electron beam, and subjected to the SEM observation.

Figure 58:
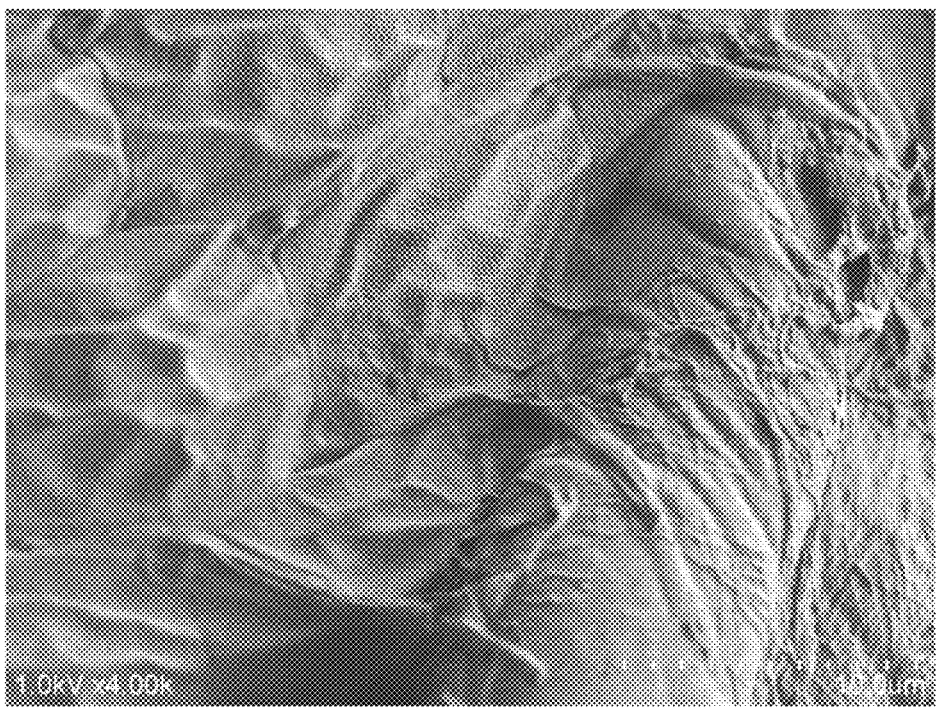
FIG. 58 is a photograph which illustrates an image of Example 35 taken by a SEM. It is an image of the developmental edge site of the *Drosophila* compound eyes in a water-containing state, which is prepared by dropping a protective agent for electron microscopic observation onto a living *Drosophila* in the compound eye developmental process of *Drosophila* and treating it with a surfactant-containing solution and observed and taken by a SEM.

FIG. 58 is an image of the developmental edge site of the *Drosophila* compound eyes, which was observed and taken in a water-containing state at a magnification of 4000-fold by a SEM.

In Example 35, it has been possible to confirm the compound eye developmental process of *Drosophila* in a water-containing state under an electron microscope.

Example 36

A protective agent for electron microscopic observation and a surfactant-containing solution were prepared in the same manner as in Example 1.

A hydra in a living state in the regenerative process of hydra head was immediately treated with the protective agent for electron microscopic observation and the surfactant-containing solution. The living hydra on which the surfactant-containing solution was dropped was introduced into the sample chamber of a SEM, irradiated with an electron beam, and subjected to the SEM observation.

Figure 59:
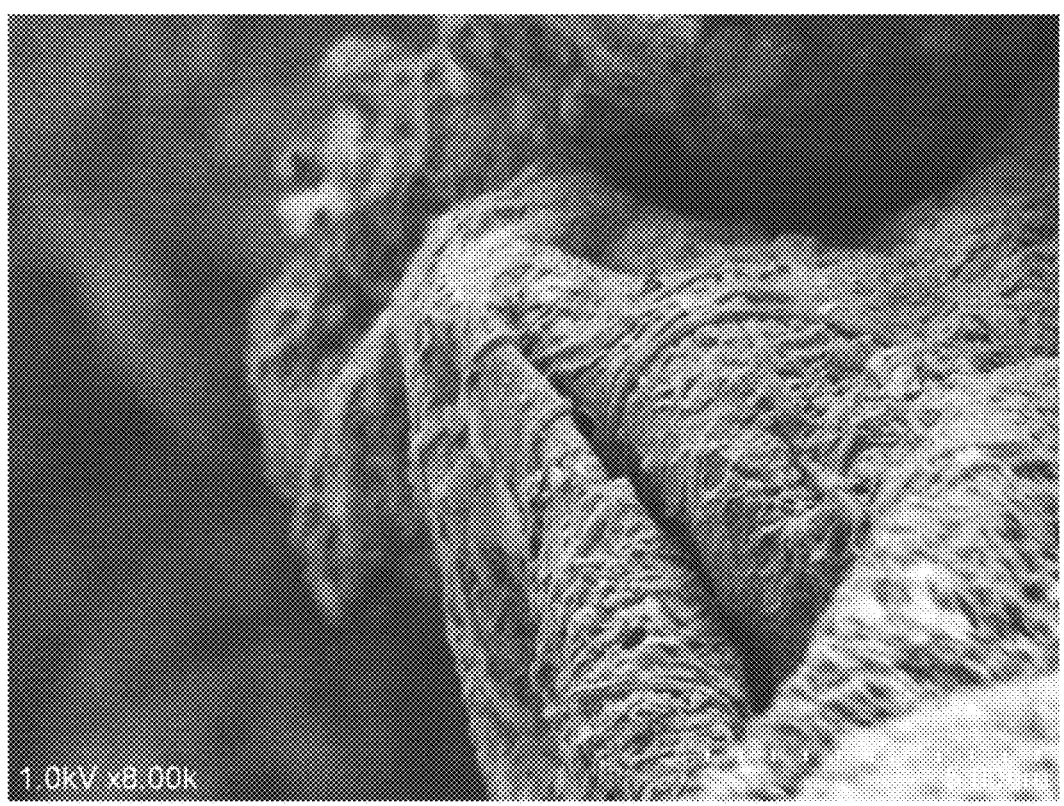
FIG. 59 is a photograph which illustrates an image of Example 36 taken by a SEM. It is an image of the regenerative tip of hydra head in a water-containing state, which is prepared by dropping a protective agent for electron microscopic observation onto a living hydra in the regenerative process of hydra and treating it with a surfactant-containing solution and observed and taken by a SEM.

FIG. 59 is an image of the regenerative tip of hydra head, which was observed and taken in a water-containing at a magnification of 8000-fold by a SEM.

In Example 36, it has been possible to confirm the regenerative process of head of a hydra in a water-containing state under an electron microscope.

Example 37

A protective agent for electron microscopic observation and a surfactant-containing solution were prepared in the same manner as in Example 1.

A culture medium containing a prokaryotic organism, Nata de coco bacteria, and yeast as a single cell were dropped on a glass plate, and immediately treated with the protective agent for electron microscopic observation. The culture medium containing a prokaryotic organism, Nata de coco bacteria, and yeast on which the protective agent for electron microscopic observation was dropped was introduced into the sample chamber of a SEM, irradiated with an electron beam, and subjected to the SEM observation. In addition, a culture medium containing *Escherichia coli* as a single cell was subjected to the same treatment and the TEM observation.

Figure 60:
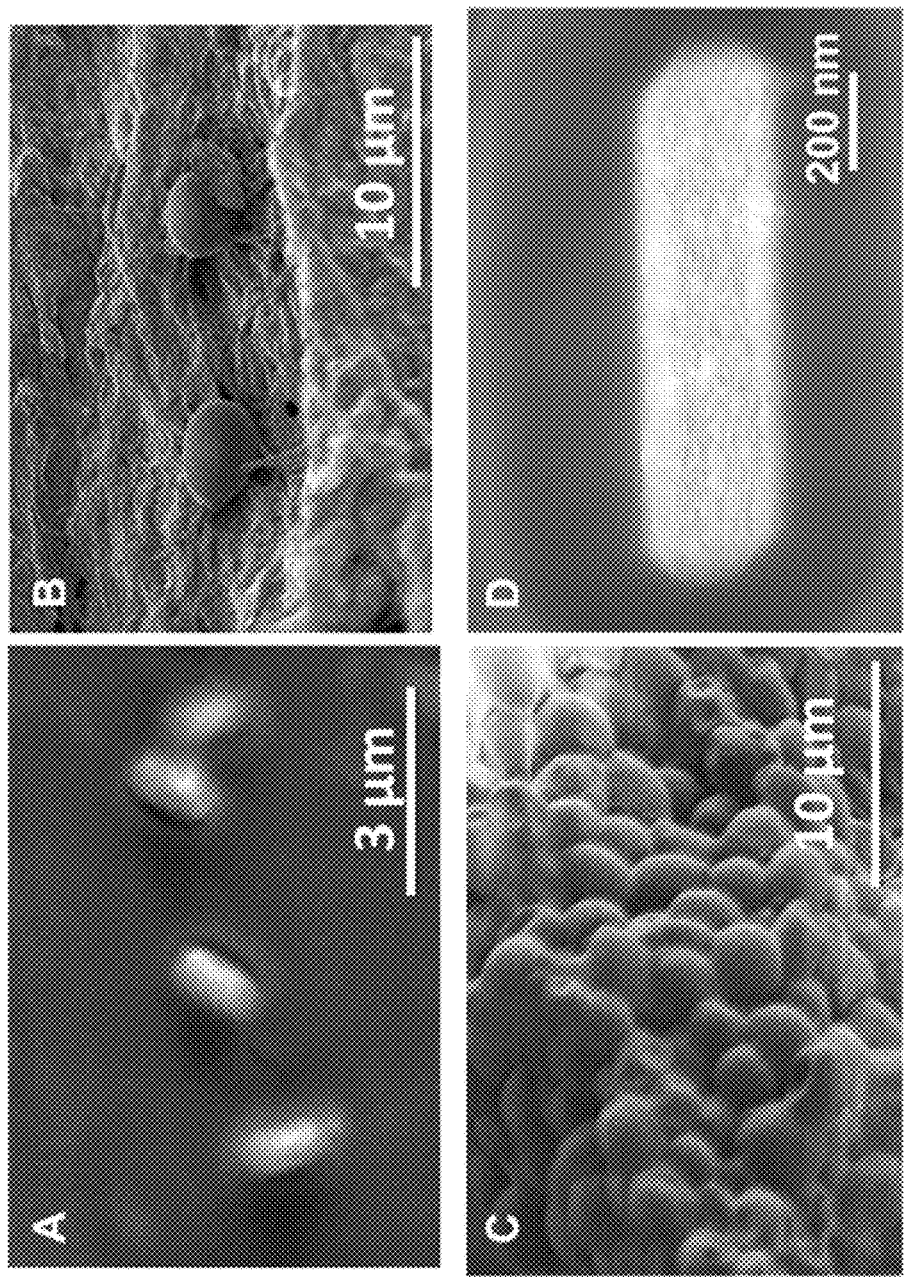
FIGS. 60(a) to 60(c) are images of Example 37 taken by a SEM, respectively.
FIG. 60(d) is an image of Example 37 taken by a TEM.

FIG. 60(*a*) is an image of a prokaryotic organism in a water-containing state taken by a SEM. The scale bar in the drawing represents 3 μm. In addition, FIG. 60(*b*) is an image of Nata de coco bacteria in a water-containing state taken by a SEM. The scale bar in the drawing represents 10 μm. FIG. 60(*c*) is an image of yeast in a water-containing state taken by a SEM. The scale bar in the drawing represents 10 μm. FIG. 60(*d*) is an image of *Escherichia coli* in a water-containing state taken by a TEM. The scale bar in the drawing represents 200 nm.

In Example 37, it has been possible to confirm a cell in the surviving state of all of a prokaryotic organism, Nata de coco bacteria, yeast, and *Escherichia coli* under an electron microscope.

Example 38 and Comparative Example 10

A protective agent for electron microscopic observation and a surfactant-containing solution were prepared in the same manner as in Example 1.

The artificial human skin obtained by sterically three-dimensionally culturing a normal human skin cell was treated with the protective agent for electron microscopic observation and the surfactant-containing solution (Example 38).

On the other hand, as a control group, the artificial human skin obtained by sterically three-dimensionally culturing a normal human skin cell was chemically fixed with glutaraldehyde of a general fixing solution for electron microscopic observation (Comparative Example 10).

The artificial human skins of Example 38 and Comparative Example 10 were observed by a SEM, respectively. Furthermore, a plurality of sites were selected from the epidermis through the dermis, and the respective sites were subjected to the elemental analysis by EDS to measure the element distribution (Na, Mg, P, S, CI, K and Ca) in the interior of the artificial skin. Incidentally, the elements of the measurement target were detected in a state of being ionized in the skin of the present test example.

Figure 61:
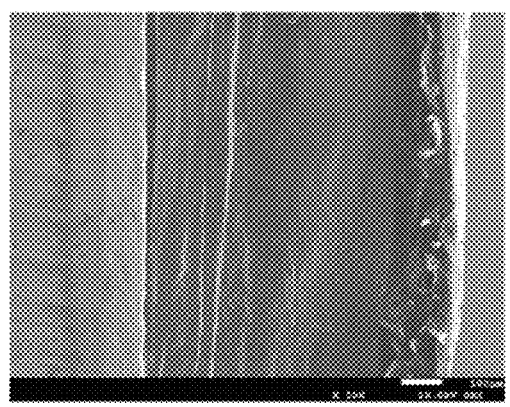
FIG. 61(a) is an image of Example 38 taken by a SEM.
FIG. 61(b) is a diagram which illustrates the site subjected to EDS analysis in Example 38.
FIG. 61(c) is the chart obtained by EDS analysis of Example 38.
Figure 61:
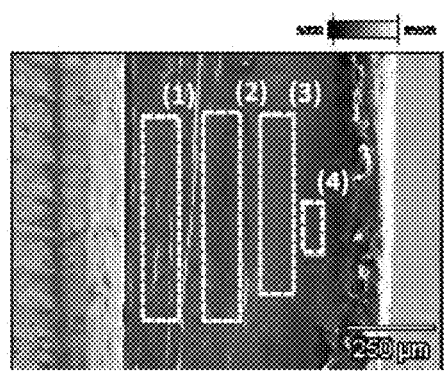
Figure 61:
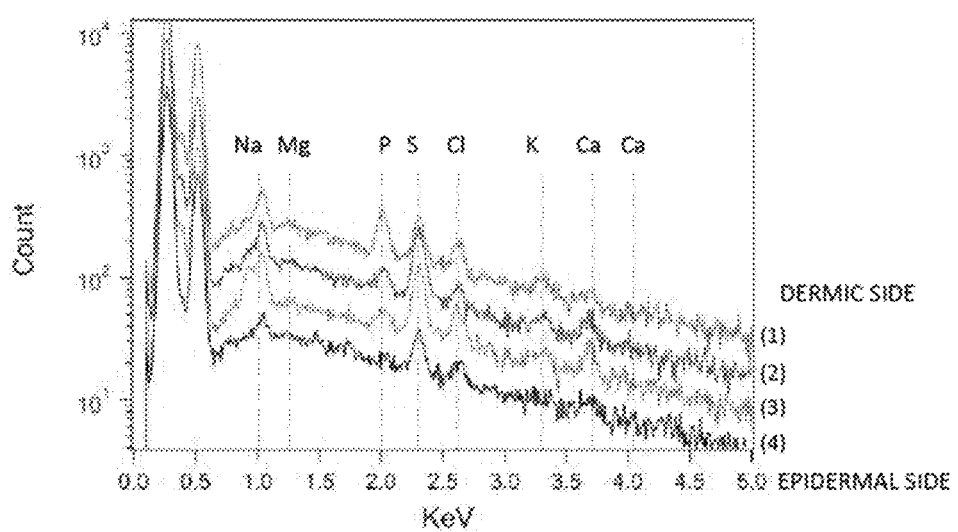

FIG. 61(*a*) is an image of Example 38 taken by a SEM, FIG. 61(*b*) is a diagram which illustrates the site subjected to the EDS analysis in Example 38, and FIG. 61(*c*) is the chart obtained by the EDS analysis of Example 38.

Figure 62:
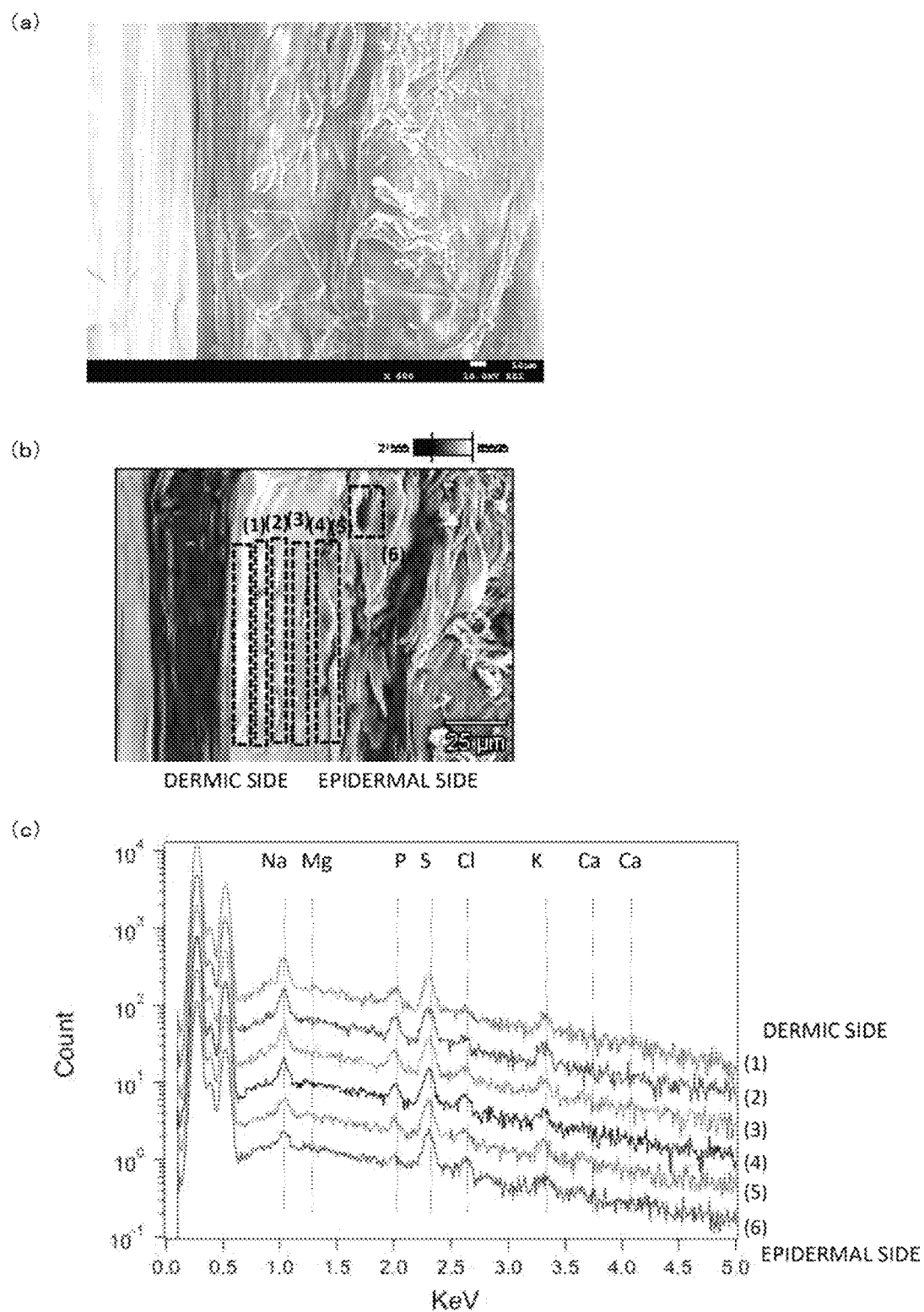
FIG. 62(a) is an image of Comparative Example 10 taken by a SEM.
FIG. 62(b) is a diagram which illustrates the site subjected to EDS analysis in Comparative Example 10.
FIG. 62(c) is the chart obtained by EDS analysis of Comparative Example 10.

FIG. 62(*a*) is an image of Comparative Example 10 taken by a SEM, FIG. 62(*b*) is a diagram which illustrates the site subjected to the EDS analysis in Comparative Example 10, and FIG. 62(*c*) is the chart obtained by the EDS analysis of Comparative Example 10.

As illustrated in FIG. 61(*c*) and FIG. 62(*c*), it has been confirmed that each ion has a characteristic gradient from the epidermal side through the dermic side in the artificial human skin. On the other hand, it can be seen that the peak profile corresponding to each ion is different when FIG. 61(*c*) and FIG. 62(*c*) are compared to each other. For example, a change in peak height of the sulfur ion and the calcium ion is seen in Example 38, but such a change is not seen in Comparative Example 10.

From the results described above, it has been suggested that the element distribution in a sample is differently affected in the case of using the protective agent for electron microscopic observation and surfactant-containing solution of the present invention and in the case of chemically fixing the sample with a fixing solution for electron microscopic observation of the prior art.

Example 39 and Comparative Example 11

A protective agent for electron microscopic observation and a surfactant-containing solution were prepared in the same manner as in Example 1.

The artificial human skin obtained by sterically three-dimensionally culturing a normal human skin cell was treated with the protective agent for electron microscopic observation and the surfactant-containing solution after 10 µM of GFT (anti-cancer drug) was added to the artificial human skin (Example 39).

On the other hand, as a control group, the artificial human skin obtained by sterically three-dimensionally culturing a normal human skin cell was chemically fixed with glutaraldehyde of a general fixing solution for electron microscopic observation after 10 µM of GFT (anti-cancer drug) was added to the artificial human skin (Comparative Example 11).

The artificial human skins of Example 39 and Comparative Example 11 were observed by a SEM, respectively. Furthermore, a plurality of sites were selected from the epidermis through the dermis, and the respective sites were subjected to the elemental analysis by EDS to measure the element distribution (Na, Mg, P, S, CI, K and Ca) in the interior of the artificial skin. Incidentally, the elements of the measurement target were detected in a state of being ionized in the skin of the present test example.

Figure 63:
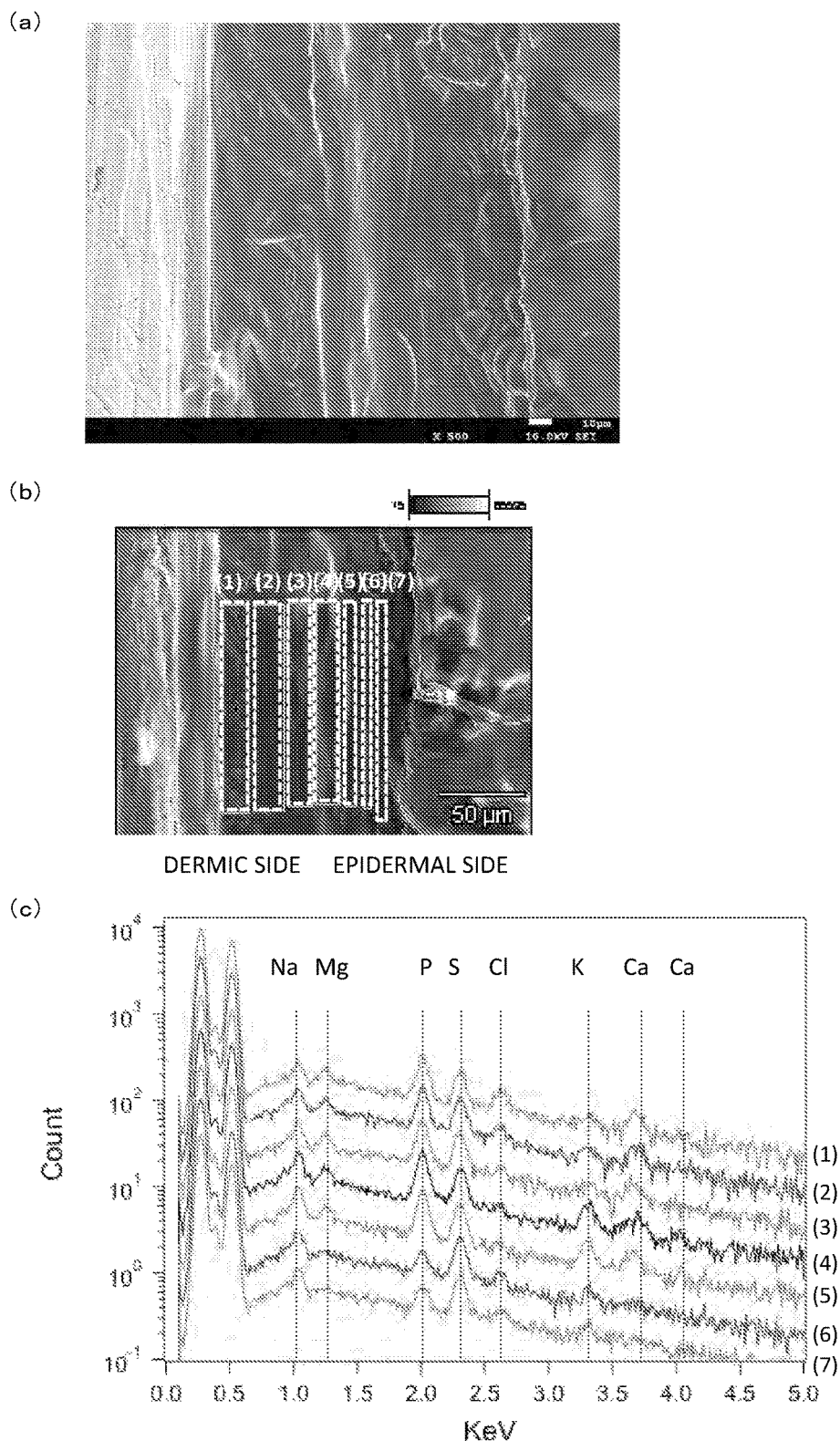
FIG. 63(a) is an image of Example 39 taken by a SEM.
FIG. 63(b) is a diagram which illustrates the site subjected to EDS analysis in Example 39.
FIG. 63(c) is the chart obtained by EDS analysis of Example 39.

FIG. 63(*a*) is an image of Example 39 taken by a SEM, FIG. 63(*b*) is a diagram which illustrates the site subjected to the EDS analysis in Example 39, and FIG. 63(*c*) is the chart obtained by the EDS analysis of Example 39.

Figure 64:
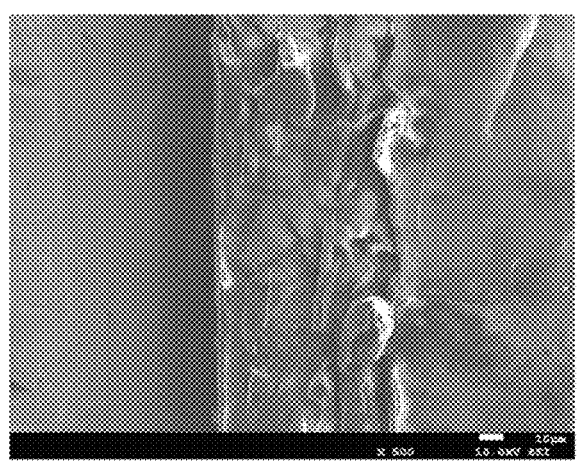
FIG. 64(a) is an image of Comparative Example 11 taken by a SEM.
FIG. 64(b) is a diagram which illustrates the site subjected to EDS analysis in Comparative Example 11.
FIG. 64(c) is the chart obtained by EDS analysis of Comparative Example 11.
Figure 64:
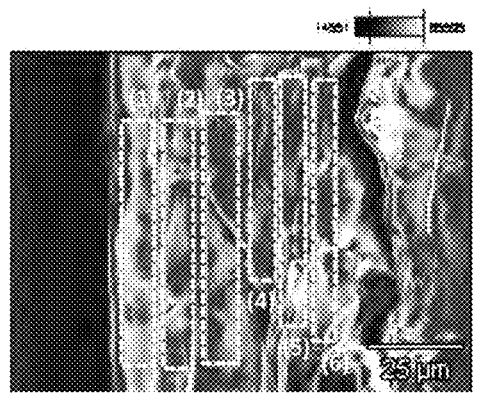
Figure 64:
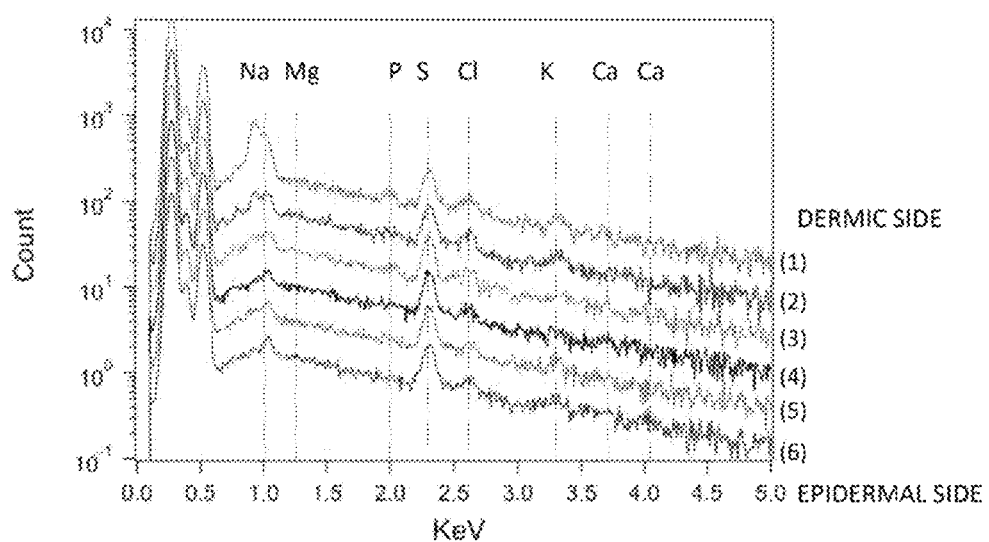

FIG. 64(*a*) is an image of Comparative Example 11 taken by a SEM, FIG. 64(*b*) is a diagram which illustrates the site subjected to the EDS analysis in Comparative Example 11, and FIG. 64(*c*) is the chart obtained by the EDS analysis of Comparative Example 11.

In Example 39, as illustrated in FIG. 63(*c*) it has been confirmed that potassium ion has a gradient from the epidermal side through the dermic side and calcium ion has a gradient from the dermic side through the epidermal side in the artificial human skin. On the other hand, in Comparative Example 11, as illustrated in FIG. 64(*c*), the gradient of potassium ion and the gradient of calcium ion as confirmed in Example 39 have not been confirmed.

From the results described above, it has become possible to more accurately measure the element distribution in the skin tissue by performing the SEM observation and EDS analysis by using the protective agent for electron microscopic observation and surfactant-containing solution of the present invention as compared to the sample that is chemically fixed with a fixing solution for electron microscopic observation of the prior art. This makes it possible to evaluate the therapeutic effect of a drug, for example, by performing the SEM observation of the skin and the EDS analysis of the interior of the skin before and after the drug is administered to the skin.

The invention claimed is:

1. A method for observing a biological sample in a water-containing state by an electron microscope, the method comprising:
   a step of coating a biological sample in a water-containing state with a protective agent for electron microscopic observation containing a component to impart the survival environment that is one or more selected from the group consisting of a polyhydric alcohol and any derivative of the polyhydric alcohol, a saccharide, and an electrolyte;
   a step of coating the biological sample in a water-containing state with a surfactant-containing solution;
   a step of placing the biological sample in a water-containing state coated with the protective agent for electron microscopic observation and the surfactant-containing solution on a sample stage and forming a thin film on a surface of the biological sample in a water-containing state by irradiating the biological sample in a water-containing state with an electron beam or plasma to cover the biological sample in a water-containing state; and a step of displaying an electron microscopic image of the biological sample in a water-containing state that is covered with the thin film and contained in a sample chamber in a vacuum on a display device;
wherein when the biological sample in a water-containing state is a cell in a water-containing state, the method further comprises the following steps prior to the coating step:
a step of bringing the cell in a water-containing state into contact with a primary antibody; and
a step of bringing the primary antibody cell into contact with a secondary antibody modified with a gold colloid,
wherein the cell bound to the primary antibody and the second antibody is coated with the protective agent for electron microscopic observation and the surfactant-containing solution, and
wherein a binding site of the cell in a water-containing state with the primary antibody is observed at the displaying step; and
wherein when the biological sample in a water-containing state is viral particle(s) in a water-containing state, the method further comprises
a step of concentrating the viral particles in a water-containing state on a substrate, wherein the viral particles are placed on the sample stage together with the substrate, and wherein the method further comprises
a step of counting viral particles in the displayed electron microscopic image of the viral particles in a water-containing state after the displaying step.

2. The method for observing a biological sample in a water-containing state by an electron microscope according to claim 1, wherein a surface of the biological sample in a water-containing state is washed with water prior to coating of the biological sample in a water-containing state with the protective agent for electron microscopic observation.

3. The method for observing a biological sample in a water-containing state by an electron microscope according to claim 1, wherein in the sample stage, the biological sample in a water-containing state on which a thin film is formed is placed on an upper surface of a cylindrical base member, a ring-shaped member having a circular opening that is substantially equal to a diameter of the cylindrical member, an opening having a diameter smaller than the opening at an upper surface portion of the ring-shaped member, and a fixing hole at a side surface portion is covered on the biological sample in a water-containing state placed on the upper surface of the cylindrical base member, and the cylindrical base member and the ring-shaped member are fixed with a fixing material.

4. The method for observing a biological sample in a water-containing state by an electron microscope according to claim 1, wherein in the sample stage, the biological sample in a water-containing state on which a thin film is formed is placed on an upper surface of a cylindrical member having a circular recess formed in a center, a disk-shaped member having a circular through hole formed in a center and a plurality of fixing holes opened on the periphery of the through hole is covered on the biological sample in a water-containing state placed on the upper surface of the cylindrical member, and the disk-shaped member and the cylindrical member are fixed with a fixing material.

5. The method for observing a biological sample in a water-containing state by an electron microscope according to claim 1, wherein a thin film is formed on a surface of the biological sample in a water-containing state by irradiating the biological sample in a water-containing state with an electron beam for sample observation in a sample chamber of an electron microscope.

6. The method for observing a biological sample in a water-containing state by an electron microscope according to claim 1, wherein a thin film is formed on a surface of the biological sample in a water-containing state by irradiating the biological sample in a water containing state with an electron beam different from an electron beam in a sample chamber of an electron microscope or plasma in advance before observation of the biological sample in a water-containing state by an electron microscope.

7. The method for observing a biological sample in a water-containing state by an electron microscope according to claim 1, wherein an electron microscopic image of the biological sample in a water-containing state is displayed on the display device without accompanying destruction of the biological sample in a water-containing state.

8. The method for observing a biological sample in a water-containing state by an electron microscope according to claim 1, wherein an electron microscopic image of the biological sample in a water-containing state is displayed on a display device without causing charge-up of the biological sample in a water-containing state by using a scanning electron microscope.

9. The method for observing a biological sample in a water-containing state by an electron microscope according to claim 1, wherein the biological sample in a water-containing state is a cancer cell in a water-containing state or a tissue including the cancer cell which is excised from a living body, and wherein the method further comprises
a step of performing image diagnosis of the displayed cancer cell in a water-containing state or the displayed tissue including the cancer cell after the displaying step.

10. The method for observing a biological sample in a water-containing state by an electron microscope according to claim 9, wherein the cancer cell in a water-containing state is one that is inoculated and cultured on a normal cell or a cell sheet.

11. The method for observing a biological sample in a water-containing state by an electron microscope according to claim 9, wherein the cancer cell in a water-containing state or the tissue including the cancer cell which is excised from a living body is chemically fixed immediately after the excision.

12. The method for observing a biological sample in a water-containing state by an electron microscope according to claim 1, wherein the biological sample in a water-containing state is a cell or cell sheet in a water-containing state, wherein the method further comprises
a step of adding a physiologically active substance or a drug to the cell or cell sheet in a water-containing state prior to the coating step, and wherein the method further comprises
a step of performing image diagnosis on an effect of the physiologically active substance or the drug to the displayed cell or cell sheet in a water-containing state after the displaying step.

13. The method for observing a biological sample in a water-containing state by an electron microscope according to claim 12, wherein the cell is a normal cell in a water-containing state and a physiologically active substance or a drug which has fewer side effects is screened by using a morphological change of the normal cell as an indicator.

14. The method for observing a biological sample in a water-containing state by an electron microscope according to claim 13, wherein the physiologically active substance or the drug is an anti-cancer drug.

15. The method for observing a biological sample in a water-containing state by an electron microscope according to claim 12, wherein the cell is a diseased cell in a water-containing state and a drug exhibiting activities is screened by using a morphological change of the diseased cell in a water-containing state as an indicator.

16. The method for observing a biological sample in a water-containing state by an electron microscope according to claim 15, wherein the diseased cell in a water-containing state is a cancer cell and the physiologically active substance or the drug is an anti-cancer drug.

17. The method for observing a biological sample in a water-containing state by an electron microscope according to claim 1, wherein an antigen that reacts with the primary antibody is a membrane protein of the cell in a water-containing state and a binding site of the cell in a water-containing state with the primary antibody is observed.

18. The method for observing a biological sample in a water-containing state by an electron microscope according to claim 1, wherein the step of concentrating viral particles in a water-containing state on a substrate is to concentrate viral particles by charging a surface of the viral particles in a water-containing state with a charge and adsorbing the viral particles in a water-containing state to a substrate having a surface charged with a charge that is opposite to this charged charge.

19. The method for observing a biological sample in a water-containing state by an electron microscope according to claim 18, wherein the surface of the viral particles in a water-containing state is charged with a positive charge by being treated with polybrene.

20. The method for observing a biological sample in a water-containing state by an electron microscope according to claim 19, wherein the surface of the substrate is charged with a negative charge by irradiating the surface with plasma.

21. The method for observing a biological sample in a water-containing state by an electron microscope according to claim 1, wherein the saccharide is one or more selected from the group consisting of a monosaccharide, a disaccharide, an oligosaccharide, a polysaccharide, and any derivative of the monosaccharide, the disaccharide, the oligosaccharide, and the polysaccharide.

22. The method for observing a biological sample in a water-containing state by an electron microscope according to claim 1, wherein the electrolyte is one or more selected from the group consisting of a metal compound, a metal complex, an inorganic salt, an organic salt, and an acid-base.

23. The method for observing a biological sample in a water-containing state by an electron microscope according to claim 1, wherein the protective agent comprises the component to impart the survival environment, the saccharide, and the electrolyte at a blending ratio of from 20:0.7:0.03 to 20:0.4:0.01.

24. The method for observing a biological sample in a water-containing state by an electron microscope according to claim 23, wherein the protective agent further comprises water at a blending ratio of 2:1 with respect to the component to impart the survival environment.

25. The method for observing a biological sample in a water-containing state by an electron microscope according to claim 23, wherein the component to impart the survival environment is glycerin, the saccharide is glucose, and the electrolyte is sodium chloride, dibasic sodium phosphate, citric acid, or calcium lactate.

* * * * *